US009884843B2

(12) United States Patent
Dixon et al.

(10) Patent No.: US 9,884,843 B2
(45) Date of Patent: Feb. 6, 2018

(54) CYCLIC SULFONE AND SULFOXIMINE ANALOGS AND USES THEREOF

(71) Applicant: Peloton Therapeutics, Inc., Dallas, TX (US)

(72) Inventors: Darryl David Dixon, Somerset, NJ (US); Jonas Grina, Coppell, TX (US); John A. Josey, Dallas, TX (US); James P. Rizzi, Irving, TX (US); Stephen T. Schlachter, Dallas, TX (US); Eli M. Wallace, Richardson, TX (US); Bin Wang, Dallas, TX (US); Paul Wehn, Dallas, TX (US); Rui Xu, Dallas, TX (US); Hanbiao Yang, Coppell, TX (US)

(73) Assignee: PELOTON THERAPEUTICS, INC., Dallas, TX (US)

( * ) Notice: Subject to any disclaimer, the term of this patent is extended or adjusted under 35 U.S.C. 154(b) by 0 days.

(21) Appl. No.: 15/037,047

(22) PCT Filed: Dec. 15, 2014

(86) PCT No.: PCT/US2014/070346
§ 371 (c)(1),
(2) Date: May 16, 2016

(87) PCT Pub. No.: WO2015/095048
PCT Pub. Date: Jun. 25, 2015

(65) Prior Publication Data
US 2016/0368893 A1 Dec. 22, 2016

Related U.S. Application Data

(60) Provisional application No. 61/916,672, filed on Dec. 16, 2013.

(51) Int. Cl.
| C07D 333/64 | (2006.01) |
| C07D 333/66 | (2006.01) |
| C07D 409/12 | (2006.01) |
| C07D 333/78 | (2006.01) |
| C07D 335/06 | (2006.01) |
| A61K 31/381 | (2006.01) |

(52) U.S. Cl.
CPC .......... C07D 333/64 (2013.01); A61K 31/381 (2013.01); C07D 333/66 (2013.01); C07D 333/78 (2013.01); C07D 335/06 (2013.01); C07D 409/12 (2013.01)

(58) Field of Classification Search
CPC .................................................. C07D 333/64
USPC ....................................................... 514/337
See application file for complete search history.

(56) References Cited

U.S. PATENT DOCUMENTS

| 4,214,103 A | 7/1980 | Garman et al. |
| 4,426,385 A | 1/1984 | Cain |
| 4,505,929 A | 3/1985 | Markley et al. |
| 4,665,097 A | 5/1987 | Cain |
| 5,059,609 A | 10/1991 | Eggler et al. |
| 2005/0070474 A1 | 3/2005 | Krissansen et al. |
| 2005/0085541 A1 | 4/2005 | Shiohara et al. |
| 2006/0058361 A1 | 3/2006 | Fliri et al. |
| 2006/0128790 A1 | 6/2006 | Chu et al. |
| 2007/0155726 A1 | 7/2007 | Arnaiz et al. |
| 2007/0244071 A1 | 10/2007 | Dennis et al. |
| 2008/0312313 A1 | 12/2008 | Carballido Herrera et al. |
| 2009/0286812 A1* | 11/2009 | Erickson ............. C07D 487/04 514/262.1 |
| 2009/0325961 A1 | 12/2009 | Duan et al. |
| 2010/0029694 A1 | 2/2010 | Herold et al. |
| 2010/0048537 A1 | 2/2010 | Matsuoka et al. |
| 2010/0168110 A1 | 7/2010 | Chhipa et al. |
| 2012/0295937 A1 | 11/2012 | Linehan et al. |
| 2013/0116275 A1 | 5/2013 | Van Meir et al. |
| 2013/0137746 A1 | 5/2013 | Govek et al. |
| 2014/0073634 A1 | 3/2014 | Jones et al. |
| 2014/0148462 A1 | 5/2014 | Eckhardt et al. |
| 2014/0163025 A1 | 6/2014 | Eckhardt et al. |
| 2014/0200218 A1 | 7/2014 | Bellingham et al. |

(Continued)

FOREIGN PATENT DOCUMENTS

| CN | 101058535 A | 10/2007 |
| DE | 705530 C | 4/1941 |

(Continued)

OTHER PUBLICATIONS

Song et al., ACS Med. Chem. Lets. (2012), vol. 3(6), pp. 450-453.*
King, Med. Chem., Principle and Practice (1994), pp. 206-208.*
Morrison and Boyd, Org. Chem., 3rd ed., (1974), pp. 353-356.*
Akincioglu, et al. Novel sulfamides as potential carbonic anhydrase isoenzymes inhibitors. Bioorg Med Chem. Mar. 15, 2013;21(6):1379-85. doi: 10.1016/j.bmc.2013.01.019. Epub Jan. 22, 2013.
International search report and written opinion dated May 12, 2016 for PCT/US2016/021060.
International search report and written opinion dated May 17, 2016 for PCT/US2016/021846.

(Continued)

*Primary Examiner* — Taofiq A Solola
(74) *Attorney, Agent, or Firm* — Wilson Sonsini Goodrich & Rosati

(57) ABSTRACT

The present disclosure relates to cyclic sulfones and sulfoximines that are HIF-2a inhibitors and methods of making and using them for treating cancers. In another aspect, the present disclosure provides a pharmaceutical composition comprising a compound described herein and a pharmaceutically acceptable carrier or excipient. The compound may exist in an amorphous form, a crystalline form, or as a salt, solvate, or hydrate. In another aspect, the present disclosure provides a method of treating renal cell carcinoma by administrating a therapeutically effective amount of a compound described herein or a pharmaceutical composition thereof to a subject in need of such treatment.

28 Claims, 5 Drawing Sheets

(56) References Cited

U.S. PATENT DOCUMENTS

| | | |
|---|---|---|
| 2014/0371319 A1 | 12/2014 | Kazuta et al. |
| 2016/0250216 A1 | 9/2016 | Bruick et al. |
| 2016/0251307 A1 | 9/2016 | Dixon et al. |
| 2016/0362390 A1 | 12/2016 | Wehn et al. |
| 2017/0217891 A1 | 8/2017 | Dixon et al. |
| 2017/0217892 A1 | 8/2017 | Dixon et al. |

FOREIGN PATENT DOCUMENTS

| | | | |
|---|---|---|---|
| FR | 1574139 A | | 7/1969 |
| GB | 2017087 A | | 10/1979 |
| JP | 558124758 A | | 7/1983 |
| WO | WO-9324434 A1 | | 12/1993 |
| WO | WO-0116097 A1 | | 3/2001 |
| WO | WO-2006027684 A1 | | 3/2006 |
| WO | WO-2006083781 A1 | | 8/2006 |
| WO | WO-2006125972 A1 | | 11/2006 |
| WO | WO-2007071441 A1 | | 6/2007 |
| WO | WO 2007/099423 A1 | | 9/2007 |
| WO | WO 2009/093133 A1 | | 7/2009 |
| WO | WO 2010/068794 A2 | | 6/2010 |
| WO | WO-2010103438 A1 | | 9/2010 |
| WO | 2010/137620 | * | 12/2010 |
| WO | WO 2010/141956 A2 | | 12/2010 |
| WO | WO 2012/123129 A1 | | 9/2012 |
| WO | WO 2012/170442 A1 | | 12/2012 |
| WO | WO 2013/011033 A1 | | 1/2013 |
| WO | 2013/040863 | * | 3/2013 |
| WO | WO 2013/057101 A1 | | 4/2013 |
| WO | WO-2013110433 A1 | | 8/2013 |
| WO | WO-2013133325 A1 | | 9/2013 |
| WO | WO 2014/078479 A2 | | 5/2014 |
| WO | WO 2015/035223 A1 | | 3/2015 |

OTHER PUBLICATIONS

International search report and written opinion dated May 20, 2016 for PCT/US2016/021061.
International search report and written opinion dated May 31, 2016 for PCT/US2016/021492.
International search report and written opinion dated Jun. 20, 2016 for PCT/US2016/021510.
International search report and written opinion dated Jul. 26, 2016 for PCT/US2016/027611.
Owens, et al. Smooth muscle cell hypertrophy versus hyperplasia in hypertension. Proc Natl Acad Sci U S A. Dec. 1981;78(12):7759-63.
CAS Registry No. 1050878-94-8 (Sep. 2008).
CAS Registry No. 1062399-04-05 (Oct. 2008).
CAS Registry No. 1090604-08-2 (Dec. 2008).
CAS Registry No. 1119387-77-7 (Mar. 2009).
CAS Registry No. 1147778-06-0 (May 2009).
CAS Registry No. 1386280-55-2 (Aug. 2012).
CAS Registry No. 879353-79-4 (Apr. 2006).
CAS Registry No. 903274-78-2 (Aug. 2006).
CAS Registry No. 950051-37-3 (Oct. 2007).
CAS Registry No. 21081-71-0, Database Registry, Chemical Abstracts Services, [retrieved on Mar. 23, 2017], Published 1968.
Co-pending U.S. Appl. No. 15/439,308, filed Feb. 22, 2017.
Co-pending U.S. Appl. No. 15/439,494, filed Feb. 22, 2017.
European Search Report dated Mar. 29, 2017 for EP Application No. 14871152.6.
European Search Report dated Mar. 8, 2017 for EP Application No. 14842085.4.
Lin, et al., Efficient in silico assay of inhibitors of hepatitis c virus RNA-dependent RNA polymerase by structure-based virtual screening and in vitro evaluation. Assay and drug development technologies. 9(3): Jun. 2011; pp. 290-298. XP55350132.
Notice of Allowance dated Apr. 6, 2017 for U.S. Appl. No. 15/177,166.
Office Action dated Apr. 28, 2017 for U.S. Appl. No. 14/905,776.
Svensson, et al., Bromination of bicyclic phenols with SO2 hetero-cyclic annelated rings, ACTA Pharmaceutica Suecica, Royal Pharmaceutical Institute, Sweden, vol. 12, No. 5-6, Jan. 1, 1975: pp. 401-406.
Co-pending U.S. Appl. No. 15/553,570, filed Aug. 24, 2017.
Co-pending U.S. Appl. No. 15/556,153, filed Sep. 6, 2017.
Co-pending U.S. Appl. No. 15/556,248, filed Sep. 6, 2017.
Co-pending U.S. Appl. No. 15/556,607, filed Sep. 7, 2017.
Co-pending U.S. Appl. No. 15/556,609, filed Sep. 7, 2017.
Co-pending U.S. Appl. No. 15/564,348, filed Oct. 4, 2017.
Notice of Allowance dated Sep. 7, 2017 for U.S. Appl. No. 15/177,166.
Office Action dated Sep. 8, 2017 for U.S. Appl. No. 14/905,776.
CAS Registry No. 81614-92-8 (Nov. 1984).
Office Action dated Dec. 16, 2016 for U.S. Appl. No. 14/905,776.
U.S. Appl. No. 14/905,776, filed Jan. 15, 2016, Dixon et al.
U.S. Appl. No. 15/177,166, filed Jun. 8, 2016, Wehn et al.
Bertout, et al. HIF2alpha inhibition promotes p53 pathway activity, tumor cell death, and radiation responses. Proc Natl Acad Sci U S A. Aug. 25, 2009;106(34):14391-6. doi: 10.1073/pnas.0907357106. Epub Aug. 12, 2009.
Bhatt, et al. Hypoxia-inducible factor-2alpha: effect on radiation sensitivity and differential regulation by an mTOR inhibitor. BJU Int. Aug. 2008;102(3):358-63. doi: 10.1111/j.1464-410X.2008.07558.x. Epub Apr. 3, 2008.
Cardoso, et al. Identification of Cys255 in HIF-1α as a novel site for development of covalent inhibitors of HIF-1α/ARNT PasB domain protein-protein interaction. Protein Sci. Dec. 2012;21(12):1885-96. doi: 10.1002/pro.2172. Epub Nov. 9, 2012.
Carew, et al. ELR510444 inhibits tumor growth and angiogenesis by abrogating HIF activity and disrupting microtubules in renal cell carcinoma. PLoS One. 2012;7(1):e31120. doi: 10.1371/journal.pone.0031120. Epub Jan. 25, 2012.
Giatromanolaki, et al. Relation of hypoxia inducible factor 1 alpha and 2 alpha in operable non-small cell lung cancer to angiogenic/molecular profile of tumours and survival. Br J Cancer. Sep. 14, 2001;85(6):881-90.
Gordon, et al. HIF-2alpha promotes hypoxic cell proliferation by enhancing c-myc transcriptional activity. Cancer Cell. Apr. 2007;11(4):335-47.
He, et al. Downregulating hypoxia-inducible factor-2α improves the efficacy of doxonthicin in the treatment of hepatocellular carcinoma. Cancer Sci. Mar. 2012;103(3):528-34. doi: 10.1111/j.1349-7006.2011.02177.x. Epub Jan. 13, 2012.
Holmquist-Mengelbier, et al. Recruitment of HIF-1alpha and HIF-2alpha to common target genes is differentially regulated in neuroblastoma: HIF-2alpha promotes an aggressive phenotype. Cancer Cell. Nov. 2006;10(5):413-23.
Hu, et al. Differential roles of hypoxia-inducible factor lalpha (HIF-1alpha) and HIF-2alpha in hypoxic gene regulation. Mol Cell Biol. Dec. 2003;23(24):9361-74.
International search report and written opinion dated Jan. 27, 2015 for PCT/US2014/054375.
International search report and written opinion dated Apr. 15, 2015 for PCT/US2014/070346.
Karoor, et al. Alveolar hypoxia promotes murine lung tumor growth through a VEGFR-2/EGFR-dependent mechanism. Cancer Prey Res (Phila). Aug. 2012;5(8):1061-71. doi: 10.1158/1940-6207.CAPR-12-0069-T. Epub Jun. 14, 2012.
Keith, et al. HIF1α and HIF2α: sibling rivalry in hypoxic tumour growth and progression. Nat Rev Cancer. Dec. 15, 2011;12(1):9-22. doi: 10.1038/nrc3183.
Key, et al. Principles of ligand binding within a completely buried cavity in HIF2alpha.PAS-B. J Am Chem Soc. Dec. 9, 2009;131(48):17647-54. doi: 10.1021/ja9073062.
Kim, et al. HIF2alpha cooperates with RAS to promote lung tumorigenesis in mice. J.Clin Invest. Aug. 2009;119(8):2160-70.
Kondo, et a. Inhibition of HIF2alpha is sufficient to suppress pVHL-defective tumor growth. PLoS Biol. Dec. 2003;1(3):E83, 439-444. Epub Dec. 22, 2003.
Kondo, et al. Inhibition of HIF is necessary for tumor suppression by the von Hippel-Lindau protein. Cancer Cell. Apr. 2002;1(3):237-46.

(56) References Cited

OTHER PUBLICATIONS

Koshiji, et al. HIF-1alpha induces cell cycle arrest by functionally counteracting Myc. EMBO J. May 5, 2004;23(9):1949-56. Epub Apr. 8, 2004.
Lee, et al. Acriflavine inhibits HIF-1 dimerization, tumor growth, and vascularization. Proc Nail Acad Sci U S A. Oct. 20, 2009;106(42):17910-5. doi: 10.1073/pnas.0909353106. Epub Oct. 1, 2009.
Li, et al. Hypoxia-inducible factors regulate tumorigenic capacity of glioma stem cells. Cancer Cell. Jun. 2, 2009;15(6):501-13. doi: 10.1016/j.ccr.2009.03.018.
Maher, et al. von Hippel-Lindau disease: a clinical and scientific review. Eur J Hum Genet. Jun. 2011;19(6):617-23. doi: 10.1038/ejhg.2010.175. Epub Mar. 9, 2011.
Mandriota, et al. HIF activation identifies early lesions in VHL kidneys: evidence for site-specific tumor suppressor function in the nephron. Cancer Cell. Jun. 2002;1(5):459-68.
Maranchie, et al. The contribution of VHL substrate binding and HIF1-alpha to the phenotype of VHL loss in renal cell carcinoma. Cancer Cell. Apr. 2002,1(3):247-55.
Mazumdar, et al. HIF-2alpha deletion promotes Kras-driven lung tumor development. Proc Natl Acad Sci U S A. Aug. 10, 2010;107(32):14182-7. doi: 10.1073/pnas.1001296107. Epub Jul. 21, 2010.
Miranda, et al. A cyclic peptide inhibitor of HIF-1 heterodimerization that inhibits hypoxia signaling in cancer cells. J Am Chem Soc. Jul. 17, 2013;135(28):10418-25. doi: 10.1021/ja402993u. Epub Jul. 9, 2013.
Nguyen, et al. Epigenetic regulation of hypoxia inducible factor in diseases and therapeutics. Arch Pharr Res. Mar. 2013;36(3):252-63. doi: 10.1007/s12272-013-0058-x. Epub Feb. 26, 2013.
Percy, et al. A gain-of-function mutation in the HIF2A gene in familial erythrocytosis. N Engl J Med. Jan. 10, 2008;358(2):162-8. doi: 10.1056/NEJMoa073123.
Percy, et al. Two new mutations in the HIF2A gene associated with erythrocytosis. Am J Hematol. Apr. 2012;87(4):439-42. doi: 10.1002/ajh.23123. Epub Feb. 24, 2012.
PubChem. Compound Summary for CID 21110550. 1-10. Create Date: Dec. 5, 2007. [retrieved on Jan. 20, 2015]. Retrieved from the Internet. <URL:http://pubchem.ncbi.nlm.nih.gov/compound/21110550>. entire document.
PubChem. Compound Summary for CID 825455. 1-11. Create Date: Jul. 9, 2005. [retrieved on Jan. 20, 2015]. Retrieved from the Internet. <URL:http://pubchem.ncb.nlm.nih.gov/compound/825455>. entire document.
Raval, et al. Contrasting properties of hypoxia-inducible factor 1 (HIF-1) and HIF-2 in von Hippel-Lindau-associated renal cell carcinoma. Mol Cell Biol. Jul. 2005;25(13):5675-86.

Rogers, et al. Development of inhibitors of the PAS-B domain of the HIF-2$\alpha$ transcription factor. J Med Chem. Feb. 28, 2013;56(4):1739-47. doi: 10.1021/jm301847z. Epub Feb. 18, 2013.
Sakairi, et al. Synthesis and SAR studies of bicyclic amine series GPR119 agonists. Bioorganic & Medicinal Chemistry Letters. 2012; 22:5123-5128.
Scheuermann, et al. Allosteric inhibition of hypoxia inducible factor-2 with small molecules. Nat Chem Biol. Apr. 2013;9(4):271-6. doi: 10.1038/nchembio.1185. Epub Feb. 24, 2013.
Scheuermann, et al. Artificial ligand binding within the HIF2alpha PAS-B domain of the HIF2 transcription factor. Proc Natl Acad Sci U S A. Jan. 13, 2009;106(2):450-5. doi: 10.1073/pnas.0808092106. Epub Jan. 7, 2009.
Semenza. Hypoxia-inducible factors: mediators of cancer progression and targets for cancer therapy. Trends Pharmacol Sci. Apr. 2012;33(4):207-14. doi: 10.1016/j.tips.2012.01.005. Epub Mar. 6, 2012.
Shen, et al. The VHL/HIF axis in clear cell renal carcinoma. Semin Cancer Biol. Feb. 2013;23(1):18-25. doi: 10.1016/j.semcancer.2012.06.001. Epub Jun. 13, 2012.
Talks, et al. The expression and distribution of the hypoxia-inducible factors HIF-alpha and HIF-2alpha in normal human tissues, cancers, and tumor-associated macrophages. Am J Pathol. Aug. 2000;157(2):411-21.
Tan, et al. Identification of a novel small-molecule inhibitor of the hypoxia-inducible factor 1 pathway. Cancer Rcs. Jan. 15, 2005;65(2):605-12.
Vanharanta, et al. Epigenetic expansion of VHL-HIF signal output drives multiorgan metastasis in renal cancer. Nat Med. Jan. 2013;19(1):50-6. doi: 10.1038/nm.3029. Epub Dec. 9, 2012.
Xue, et al. Hypoxia-inducible factor-2$\alpha$ activation promotes colorectal cancer progression by dysregulating iron homeostasis. Cancer Res. May 1, 2012;72(9):2285-93. doi: 10.1158/0008-5472.CAN-11-3836. Epub Mar. 14, 2012.
Xue, et al. Hypoxia-inducible factor-2$\alpha$ is essential in activating the COX2/mPGES-1/PGE2 signaling axis in colon cancer. Carcinogenesis. Jan. 2013;34(1):163-9. doi: 10.1093/carcin/bgs313. Epub Oct. 5, 2012.
Zhuang, et al. Somatic HIF2A gain-of-function mutations in paraganglioma with polycythemia. N Engl J Isiled. Sep. 6, 2012;367(10):922-30. doi: 10.1056/NEJMoa1205119.
Zimmer, et al. Inhibition of hypoxia-inducible factor is sufficient for growth suppression of VHL-/- tumors. Mol Cancer Res. Feb. 2004;2(2):89-95.
Zimmer, et al. Small-molecule inhibitors of HIF-2a translation link its 5'UTR iron-responsive clement to oxygen sensing. Mol Cell. Dec. 26, 2008;32(6):838-48. doi: 10.1016/j.molce1.2008.12.004.

\* cited by examiner

CYCLIC SULFONE AND SULFOXIMINE ANALOGS AND USES THEREOF

The present application is a National Stage Entry of PCT/US2014/070346, filed Dec. 15, 2014, which claims benefit of priority to U.S. Provisional Application Ser. No. 61/916,672, filed on Dec. 16, 2013, the entire contents of each application being hereby incorporated by reference.

This invention was in part funded by a grant from Cancer Prevention Research Institute of Texas (Grant number R1009).

Intratumoral hypoxia is a driving force in cancer progression and is closely linked to poor patient prognosis and resistance to chemotherapy and radiation treatment. Progress over the past several decades in mapping the molecular mechanisms that enable cellular adaptation to chronic oxygen deprivation has intensified interest in identifying drugs that effectively block the hypoxic response pathway in tumors. Hypoxia-Inducible Factors (HIF-1α and HIF-2α) are transcription factors that play central roles in this pathway, and thus represent attractive targets for therapeutic intervention. The half-life of HIF-α proteins is tightly regulated by the oxidative status within the cell. Under normoxic conditions, specific proline residues on the HIF proteins are hydroxylated by the oxygen sensitive HIF-specific prolyl-hydroxylases (PHD). The tumor suppressor von Hippel-Lindau (VHL) protein binds to the specific hydroxylated proline residues and recruits E3 ubiquition-ligase complex that targets HIF-α proteins for proteasomal degradation. Because PHDs require oxygen to function, under hypoxic conditions, HIF-α proteins accumulate and enter the nucleus to activate gene expression. Genetic mutations of the VHL gene that result in loss of function lead to constitutively active HIF-α proteins regardless of oxygen levels. Upon activation, these transcription factors stimulate the expression of genes that coordinately regulate anaerobic metabolism, angiogenesis, cell proliferation, cell survival, extracellular matrix remodeling, pH homeostasis, amino acid and nucleotide metabolism, and genomic instability. While many gene products involved in the hypoxic response have been explored individually as therapeutic targets for cancer, broad inhibition of the pathway through direct targeting of HIF-α proteins offers an exciting opportunity to attack tumors on multiple fronts (Keith, et al. *Nature Rev. Cancer* 12: 9-22, 2012).

Both HIF-1α and HIF-2α form a dimeric complex with HIF-1β (or ARNT: aryl hydrocarbon receptor nuclear translocator) and subsequently bind to hypoxia response elements (HRE) in target genes. Because the level of HIF-1β is unaffected by oxygen levels or VHL, transcriptional activity of the complex is largely driven by the availability of the HIF-α proteins. While HIF-1α and HIF-2α share significant sequence homology, they differ in tissue distribution, sensitivity to hypoxia, timing of activation and target gene specificity (Hu, et al. *Mol. Cell Biol.* 23: 9361-9374, 2003; and Keith, et al., *Nature Rev. Cancer* 12: 9-22, 2012). Whereas HIF-1α mRNA is ubiquitously expressed, the expression of HIF-2α mRNA is found primarily in kidney fibroblasts, hepatocytes and intestinal lumen epithelial cells. Consistent with the tight regulation of the HIF-α proteins under normal physiology, neither is detected in normal tissue with the exception of HIF-2α in macrophages (Talks, et al. *Am. J. Pathol.* 157: 411-421, 2000). However, HIF-2α protein has been detected in various human tumors of the bladder, breast, colon, liver, ovaries, pancreas, prostate and kidney as well as tumor-associated macrophages (Talks, et al. *Am. J. Pathol.* 157: 411-421, 2000). HIF-1α has been reported to give a transient, acute transcriptional response to hypoxia while HIF-2α provides more prolonged transcriptional activity. Furthermore, HIF-2α has greater transcriptional activity than HIF-1α under moderately hypoxic conditions such as those encountered in end capillaries (Holmquist-Mengelbier, et al. *Cancer Cell* 10: 413-423, 2006). Whereas some hypoxia-regulated genes are controlled by both HIF-1α and HIF-2α, some are only responsive to specific HIF-α proteins. For example, lactate dehydrogenase A (LDHA), phosphoglycerate kinase (PGK) and pyruvate dehydrogenase kinase 1 (PDK1) are uniquely controlled by HIF-1α whereas Oct-4 and erythropoietin (EPO) by HIF-2α. Often the relative contributions of the HIF-α proteins to gene transcription are cell type-, and disease-specific. More importantly, the HIF-α proteins may play contrasting roles in tumor genesis. For example, the oncogene MYC is a transcription factor that controls cell cycle G1/S transition. MYC is overexpressed in 40% of human cancer. It has been shown that HIF-2α activity increases MYC transcription activity whereas HIF-1α inhibits MYC activity. As a result, in MYC driven tumors, HIF-2α inhibition reduced proliferation whereas HIF-1α inhibition increased growth (Gordan, et al. *Cancer Cell* 11: 335-347, 2007; and Koshiji et al. *EMBO J.* 23: 1949-1956, 2004).

Therefore, it is desirable to identify effective small molecules which can modulate the activity of HIF-2α.

SUMMARY

In one aspect, the present disclosure provides a compound of Formula I,

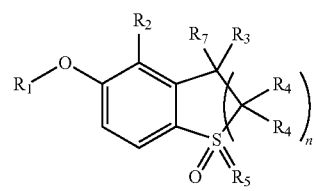

or a pharmaceutically acceptable salt thereof,
wherein:
$R_1$ is alkyl, heteroalkyl, cycloalkyl, heterocycloalkyl, aryl or heteroaryl;
$R_2$ is hydrogen, nitro, cyano, halo, alkyl, heteroalkyl, alkynyl or alkenyl;
$R_3$ is hydrogen, hydroxy or amino;
each of $R_4$ is independently selected from the group consisting of hydrogen, halo, alkyl, heteroalkyl and cycloalkyl, or the two $R_4$s and the carbon they are attached to form C3-C8 cycloalkyl or C5-C8 heterocycloalkyl;
$R_5$ is O or $NR_6$, wherein $R_6$ is selected from the group consisting of hydrogen, alkyl, cycloalkyl, cyano, heterocycloalkyl, heteroaryl and heteroalkyl;
$R_7$ is hydrogen, deuterium or alkyl; and
n is 1 or 2.

In another aspect, the present disclosure provides a pharmaceutical composition comprising a compound described herein and a pharmaceutically acceptable carrier or excipient. The compound may exist in an amorphous form, a crystalline form, or as a salt, solvate, or hydrate.

In another aspect, the present disclosure provides a method of treating renal cell carcinoma by administrating a therapeutically effective amount of a compound described herein or a pharmaceutical composition thereof to a subject in need of such treatment. The compound may exist in an amorphous form, a crystalline form, or as a salt, solvate, or hydrate. In some embodiments, the subject is a human.

In another aspect, the present disclosure provides a method of inhibiting the activities of HIF-2α in a cell, comprising contacting the cell with an effective amount of a compound described herein.

In another aspect, the present disclosure provides a kit comprising a pharmaceutical composition comprising a compound described herein and a pharmaceutically acceptable carrier or excipient and an instruction for using the composition to treat a subject suffering from cancer. In some embodiments, the cancer is renal cell carcinoma. In some embodiments, the subject is a human.

BRIEF DESCRIPTION OF FIGURES

FIG. 1 shows that Compound 3 treatment of renal cell carcinoma 786-0 xenograft bearing mice reduced the mRNA levels of HIF-2α and HIF-2α-regulated genes (PAI-1 and CCND1) in the tumor. Compound 3 had no significant effect on the mRNA level of HIF-1α or non-HIF-2α-regulated genes (PGK1 and PDK1).

FIG. 2 shows that Compound 3 treatment of 786-O xenograft bearing mice reduced the plasma level of human VEGFA compared to the vehicle treatment group.

FIG. 3 shows that Compound 3 treatment of 786-O xenograft bearing mice as a single agent led to tumor size reduction and regression compared to the vehicle treatment group.

DETAILED DESCRIPTION OF THE INVENTION

Figure 1:
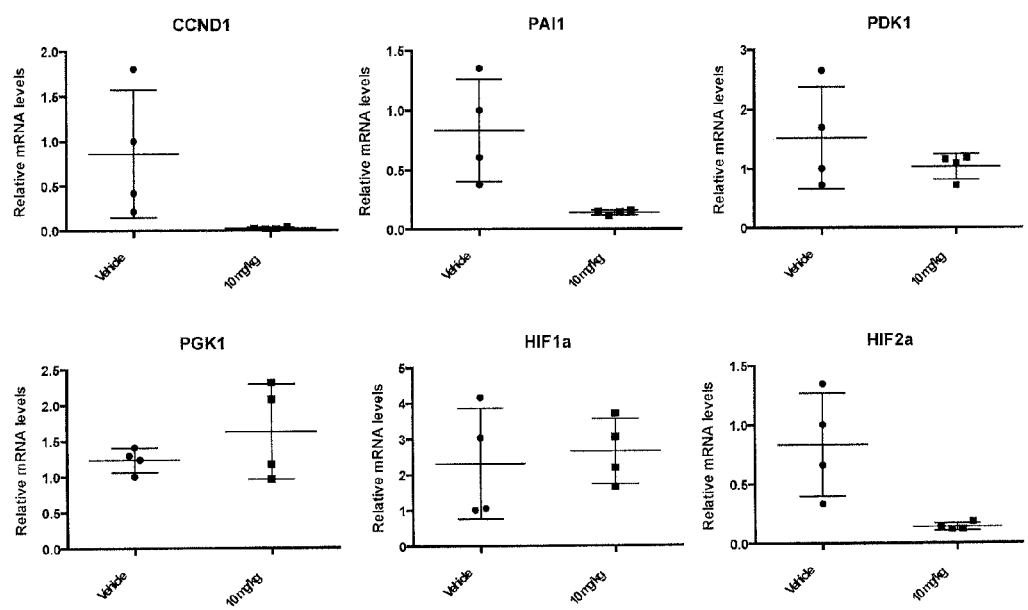
FIG. 1 shows treatment of renal cell carcinoma 786-O xenograft bearing mice at 0 mg/kg (denoted as "Vehicle") and 10 mg/kg of Compound 3, three times each at 12 hour intervals.

For purposes of interpreting this disclosure, the following definitions will apply.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF2A, PASD2, HIF-2-Alpha, HIF2-Alpha, HLF, Hypoxia-Inducible Factor 2-Alpha, HIF-1alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "scintillation proximity assay" (SPA) refers to a homogenous assay in which light is emitted when a radiolabeled ligand is brought into close proximity to a radio-sensitive bead. The assay typically contains a target protein that contains a tag (e.g., His Tag, Glutathione S-transferase Tag). The tag on the protein is used to bind the target protein to the scintillation bead. Radiolabeled ligand (e.g., labeled with tritium) that binds to the protein is now in close proximity to the bead, and when the raidolabel (e.g., tritium) decays, the high energy particle hits the bead resulting in the emission of light that is detected by a detector, such as photomultiplier tube or CCD camera. When unlabeled ligands or compounds that bind to the protein are used in the assay, they displace the radiolabeled ligand, resulting in loss of signal. For a general reference describing the assay, see Park, et al. *Analytical Biochemistry* 269: 94-104, 1999.

HIF-2α activity as used herein has its ordinary meaning in the art. HIF-2α activity, for example, includes activation of gene transcription mediated by HIF-2α.

The term "inhibiting HIF-2α activity", as used herein, refers to slowing, reducing, altering, as well as completely eliminating and/or preventing HIF-2α activity.

As used herein, the terms "treatment", "treating", "palliating" and "ameliorating" are used interchangeably. These terms refer to an approach for obtaining beneficial or desired results including, but are not limited to, any therapeutic and/or prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

The term "alkyl" refers to a straight or branched hydrocarbon chain radical comprised of carbon and hydrogen atoms, containing no unsaturation, and having from one to ten carbon atoms (i.e., C1-C10 alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a C1-C4 alkyl group. Typical alkyl groups include, but are in no way limited to, methyl, ethyl, n-propyl, iso-propyl, n-butyl, iso-butyl, sec-butyl, tertiary butyl, pentyl, iso-pentyl, neo-pentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)—OR$^a$, —OC(=O)—N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, cycloalkyl, heterocycloalkyl, aryl or heteroaryl. In some embodiments, the alkyl is substituted with an aryl. In a further embodiment, the aryl is a phenyl, which may optionally be further substituted. In some embodiments, the alkyl is fluoroalkyl.

The term "aromatic" or "aryl" refers to an aromatic radical with six to ten ring atoms (i.e., C6-C10 aromatic or C6-C10 aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)—OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$N(R$^a$)$_2$ (where t is 1 or 2), —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, cycloalkyl, heterocycloalkyl, aryl or heteroaryl.

The term "heteroaryl" or, alternatively, "heteroaromatic" refers to a 5- to 18-membered aromatic radical (i.e., C5-C18 heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —SR$^a$, —OC(=O)R$^a$, —OC(=O)OR$^a$, —N(R$^a$)$_2$, —C(=O)OR$^a$, —OC(=O)N(R$^a$)$_2$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, cycloalkyl, heterocycloalkyl, aryl or heteroaryl. Examples of monocyclic heteroaryls include, but are not limited to, imidazolyl, pyridinyl, pyrrolyl, pyrazinyl, pyrimidinyl, thiazolyl, furanyl and thienyl.

The term "acyl" refers to a —C(=O)R radical, wherein R is alkyl, cycloalkyl, aryl, heteroaryl, heteroalkyl, or heterocycloalkyl, which are as described herein. The R group is joined to the carbonyl through a carbon-carbon single bond. In some embodiments, it is a C1-C10 acyl radical which refers to the total number of chain or ring atoms of the alkyl, cycloalkyl, heteroalkyl, aryl, heteroaryl or heterocyclyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, heteroaryl, hydroxy, halo, cyano, trifluoromethyl, trifluoromethoxy, nitro, trimethylsilanyl, —OR$^a$, —SR$^a$, —OC(=O)R$^a$, —OC(=O)OR$^a$, —N(R$^a$)$_2$, —C(=O)R$^a$, —C(=O)OR$^a$, —OC(=O)N(R$^a$)$_2$, —C(=O)N(R$^a$)$_2$, —N(R$^a$)C(=O)OR$^a$, —N(R$^a$)C(=O)R$^a$, —N(R$^a$)C(=O)N(R$^a$)$_2$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), or —P(=O)

(OR$^a$)$_2$, wherein each R$^a$ is independently hydrogen, alkyl, cycloalkyl, heterocycloalkyl, aryl or heteroaryl.

The term "halo", "halide", or alternatively, "halogen" means fluoro, chloro, bromo or iodo. The term "haloalkyl" refers to alkyl structures that are substituted with one or more halo groups or combinations thereof. The term "haloalkoxy" refers to alkoxy structures that are substituted with one or more halo groups or combinations thereof. The term "fluoroalkyl" or "fluoroalkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$.

The term "cyano" refers to a —CN radical.

The term "alkoxy" refers to an —O-alkyl radical, wherein alkyl is as described herein and contains 1 to 10 carbons (e.g., C1-C10 alkoxy). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a C$_1$-C$_4$ alkoxy group. Unless stated otherwise specifically in the specification, an alkoxy moiety may be substituted by one or more of the substituents described as suitable substituents for an alkyl radical.

The term "sulfonyl" refers to a —S(=O)$_2$—R radical, wherein R is selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R group may be substituted by one or more of the substituents described as suitable substituents for an alkyl, an aryl or a heteroaryl radical.

The term "sulfoximinyl" refers to a —S(=O)(=NR$^a$)—R$^b$ radical, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroaryl (bonded through a ring carbon) and heterocycloalkyl (bonded through a ring carbon). Unless stated otherwise specifically in the specification, the R$^a$ and R$^b$ group may be substituted by one or more of the substituents described as suitable substituents for an alkyl, an aryl or a heteroaryl radical.

The term "cycloalkyl" refers to a monocyclic or polycyclic non-aromatic radical that contains only carbon and hydrogen, and may be saturated, or partially unsaturated. Cycloalkyl groups include groups having from 3 to 10 ring atoms (i.e., C3-C10 cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a C3-C6 cycloalkyl radical. Illustrative examples of cycloalkyl groups include, but are not limited to the following moieties: cyclopropyl, cyclobutyl, cyclopentyl, cyclohexyl, cycloseptyl, cyclooctyl, cyclononyl, cyclodecyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)R$^a$, —N(R$^a$)C(=O)N(R$^a$)$_2$, —N(R$^a$)C(=O)OR$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, cycloalkyl, heteroalkyl, heterocycloalkyl, aryl or heteroaryl.

The term "heterocyclyl" or "heterocycloalkyl" refers to a stable and not fully aromatic 3- to 18-membered ring (i.e., C3-C18 heterocycloalkyl) radical that comprises two to twelve ring carbon atoms and from one to six ring heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, 5 ring atoms, etc., up to and including 18 ring atoms. In some embodiments, it is a C5-C10 heterocycloalkyl. In some embodiments, it is a C4-C10 heterocycloalkyl. In some embodiments, it is a C3-C10 heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, I-oxothiomorpholinyl, and 1,1-dioxothiomorpholinyl. Unless stated otherwise specifically in the specification, a heterocycloalkyl moiety is optionally substituted by one or more substituents which independently are alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, heteroalkyl, cycloalkyl, heterocycloalkyl, aryl or heteroaryl.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range which refers to the chain length in total may be given. For example, a —CH$_2$OCH$_2$CH$_3$ radical is referred to as a "C4 heteroalkyl", which includes the heteroatom in the atom chain length description. Connection to the rest of the molecule is through a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, heteroalkyl, cycloalkyl, heterocycloalkyl, aryl or heteroaryl.

The term "amino" or "amine" refers to a —NHR$^a$ radical group, wherein R$^a$ is independently selected from hydrogen, alkyl, heteroalkyl, cycloalkyl, or heteroalkyl.

The term "acyloxy" refers to a RC(=O)O— radical wherein R is alkyl, cycloalkyl, heteroalkyl, aryl, heteroaryl or heterocycloalkyl, which are as described herein. In some embodiments, it is a C2-C4 acyloxy radical, wherein the C2-C4 refers to the total number, i.e., 1-3 of the chain or ring atoms of the alkyl, cycloalkyl, heteroalkyl, aryl, heteroaryl or heterocycloalkyl portion of the acyloxy group plus the carbonyl carbon of acyl, i.e., the ring or chain atoms plus carbonyl. If the R radical is heteroaryl or heterocyclyl, the hetero ring or chain atoms contribute to the total number of chain or ring atoms. Unless stated otherwise specifically in the specification, the R of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) where each R$^a$ is independently hydrogen, alkyl, heteroalkyl, cycloalkyl, heterocycloalkyl, aryl or heteroaryl.

The term "alkenyl" refers to a straight or branched hydrocarbon chain radical group comprising carbon and hydrogen atoms, containing at least one double bond, and having from two to ten carbon atoms (i.e., C2-C10 alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., C2-C8 alkenyl). In other embodiments, an alkenyl comprises two to five carbon atoms (i.e., C2-C5 alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, cycloalkyl, heterocycloalkyl, aryl or heteroaryl.

The term "alkynyl" refers to a straight or branched hydrocarbon chain radical group comprising carbon and hydrogen atoms, containing at least one triple bond, and having from two to ten carbon atoms (i.e., C2-C10 alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., C2-C8 alkynyl). In other embodiments, an alkynyl has two to five carbon atoms (i.e., C2-C5 alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each R$^a$ is independently hydrogen, alkyl, cycloalkyl, heterocycloalkyl, aryl or heteroaryl.

The term "amide" or "amido" refers to a chemical moiety with formula —C(=O)N(R$^a$)$_2$ or —NR$^a$C(=O)R$^a$, wherein each of R$^a$ is independently selected from the group consisting of hydrogen, alkyl, cycloalkyl, aryl, heteroaryl (bonded through a ring carbon) and heterocycloalkyl (bonded through a ring carbon). Two R$^a$s, together with the atoms they are attached to, optionally form a 5-10 membered ring. In some embodiments, it is a C1-C4 amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amino acid or a peptide molecule may be attached to a compound having an amine or a carboxylic acid moiety, thereby forming a prodrug. The procedures and specific groups to make such amides are known to those of skilled in the art and can readily be found in reference sources such as Greene and Wuts, *Protective Groups in Organic Synthesis*, 3rd Ed., John Wiley & Sons, New York, N.Y., 1999.

"Carboxaldehyde" refers to a —(C=O)H radical.
"Carboxylic acid" refers to a —(C=O)OH radical.

"Ester" refers to a chemical radical of formula —OC(=O)R or —C(=O)OR, wherein R is selected from the group consisting of alkyl, cycloalkyl, aryl, heteroaryl (bonded through a ring carbon) and heteroalkyl (bonded through a ring carbon). A hydroxy or carboxylic acid moiety on the compounds described herein may be esterified. The procedures and specific groups to make such esters are known to those skilled in the art and can readily be found in reference sources such as Greene and Wuts, *Protective Groups in Organic Synthesis*, 3rd Ed., John Wiley & Sons, New York, N.Y., 1999. Unless stated otherwise specifically in the specification, an ester group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$OR^a$, —$SR^a$, —OC(=O)$R^a$, —OC(=O)$OR^a$, —OC(=O)N($R^a$)$_2$, —N($R^a$)$_2$, —C(=O)$R^a$, —C(=O)$OR^a$, —C(=O)N($R^a$)$_2$, —N($R^a$)C(=O)$OR^a$, —N($R^a$)C(=O)N($R^a$)$_2$, —N($R^a$)C(=O)$R^a$, —N($R^a$)S(=O)$_t R^a$ (where t is 1 or 2), —N($R^a$)S(=O)$_t$N($R^a$)$_2$ (where t is 1 or 2), —S(=O)$_t R^a$ (where t is 1 or 2), —S(=O)$_t$N($R^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron) wherein each $R^a$ is independently hydrogen, alkyl, cycloalkyl, heterocycloalkyl, aryl or heteroaryl.

"Imino" refers to a =N—$R^a$ radical, wherein $R^a$ is hydrogen, alkyl, heteroalkyl, cycloalkyl, cyano, heterocycloalkyl, aryl or heteroaryl.

"Isocyanato" refers to a —NCO radical.

"Isothiocyanato" refers to a —NCS radical.

"Mercaptyl" refers to an (alkyl)S— or (H)S— radical.

"Moiety" refers to a specific segment or functional group of a molecule. Chemical moieties are often recognized chemical entities embedded in or appended to a molecule.

"Hydroxy" refers to a —OH radical.

"Oxa" refers to a —O— radical.

"Oxo" refers to a =O radical.

"Nitro" refers to a —NO$_2$ radical.

"Sulfinyl" refers to a —S(=O)—R radical, where R is selected from the group consisting of alkyl, cycloalkyl, aryl, heteroalkyl, heteroaryl (bonded through a ring carbon) and heterocyclyl (bonded through a ring carbon). In some embodiments, R is fluoroalkyl.

"Thiocyanato" refers to a —CNS radical.

"Thioxo" refers to a =S radical.

"Sulfoxyl" refers to a —S(=O)$_2$OH radical.

"Sulfonate" refers to a —S(=O)$_2$—OR radical, where R is selected from the group consisting of alkyl, cycloalkyl, heteroalkyl, aryl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl respectively.

"Substituted" means that the referenced group may be substituted with one or more additional group(s). Without being limiting, the one or more additional groups may be individually and independently selected from acyl, alkyl, heteroalkyl, cycloalkyl, heterocycloalkyl, aryl, heteroaryl, hydroxy, alkoxy, mercapto, alkylthio, arylthio, cyano, halo, carbonyl, ester, thiocarbonyl, isocyanato, thiocyanato, isothiocyanato, nitro, perhaloalkyl, fluoroalkyl, perfluoroalkyl, phosphate, silyl, sulfinyl, sulfonyl, sulfonamide, sulfoximinyl, alkylamino, amino, and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts cited herein.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

The methods and formulations described herein include the use of N-oxides, crystalline forms (also known as polymorphs), or pharmaceutically acceptable salts of compounds having the structure of formulae described herein, as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds described herein may exhibit their natural isotopic abundance, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*; Vol. 7; Wiley, ISBN-10: 0471495018, 2001.

The term "pharmaceutically acceptable" means that a chemical entity, such as a compound, a carrier, an additive or a salt, is acceptable for being administrated to a subject.

The term "pharmaceutically acceptable salts" refers to salts prepared from pharmaceutically acceptable bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts derived from pharmaceutically acceptable organic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylene-diamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When chemical entities disclosed herein are basic, salts may be prepared using at least one pharmaceutically acceptable acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, trifluoroacetic acid, and p-toluenesulfonic acids. In some embodiments, such acid may be selected, for example, from citric, hydrobromic, hydrochloric, maleic, phosphoric, sulfuric, fumaric, and tartaric acids.

The term "pharmaceutically acceptable carrier" as used herein means a diluent, excipient, encapsulating material or formulation auxiliary. The pharmaceutically acceptable carrier may be non-toxic, and/or inert. The pharmaceutically acceptable carrier may not have undesirable effect on a subject, preferably a mammal, more preferably a human. The pharmaceutically acceptable carrier may be suitable for delivering an active agent to the target site without affecting the activity of the agent.

The term "enantiomeric excess" or "e.e.", as used herein, is the percent excess of one enantiomer compared to that of the other enantiomer in a mixture, and can be calculated using the following equation: enantiomeric excess=((R−S)/(R+S))×100=% (R*)−% (S*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess is 74%.

The term "effective amount" or "therapeutically effective amount" refers to an amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

The term "about" refers to ±10% of a stated number or value.

The following abbreviations and terms have the indicated meanings throughout:
DAST=Diethylaminosulfur trifluoride
DCM or CH$_2$Cl$_2$=Dichloromethane
MTBE=Methyl t-butyl ether
NBS=N-Bromosuccinimide
NMP=N-Methyl-2-pyrrolidone
e.e. or ee=Enantiomeric excess
PPTS=Pyridinium p-toluenesulfonate
DMAP=4-Dimethylaminopyridine
Et$_2$O=Diethyl ether
CH$_3$CN or MeCN=Acetonitrile
EtOAc=Ethyl acetate
MeOH=Methanol
EtOH=Ethanol
TLC=Thin layer chromatography
THF=Tetrahydrofuran
DMSO=Dimethyl sulfoxide
CDCl$_3$=Deuterated chloroform
DMF=N,N-Dimethylformamide Compounds When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

When "⧸" is drawn across a bond, it denotes where a bond disconnection or attachment occurs. For example, in the chemical structure shown below,

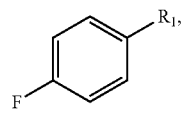

R$_1$ group is attached to the para position of a fluorophenyl ring through a single bond. When R$_1$ is phenyl, it can also be drawn as

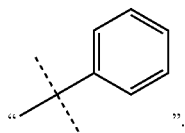

The waved line "∿" means a bond with undefined stereochemistry. For example,

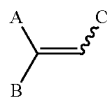

represents a mixture of

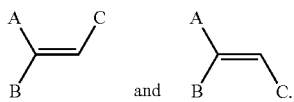

When a bond is drawn across a ring, it means substitution at a non-specific ring atom or position. For example, in the structure shown below,

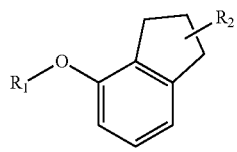

R$_2$ may be attached to any one of the —CH$_2$— of the five-membered ring.

In one aspect, the present disclosure provides a compound having the structure of Formula I,

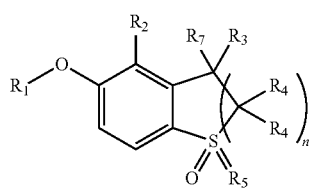

or a pharmaceutically acceptable salt thereof,
wherein:

R$_1$ is alkyl, heteroalkyl, cycloalkyl, heterocycloalkyl, aryl or heteroaryl;

R$_2$ is hydrogen, nitro, cyano, halo, alkyl, heteroalkyl, alkynyl or alkenyl;

R$_3$ is hydrogen, hydroxy or amino;

each of R$_4$ is independently selected from the group consisting of hydrogen, halo, alkyl, heteroalkyl and cycloalkyl, or two R$_4$s and the carbon they are attached to form C3-C8 cycloalkyl or C5-C8 heterocycloalkyl;

R$_5$ is O or NR$_6$, wherein R$_6$ is selected from the group consisting of hydrogen, alkyl, and cyano;

R$_7$ is hydrogen, deuterium, alkyl or R$_3$ and R$_7$ in combination form oxo; and n is 1 or 2.

In some embodiments, R$_1$ is alkyl, cycloalkyl, heterocycloalkyl, aryl or heteroaryl. In some embodiments, R$_1$ is cycloalkyl, heterocycloalkyl, aryl or heteroaryl. In some embodiments, R$_1$ is heterocycloalkyl, aryl or heteroaryl. In some embodiments, R$_1$ is cycloalkyl, aryl or heteroaryl. In some embodiments, R$_1$ is aryl or heteroaryl. In a further embodiment, R$_1$ is phenyl. In another further embodiment, R$_1$ is pyridyl. In a still further embodiment, the phenyl or pyridyl is substituted with at least one substituent selected from the group consisting of halo, alkoxy, cyano and alkyl.

In some embodiment, R$_1$ is selected from the group consisting of cyclobutyl, cyclohexyl, tetrahydrofuranyl and tetrahydropyranyl.

In some embodiments, R$_1$ is

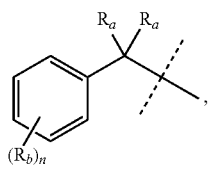

wherein each of R$_a$ is independently hydrogen or C1-C4 alkyl, or two R$_a$s and the carbon atom that they are attached to form a 4-8 membered all carbon or heterocyclic ring system, n is 0, 1, 2, 3, or 4, and each of R$_b$ is independently selected from the group consisting of halo, alkoxy, cyano, and alkyl when multiple R$_b$s are present.

In some embodiments, R$_1$ is selected from the group consisting of:

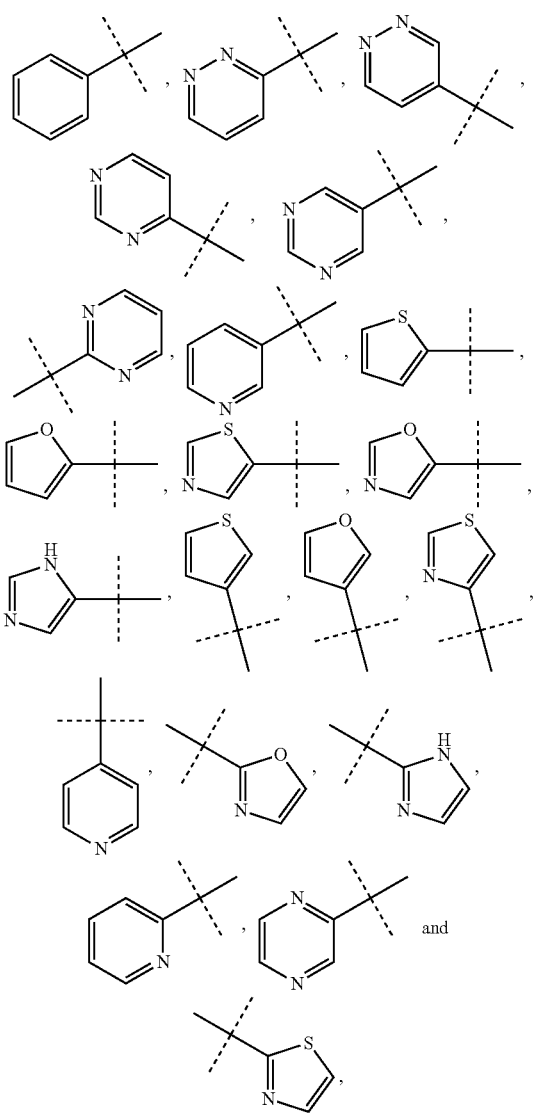

and the rings specified for R$_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_2$ is nitro, cyano, halo, alkyl, heteroalkyl, alkynyl or alkenyl. In some embodiments, $R_2$ is cyano, halo, alkyl, heteroalkyl, or alkynyl. In some embodiments, $R_2$ is cyano, halo, or alkyl. In some embodiments, $R_2$ is halo, or alkyl. In a further embodiment, $R_2$ is fluoroalkyl. In a still further embodiment, $R_2$ is C1-C4 fluoroalkyl. Exemplary C1-C4 fluoroalkyl includes, but is not limited to, —CH$_2$F, —CHF$_2$, —CF$_2$CH$_3$, and the like.

In some embodiments, $R_3$ is hydroxy or amino. In some embodiments, $R_3$ is hydroxy. In some embodiments, $R_3$ is amino. In a further embodiment, $R_3$ is NH$_2$.

In some embodiments, each of $R_4$ is independently hydrogen or fluoro. In some embodiments, each of $R_4$ is hydrogen. In some embodiments, each of $R_4$ is fluoro. In some embodiments, at least one $R_4$ is fluoro.

In some embodiments, $R_5$ is O, N—CN, or NH. In some embodiments, $R_5$ is O. In some embodiments, $R_5$ is NH. In some embodiments, $R_5$ is N—CN.

In some embodiments, $R_7$ is hydrogen or deuterium. In some embodiments, $R_7$ is hydrogen. In a further embodiment, $R_7$ is C1-C4 alkyl.

In some embodiments, $R_3$ is hydroxy or amino and $R_7$ is hydrogen. In some further embodiments, $R_1$ is aryl or heteroaryl. In a further embodiment, $R_2$ is cyano, halo or alkyl. In a still further embodiment, $R_4$ is fluoro.

In some embodiments, $R_3$ is hydroxy or amino and $R_2$ is cyano, halo or alkyl. In a further embodiment, $R_2$ is fluoroalkyl. In a still further embodiment, at least one $R_4$ is fluoro. In a yet still further embodiment, n is 1.

In some embodiments, $R_5$ is O or NH and $R_7$ is hydrogen. In some further embodiments, $R_1$ is aryl or heteroaryl. In a further embodiment, $R_2$ is cyano, halo or alkyl. In a still further embodiment, at least one of $R_4$ is fluoro.

In some embodiments, n is 1. In some further embodiments, $R_3$ is hydroxy or amino and $R_4$ is fluoro. In a further embodiment, $R_1$ is aryl or heteroaryl. In a still further embodiment, $R_1$ is phenyl or pyridyl, optionally substituted with one or more substituents selected from the group consisting of halo, alkoxy, cyano and alkyl.

In another aspect, the present invention provides a compound having the structure of Formula II

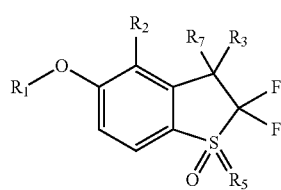

II or a pharmaceutically acceptable salt thereof, wherein:
$R_1$ is alkyl, heteroalkyl, cycloalkyl, heterocycloalkyl, aryl or heteroaryl;
$R_2$ is hydrogen, nitro, cyano, halo, alkyl, heteroalkyl, alkynyl or alkenyl;
$R_3$ is hydrogen, hydroxy or amino;
$R_5$ is O or NR$_6$, wherein R$_6$ is selected from the group consisting of hydrogen, alkyl, and cyano; and
$R_7$ is hydrogen, deuterium, alkyl or $R_3$ and $R_7$ in combination form oxo.

In some embodiments, $R_1$ is alkyl, cycloalkyl, heterocycloalkyl, aryl or heteroaryl. In some embodiments, $R_1$ is cycloalkyl, heterocycloalkyl, aryl or heteroaryl. In some embodiments, $R_1$ is heterocycloalkyl, aryl or heteroaryl. In some embodiments, $R_1$ is cycloalkyl, aryl or heteroaryl. In some embodiments, $R_1$ is aryl or heteroaryl. In a further embodiment, $R_1$ is phenyl. In another further embodiment, $R_1$ is pyridyl. In a still further embodiment, the phenyl or pyridyl is substituted with at least one substituent selected from the group consisting of halo, alkoxy, cyano and alkyl.

In some embodiment, $R_1$ is selected from the group consisting of cyclobutyl, cyclohexyl, tetrahydrofuranyl and tetrahydropyranyl.

In some embodiments, $R_1$ is

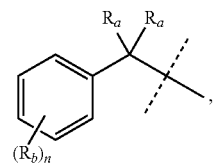

wherein each of $R^a$ is independently hydrogen or C1-C4 alkyl, or two $R_a$s and the carbon atom that they are attached to form a 4-8 membered all carbon or heterocyclic ring system, n is 0, 1, 2, 3, or 4, and each of $R_b$ is independently selected from the group consisting of halo, alkoxy, cyano and alkyl when multiple $R_b$s are present.

In some embodiments, $R_1$ is selected from the group consisting of:

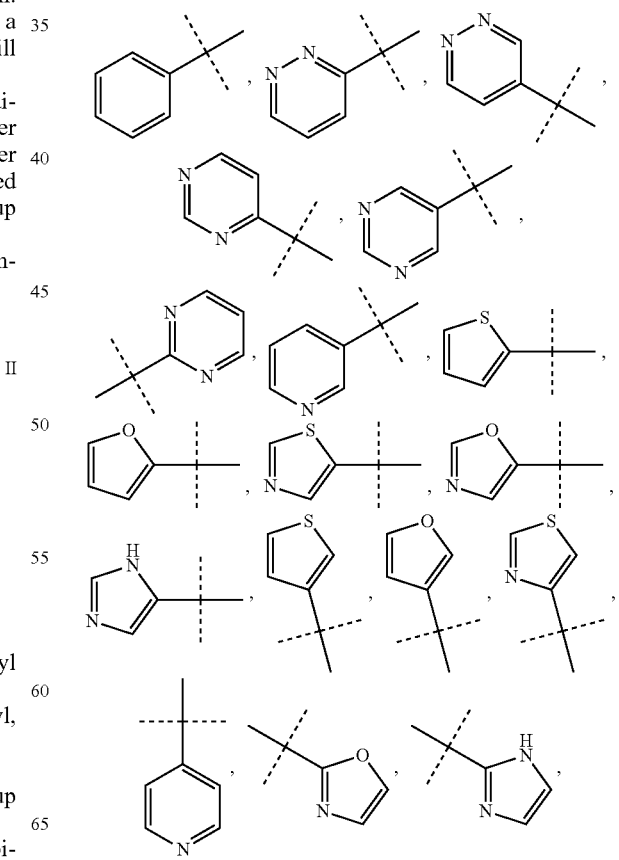

-continued

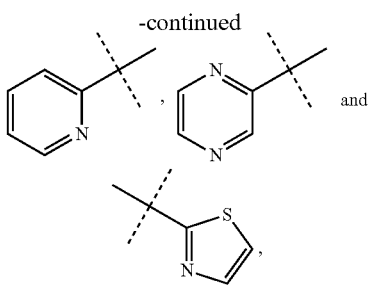

and the rings specified for $R_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_2$ is nitro, cyano, halo, alkyl, heteroalkyl, alkynyl or alkenyl. In some embodiments, $R_2$ is cyano, halo, alkyl, heteroalkyl, or alkynyl. In some embodiments, $R_2$ is cyano, halo, or alkyl. In some embodiments, $R_2$ is halo, or alkyl. In a further embodiment, $R_2$ is fluoroalkyl. In a still further embodiment, $R_2$ is C1-C4 fluoroalkyl. Exemplary C1-C4 fluoroalkyl includes, but is not limited to, —CH$_2$F, —CHF$_2$, —CF$_3$, —CF$_2$CH$_3$, and the like.

In some embodiments, $R_3$ is hydroxy or amino. In some embodiments, $R_3$ is hydroxy. In some embodiments, $R_3$ is amino. In a further embodiment, $R_3$ is NH$_2$.

In some embodiments, $R_5$ is O, N—CN, or NH. In some embodiments, $R_5$ is O. In some embodiments, $R_5$ is NH. In some embodiments, $R_5$ is N—CN.

In some embodiments, $R_7$ is hydrogen or deuterium. In some embodiments, $R_7$ is alkyl. In a further embodiment, $R_7$ is C1-C4 alkyl.

In some embodiments, $R_5$ is O or NH and $R_7$ is hydrogen. In a further embodiment, $R_3$ is hydroxy.

In another aspect, the present invention provides a compound having the structure of Formula III

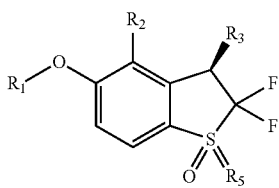

III or a pharmaceutically acceptable salt thereof,
wherein:
$R_1$ is alkyl, heteroalkyl, cycloalkyl, heterocycloalkyl, aryl or heteroaryl;
$R_2$ is hydrogen, nitro, cyano, halo, alkyl, heteroalkyl, alkynyl or alkenyl;
$R_3$ is hydroxy or amino; and
$R_5$ is O or NR$_6$, wherein $R_6$ is selected from the group consisting of hydrogen, alkyl and cyano.

In some embodiments, $R_1$ is alkyl, cycloalkyl, heterocycloalkyl, aryl or heteroaryl. In some embodiments, $R_1$ is cycloalkyl, heterocycloalkyl, aryl or heteroaryl. In some embodiments, $R_1$ is heterocycloalkyl, aryl or heteroaryl. In some embodiments, $R_1$ is cycloalkyl, aryl or heteroaryl. In some embodiments, $R_1$ is aryl or heteroaryl. In a further embodiment, $R_1$ is phenyl. In another further embodiment, $R_1$ is pyridyl. In a still further embodiment, the phenyl or pyridyl is substituted with at least one substituent selected from the group consisting of halo, alkoxy, cyano and alkyl.

In some embodiments, $R_1$ is selected from the group consisting of cyclobutyl, cyclohexyl, tetrahydrofuranyl and tetrahydropyranyl.

In some embodiments, $R_1$ is

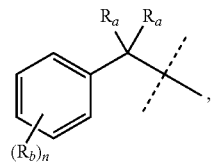

wherein each of $R_a$ is independently hydrogen or C1-C4 alkyl, or two $R_a$s and the carbon atom they are attached to form a 4-8 membered all carbon or heterocyclic ring system, n is 0, 1, 2, 3, or 4, and each of $R_b$ is independently selected from the group consisting of halo, alkoxy, cyano and alkyl when multiple $R_b$s are present.

In some embodiments, $R_1$ is selected from the group consisting of:

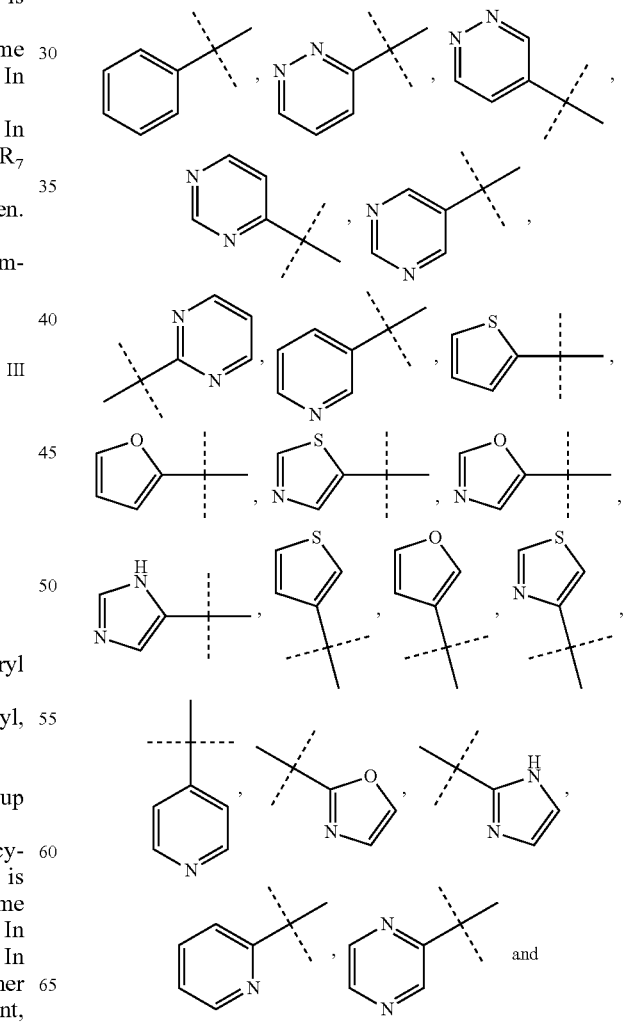

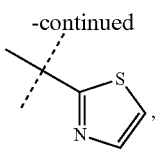

and the rings specified for $R_1$ may optionally be substituted by one or more substituents described for aryl and heteroaryl. In a further embodiment, the substituent(s) is selected from the group consisting of halo, C1-C4 alkyl, C1-C4 alkoxy, and cyano.

In some embodiments, $R_2$ is nitro, cyano, halo, alkyl, heteroalkyl, alkynyl or alkenyl. In some embodiments, $R_2$ is cyano, halo, alkyl, heteroalkyl, or alkynyl. In some embodiments, $R_2$ is cyano, halo, or alkyl. In some embodiments, $R_2$ is halo, or alkyl. In a further embodiment, $R_2$ is fluoroalkyl. In a still further embodiment, $R_2$ is C1-C4 fluoroalkyl. Exemplary C1-C4 fluoroalkyl includes, but is not limited to, —CH$_2$F, —CHF$_2$, —CF$_2$CH$_3$, and the like.

In some embodiments, $R_3$ is hydroxy. In some embodiments, $R_3$ is amino. In a further embodiment, $R_3$ is NH$_2$.

In some embodiments, $R_5$ is O, N—CN, or NH. In some embodiments, $R_5$ is O. In some embodiments, $R_5$ is NH. In some embodiments, $R_5$ is N—CN.

The compound of Formula III may have an enantiomeric excess of at least about 50%. In some embodiments, $R_5$ is O and the compound has an enantiomeric excess of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%. In a further embodiment, the compound has an enantiomeric excess of at least about 90%.

In another aspect, the present disclosure provides a compound or pharmaceutically acceptable salt selected from the group consisting of the following compounds:

| Structure | Example Number | IUPAC Name |
|---|---|---|
| 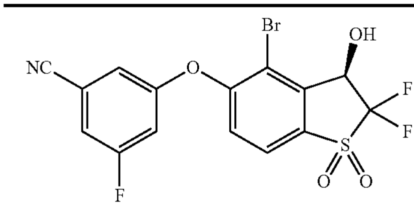 | 1 | (R)-3-((4-bromo-2,2-difluoro-3-hydroxy-1,1-dioxido-2,3-dihydrobenzo[b]thiophen-5-yl)oxy)-5-fluorobenzonitrile |
| 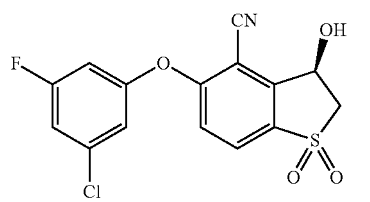 [SMILES: N#Cc1c(Oc2cc(F)cc(Cl)c2)ccc2c1[C@@H](O)CS2(=O)=O] | 2 | (3R)-5-(3-chloro-5-fluoro-phenoxy)-3-hydroxy-1,1-dioxo-2,3-dihydrobenzothiophene-4-carbonitrile |
| 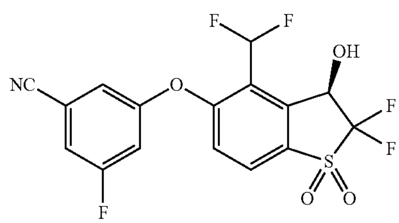 [SMILES: N#Cc1cc(F)cc(Oc2ccc3c(c2C(F)F)[C@@H](O)C(F)(F)S3(=O)=O)c1] | 3 | (R)-3-((4-(difluoromethyl)-2,2-difluoro-3-hydroxy-1,1-dioxido-2,3-dihydrobenzo[b]thiophen-5-yl)oxy)-5-fluorobenzonitrile |
| 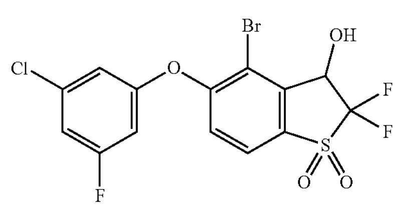 [SMILES: O=S1(=O)c2ccc(Oc3cc(F)cc(Cl)c3)c(Br)c2C(O)C1(F)F] | 9 | 4-Bromo-5-(3-chloro-5-fluorophenoxy)-2,2-difluoro-3-hydroxy-2,3-dihydrobenzo[b]thiophene 1,1-dioxide |
| 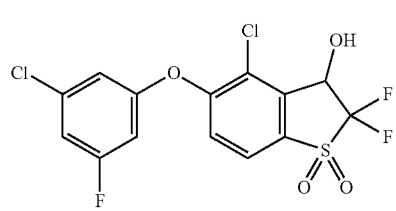 [SMILES: O=S1(=O)c2ccc(Oc3cc(F)cc(Cl)c3)c(Cl)c2C(O)C1(F)F] | 11 | 4-Chloro-5-(3-chloro-5-fluorophenoxy)-2,2-difluoro-3-hydroxy-2,3-dihydrobenzo[b]thiophene 1,1-dioxide |

-continued

| Structure | Example Number | IUPAC Name |
|---|---|---|
| 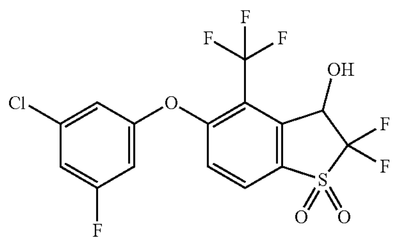 [SMILES: O=S1(=O)c2ccc(Oc3cc(F)cc(Cl)c3)c(C(F)(F)F)c2C(O)C1(F)F] | 14 | 5-(3-Chloro-5-fluorophenoxy)-2,2-difluoro-3-hydroxy-4-(trifluoromethyl)-2,3-dihydrobenzo[b]thiophene 1,1-dioxide |
| 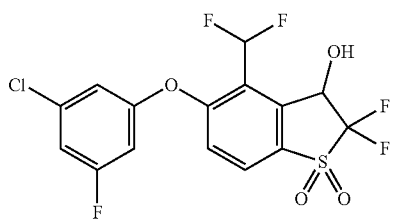 [SMILES: O=S1(=O)c2ccc(Oc3cc(F)cc(Cl)c3)c(C(F)F)c2C(O)C1(F)F] | 18 | 5-(3-Chloro-5-fluorophenoxy)-4-(difluoromethyl)-2,2-difluoro-3-hydroxy-2,3-dihydrobenzo[b]thiophene 1,1-dioxide |
| 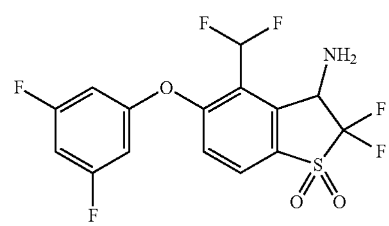 [SMILES: NC1c2c(ccc(Oc3cc(F)cc(F)c3)c2C(F)F)S(=O)(=O)C1(F)F] | 19 | 3-Amino-4-(difluoromethyl)-5-(3,5-difluorophenoxy)-2,2-difluoro-2,3-dihydrobenzo[b]thiophene 1,1-dioxide |
| 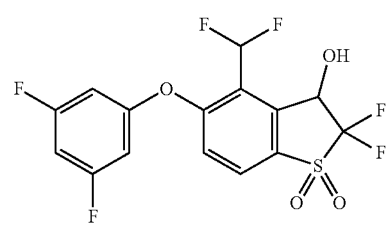 [SMILES: O=S1(=O)c2ccc(Oc3cc(F)cc(F)c3)c(C(F)F)c2C(O)C1(F)F] | 22 | 4-(Difluoromethyl)-5-(3,5-difluorophenoxy)-2,2-difluoro-3-hydroxy-2,3-dihydrobenzo[b]thiophene 1,1-dioxide |
| 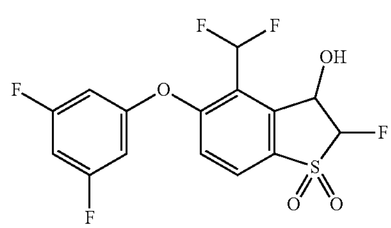 [SMILES: O=S1(=O)c2ccc(Oc3cc(F)cc(F)c3)c(C(F)F)c2C(O)C1F] | 23 | 4-(Difluoromethyl)-5-(3,5-difluorophenoxy)-2-fluoro-3-hydroxy-2,3-dihydrobenzo[b]thiophene 1,1-dioxide |
| 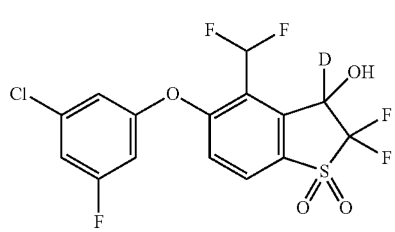 [SMILES: [2H]C1(O)c2c(ccc(Oc3cc(F)cc(Cl)c3)c2C(F)F)S(=O)(=O)C1(F)F] | 25 | 5-(3-Chloro-5-fluorophenoxy)-4-(difluoromethyl)-2,2-difluoro-3-hydroxy-2,3-dihydrobenzo[b]thiophene 1,1-dioxide-3-d |

| Structure | Example Number | IUPAC Name |
|---|---|---|
| 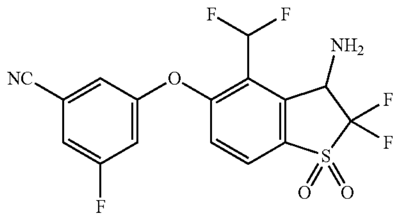 | 26 | 3-((3-Amino-4-(difluoromethyl)-2,2-difluoro-1,1-dioxido-2,3-dihydrobenzo[b]thiophen-5-yl)oxy)-5-fluorobenzonitrile |
| 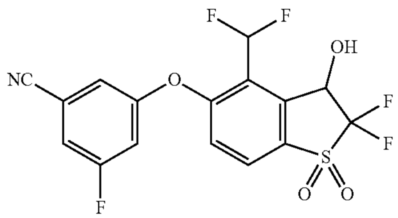 [SMILES: N#Cc1cc(F)cc(Oc2ccc3c(c2C(F)F)C(O)C(F)(F)S3(=O)=O)c1] | 29 | 3-((4-(Difluoromethyl)-2,2-difluoro-3-hydroxy-1,1-dioxido-2,3-dihydrobenzo[b]thiophen-5-yl)oxy)-5-fluorobenzonitrile |
| 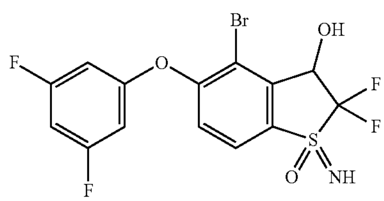 [SMILES: N=S1(=O)c2ccc(Oc3cc(F)cc(F)c3)c(Br)c2C(O)C1(F)F] | 32 | 4-bromo-5-(3,5-difluorophenoxy)-2,2-difluoro-3-hydroxy-1-imino-2,3-dihydro-1H-1$\lambda^4$-benzo[b]thiophene 1-oxide |
| 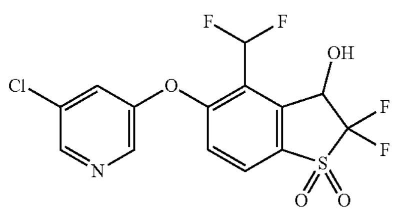 [SMILES: O=S1(=O)c2ccc(Oc3cncc(Cl)c3)c(C(F)F)c2C(O)C1(F)F] | 35 | 5-((5-Chloropyridin-3-yl)oxy)-4-(difluoromethyl)-2,2-difluoro-3-hydroxy-2,3-dihydrobenzo[b]thiophene 1,1-dioxide |
| 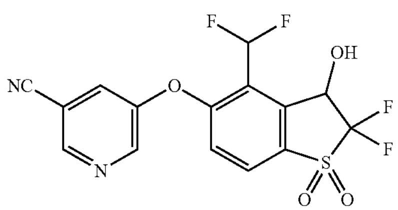 [SMILES: N#Cc1cncc(Oc2ccc3c(c2C(F)F)C(O)C(F)(F)S3(=O)=O)c1] | 37 | 5-((4-(Difluoromethyl)-2,2-difluoro-3-hydroxy-1,1-dioxido-2,3-dihydrobenzo[b]thiophen-5-yl)oxy)nicotinonitrile |
| 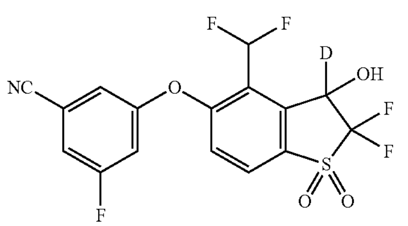 [SMILES: [2H]C1(O)c2c(ccc(Oc3cc(F)cc(C#N)c3)c2C(F)F)S(=O)(=O)C1(F)F] | 40 | 3-((4-(Difluoromethyl)-2,2-difluoro-3-hydroxy-1,1-dioxido-2,3-dihydrobenzo[b]thiophen-5-yl-3-d)oxy)-5-fluorobenzonitrile |
| 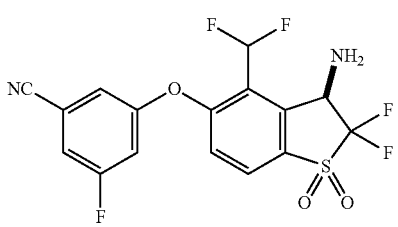 [SMILES: N#Cc1cc(F)cc(Oc2ccc3c(c2C(F)F)[C@@H](N)C(F)(F)S3(=O)=O)c1] | 41 | (R)-3-((3-Amino-4-(difluoromethyl)-2,2-difluoro-1,1-dioxido-2,3-dihydrobenzo[b]thiophen-5-yl)oxy)-5-fluorobenzonitrile |

-continued

| Structure | Example Number | IUPAC Name |
|---|---|---|
| 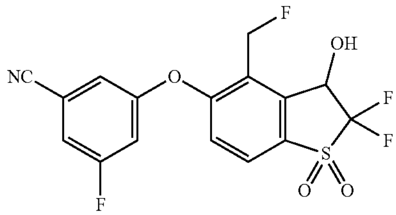 [SMILES: N#Cc1cc(F)cc(Oc2ccc3c(c2CF)C(O)C(F)(F)S3(=O)=O)c1] | 42 | 3-((2,2-Difluoro-4-(fluoromethyl)-3-hydroxy-1,1-dioxido-2,3-dihydrobenzo[b]thiophen-5-yl)oxy)-5-fluorobenzonitrile |
| 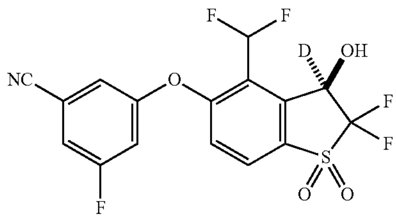 [SMILES: [2H][C@@]1(O)c2c(ccc(Oc3cc(F)cc(C#N)c3)c2C(F)F)S(=O)(=O)C1(F)F] | 43 | (R)-3-((4-(Difluoromethyl)-2,2-difluoro-3-hydroxy-1,1-dioxido-2,3-dihydrobenzo[b]thiophen-5-yl-3-d)oxy)-5-fluorobenzonitrile |
| 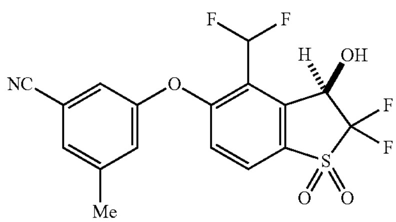 [SMILES: Cc1cc(C#N)cc(Oc2ccc3c(c2C(F)F)[C@@H](O)C(F)(F)S3(=O)=O)c1] | 46 | (R)-3-((4-(Difluoromethyl)-2,2-difluoro-3-hydroxy-1,1-dioxido-2,3-dihydrobenzo[b]thiophen-5-yl)oxy)-5-methylbenzonitrile |
| 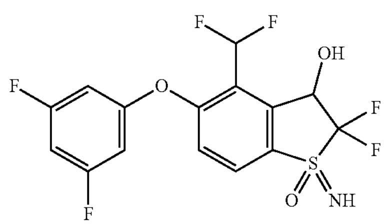 [SMILES: N=S1(=O)c2ccc(Oc3cc(F)cc(F)c3)c(C(F)F)c2C(O)C1(F)F] | 52 | 4-(Difluoromethyl)-5-(3,5-difluorophenoxy)-2,2-difluoro-3-hydroxy-1-imino-2,3-dihydro-1H-1λ$^4$-benzo[b]thiophene 1-oxide |
| 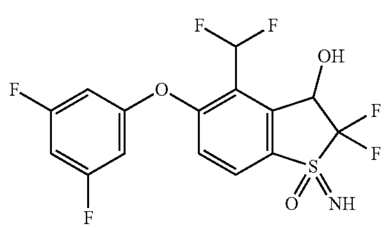 [SMILES: N=S1(=O)c2ccc(Oc3cc(F)cc(F)c3)c(C(F)F)c2C(O)C1(F)F] | 53 | 4-(Difluoromethyl)-5-(3,5-difluorophenoxy)-2,2-difluoro-3-hydroxy-1-imino-2,3-dihydro-1H-1λ$^4$-benzo[b]thiophene 1-oxide |
| 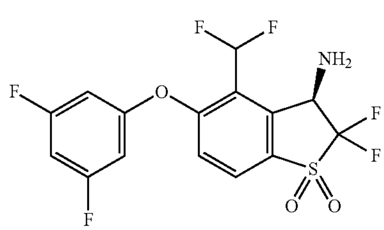 [SMILES: N[C@@H]1c2c(ccc(Oc3cc(F)cc(F)c3)c2C(F)F)S(=O)(=O)C1(F)F] | 55 | (R)-3-Amino-4-(difluoromethyl)-5-(3,5-difluorophenoxy)-2,2-difluoro-2,3-dihydrobenzo[b]thiophene 1,1-dioxide |

-continued

| Structure | Example Number | IUPAC Name |
|---|---|---|
| 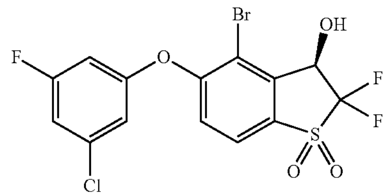 [SMILES: O=S1(=O)c2ccc(Oc3cc(F)cc(Cl)c3)c(Br)c2[C@@H](O)C1(F)F] | 57 | (R)-4-Bromo-5-(3-chloro-5-fluoro-phenoxy)-2,2-difluoro-1,1-dioxo-3H-benzothiophen-3-ol |
| 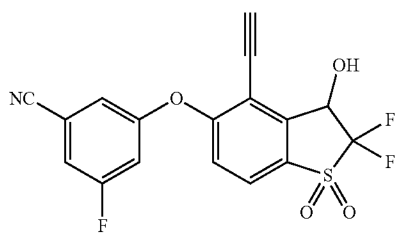 [SMILES: C#Cc1c(Oc2cc(F)cc(C#N)c2)ccc2c1C(O)C(F)(F)S2(=O)=O] | 63 | 3-((4-Ethynyl-2,2-difluoro-3-hydroxy-1,1-dioxido-2,3-dihydrobenzo[b]thiophen-5-yl)oxy)-5-fluorobenzonitrile |
| 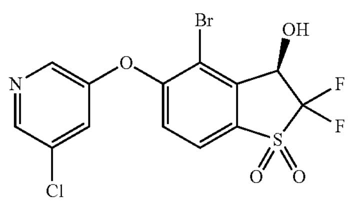 [SMILES: O=S1(=O)c2ccc(Oc3cncc(Cl)c3)c(Br)c2[C@@H](O)C1(F)F] | 75 | (R)-4-bromo-5-((5-chloropyridin-3-yl)oxy)-2,2-difluoro-3-hydroxy-2,3-dihydrobenzo[b]thiophene 1,1-dioxide |
| 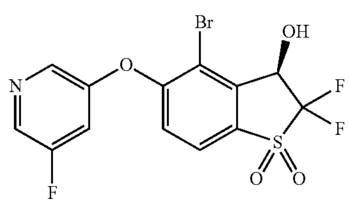 [SMILES: O=S1(=O)c2ccc(Oc3cncc(F)c3)c(Br)c2[C@@H](O)C1(F)F] | 77 | (R)-4-bromo-2,2-difluoro-5-((5-fluoropyridin-3-yl)oxy)-3-hydroxy-2,3-dihydrobenzo[b]thiophene 1,1-dioxide |
| 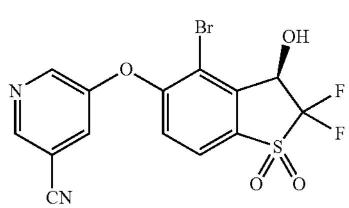 [SMILES: N#Cc1cncc(Oc2ccc3c(c2Br)[C@@H](O)C(F)(F)S3(=O)=O)c1] | 78 | (R)-5-((4-Bromo-2,2-difluoro-3-hydroxy-1,1-dioxido-2,3-dihydrobenzo[b]thiophen-5-yl)oxy)nicotinonitrile |
| 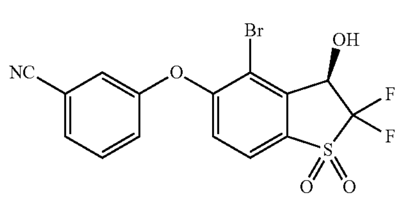 [SMILES: N#Cc1cccc(Oc2ccc3c(c2Br)[C@@H](O)C(F)(F)S3(=O)=O)c1] | 84 | (R)-3-((4-bromo-2,2-difluoro-3-hydroxy-1,1-dioxido-2,3-dihydrobenzo[b]thiophen-5-yl)oxy)benzonitrile |

| Structure | Example Number | IUPAC Name |
|---|---|---|
| 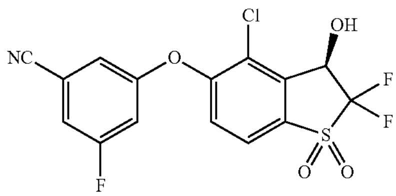 | 85 | (R)-3-((4-chloro-2,2-difluoro-3-hydroxy-1,1-dioxido-2,3-dihydrobenzo[b]thiophen-5-yl)oxy)-5-fluorobenzonitrile |
| 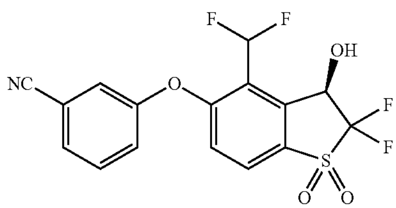 [SMILES: N#Cc1cccc(Oc2ccc3c(c2C(F)F)[C@@H](O)C(F)(F)S3(=O)=O)c1] | 89 | (R)-3-((4-(difluoromethyl)-2,2-difluoro-3-hydroxy-1,1-dioxido-2,3-dihydrobenzo[b]thiophen-5-yl)oxy)benzonitrile |
| 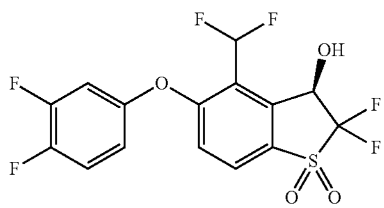 [SMILES: O=S1(=O)c2ccc(Oc3ccc(F)c(F)c3)c(C(F)F)c2[C@@H](O)C1(F)F] | 90 | (R)-4-(Difluoromethyl)-5-(3,4-difluorophenoxy)-2,2-difluoro-3-hydroxy-2,3-dihydrobenzo[b]thiophene 1,1-dioxide |
| 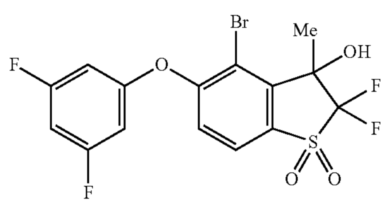 [SMILES: CC1(O)c2c(ccc(Oc3cc(F)cc(F)c3)c2Br)S(=O)(=O)C1(F)F] | 98 | 4-Bromo-5-(3,5-difluorophenoxy)-2,2-difluoro-3-hydroxy-3-methyl-2,3-dihydrobenzo[b]thiophene 1,1-dioxide |
| 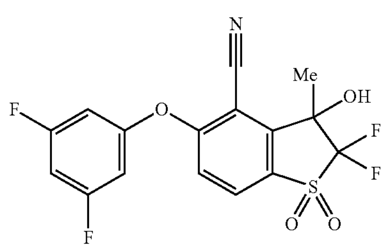 [SMILES: CC1(O)c2c(ccc(Oc3cc(F)cc(F)c3)c2C#N)S(=O)(=O)C1(F)F] | 100 | 5-(3,5-Difluorophenoxy)-2,2-difluoro-3-hydroxy-3-methyl-2,3-dihydrobenzo[b]thiophene-4-carbonitrile 1,1-dioxide |
| 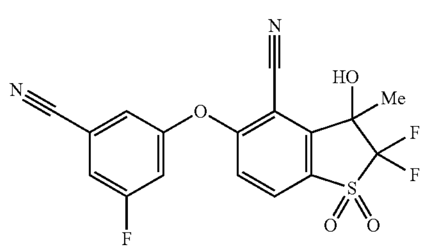 [SMILES: CC1(O)c2c(ccc(Oc3cc(F)cc(C#N)c3)c2C#N)S(=O)(=O)C1(F)F] | 105 | 5-(3-cyano-5-fluoro-phenoxy)-2,2-difluoro-3-hydroxy-3-methyl-1,1-dioxo-benzothiophene-4-carbonitrile |

-continued

| Structure | Example Number | IUPAC Name |
|---|---|---|
| 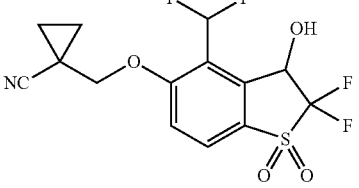 | 109 | 1-[[4-(difluoromethyl)-2,2-difluoro-3-hydroxy-1,1-dioxo-3H-benzothiophen-5-yl]oxymethyl]cyclopropanecarbonitrile |
| 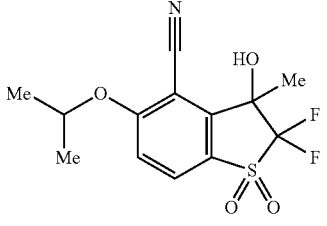 [SMILES: CC(C)Oc1ccc2c(c1C#N)C(C)(O)C(F)(F)S2(=O)=O] | 110 | 2,2-difluoro-3-hydroxy-5-isopropoxy-3-methyl-1,1-dioxo-benzothiophene-4-carbonitrile |
| 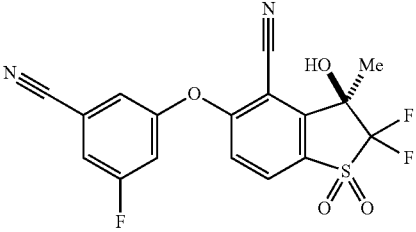 [SMILES: C[C@@]1(O)c2c(ccc(Oc3cc(F)cc(C#N)c3)c2C#N)S(=O)(=O)C1(F)F] | 112 | (3R)-5-(3-cyano-5-fluoro-phenoxy)-2,2-difluoro-3-hydroxy-3-methyl-1,1-dioxo-benzothiophene-4-carbonitrile |
| 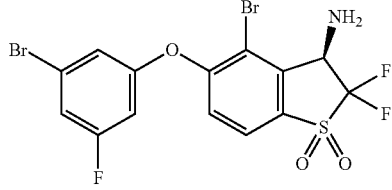 [SMILES: N[C@@H]1c2c(ccc(Oc3cc(F)cc(Br)c3)c2Br)S(=O)(=O)C1(F)F] | 116 | (3R)-4-bromo-5-(3-bromo-5-fluoro-phenoxy)-2,2-difluoro-2,2-dioxo-3H-benzothiophen-3-amine |
| 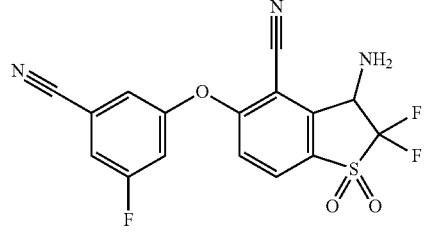 [SMILES: N#Cc1cc(F)cc(Oc2ccc3c(c2C#N)C(N)C(F)(F)S3(=O)=O)c1] | 118 | 3-amino-5-(3-cyano-5-fluoro-phenoxy)-2,2-difluoro-1,1-dioxo-3H-benzothiophene-4-carbonitrile |

The chemical entities described herein are useful for the treatment, or in the preparation of a medicament for the treatment of HIF-2α mediated diseases, including but are not limited to, cancers. A role of HIF-2α in tumor genesis and tumor progression has been implicated in many human cancers. One of the strongest links between HIF-2α activity and disease is in renal cell carcinoma (RCC), including clear cell renal cell carcinoma (ccRCC) (reviewed in Shen and Kaelin, *Seminars in Cancer Biology* 23: 18-25, 2013). Greater than eighty percent of ccRCC have defective VHL either through deletion, mutation or post-translational modification. Defective VHL in ccRCC results in constitutively active HIF-α proteins regardless of the oxygen level. A series of studies using gain-of-function and loss-of-function approaches in xenograft mouse models have clearly demonstrated that HIF-2α is the key oncogenic substrate of VHL (Kondo, et al. *Cancer Cell* 1: 237-246, 2002; Kondo, et al. *PLoS Biology* 1: 439-444, 2002; Maranchi, et al. *Cancer Cell* 1: 247-255, 2002; and Zimmer, et al. *Mol. Cancer Res.* 2: 89-95, 2004). In these studies, biological knockdown of HIF-2α in VHL null tumors inhibited tumor formation in a manner analogous to reintroduction of VHL. And, overexpression of HIF-2α overcame the tumor suppressive role of VHL. In addition, single nucleotide polymorphism in HIF-2α that rendered HIF-2α refractory to PHD-mediated degradation have been linked to increased risk of kidney cancer.

Furthermore, immunohistochemical analyses of morphologically normal renal tubular cells show HIF activation thereby supporting an early, dominant pathologic role in the disease (Mandriota, et al. *Cancer Cell* 1: 459-468, 2002; Raval, et al. *Mol. Cell. Biol.* 25: 5675-5686, 2005). In addition to their role in tumor initiation, the VHL-HIF-2α axis has been implicated in ccRCC tumor metastasis (Vanharanta et al. *Nature Medicine* 19: 50-59, 2013). Genetic studies on HIF-1α have led to the hypothesis that HIF-1α acts as a tumor suppressor in kidney cancer. HIF-1α resides on a frequently deleted chromosome in ccRCC and deletion of HIF-1α increased tumor growth in mice (reviewed in Shen and Kaelin, *Seminars in Cancer Biology* 23: 18-25, 2013). Taken together, these data support the potential therapeutic utility of HIF-2α-targeted agents for the treatment of ccRCC.

VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19: 617-623, 2011). HIF-2α has been linked to cancers of the retina, adrenal gland and pancreas through both VHL disease and activating mutations. Recently, gain-of-function HIF-2α mutations have been identified in erythrocytosis and paraganglioma with polycythemia (Zhuang, et al. *NEJM* 367: 922-930, 2012; Percy, et al. *NEJM* 358:162-168, 2008; and Percy, et al. *Am. J. Hematol.* 87: 439-442, 2012). Notably, a number of known HIF-2α target gene products (e.g., VEGF, PDGF, and cyclin Dl) have been shown to play pivotal roles in cancers derived from kidney, liver, colon, lung and brain. In fact, therapies targeted against one of the key HIF-2α regulated gene products, VEGF, have been approved for the treatment of these cancers.

Due to poor vascularization, the intratumor environment of rapidly growing tumors are normally hypoxic, a condition that activates HIF-α, which supports tumor cell survival and proliferation. Studies have demonstrated a correlation between HIF-2α overexpression and poor prognosis in multiple cancers including astrocytoma, breast, cervical, colorectal, glioblastoma, glioma, head and neck, hepatocellular, non-small cell lung, melanoma, neuroblastoma, ovarian, and prostate, thereby providing support for HIF-2α as a therapeutic target for these diseases (reviewed in Keith, et al. *Nature Rev. Cancer* 12: 9-22, 2012). Also, epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (reviewed in Nguyen, et al. *Arch. Pharm. Res* 36: 252-263, 2013).

Specifically, HIF-2α has been demonstrated to play an important role in APC mutant colorectal cancer through control of genes involved in proliferation, iron utilization and inflammation (Xue, et al. *Cancer Res.* 72: 2285-2293, 2012; and Xue and Shah, Carcinogenesis 32: 163-169, 2013). In hepatocellular carcinoma (HCC), knock-down of HIF-2α in preclinical models reduced the expression of VEGF and cyclin D1 genes both in vitro and in vivo resulting in inhibition of cell proliferation and tumor growth (He, et al. *Cancer Sci.* 103: 528-534, 2012). Additionally, fifty percent of NSCLC patients have overexpression of HIF-2α protein, which correlates strongly with VEGF expression and most importantly poor overall survival. HIF-1α is also overexpressed in many lung cancer patients. However, in contrast to HIF-2α, HIF-1α expression does not correlate with reduced overall survival (Giatromanolaki, et al. *Br. J. Cancer* 85: 881-890, 2001). In mice engineered with both non-degradable HIF-2α and mutant KRAS tumors, increased tumor burden and decreased survival were observed when compared to mice with only mutant KRAS expression (Kim, et al. *J. Clin. Invest.* 119: 2160-2170, 2009). This research demonstrates that HIF-2α contributes to tumor growth and progression in lung cancer and suggests a relationship with clinical prognosis in NSCLC. Furthermore, HIF-2α activity has been linked to the progression of chronic obstructive pulmonary disease (COPD) and lung cancer in mouse models (Karoor, et al. *Cancer Prev. Res.* 5: 1061-1071, 2012). However, genetic deletion of HIF-2α in a KRAS mutant mouse model increased tumor growth through the reduction of Scgb3a1 tumor suppressor gene (Mazumdar, et al. *PNAS* 107: 14182-14187, 2010). In total, these studies implicate HIF-2α in lung cancer progression but suggest that maintenance of the basal HIF-2α level maybe beneficial. HIF-2α activity has also been demonstrated to be important in central nervous system cancers (Holmquist-Mengelbier, et al. *Cancer Cell* 10: 413-423, 2006; and Li, et al. *Cancer Cell* 15: 501-513, 2009). In preclinical animal models of neuroblastoma, HIF-2α knockdown reduced tumor growth. Additionally, high protein levels of HIF-2α were correlated with advanced disease, poor prognosis and high VEGF levels. Similarly, poor survival in glioma correlated with HIF-2α expression. And, inhibition of HIF-2α in glioma stem cells reduced cell proliferation, and survival in vitro and tumor initiation in vivo. Interestingly, while HIF-1α is expressed in both neural progenitors and brain tumor stem cells, HIF-2α is only expressed in the latter. Moreover, glioma survival is correlated to HIF-2α but not HIF-1α levels.

Approximately 50% of cancer patients receive radiation treatment, either alone or in combination with other therapies. Tumor hypoxia has long been associated with resistance to radiation therapy. Therefore, inhibition of HIF-2α could improve radiation response of cancer/tumor cells. Bhatt and co-workers showed that decreasing levels of HIF-2α leads to increased sensitivity to ionizing radiation in renal cell carcinoma cell lines (Bhatt, et al. *BJU Int.* 102: 358-363, 2008). Furthermore, Bertout and co-workers demonstrated that HIF-2α inhibition enhances effectiveness of radiation through increased p53-dependent apoptosis (Bertout, et al. *PNAS* 106: 14391-14396, 2009).

Multiple groups have reported attempts to discover inhibitors of HIF-α activity. These efforts include irreversible inhibitors, small molecules, cyclic peptides and natural products (Cardoso, et al. *Protein Sci.* 21: 1885-1896, 2012; Miranda, et al. *J. Am. Chem. Soc.* 135: 10418-10425, 2013; Tan, et al. *Cancer Res.* 65: 605-612, 2005; WO2013011033; and WO2013057101). Some indirect, non-specific approaches to block HIF-α protein activity have also been described (Zimmer, et al. *Mole Cell* 32: 838-848, 2008; and Carew, et al. *PLoS ONE* 7: e31120, 2012). The reported molecular mechanisms of these approaches include decreased HIF-1α mRNA levels, decreased HIF-1α protein synthesis, increased HIF-1α degradation, decreased HIF subunit heterodimerization, decreased HIF binding to DNA, and decreased HIF transcriptional activity. For example, acriflavine, an antibacterial agent, is reported to bind directly to the PAS-B domain of HIF-1α and HIF-2α and block their interaction with HIF-1β, thereby blocking HIF-dependent gene transcription and leading to impaired tumor growth and vascularization (Lee, et al. PNAS 106: 17910-17915, 2009). Furthermore, HIF-1α protein synthesis has reported to be blocked by various molecules including rapamycin, temsirolimus, everolimus, cardiac glycosides, microtubule targeting agents (taxotere), and topoisomerase inhibitors (topotecan). Drugs that induce degradation of HIF-1α include HSP90 inhibitors, e.g., 17-allylamino-17-demethoxygeldanamycin, and antioxidants, such as ascorbate. Anthracyclines, such as doxorubicin and daunorubicin, bind to DNA and block the binding of HIF-1α and HIF-2α in cultured cells and also block HIF-1α -dependent expression of angiogenic growth factors, leading to impaired tumor growth (Semenza, Trends Pharmacol. Sci. 33: 207-214, 2012). However, attempts to identify selective molecules that directly interfere with HIF-2α function have been met with little success, evidenced by the current paucity of clinical (or pre-clinical) programs targeting this transcription factor.

Recent work from Professors Kevin Gardner and Richard Bruick at the University of Texas Southwestern Medical Center has revealed a unique ligand-binding pocket in a select domain of HIF-2α that is required for HIF-2α transcriptional activity. High-resolution structural data gathered against one of the isolated HIF-2α PAS domains, both alone and in complexes, revealed a large internal hydrated cavity (280 $A^3$)—highly unusual for a protein of this size (Scheuermann et al. PNAS 106: 450-455, 2009; and Key et al. J. Am. Chem. Soc., 131: 17647-17654, 2009). Furthermore, small molecule HIF-2α PAS B domain binders have been identified (Rogers, et al. J. Med. Chem. 56: 1739-1747, 2013). Binding of these ligands leads to inhibition of HIF-2α transcriptional activity in cells (Scheuermann, et al. Nat. Chem. Biol. 9: 271-276, 2013).

In one aspect, the compounds or their pharmaceutical compositions described herein are useful as inhibitors of HIF-2α. Thus, without wishing to be bound by any particular theory, the compounds or their pharmaceutical compositions described herein are particularly useful for treating or lessening the severity of a disease, condition, or disorder where activation of HIF-2α and/or one or more downstream processes associated with the activation or over activation of HIF-2α are implicated in the disease, condition, or disorder. Accordingly, the present invention provides a method for treating or lessening the severity of a disease, condition, or disorder where activation or over activation of HIF-2α is implicated in the disease state.

In another aspect, the present disclosure provides a method of treating renal cell carcinoma of a subject with a compound described herein or a pharmaceutically acceptable salt thereof. RCC is one of the most common forms of kidney cancer arising from the proximal convoluted tubule. RCC is also known as hypemephroma. Initial treatment is commonly a radical or partial nephrectomy and remains the mainstay of curative treatment. Where the tumor is confined to the renal parenchyma, the 5-year survival rate is 60-70%, but this is lowered considerably where metastasis have spread. RCC is generally resistant to radiation therapy and chemotherapy, although some cases respond to immunotherapy. Targeted cancer therapies such as sunitinib, temsirolimus, bevacizumab, axitinib, pazopanib, interferon-alpha, and sorafenib have improved the outlook for RCC (progression-free survival), although they have not yet demonstrated improved survival rate. Subtypes of RCC include, but are not limited to, clear cell renal cell carcinoma, papillary renal cell carcinoma, and chromophobe renal cell carcinoma.

A compound or a pharmaceutically acceptable salt thereof may be formulated as a pharmaceutical composition prior to being administered to a subject. The pharmaceutical composition may comprise additional additives such as pharmaceutically acceptable excipients, carriers, and vehicles. Suitable pharmaceutically acceptable excipients, carriers, and vehicles include but are not limited to processing agents and drug delivery modifiers, for example, ethylene glycol, polyethylene glycol (PEG), calcium phosphate, magnesium stearate, talc, monosaccharides, disaccharides, starch, gelatin, cellulose, methyl cellulose, hydroxypropyl cellulose, sodium carboxymethyl cellulose, dextrose, hydroxypropyl-β-cyclodextrin, polyvinylpyrrolidine, low melting waxes, ion exchange resins, and the like, as well as combinations of any two or more thereof.

A pharmaceutical composition comprising a compound or a pharmaceutically acceptable salt thereof may be administered enterally, orally, parenterally, sublingually, rectally, or topically in a unit dosage containing pharmaceutically acceptable excipients, carriers, or vehicles. Generally, the unit dosage is a dose sufficient for the compound or its pharmaceutically acceptable salt to achieve desired therapeutic effect. Suitable modes of administration include oral, subcutaneous, intra-arterial, intramuscular, intraperitoneal, intranasal, intraocular, subdural, vaginal, gastrointestinal, and the like. The compound or its salt can also be administered as prodrugs, wherein the prodrugs undergo transformation in the body of the treated subject to form a therapeutically active ingredient.

A pharmaceutical composition comprising a compound or a pharmaceutically acceptable salt described herein may be in any form suitable for the intended purpose of administration, including, for example, a solid or a liquid dosage form. The liquid dosage form may include solution, suspension, softgel, syrup, elixir, or emulsion. Liquid carriers are typically used in preparing solutions, suspensions, and emulsions. Liquid carriers contemplated for use in the practice of the present invention include, for example, water, saline, ethylene glycol, propylene glycol, pharmaceutically acceptable organic solvents, pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, sunflower oil, and the like. For parenteral administration, the carrier can also be an oily ester such as isopropyl myristate, and the like. Compositions of the present invention may also be in the form of nanoparticles, microparticles, microcapsules, liposomal encapsulates, and the like, as well as combinations of any two or more thereof. Solid dosage forms for oral administration may include capsule, tablet, pill, powder, and granule. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

In cases of a solid dosage form, examples of daily dosages of the compounds described herein which can be used are an effective amount within the dosage range of about 0.001 mg to about 2 mg per kilogram of body weight, about 0.001 mg to about 5 mg per kilogram of body weight, about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight, or about 0.001 mg to about 300 mg per kilogram of body weight. When administered orally or by inhalation, examples of daily dosages are an effective amount within the dosage range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g, or about 20 mg to 300 mg, or about 20 mg to 500 mg, or about 20 mg to 700 mg, or about 20 mg to 1000 mg, or about 50 mg to 1500 mg, or about 50 mg to 2000 mg. Preferred fixed daily doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, or about 1000 mg, about 1200 mg, about 1500 mg, or about 2000 mg, independent of body weight. However, it is understood that pediatric patients may require smaller dosages, and depending on the severity of the disease and condition of the patient, dosages may vary. The compound will preferably be administered once daily, but may be administered two, three or four times daily, or every other day, or once or twice per week.

When formulated as a liquid, the concentration of the compounds described herein may be about 0.01 mg/ml to about 0.1 mg/ml or about 0.1 mg/ml to about 1 mg/ml, but can also be about 1 mg/ml to about 10 mg/ml or about 10 mg/ml to about 100 mg/ml. The liquid formulation could be a solution or a suspension. When formulated as a solid, for example as a tablet or as a powder for inhalation, the concentration, expressed as the weight of a compound divided by total weight, will typically be about 0.01% to about 0.1%, about 0.1% to about 1%, about 1% to about 10%, about 10% to about 20%, about 20% to about 40%, about 40% to about 60%, about 60% to about 80%, or about 80% to about 100%.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed.; *Methods in Cell Biology*; Volume XIV; ISBN: 978-0-12-564114-2; Academic Press, New York, N.W.; 1976 and Medina, Zhu, and Kairemo; *Targeted Liposomal Drug Delivery in Cancer*; in *Current Pharm. Des.* 10: 2981-2989, 2004. For additional information regarding drug formulation and administration, see *Remington: The Science and Practice of Pharmacy*; Lippincott Williams & Wilkins; 21$^{st}$ Edition; Philadelphia, ISBN-10: 0781746736; 2005.

Compounds disclosed herein may be prepared by routes described below. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-4, the steps in some cases may be performed in a different order than the order shown in Schemes 1-4. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

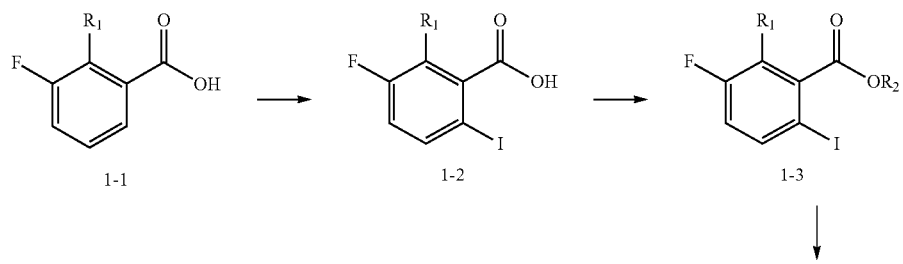

Scheme 1

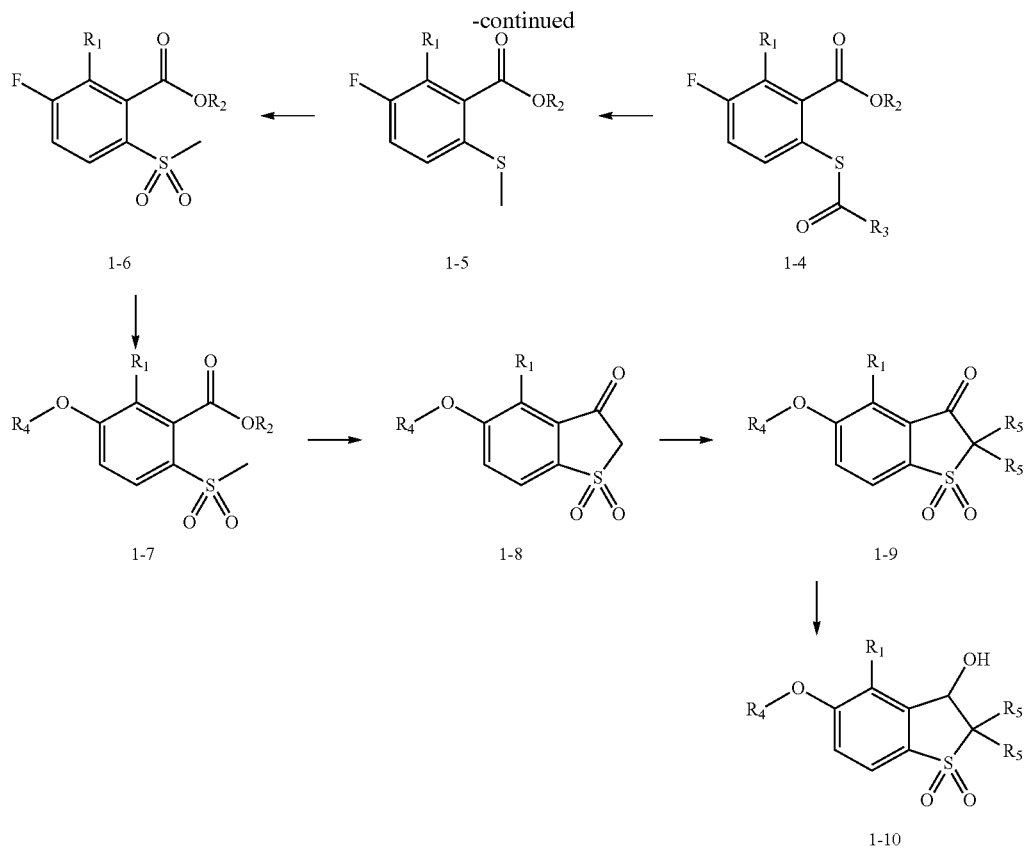

In some embodiments, compounds of Formula 1-10 are prepared according to steps outlined in Scheme 1, wherein $R_1$ is halo, cyano, alkyl, alkenyl or alkynyl, $R_4$ is alkyl, cycloalkyl, heterocycloalkyl, aryl, or heteroaryl, and $R_5$ is fluoro or alkyl, or two R5s and the carbon they are attached to form C3-C8 cycloalkyl or C5-C8 heterocycloalkyl. The synthesis commences with compounds of Formula 1-1. Orthoiodination of 1-1 provides compounds of Formula 1-2. The reaction may be carried out in a suitable organic solvent in the presence of iodine and a palladium catalyst at an elevated temperature if needed. After esterification of 1-2, the resulting ester 1-3 may undergo a transition-metal catalyzed coupling reaction with a thioate, e.g., potassium ethanethioate or sodium ethanethioate, to give compounds of Formula 1-4. Suitable transition-metal catalysts include but are not limited to Pd(PPh$_3$)$_4$, Pd$_2$(dba)$_3$ chloroform complex or Pd(OAc)$_2$ in the presence or absence of a suitable ligand. Hydrolysis of compounds of Formula 1-4 followed by alkylation of the resulting thiophenol intermediate with an alkyl halide, e.g., methyl iodide, gives compounds of Formula 1-5. The hydrolysis and alkylation may be carried out in a one-pot procedure without purification. In some embodiments, this is carried out by treating compounds of Formula 1-4 with a carbonate base in a suitable solvent at or near room temperature for a period ranging from 0.1 to 24 hours followed by addition of an alkyl halide. Carbonate bases include but are not limited to sodium carbonate, potassium carbonate, cesium carbonate, potassium bicarbonate and cesium bicarbonate. Oxidation of compounds of Formula 1-5 to give compounds of Formula 1-6 may be accomplished by a variety of methods known in the art, including but are not limited to, RuCl$_3$ catalyzed oxidation in the presence of NaIO$_4$, oxidation with m-chloroperbenzoic acid (mCPBA), and oxidation with Oxone®. Compounds of Formula 1-6 are then subjected to a nucleophilic aromatic substitution (SNAr) reaction with R$_4$OH (wherein R$_4$ is alkyl, aryl or heteroaryl) to give compounds of Formula 1-7. Temperature for carrying out the SNAr reaction may depend on the reactivity of both R$_4$OH and/or compounds of Formula 1-6. The reaction may be carried out in a temperature ranging from −10° C. to 200° C. In some embodiments, the temperature range is from 30° C. to 120° C. In some other embodiments, the temperature range is from 0° C. to room temperature. Cyclization of compounds of Formula 1-7 may be effected with a base, e.g., sodium hydride, in a suitable solvent to yield compounds of Formula 1-8. After the cyclization, a variety of R$_5$ groups may be introduced. In some embodiments, compounds of Formula 1-8 are difluorinated to give compounds of Formula 1-9 by treating with a fluorinating agent, e.g., 1-(chloromethyl)-4-fluoro-1,4-diazo niabicyclo[2.2.2]octane ditetrafluoroborate (Selectfluor®), in the presence of suitable base, e.g., sodium carbonate. Reduction of compounds of Formula 1-9 yields compounds of Formula 1-10. In some embodiments, the reduction is carried out with a hydride, e.g., sodium borohydride and sodium triacetoxyborohydride, to give a racemic mixture. In some embodiments, asymmetric reduction are carried out to give an enantiomer having an enantiomeric excess as disclosed herein. Asymmetric reduction of com pounds of Formula 1-10 may be accomplished chemically or enzymatically. For a recent review on enzymatic reduction of ketones, see Moore, et al. *Acc. Chem. Res.* 40: 1412-1419, 2007. Examples of chemical asymmetric reduction of ketones include, but are not limited to, Corey-Bakshi-Shibata (CBS) reduction, asymmetric hydrogenation, and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R configuration):

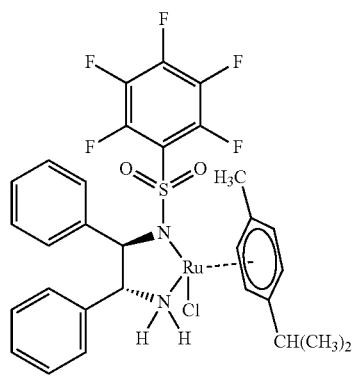

RuCl(FsDPEN)(p-cymene)

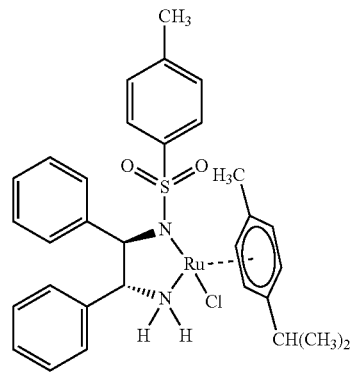

RuCl(TsDPEN)(p-cymene)

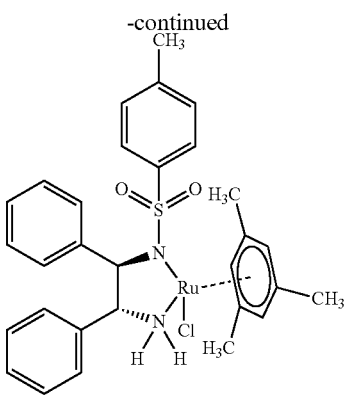

RuCl(TsDPEN)(mesitylene)

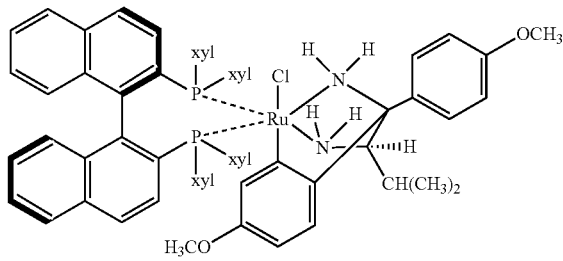

RUCY™

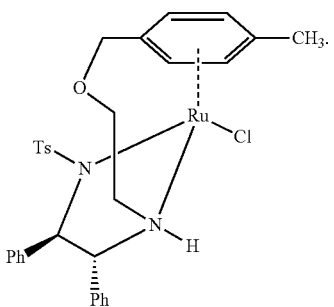

Ts-DENEB

The asymmetric transfer hydrogenation may be carried out at or below room temperature. In some embodiments, the asymmetric transfer hydrogenation is carried out about 4° C. The alcohol product may have an enantiomeric excess of at least about 80%, at least about 85%, at least about 88%, at least about 90%, at least about 91%, at least about 92%, at least about 93%, at least about 94%, at least about 95%, at least about 96%, at least about 97%, at least about 98% or even higher. It is well understood by one skilled in the art that changing the catalyst configuration will lead to a product with the opposite configuration.

Scheme 2

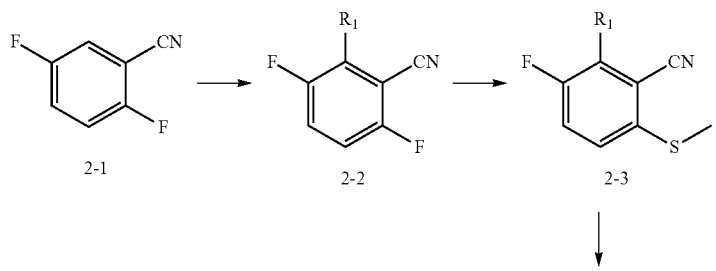

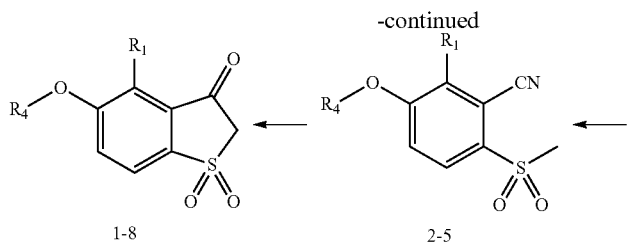

Alternatively, compounds of Formula 1-8 are prepared according to Scheme 2. For example, lithiation of compound 2-1 followed by trapping the resulting lithio intermediate with a suitable electrophile gives compounds of Formula 2-2. In some embodiments, the electrophile is N,N-dimethylformamide and the $R_1$ is —CHO. In a further embodiment, —CHO is converted to —CHF$_2$ by treating with a fluorinating reagent, e.g., diethylaminosulfur trifluoride. One of the fluorines in compounds of Formula 2-2 may be selected displaced with a thiomethoxide, e.g., sodium thiomethoxide, to give compounds of Formula 2-3. The reaction temperature may be in a range of −50 to 40° C. In some embodiments, the temperature is at or about 0° C. Oxidation of compounds of Formula 2-3, followed by SNAr reaction with $R_4$OH and based-mediated cyclization, provides compounds of Formula 1-8.

oxidation may be accomplished with Oxone® or mCPBA. The amount of oxidant used for the oxidation may be about 1.5 equivalent, about 1.4 equivalent, about 1.3 equivalent, about 1.2 equivalent, about 1.1 equivalent or about 1.0 equivalent. SNAr reaction of compounds of Formula 3-1 with $R_4$OH (wherein $R_4$ is alkyl, cycloalkyl, heterocycloalkyl, aryl or heteroaryl) in the presence of a base gives compounds of Formula 3-2. At this stage, sulfoximine moiety may be introduced to give compounds of Formula 3-3 through transition-metal catalyzed insertion reaction of a suitable nitrogen donor. Suitable transition-metal catalysts include but are not limited to copper and rhodium catalysts, e.g., bis(rhodium(α,α,α',α'-tetramethyl-1,3-benezenedipropionic acid)) and dirhodium tetraacetate. Suitable nitrogen donors include but are not limited to PhI=NNs, cyanamide, and fluoroalkylamides, e.g., trifluoromethyl acetamide.

Scheme 3

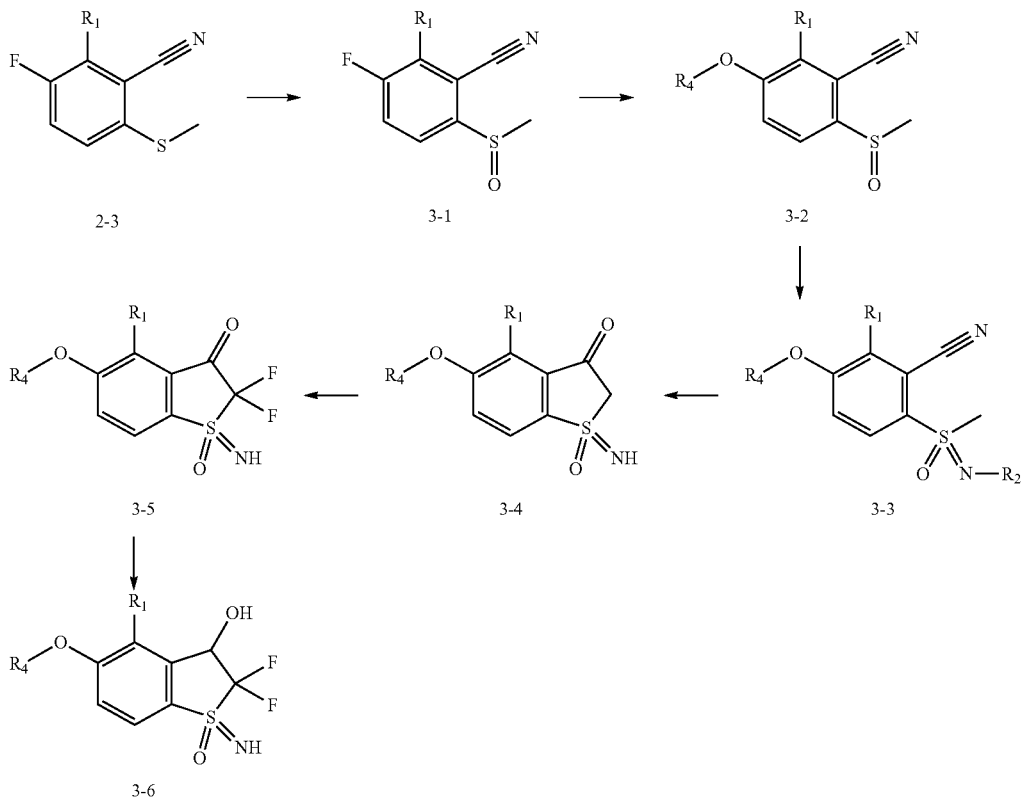

In some embodiments, compounds of Formula 3-6 are prepared according to Scheme 3. Oxidation of compounds of Formula 2-3 gives compounds of Formula 3-1. The Cyclization of compounds of Formula 3-3 to give compounds of Formula 3-4 may be achieved with a base, e.g., sodium hydride, at about room temperature. Finally, reduction of compounds of Formula 3-5 as outlined in Scheme 1 provides compounds of Formula 3-6. Compounds of Formula 3-6 may exist as a mixture of diastereomers and/or enantiomers. Diastereomers may be separated by conventional column chromatography while enantiomers may be separated by chiral column chromatography.

254 nm. Samples were prepared as a solution in about 1:1 (v/v) acetonitrile:water mixture. Flow rate was about 0.8 mL/minute. Elution solvents were acetonitrile and water each containing 0.1% formic acid. In a typical run, a linear gradient starting with 5% acetonitrile and 95% water and ending with 95% acetonitrile and 5% water over 12 minutes Scheme 4

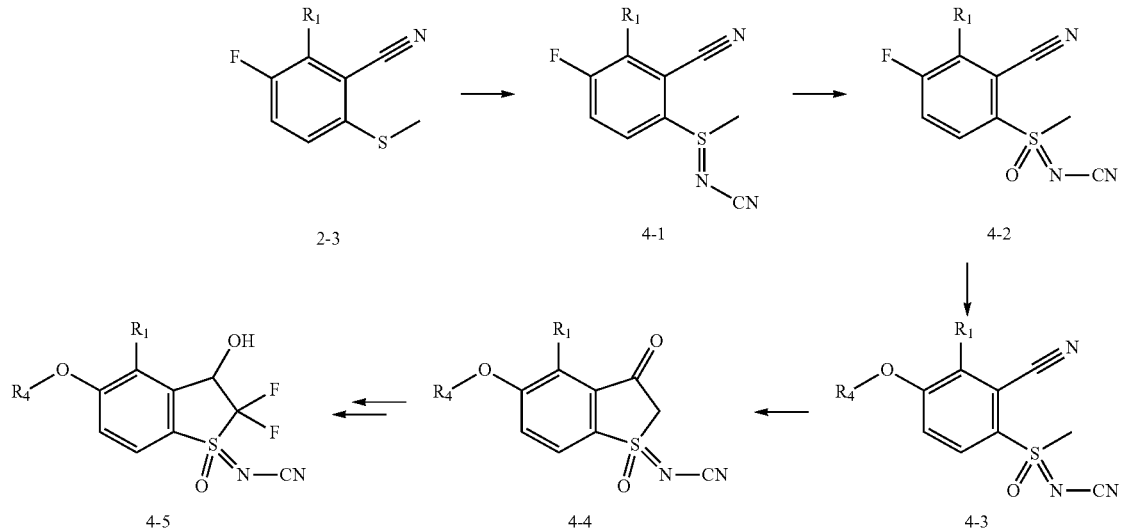

In some embodiments, compounds of Formula 4-5 are prepared according to Scheme 4. Reaction of compounds of Formula 2-3 with cyanamide in the presence of an oxidant, e.g., (diacetoxyiodo)benzene, affords compounds of Formula 4-1. Further oxidation of compounds of Formula 4-1 provides compounds of Formula 4-2, which undergoes SNAr reaction, cyclization, and reduction to give compounds of Formula 4-5.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be taken into account.

$^1$H and $^{19}$F NMR analysis of intermediates and exemplified compounds were performed on an Agilent Technologies 400/54 magnet system (operating at 399.85 MHz or 376.24 MHz), Vnmrj VERSION 3.2 software. Pulse sequences were selected from the default experiment set. Reference frequency was set using TMS as an internal standard. Typical deuterated solvents were utilized as indicated in the individual examples.

LCMS analysis of intermediates and exemplified compounds was performed on an Agilent Technologies 1200 Series HPLC system coupled to an Agilent Technologies 6150 Quadrapole LC/MS detector. Analytes were detected by UV absorbance at 220 and 254 nm. Analyte ions were detected by mass spectrometry in both negative and positive modes (110-800 amu scan range, API-ES ionization). A long HPLC method was run on a Phenomenex® Kinetex 2.6 µm C18 100 Å, 30×3.00 mm column. The column temperature was set at 40° C. UV absorptions were detected at 220 and was carried out. At the end of each run, the column was washed with 95% acetonitrile and 5% water for 2 minutes.

Enantiomeric excess was determined by Mosher ester analysis or with chiral HPLC. The chiral HPLC analysis was performed on an Agilent Technologies 1200 Series HPLC system. Analytes were detected by UV absorbance at 220 and 254 nm. A detailed description of the analytical method is provided below:

Column: Lux® 5 u Cellulose-4 5.0 µm 1000 Å, 150×4.60 mm
Flow rate: 1.5 mL/min
Mobile phase A: 0.1% formic acid in water
Mobile phase B: 0.1% formic acid in acetonitrile
Strong needle wash: 90% acetonitrile, 10% water
Weak needle wash: 10% water, 90% acetonitrile
Injection volume: 2 µL
Column temperature: 40° C.
Autosampler temperature: Room temperature
Run time: 5.0 min
Gradient: 60% mobile phase A and 40% moble phase B Routine chromatographic purification was performed using Biotage® Isolera™ One automated systems running Biotage® Isolera™ One 2.0.6 software (Biotage LLC, Charlotte, N.C.). Flow rates were the default values specified for the particular column in use. Reverse phase chromatography was performed using elution gradients of water and acetonitrile on KP-C18-HS Flash+ columns (Biotage LLC) of various sizes. Typical loading was between 1:50 and 1:1000 crude sample: RP SiO$_2$ by weight. Normal phase chromatography was performed using elution gradients of various solvents (e.g., hexane, ethyl acetate, methylene chloride, methanol, chloroform, MTBE, etc.). The columns were SNAP Cartridges containing KP-SIL or SNAP Ultra (25 µm spherical particles) of various sizes (Biotage LLC). Typical loading was between 1:10 to 1:150 crude sample: SiO$_2$ by weight.

Example 1

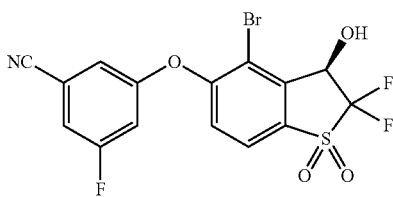 [SMILES: N#Cc1cc(F)cc(Oc2ccc3c(c2Br)[C@@H](O)C(F)(F)S3(=O)=O)c1]

(R)-3-((4-bromo-2,2-difluoro-3-hydroxy-1,1-dioxido-2,3-dihydrobenzo[b]thiophen-5-yl)oxy)-5-fluorobenzonitrile (Compound 1)

Step A: Preparation of methyl 2-bromo-3-(3-cyano-5-fluorophenoxy)-6-(methylsulfonyl)benzoate: Methyl 2-bromo-3-fluoro-6-methylsulfonyl-benzoate (200 mg, 0.64 mmol) was combined with 3-fluoro-5-hydroxy-benzonitrile (132 mg, 0.96 mmol) and N, N-dimethylformamide (2.5 mL). The solution was treated in a single portion with sodium bicarbonate (108 mg, 1.3 mmol) and the reaction mixture was heated to 90° C. for 16 hours. The reaction mixture was cooled, diluted with Et₂O and water and then separated. The aqueous layer was washed with Et₂O, then the combined organics were washed with water, 10% K₂CO₃, saturated NaCl, dried over Na₂SO₄ and concentrated in vacuo to provide methyl 2-bromo-3-(3-cyano-5-fluorophenoxy)-6-(methylsulfonyl)benzoate as an orange oil (276 mg, quant.). ¹H NMR (400 MHz, CDCl₃): δ 8.03 (d, 1H), 7.25-7.22 (m, 1H), 7.14 (d, 1H), 7.10-7.09 (m, 1H), 7.03-7.00 (m, 1H), 4.04 (s, 3H), 3.20 (s, 3H).

Step B: Preparation of 3-((4-bromo-1,1-dioxido-3-oxo-2,3-dihydrobenzo[b]thiophen-5-yl)oxy)-5-fluorobenzonitrile: Sodium hydride (60% in mineral oil, 77 mg, 1.9 mmol) was washed three times with hexane, then resuspended in tetrahydrofuran (3.5 mL). The suspension was cooled to 0° C. and treated dropwise with a solution of methyl 2-bromo-3-(3-cyano-5-fluoro-phenoxy)-6-methylsulfonyl-benzoate (276 mg, 0.64 mmol) dissolved in tetrahydrofuran (3.7 mL). After the addition, the reaction was warmed to ambient temperature and stirred for 5 hours. The reaction was quenched with saturated NH₄Cl and concentrated in vacuo. Ethyl acetate and some water were added, the solids were resolubilized, then the pH of the aqueous was adjusted to 3-4 with 10% KHSO₄. After separation, the aqueous was washed twice with ethyl acetate. The combined organics were washed twice with water, saturated NaCl, dried over Na₂SO₄ and concentrated in vacuo to give 3-((4-bromo-1,1-dioxido-3-oxo-2,3-dihydrobenzo[b]thiophen-5-yl)oxy)-5-fluorobenzonitrile as a pale yellow solid (214 mg, 84%). ¹H NMR (400 MHz, CDCl₃): δ 8.00-7.98 (m, 1H), 7.52-7.50 (m, 1H), 7.25-7.22 (m, 1H), 7.06-7.04 (m, 1H), 6.99-6.95 (m, 1H), 4.22 (m, 2H).

Step C: Preparation of 3-((4-bromo-2,2-difluoro-1,1-dioxido-3-oxo-2,3-dihydrobenzo[b]thiophen-5-yl)oxy)-5-fluorobenzonitrile: A mixture of 3-((4-bromo-1,1-dioxido-3-oxo-2,3-dihydrobenzo[b]thiophen-5-yl)oxy)-5-fluorobenzonitrile (84 mg, 0.21 mmol) in acetonitrile (1.2 mL) was treated with Selectfluor® (225 mg, 0.64 mmol) and sodium carbonate (67 mg, 0.64 mmol). The resulting suspension was stirred at ambient temperature for 2 hours. The mixture was diluted with water and ethyl acetate and then separated. The aqueous layer was washed with ethyl acetate. The combined organic layers were washed with saturated NaHCO₃, saturated NaCl, dried over Na₂SO₄ and concentrated in vacuo to a light yellow film. The material was chromatographed on SiO₂ eluting with a gradient of ethyl acetate/hexane to give 3-((4-bromo-2,2-difluoro-1,1-dioxido-3-oxo-2,3-dihydrobenzo[b]thiophen-5-yl)oxy)-5-fluorobenzonitrile as an off-white solid (68 mg, 42%). ¹H NMR (400 MHz, CDCl₃): δ 8.05 (d, 1H), 7.56 (d, 1H), 7.32-7.28 (m, 1H), 7.14-7.11 (m, 1H), 7.06-7.02 (m, 1H).

Step D: Preparation of (R)-3-((4-bromo-2,2-difluoro-3-hydroxy-1,1-dioxido-2,3-dihydrobenzo[b]thiophen-5-yl)oxy)-5-fluorobenzonitrile: 3-((4-Bromo-2,2-difluoro-1,1-dioxido-3-oxo-2,3-dihydrobenzo[b]thiophen-5-yl)oxy)-5-fluorobenzonitrile (34 mg, 0.08 mmol) was dissolved in dichloromethane (freshly degassed by sparging with nitrogen, 0.6 mL) and the solution was treated with triethylamine (22 μL, 0.16 mmol) and formic acid (8.9 μL, 0.24 mmol). After cooling to 0° C., the solution was treated with a pre-cooled (0° C.) solution of N-[(1R,2R)-1,2-diphenyl-2-(2-(4-methylbenzyloxy)ethylamino)-ethyl]-4-methylbenzene sulfonamide(chloro)ruthenium(II) ((R,R)-Ts-DENEB™, 0.51 mg, 0.8 μmol) dissolved in dichloromethane (0.6 mL). The resulting suspension was placed in the refrigerator and allowed to stand at 4° C. for 32 hours. The reaction was concentrated with a stream of nitrogen gas, then chromatographed on SiO₂ eluting with a gradient of ethyl acetate/chloroform to give Compound 1 as a white solid (28 mg, 82%, >89% ee by Mosher ester analysis). ¹H NMR (400 MHz, CDCl₃): δ 7.86 (d, 1H), 7.27 (d, 1H), 7.27-7.24 (m, 1H), 7.13-7.11 (m, 1H), 7.04-7.00 (m, 1H), 5.41-5.37 (m, 1H), 3.06 (d, 1H).

Example 2

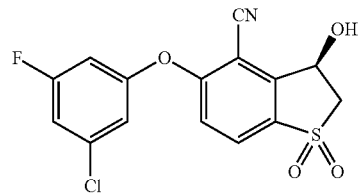

(3R)-5-(3-Chloro-5-fluoro-phenoxy)-3-hydroxy-1,1-dioxo-2,3-dihydrobenzothiophene-4-carbonitrile (Compound 2)

Step A: Preparation of 2-bromo-3-fluoro-6-iodobenzoic acid: To a flask containing 2-bromo-3-fluorobenzoic acid (2.5 g, 11.4 mmol), palladium (II) acetate (128 mg, 5 mol %), iodine (2.9 g, 11.4 mmol), and diacetoxy iodobenzene (3.68 g, 11.4 mmol) were added, followed by N,N-dimethylformamide (55 mL). The resulting suspension was stirred for 24 hours at 100° C. After cooling, the reaction mixture was concentrated under reduced pressure to near dryness. The remaining residue was poured into 0.1 M HCl, then extracted four times with diethyl ether (100 mL portions). The combined organics were washed with 1 M Na₂S₂O₃ solution until the purple color of the iodine was dissipated, then washed with saturated NaCl, dried over MgSO₄, filtered, and concentrated to provide 2-bromo-3-fluoro-6-iodobenzoic acid as a beige solid (1.2 g, 30% yield). The crude solid was used without further purification.

Step B: Preparation of methyl 2-bromo-3-fluoro-6-iodobenzoate: 2-Bromo-3-fluoro-6-iodo-benzoic acid (0.81 g, 2.3 mmol) was dissolved in N,N-dimethylformamide (5 mL), then treated with potassium carbonate (970 mg, 7.0 mmol) and iodomethane (0.44 mL, 7.0 mmol). The mixture was stirred at ambient temperature for 60 hours. The suspension was dissolved in diethyl ether and water and separated. The organic layer was washed five times with water, then with saturated NaCl, dried over $Na_2SO_4$ and concentrated in vacuo to a white solid (0.76 g, 90% yield). LCMS ESI (+) m/z 359, 361 (M+H).

Step C: Preparation of methyl 6-(acetylthio)-2-bromo-3-fluorobenzoate: Methyl 2-bromo-3-fluoro-6-iodobenzoate (1.26 g, 3.5 mmol) and 4,5-bis(diphenylphosphino)-9,9-dimethylxanthene (Xantphos, 243 mg, 0.42 mmol) were suspended in 2:1 toluene/acetone (17 mL). The mixture was sparged with argon, then treated with tris(dibenzylideneacetone)dipalladium(0) ($Pd_2dba_3$, 192 mg, 0.21 mmol) and potassium ethanethioate (500 mg, 4.4 mmol). The reaction mixture was sealed in a tube, stirred vigorously, and heated to 70° C. for 2 hours. The reaction was cooled, diluted with methylene chloride, treated with celite, then filtered through a pad of celite. The filtrate was concentrated in vacuo to orange oil. The crude mixture was chromatographed on $SiO_2$ eluting with a gradient of hexanes/ethyl acetate. Methyl 6-(acetylthio)-2-bromo-3-fluorobenzoate was obtained as a yellow oil (0.71 g, quant.). $^1$H NMR (400 MHz, $CDCl_3$): δ 7.44-7.41 (m, 1H), 7.25-7.21 (m, 1H), 3.95 (s, 3H), 2.41 (s, 3H).

Step D: Preparation of methyl 2-bromo-3-fluoro-6-(methylthio)benzoate: Methyl 6-(acetylthio)-2-bromo-3-fluorobenzoate (1.21 g, 3.9 mmol) was dissolved in methanol (12 mL) and degassed with bubbling argon for 5 minutes. The solution was treated with cesium carbonate (1.66 g, 5.1 mmol), then the solution was stirred at ambient temperature for 55 minutes. The reaction mixture was treated with iodomethane (1.22 mL, 20 mmol) and stirred overnight under argon. The reaction mixture was concentrated in vacuo and redissolved in diethyl ether and water. The layers were separated and the aqueous was washed with diethyl ether. The combined organic layers were washed with saturated $NaHCO_3$, saturated NaCl, dried over $Na_2SO_4$, and concentrated in vacuo. Methyl 2-bromo-3-fluoro-6-(methylthio)benzoate was obtained as a yellow oil (0.97 g, 88%). $^1$H NMR (400 MHz, $CDCl_3$): δ 7.38-7.35 (m, 1H), 7.16-7.11 (m, 1H), 3.98 (s, 3H), 2.45 (s, 3H).

Step E: Preparation of methyl 2-bromo-3-fluoro-6-(methylsulfonyl)benzoate: A solution of methyl 2-bromo-3-fluoro-6-(methylthio)benzoate (3.57 g, 12.8 mmol) in methanol (63 mL) was added dropwise to a solution of Oxone® (23.6 g, 38.4 mmol) in water (63 mL). The reaction mixture was stirred at ambient temperature for 20 hours, and then heated at 60° C. for 6 hours. The reaction mixture was concentrated in vacuo. The residue was diluted with water and ethyl acetate and then separated. The aqueous layer was washed with a second portion of ethyl acetate and then the combined organics were washed with saturated $NaHCO_3$, saturated NaCl, dried over $Na_2SO_4$ and concentrated in vacuo to a yellowish solid (3.7 g). The crude material was chromatographed on $SiO_2$ eluting with ethyl acetate/hexane to give methyl 2-bromo-3-fluoro-6-(methylsulfonyl)benzoate as a white solid (3.07 g, 77%).
$^1$H NMR (400 MHz, $CDCl_3$): δ 8.04-8.01 (m, 1H), 7.37-7.33 (m, 1H), 4.02 (s, 3H), 3.17 (s, 3H).

Step F: Preparation of methyl 2-bromo-3-(3-chloro-5-fluoro-phenoxy)-6-methylsulfonyl-benzoate: Methyl 2-bromo-3-fluoro-6-methylsulfonyl-benzoate (400 mg, 1.29 mmol) was combined with 3-chloro-5-fluoro-phenol (245 mg, 1.67 mmol) and N,N-dimethylformamide (3.0 mL). The solution was treated in a single portion with sodium bicarbonate (216 mg, 2.57 mmol) and the reaction mixture was heated to 90° C. for 24 hours. The reaction mixture was cooled to room temperature, then purified directly on reverse phase silica gel (40+M, 14 CV, 20-100% acetonitrile/water) affording methyl 2-bromo-3-(3-chloro-5-fluoro-phenoxy)-6-methylsulfonyl-benzoate (510 mg, 1.17 mmol, 91% yield). LCMS ESI (+) m/z 435, 437, 439.

Step G: Preparation of 4-bromo-5-(3-chloro-5-fluoro-phenoxy)-1,1-dioxo-benzothiophen-3-one: Sodium hydride (60% in mineral oil, 140 mg, 3.5 mmol) was washed three times with hexane, then resuspended in tetrahydrofuran (3.0 mL). The suspension was cooled to 0° C. and treated dropwise with a solution of methyl 2-bromo-3-(3-chloro-5-fluoro-phenoxy)-6-methylsulfonyl-benzoate (510 mg, 1.17 mmol) dissolved in tetrahydrofuran (7.0 mL). After the addition, the reaction mixture was warmed to ambient temperature and stirred for 1 hour. The reaction was quenched with saturated $NH_4Cl$ and concentrated in vacuo. Ethyl acetate and some water were added, the solids were resolubilized, then the pH of the aqueous was adjusted to 3-4 with 10% $KHSO_4$. After separation, the aqueous was washed twice with ethyl acetate. The combined organics were washed twice with water, saturated NaCl, dried over $Na_2SO_4$ and concentrated in vacuo to give 4-bromo-5-(3-chloro-5-fluoro-phenoxy)-1,1-dioxo-benzothiophen-3-one (333 mg, 0.82 mmol, 70% yield). LCMS ESI (−) m/z 403, 405, 407.

Step H: Preparation of (3R)-4-bromo-5-(3-chloro-5-fluoro-phenoxy)-1,1-dioxo-2,3-dihydrobenzothiophen-3-ol: An ice cold solution of N-[(1R,2R)-1,2-Diphenyl-2-(2-(4-methylbenzyloxy)ethylamino)-ethyl]-4-methylbenzene sulfonamide(chloro)ruthenium(II) ((R,R)-Ts-DENEB™, 0.8 mg, 0.001 mmol) in dichloromethane (0.3 mL) was added by syringe to an ice cold solution of 4-bromo-5-(3-chloro-5-fluoro-phenoxy)-1,1-dioxo-benzothiophen-3-one (25 mg, 0.06 mmol), triethylamine (17 µL, 0.12 mmol) and formic acid (7 µL, 0.18 mmol) in dichloromethane (0.3 mL) under nitrogen. The reaction vial was then placed in a 4° C. refrigerator overnight. The reaction mixture was warmed to room temperature, then purified directly on silica gel (10 g SNAP, 14 CV, 5-50% ethyl acetate/hexane) affording (3R)-4-bromo-5-(3-chloro-5-fluoro-phenoxy)-1,1-dioxo-2,3-dihydrobenzothiophen-3-ol (21 mg, 0.05 mmol, 84% yield). The e.e. was determined to be 80% by $^{19}$F NMR analysis of the corresponding Mosher ester. LCMS ESI (−) m/z 451, 453, 455 (M−H).

Step I: Preparation of (3R)-5-(3-chloro-5-fluoro-phenoxy)-3-hydroxy-1,1-dioxo-2,3-dihydrobenzothiophene-4-carbonitrile (Compound 2): Copper (I) cyanide (31 mg, 0.34 mmol) was added to (3R)-4-bromo-5-(3-chloro-5-fluoro-phenoxy)-1,1-dioxo-2,3-dihydrobenzothiophen-3-ol (100 mg, 0.25 mmol) in a microwave vial equipped with a stir bar. 1-Methyl-2-pyrrolidone (1.0 mL) was added followed by flushing with nitrogen and sealing the vial with a teflon lined crimp cap. The reaction mixture was warmed to 160° C. for 75 minutes under microwave irradiation. The reaction mixture was cooled to room temperature, then purified directly on reverse phase silica gel (25+M, 14 CV, 20-100% acetonitrile/water) affording Compound 2 (69 mg, 0.20 mmol, 80% yield). Dichloromethane (0.2 mL) was added to the obtained oil and after standing for 10 minutes, a white solid formed.

After drying, the e.e. was determined to be 80% by 19F NMR analysis of the corresponding Mosher ester. LCMS ESI (-) m/z 352, 354 (M-H); $^1$H NMR (CDCl$_3$, 400 MHz) δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H).

Example 3

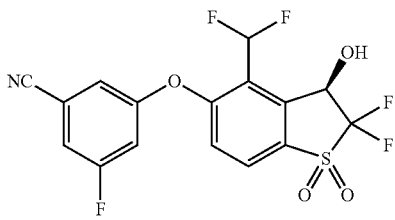 [SMILES: N#Cc1cc(F)cc(Oc2ccc3c(c2C(F)F)[C@@H](O)C(F)(F)S3(=O)=O)c1]

(R)-3-((4-(Difluoromethyl)-2,2-difluoro-3-hydroxy-1,1-dioxido-2,3-dihydrobenzo[b]thiophen-5-yl)oxy)-5-fluorobenzonitrile (Compound 3)

Step A: Preparation of 2-bromo-3-(difluoromethyl)-1,4-difluorobenzene: A solution of 2-bromo-3,6-difluorobenzaldehyde (40.0 g, 181 mmol) dissolved in dichloromethane (800 mL) was cooled to 0° C., then treated with (diethylamino)sulfur trifluoride (70.0 g, 454 mmol). After the addition, the reaction mixture was warmed to ambient temperature and stirred at this temperature for 4 hours. Saturated aqueous sodium bicarbonate solution was added slowly until the pH was 8-9. The organic layer was separated, dried over sodium sulfate, filtered and concentrated under reduced pressure to give 2-bromo-3-(difluoromethyl)-1,4-difluorobenzene (44.0 g, quant.) as solid which was used immediately in the next step without purification. $^1$H NMR (400 MHz, CDCl$_3$): δ 7.28-7.22 (m, 1H), 7.17-7.10 (m, $^1$H), 7.04 (t, 1H).

Step B: Preparation of 2-(difluoromethyl)-3,6-difluorobenzonitrile: A suspension of 2-bromo-3-(difluoromethyl)-1,4-difluorobenzene (44.0 g, 181 mmol) and copper (I) cyanide (21.1 g, 235 mmol) in 1-methyl-2-pyrrolidinone (400 mL) was heated to 180° C. for 2 hours. After cooling to ambient temperature, the reaction mixture was poured into water and extracted with diethyl ether. The organic layer was washed with brine, dried over sodium sulfate, filtered and then concentrated under reduced pressure. The crude product was purified by flash chromatography on silica gel eluting with hexane/ethyl acetate to give 2-(difluoromethyl)-3,6-difluorobenzonitrile as a solid (23 g, 67%). $^1$H NMR (400 MHz, CDCl$_3$): δ 7.48-7.35 (m, 2H), 6.98 (t, 1H).

Step C: Preparation of 2-(difluoromethyl)-3-fluoro-6-(methylthio)benzonitrile: A solution of 2-(difluoromethyl)-3,6-difluorobenzonitrile (31.3 g, 65.5 mmol) in acetonitrile (500 mL) was cooled to -30° C., then treated with sodium methanethiolate (12.8 g, 174 mmol). After addition of the solid, the reaction mixture was stirred for 7 hours while maintaining the temperature between -30° C. and -40° C. A mixture of water (200 mL) and methyl t-butyl ether (500 mL) were added and the reaction mixture was warmed to ambient temperature. The organic layer was separated, washed with brine, dried over sodium sulfate, filtered and concentrated under reduced pressure to give 2-(difluoromethyl)-3-fluoro-6-methylsulfanyl-benzonitrile as yellow solid (36.3 g, 150 mmol, 91%). $^1$H NMR (400 MHz, CDCl$_3$): δ 7.47-7.44 (m, 1H), 7.36-7.32 (m, 1H), 6.99 (t, 1H), 2.58 (s, 3H).

Step D: Preparation of 2-(difluoromethyl)-3-fluoro-6-(methylsulfonyl)benzonitrile: A slurry of 2-(difluoromethyl)-3-fluoro-6-methylsulfanyl-benzonitrile (36.3 g, 167 mmol) in acetonitrile (350 mL) and water (175 mL) was treated with Oxone® (257 g, 418 mmol), then the mixture was heated at 56° C. for 4 hours. After cooling to ambient temperature, the remaining solids were removed by filtration and washed with dichloromethane (300 mL). The filtrate was concentrated in vacuo to remove volatile solvents. The resulting aqueous solution was extracted with dichloromethane (400 mL). The organic layer was dried over sodium sulfate, filtered and concentrated under reduced pressure. The resulting solid was suspended in 4:1 hexane/methyl t-butyl ether (200 mL) and stirred for 10 minutes at ambient temperature. The undissolved solid was collected by filtration and air-dried to give 2-(difluoromethyl)-3-fluoro-6-(methylsulfonyl)benzonitrile (29.9 g, 71%). $^1$H NMR (400 MHz, CDCl$_3$): δ 8.41-8.37 (m, 1H), 7.66-7.61 (m, 1H), 7.11 (t, 1H), 3.34 (s, 3H).

Step E: Preparation of 3-(3-cyano-5-fluorophenoxy)-2-(difluoromethyl)-6-(methylsulfonyl)benzonitrile: A suspension of 2-(difluoromethyl)-3-fluoro-6-(methylsulfonyl)benzonitrile (9.52 g, 38.2 mmol), 3-fluoro-5-hydroxybenzonitrile (5.23 g, 38.2 mmol), and cesium carbonate (7.77 g, 40.1 mmol) in N, N-dimethylformamide (76 mL) was heated to 45° C. for 3 hours. Additional cesium carbonate (0.46 g, 1.4 mmol) was added and the reaction mixture was heated at 45° C. for three hours, then stirred at ambient temperature for 54 hours. The reaction mixture was vigorously stirred while water (800 mL) was added. The resulting suspension was stirred for 30 minutes, then the solids were collected by filtration, washed with water (1.2 L), and dried under high vacuum to give 3-(3-cyano-5-fluorophenoxy)-2-(difluoromethyl)-6-(methylsulfonyl)benzonitrile as a white solid (13.3 g, 96%). LCMS ESI (+) m/z 384 (M+NH$_4$). $^1$H NMR (400 MHz, DMSO-d$_6$): δ 8.22 (d, 1H), 7.86-7.82 (m, 1H), 7.72-7.62 (m, 3H), 7.49 (t, 1H), 3.44 (s, 3H).

Step F: Preparation of 3-((4-(difluoromethyl)-1,1-dioxido-3-oxo-2,3-dihydrobenzo[b]thiophen-5-yl)oxy)-5-fluorobenzonitrile: A solution of 3-(3-cyano-5-fluorophenoxy)-2-(difluoromethyl)-6-(methylsulfonyl)benzonitrile (13.3 g, 36 mmol) was dissolved in tetrahydrofuran (380 mL) and treated with sodium hydride (60% in mineral oil, 2.26 g, 56 mmol) in two equal portions at five minute intervals. The resulting suspension was stirred at ambient temperature for 60 minutes. The reaction mixture was quenched by addition of a mixture of 4:1 methanol/10% aqueous HCl (200 mL) and the resulting suspension was stirred for 1 hour. The mixture was concentrated to remove volatile solvents, then the remaining slurry was diluted with additional water (800 mL) and stirred for an additional 30 minutes. The solids were recovered by filtration and washed with additional water and the resulting beige solid was dried under high vacuum in the presence of solid NaOH. 3-((4-(Difluoromethyl)-1,1-dioxido-3-oxo-2,3-dihydrobenzo[b]thiophen-5-yl)oxy)-5-fluorobenzonitrile was obtained as a beige solid (13.3 g, quant.) and was used without further purification. LCMS ESI (-) m/z 366 (M-H). $^1$H NMR (400 MHz, DMSO-d$_6$): δ 8.35 (d, 1H), 7.79 (d, 1H), 7.76 (t, 1H), 7.76-7.72 (m, 1H), 7.56-7.50 (m, 2H), 4.72 (s, 2H).

Step G: Preparation of 3-((4-(difluoromethyl)-2,2-difluoro-1,1-dioxido-3-oxo-2,3-dihydrobenzo[b]thiophen-5-yl)oxy)-5-fluorobenzonitrile: A solution of 3-((4-(difluoromethyl)-1,1-dioxido-3-oxo-2,3-dihydrobenzo[b]thiophen-5-yl)oxy)-5-fluorobenzonitrile (1.40 g, 3.82 mmol) dissolved in acetonitrile (38 mL) was treated at ambient temperature with sodium carbonate (890 mg, 8.4 mmol) followed by Selectfluor® (2.98 g, 8.4 mmol). The reaction mixture was stirred at ambient temperature for 90 minutes. The reaction mixture was concentrated in vacuo to remove volatile solvents, then the residue was diluted with water (100 mL) and extracted three times with ethyl acetate (50 mL portions). The combined organic layers were washed with saturated NaCl, dried over MgSO$_4$, filtered and concentrated in vacuo to give 3-((4-(difluoromethyl)-2,2-difluoro-1,1-dioxido-3-oxo-2,3-dihydrobenzo[b]thiophen-5-yl)oxy)-5-fluorobenzonitrile as a solid (1.48 g, quant.).

$^1$H NMR (400 MHz, DMSO-d$_6$, sample exists as hydrate): δ 8.81 (s, 2H), 8.29 (d, 1H), 7.80-7.76 (m, 1H), 7.74 (t, 1H), 7.57-7.50 (m, 3H).

Step H: Preparation of 3-((4-(difluoromethyl)-2,2-difluoro-3-hydroxy-1,1-dioxido-2,3-dihydrobenzo[b]thiophen-5-yl)oxy)-5-fluorobenzonitrile: A solution of 3-((4-(difluoromethyl)-2,2-difluoro-1,1-dioxido-3-oxo-2,3-dihydrobenzo[b]thiophen-5-yl)oxy)-5-fluorobenzonitrile (1.48 g, 3.67 mmol) in methanol (37 mL) was cooled to 0° C., then treated with sodium borohydride (139 mg, 3.7 mmol) and stirred for 1 hour. The reaction was quenched by addition of water (0.5 mL) and saturated NH$_4$Cl (0.25 mL). The reaction mixture was concentrated in vacuo to remove volatile solvents, then diluted with 0.5 M NaOH (10 mL). The aqueous was extracted three times with ethyl acetate and the combined organic layers were washed with saturated NaCl, dried over MgSO$_4$, filtered and concentrated in vacuo. The crude product was chromatographed on SiO$_2$ eluting with a gradient of ethyl acetate/hexane to give 3-((4-(difluoromethyl)-2,2-difluoro-3-hydroxy-1,1-dioxido-2,3-dihydrobenzo[b]thiophen-5-yl)oxy)-5-fluorobenzonitrile as a white solid (1.24 g, 83%).

Step I: Preparation of (R)-3-((4-(difluoromethyl)-2,2-difluoro-3-hydroxy-1,1-dioxido-2,3-dihydrobenzo[b]thiophen-5-yl)oxy)-5-fluorobenzonitrile: 3-((4-(Difluoromethyl)-2,2-difluoro-3-hydroxy-1,1-dioxido-2,3-dihydrobenzo[b]thiophen-5-yl)oxy)-5-fluorobenzonitrile was resolved using preparative SFC chromatography under the following conditions: ChiralPak AS(—H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 3 was recovered as the first peak (1.50 minutes) to elute from the column. LCMS ESI (–) m/z 404 (M–H). $^1$H NMR (400 MHz, CDCl$_3$): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H).

Example 4

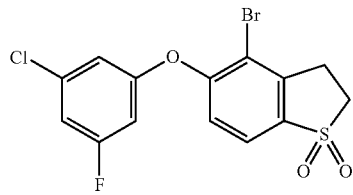 [SMILES: O=S1(=O)CCc2c1ccc(Oc1cc(F)cc(Cl)c1)c2Br]

4-Bromo-5-(3-chloro-5-fluorophenoxy)-2,3-dihydrobenzo[b]thiophene 1,1-dioxide (Compound 4)

Step A: Preparation of 2-bromo-3-fluoro-6-iodobenzoic acid: 2-Bromo-3-fluoro-benzoic acid (7.5 g, 34.3 mmol) was combined with palladium (II) acetate (384 mg, 1.7 mmol), iodine (8.7 g, 34.3 mmol), diacetoxy iodobenzene (11.0 g, 34.3 mmol) and N, N-dimethylformamide (165 mL). The resulting suspension was heated to 120° C. for 28 hours, then stirred at ambient temperature for 40 hours. The reaction mixture was concentrated to remove most of the N, N-dimethylformamide, then the residue was poured into 0.1 M HCl (resultant pH<3) and solid Na$_2$S$_2$O$_3$ was added to dissipate some of the iodine color. The aqueous layer was washed three times with Et$_2$O (100 mL each), then the combined organic layers were washed with 1M Na$_2$S$_2$O$_3$ to remove the remaining purple color. The organic layer was washed with saturated NaCl, dried over Na$_2$SO$_4$ and concentrated in vacuo. The crude product solidified after standing under vacuum (8 g, 67%).

Step B: Preparation of 2-bromo-3-fluoro-6-iodobenzamide: 2-Bromo-3-fluoro-6-iodobenzoic acid (2.33 g, 6.76 mmol) was dissolved in tetrahydrofuran (20 mL) and cooled to 0° C. The solution was treated with N, N-dimethylformamide (10 drops) followed by dropwise addition of thionyl chloride (1.0 mL, 10.1 mmol), then stirred for 10 minutes. The reaction mixture was warmed to ambient temperature, stirred for two hours, cooled to 0° C. and treated with concentrated ammonium hydroxide (5 mL). The resulting mixture was allowed to warm to ambient temperature with the bath and stirred overnight. The mixture was concentrated in vacuo, then redissolved in saturated NaHCO$_3$ and ethyl acetate. The layers were separated and the organic phase was washed with saturated NaHCO$_3$, saturated NaCl, dried over Na$_2$SO$_4$ and concentrated in vacuo to give a white solid (2.20 g, 94%).

Step C: Preparation of 2-bromo-3-fluoro-6-iodobenzonitrile: 2-Bromo-3-fluoro-6-iodobenzamide (10 g, 29 mmol) was suspended in phosphorus oxychloride (41 mL), treated with triethylamine (12.2 mL, 87.2 mmol) then the mixture was heated to 75° C. for 3 hours. The reaction mixture was cooled to ambient temperature with the bath and stirred overnight. The mixture was concentrated in vacuo to remove excess POCl$_3$, then the semi-dry residue was treated with a combination of ice and water. The mixture was stirred until the ice melted and the beige solid was collected by filtration, washed with water and air-dried (8.04 g, quant.).

Step D: Preparation of 2-bromo-3-fluoro-6-iodobenzaldehyde: A sample of 2-bromo-3-fluoro-6-iodobenzonitrile (100 mg, 0.307 mmol) was dissolved in CH$_2$Cl$_2$ (2 mL) and cooled to 0° C. The resulting solution was treated with diisobutylaluminum hydride (~1.0 M in heptanes, 370 μL, 0.37 mmol). The reaction was allowed to warm to room temperature after the addition for one hour, then 10% aqueous HCl (1 mL) was added to the reaction mixture and it was vigorously stirred for 1 hour. A solution of 20% sodium potassium tartrate (1 mL) was added and the reaction was stirred vigorously for an additional hour. The resulting solution was made basic by the addition of 10% NaOH solution. The reaction mixture was extracted with 3×20 mL CH$_2$Cl$_2$. The combined organics were rinsed with 20 mL of brine, dried with MgSO$_4$, filtered, and concentrated to dryness. The product was used without further purification.

Step E: Preparation of 2-bromo-1-fluoro-4-iodo-3-vinylbenzene: A sample of bromo(methyl)triphenylphosphorane (130 mg, 0.37 mmol) in anhydrous tetrahydrofuran (3.7 mL) was cooled to −40° C. and treated with ~2.5 M n-butyl lithium in hexane (140 μL, 0.34 mmol) by dropwise addition. The resulting solution was allowed to warm to −10° C. and stirred for 30 minutes at that temperature. The reaction mixture was cooled to −30° C. and treated with a solution of 2-bromo-3-fluoro-6-iodobenzaldehyde (75 mg, 0.23 mmol) in anhydrous tetrahydrofuran (3.7 mL) by dropwise addition. The reaction mixture was allowed to warm to room temperature and stirred overnight. The reaction mixture was poured into 30 mL of saturated aqueous $NH_4Cl$ and extracted with 3×20 mL $Et_2O$. The combined organics were rinsed with 20 mL of brine, dried with $MgSO_4$, filtered, and concentrated to dryness. The crude residue was purified on silica using 0-40% $CH_2Cl_2$/hexane to afford 2-bromo-1-fluoro-4-iodo-3-vinylbenzene (54 mg, 72% yield).

Step F: Preparation of S-(3-bromo-4-fluoro-2-vinylphenyl) ethanethioate: A reaction vial was charged with 2-bromo-1-fluoro-4-iodo-3-vinylbenzene (54 mg, 0.17 mmol) and (9,9-dimethyl-9H-xanthene-4,5-diyl)bis(diphenylphosphine) (11.5 mg, 0.02 mmol). The mixture was suspended in 1 mL of a 2:1 mixture of toluene/acetone and then sparged by bubbling nitrogen through the mixture for 3 minutes. Under continuous stream of nitrogen, tris(dibenzylideneacetone)dipalladium(0) (9.0 mg, 0.009 mmol) and potassium ethanethioate (23.6 mg, 0.21 mmol) were added. The vessel was sealed and heated to 70° C. After 2 hours of heating, the reaction mixture was filtered. The filtered residue was rinsed with excess $CH_2Cl_2$ and the combined filtrates were concentrated. The crude residue was purified directly on silica using 10-50% $CH_2Cl_2$/hexane as eluent. S-(3-Bromo-4-fluoro-2-vinylphenyl) ethanethioate was isolated as a yellow solid (45.4 mg, 98%). LCMS ESI (−) (M−H) m/z 273, 275.

Step G: Preparation of 3-bromo-4-fluoro-2-vinylbenzenethiol: To a round bottom flask containing S-(3-bromo-4-fluoro-2-vinyl-phenyl) ethanethioate (45 mg, 0.17 mmol) dissolved in 2 mL of degassed tetrahydrofuran (sparged with nitrogen for 5 minutes) was added ammonium hydroxide (ACS reagent, 0.06 mL, 1.65 mmol). The resulting reaction mixture was stirred for 40 minutes under nitrogen atmosphere. The reaction mixture was poured into 20 mL of a 1:1 mixture of brine and 1 M HCl and extracted with 3×15 mL of EtOAc. The combined organics were dried with $MgSO_4$, filtered, and concentrated to dryness. The product was used without further purification. LCMS ESI (−) (M−H) m/z 231, 233.

Step H: Preparation of 4-bromo-5-fluoro-2,3-dihydrobenzo[b]thiophene 1-oxide: A solution of 3-bromo-4-fluoro-2-vinyl-benzenethiol (28 mg, 0.12 mmol) and azobisisobutyronitrile (4 mg, 0.02 mmol) in benzene (2 mL) was sparged with nitrogen for 5 minutes. The vessel was sealed and heated to 80° C. for 4 hours. The reaction mixture was concentrated to dryness and the product residue was dissolved in 2 mL of MeOH and 1 mL of water. Oxone® (18.7 mg, 0.06 mmol) was added and the resulting mixture was stirred for 2 hours at room temperature. The reaction mixture was concentrated to dryness and the residue purified directly on reverse phase by injection as a solution in N,N-dimethylformamide (Biotage® Isolera™ One unit, C18 Flash 12+M column, 0-100% $CH_3CN$/water, 8.5 mg, 30%). LCMS ESI (+) (M+H) m/z 249, 251.

Step I: Preparation of 4-bromo-5-fluoro-2,3-dihydrobenzo[b]thiophene 1,1-dioxide: A solution of 4-bromo-5-fluoro-2,3-dihydrobenzothiophene[b] 1-oxide (8.5 mg, 0.03 mmol) in dichloromethane (1 mL) was treated with 3-chloroperbenzoic acid (9.2 mg, 0.04 mmol) and stirred at 25° C. overnight. The reaction mixture was poured into 10 mL of 1 M NaOH and extracted with 3×20 mL EtOAc. The combined organics were rinsed with 20 mL of brine, dried with $MgSO_4$, filtered, and concentrated to dryness. The product was used without further purification. LCMS ESI (+) (M+H) m/z 265, 267.

Step J: Preparation of 4-bromo-5-(3-chloro-5-fluorophenoxy)-2,3-dihydrobenzo[b]thiophene 1,1-dioxide: A solution of 4-bromo-5-fluoro-2,3-dihydrobenzothiophene[b] 1,1-dioxide (9.0 mg, 0.03 mmol) and 3-chloro-5-fluorophenol (6.0 mg, 0.04 mmol) in N,N-dimethylformamide (0.7 mL) was treated with potassium carbonate (5.6 mg, 0.04 mmol) and stirred at 90° C. for 4 hours. The reaction mixture was poured into 30 mL of water and extracted with 3×20 mL $Et_2O$. The combined organics were rinsed with 20 mL of brine, dried with $MgSO_4$, filtered, and concentrated to dryness. The residue was purified directly on reverse phase by injection as a solution in N,N-dimethylformamide (Biotage® Isolera™ One unit, C18 Flash 12+M column, 20-90% $CH_3CN$/water) to afford Compound 4 as a white solid (7.4 mg, 56%). LCMS ESI (+) (M+H) m/z 391, 393, 395; $^1H$ NMR (400 MHz, $CDCl_3$): δ 7.70 (d, 1H), 7.10 (d, 1H), 6.93 (ddd, 1H), 6.78-6.76 (m, 1H), 6.63 (dt, 1H), 3.62-3.58 (m, 2H), 3.42-3.37 (m, 2H).

Example 5

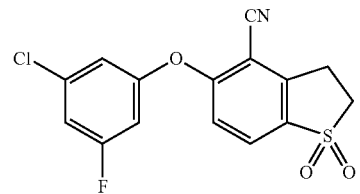 [SMILES: N#Cc1c(Oc2cc(F)cc(Cl)c2)ccc2c1CCS2(=O)=O]

5-(3-Chloro-5-fluorophenoxy)-2,3-dihydrobenzo[b]thiophene-4-carbonitrile 1,1-dioxide (Compound 5)

A solution of zinc cyanide (2.3 mg, 0.02 mmol) and 4-bromo-5-(3-chloro-5-fluoro-phenoxy)-2,3-dihydrobenzo[b]thiophene 1,1-dioxide (6.5 mg, 0.02 mmol) in N, N-dimethylformamide (0.2 mL) was treated with 1,1'-bis(diphenylphosphino)ferrocene-palladium(II)dichloride dichloromethane complex (4.1 mg, 30 mol %) and heated at 170° C. by microwave irradiation for 45 minutes. The reaction mixture was purified directly by reverse phase chromatography by injection of the dimethylformamide reaction solution (Biotage® Isolera™ One unit, C18 Flash 12+M column, 20-80% $CH_3CN$/water) to afford 5-(3-chloro-5-fluorophenoxy)-2,3-dihydrobenzo[b]thiophene-4-carbonitrile 1,1-dioxide as a beige solid (2.8 mg, 50%). LCMS ESI (−) (M−H) m/z 336, 338; $^1H$ NMR (400 MHz, $CDCl_3$): δ 7.87 (d, 1H), 7.06 (dt, 1H), 7.03 (d, 1H), 6.94-6.92 (m, 1H), 6.78 (dt, 1H), 3.66-3.61 (m, 2H), 3.60-3.55 (m, 2H).

Example 6

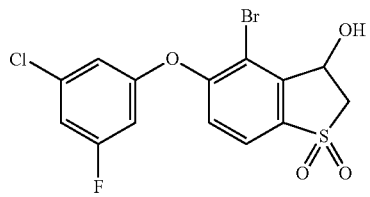 [SMILES: O=S1(=O)CC(O)c2c1ccc(Oc1cc(F)cc(Cl)c1)c2Br]

4-Bromo-5-(3-chloro-5-fluorophenoxy)-3-hydroxy-
2,3-dihydrobenzo[b]thiophene 1,1-dioxide (Compound 6)

A solution of 4-bromo-5-(3-chloro-5-fluoro-phenoxy)-1,1-dioxo-benzo[b]thiophen-3-one (31 mg, 0.08 mmol, prepared similarly according to Example 1, Steps A-G) in methanol (1.5 mL) and dichloromethane (0.75 mL) at 0° C. was treated with sodium borohydride (1.5 mg, 0.04 mmol) and stirred at 0° C. for 45 minutes. The reaction mixture was quenched by the addition of 1 mL of water. Volatiles were removed by concentration under reduced pressure. The reaction mixture was poured into 10 mL of water and extracted with 3×15 mL EtOAc. The combined organics were rinsed with 10 mL of brine, dried with MgSO$_4$, filtered, and concentrated to dryness. Purification was achieved by chromatography on silica using 20-70% EtOAc/hexane to give Compound 6 as a clear thin film (22 mg, 71%). LCMS ESI (+) (M+NH$_4$) m/z 424, 426, 428; $^1$H NMR (400 MHz, CDCl$_3$): δ 7.72 (d, 1H), 7.19 (d, 1H), 6.98-6.94 (ddd, 1H), 6.82-6.80 (m, 1H), 6.67 (dt, 1H), 5.60 (td, 1H), 3.80 (dd, 1H), 3.68 (dd, 1H), 2.89 (d, 1H).

Example 7

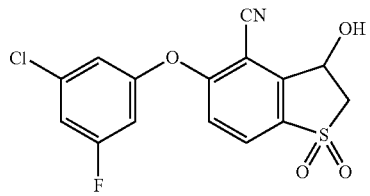 [SMILES: N#Cc1c(Oc2cc(F)cc(Cl)c2)ccc2c1C(O)CS2(=O)=O]

5-(3-chloro-5-fluorophenoxy)-3-hydroxy-2,3-dihydrobenzo[b]thiophene-4-carbonitrile 1,1-dioxide (Compound 7)

A solution of 4-bromo-5-(3-chloro-5-fluoro-phenoxy)-1,1-dioxo-2,3-dihydrobenzothiophen-3-ol (17.3 mg, 0.04 mmol) in 1-methyl-2-pyrrolidone (0.25 mL) was treated with copper (I) cyanide (4.6 mg, 0.05 mmol) and heated at 160° C. by microwave irradiation for 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 20-60% EtOAc/hexane to afford Compound 7 as a white solid (9.7 mg, 65%). LCMS ESI (−) (M−H) m/z 352, 354; $^1$H NMR (400 MHz, CDCl$_3$): δ 7.89 (d, 1H), 7.13 (d, 1H), 7.07 (ddd, 1H), 6.97-6.94 (m, 1H), 6.80 (dt, 1H), 5.79-5.72 (m, 1H), 3.91 (dd, 1H), 3.64 (dd, 1H), 3.57 (br d, 1H).

Example 8

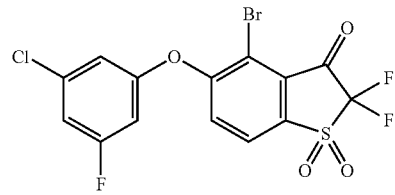 [SMILES: O=C1c2c(ccc(Oc3cc(F)cc(Cl)c3)c2Br)S(=O)(=O)C1(F)F]

4-Bromo-5-(3-chloro-5-fluorophenoxy)-2,2-difluorobenzo[b]thiophen-3(2H)-one 1,1-dioxide (Compound 8)

Compound 8 was prepared similarly according to Example 1, Steps A-H, substituting 3-chloro-5-fluorophenol for 3-fluoro-5-hydroxy-benzonitrile. Purification was achieved by chromatography on silica using 10-30% EtOAc/hexane to afford Compound 8 as a white solid (26.6 mg, 31%). $^1$H NMR (400 MHz, CDCl$_3$): δ 7.89 (d, 1H), 7.50 (d, 1H), 7.06 (ddd, 1H), 6.89-6.86 (m, 1H), 6.73 (dt, 1H).

Example 9

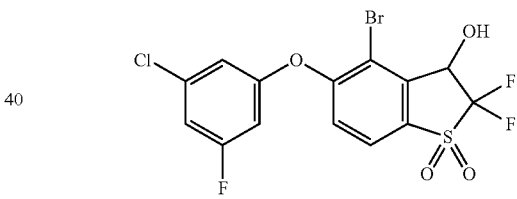

4-Bromo-5-(3-chloro-5-fluorophenoxy)-2,2-difluoro-3-hydroxy-2,3-dihydrobenzo[b]thiophene 1,1-dioxide (Compound 9)

A solution of 4-bromo-5-(3-chloro-5-fluoro-phenoxy)-2,2-difluoro-1,1-dioxo-benzo[b]thiophen-3-one (18 mg, 0.04 mmol) in methanol (2.0 mL) at 0° C. was treated with sodium borohydride (1.5 mg, 0.04 mmol) and stirred at 0° C. for 30 minutes. The reaction mixture was quenched by the addition of 0.5 mL of water. Volatiles were removed by concentration under reduced pressure. The mixture was poured into 10 mL of water and extracted with 3×20 mL EtOAc. The combined organics were rinsed with 10 mL of brine, dried with MgSO$_4$, filtered, and concentrated to dryness. Purification was achieved by chromatography on silica using 10-30% EtOAc/hexane to afford Compound 9 as a white solid (13 mg, 72%). LCMS ESI (+) (M−OH) m/z 425, 427, 429; $^1$H NMR (400 MHz, CDCl$_3$): δ 7.80 (d, 1H), 7.22 (d, 1H), 7.01 (dt, 1H), 6.87-6.85 (m, 1H), 6.71 (dt, 1H), 5.38 (d, 1H), 2.98 (br s, 1H).

Example 10

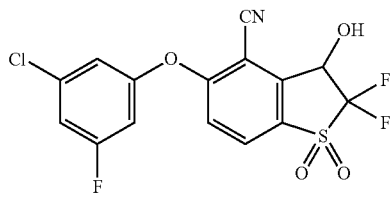 [SMILES: N#Cc1c(Oc2cc(F)cc(Cl)c2)ccc2c1C(O)C(F)(F)S2(=O)=O]

5-(3-chloro-5-fluorophenoxy)-2,2-difluoro-3-hydroxy-2,3-dihydrobenzo[b]thiophene-4-carbonitrile 1,1-dioxide (Compound 10)

A solution of 4-bromo-5-(3-chloro-5-fluoro-phenoxy)-2,2-difluoro-1,1-dioxo-3H-benzothiophen-3-ol (18.9 mg, 0.04 mmol) in 1-methyl-2-pyrrolidone (0.25 mL) was treated with copper (I) cyanide (4.6 mg, 0.05 mmol) and heated at 160° C. by microwave irradiation for 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-30% EtOAc/hexane to afford Compound 10 as a white solid (2.9 mg, 17%). LCMS ESI (−) (M−H) m/z 388, 390; $^1$H NMR (400 MHz, CDCl$_3$): δ 7.97 (d, 1H), 7.19 (d, 1H), 7.12 (ddd, 1H), 6.99-6.97 (m, 1H), 6.83 (dt, 1H), 5.58-5.51 (m, 1H), 3.51 (br d, 1H).

Example 11

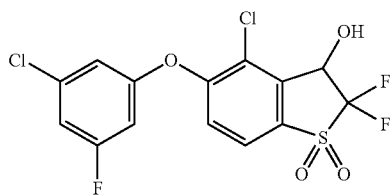

4-Chloro-5-(3-chloro-5-fluorophenoxy)-2,2-difluoro-3-hydroxy-2,3-dihydrobenzo[b]thiophene 1,1-dioxide (Compound 11)

A solution of 4-bromo-5-(3-chloro-5-fluoro-phenoxy)-2,2-difluoro-1,1-dioxo-3H-benzo[b]thiophen-3-ol (5.8 mg, 0.013 mmol) in 1-methyl-2-pyrrolidone (0.5 mL) was treated with copper(I) chloride (12.9 mg, 0.13 mmol) and stirred at 170° C. by microwave irradiation for 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 0-10% EtOAc/CH$_2$Cl$_2$ to afford Compound 11 as a white solid (2.6 mg, 50%). LCMS ESI (−) (M−H) m/z 397, 399; $^1$H NMR (400 MHz, CDCl$_3$): δ 7.76 (d, 1H), 7.26 (d, 1H), 7.01 (ddd, 1H), 6.87-6.85 (m, 1H), 6.71 (dt, 1H), 5.44 (dd, 1H), 2.94 (d, 1H).

Example 12

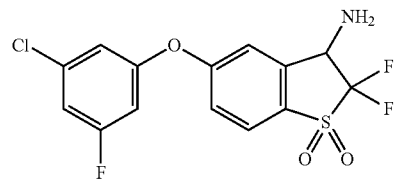

3-Amino-5-(3-chloro-5-fluorophenoxy)-2,2-difluoro-2,3-dihydrobenzo[b]thiophene 1,1-dioxide (Compound 12)

A solution of 4-bromo-5-(3-chloro-5-fluoro-phenoxy)-2,2-difluoro-1,1-dioxo-benzo[b]thiophen-3-one (18.8 mg, 0.043 mmol) in toluene (0.45 mL) at 25° C. was treated with lithium bis(trimethylsilyl)amide (1.0 M in tetrahydrofuran, 50 μL, 0.05 mmol) by dropwise addition over a 10 minutes period. The reaction was left to stir for 25 minutes at room temperature and was then treated with borane dimethylsulfide complex (10 μL, 0.09 mmol). The reaction mixture stirred for 30 minutes. The reaction mixture was then cooled to 0° C. and carefully treated with 2 N NaOH (1 mL) and stirred for 90 minutes. The reaction mixture was poured into 5 mL of 2 N NaOH and extracted with 3×10 mL EtOAc. The combined organics were rinsed with 10 mL of brine, dried with MgSO$_4$, filtered, and concentrated to dryness. Purification was achieved by chromatography on silica using 5-20% EtOAc/hexane to afford Compound 12 as a thin film (2.2 mg, 14%). LCMS ESI (+) (M+H) m/z 364, 366; $^1$H NMR (400 MHz, CDCl$_3$): δ 7.81 (d, 1H), 7.36 (dd, 1H), 7.20 (ddd, 1H), 6.99 (ddd, 1H), 6.89-6.86 (m, 1H), 6.71 (dt, 1H), 4.73-4.61 (m, 1H), 1.79 (br d, 2H).

Example 13

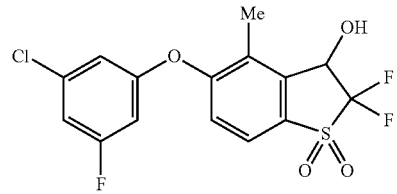 [SMILES: O=S1(=O)c2ccc(Oc3cc(F)cc(Cl)c3)c(Cl)c2C(O)C1(F)F]

5-(3-Chloro-5-fluorophenoxy)-2,2-difluoro-3-hydroxy-4-methyl-2,3-dihydrobenzo[b]thiophene 1,1-dioxide (Compound 13)

A solution of 4-bromo-5-(3-chloro-5-fluoro-phenoxy)-2,2-difluoro-1,1-dioxo-3H-benzothiophen-3-ol (10.6 mg, 0.024 mmol) and potassium trifluoro(methyl)boranuide (4.4 mg, 0.036 mmol) in 1,4-dioxane (0.5 mL) and water (50 μL) was sparged with nitrogen for 3 minutes. The reaction mixture was then treated sequentially with cesium carbonate (39 mg, 0.12 mmol) and dichloro[1;1'-bis(diphenylphosphino)ferrocene]palladium(II) dichloromethane (1.9 mg, 10 mol %) adduct under continuous nitrogen stream. The vessel was sealed and heated to 100° C. overnight. The reaction mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 10-15% EtOAc/hexane to afford Compound 13 as a white solid (2.5 mg, 28%). LCMS ESI (−) (M−H) m/z 377, 379; $^1$H NMR (400 MHz, CDCl$_3$): δ 7.70 (d, 1H), 7.16 (d, 1H), 6.95 (ddd, 1H), 6.80-6.78 (m, 1H), 6.64 (dt, 1H), 5.30 (dd, 1H), 2.72 (dd, 1H), 2.43 (s, 3H).

Example 14

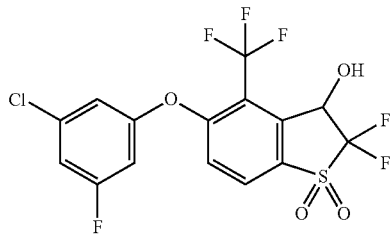 [SMILES: O=S1(=O)c2ccc(Oc3cc(F)cc(Cl)c3)c(C(F)(F)F)c2C(O)C1(F)F]

5-(3-Chloro-5-fluorophenoxy)-2,2-difluoro-3-hydroxy-4-(trifluoromethyl)-2,3-dihydrobenzo[b]thiophene 1,1-dioxide (Compound 14)

Step A: Preparation of 5-(3-chloro-5-fluorophenoxy)-2,2-difluoro-3-hydroxy-4-iodo-2,3-dihydrobenzo[b]thiophene 1,1-dioxide: A solution of 4-bromo-5-(3-chloro-5-fluorophenoxy)-2,2-difluoro-1,1-dioxo-3H-benzothiophen-3-ol (32.4 mg, 0.07 mmol) in 1-methyl-2-pyrrolidone (1.5 mL) was treated with copper (I) iodide (208 mg, 1.1 mmol) and heated at 180° C. by microwave irradiation for 1 hour. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 5-20% EtOAc/hexane to afford 5-(3-chloro-5-fluorophenoxy)-2,2-difluoro-3-hydroxy-4-iodo-2,3-dihydrobenzo[b]thiophene 1,1-dioxide as a beige solid (20 mg, 56%). LCMS ESI (−) (M−H) m/z 489, 491.

Step B: Preparation of 5-(3-chloro-5-fluorophenoxy)-2,2-difluoro-3-hydroxy-4-(trifluoromethyl)-2,3-dihydrobenzo[b]thiophene 1,1-dioxide: A solution of 5-(3-chloro-5-fluoro-phenoxy)-2,2-difluoro-4-iodo-1,1-dioxo-3H-benzothiophen-3-ol (20 mg, 0.04 mmol) in N,N-dimethylformamide (0.8 mL) was sparged with nitrogen for 3 minutes, treated with (1,10-phenanthroline)(trifluoromethyl)copper(I) (19 mg, 0.06 mmol) under a stream of nitrogen, sealed, and stirred overnight at 50° C. After 18 hours, the reaction mixture was diluted with Et$_2$O and filtered through a pad of celite. The celite pad was washed with Et$_2$O. The combined filtrate was washed sequentially with 1M aqueous HCl, saturated aqueous NaHCO$_3$ solution and brine, and dried over Na$_2$SO$_4$. After filtration and evaporation of the solvent, the crude mixture was purified by flash silica gel column chromatography using 10-20% EtOAc/hexane to afford Compound 14 as a thin film (4.9 mg, 28%). LCMS ESI (−) (M−H) m/z 431, 433; $^1$H NMR (400 MHz, CDCl$_3$): δ 8.00 (d, 1H), 7.29 (d, 1H), 7.04 (ddd, 1H), 6.91-6.89 (m, 1H), 6.74 (dt, 1H), 5.58 (d, 1H), 3.16 (br s, 1H).

Example 15

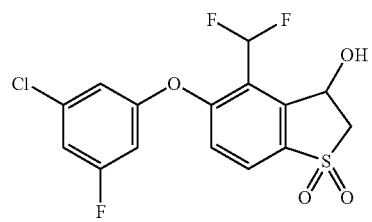 [SMILES: O=S1(=O)CC(O)c2c1ccc(Oc1cc(F)cc(Cl)c1)c2C(F)F]

5-(3-Chloro-5-fluorophenoxy)-4-(difluoromethyl)-3-hydroxy-2,3-dihydrobenzo[b]thiophene 1,1-dioxide (Compound 15)

A solution of 5-(3-chloro-5-fluoro-phenoxy)-4-(difluoromethyl)-1,1-dioxo-benzothiophen-3-one (14.7 mg, 0.04 mmol, prepared similarly according to Example 3, Steps A-F) in methanol (2.5 mL) at 0° C. was treated with sodium borohydride (1.5 mg, 0.04 mmol) and stirred at 0° C. for 1 hour. The reaction mixture was quenched by the addition of 0.5 mL of water and 0.25 mL of saturated aqueous NH$_4$Cl. Volatiles were removed by concentration under reduced pressure. The reaction mixture was poured into 10 mL of water and extracted with 3×15 mL EtOAc. The combined organics were rinsed with 10 mL of brine, dried with MgSO$_4$, filtered, and concentrated to dryness. Purification was achieved by chromatography on silica using 15-50% EtOAc/hexane to afford Compound 15 as a white solid (8.9 mg, 57%). LCMS ESI (−) (M−H) m/z 377, 379; $^1$H NMR (400 MHz, CDCl$_3$): δ 7.85 (d, 1H), 7.22 (t, 1H), 7.14 (dt, 1H), 7.01 (ddd, 1H), 6.87-6.85 (m, 1H), 6.71 (dt, 1H), 5.90-5.85 (m, 1H), 3.77 (ddd, 1H), 3.67 (dd, 1H), 2.87 (t, 1H).

Example 16

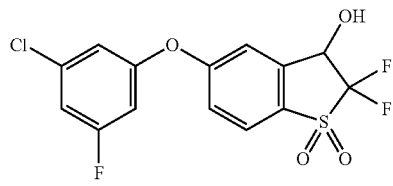 [SMILES: O=S1(=O)c2ccc(Oc3cc(F)cc(Cl)c3)cc2C(O)C1(F)F]

5-(3-Chloro-5-fluorophenoxy)-2,2-difluoro-3-hydroxy-2,3-dihydrobenzo[b]thiophene 1,1-dioxide (Compound 16)

A solution of 4-bromo-5-(3-chloro-5-fluoro-phenoxy)-2,2-difluoro-1,1-dioxo-3H-benzothiophen-3-ol (12 mg, 0.03 mmol) in toluene (0.4 mL) at 25° C. was treated with borane methylsulfanylmethane (0.15 mL, 1.58 mmol) and stirred at 25° C. overnight. Lithium borohydride solution (~1.0 M in tetrahydrofuran, 270 μL, 0.27 mmol) was added. The resulting mixture was heated to 60° C. for 1 day. Volatiles were removed by concentration under reduced pressure. The remaining residue was solubilized with 30 mL 3 of 10% aqueous HCl and extracted with 3×15 mL EtOAc. The combined organics were rinsed with 10 mL of brine, dried with MgSO$_4$, filtered, and concentrated to dryness. Repeated purifications (3×) by chromatography on silica using 10-15% EtOAc/hexane afforded Compound 16 as a thin film (1.6 mg, 15%). LCMS ESI (−) (M−H) m/z 363, 365; $^1$H NMR (400 MHz, CDCl$_3$): δ 7.84 (d, 1H), 7.27-7.23 (m, 2H), 7.01 (dt, 1H), 6.90-6.88 (m, 1H), 6.72 (dt, 1H), 5.35 (q, 1H), 2.79 (dd, 1H).

Example 17

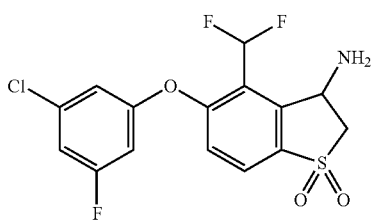 [SMILES: NC1CS(=O)(=O)c2ccc(Oc3cc(F)cc(Cl)c3)c(C(F)F)c21]

3-Amino-5-(3-chloro-5-fluorophenoxy)-4-(difluoromethyl)-2,3-dihydrobenzo[b]thiophene 1,1-dioxide (Compound 17)

Step A: Preparation of 3-amino-5-(3-chloro-5-fluorophenoxy)-4-(difluoromethyl)benzo[b]thiophene 1,1-dioxide: A solution of 3-(3-chloro-5-fluoro-phenoxy)-2-(difluoromethyl)-6-methylsulfonyl-benzonitrile (16.5 mg, 0.044 mmol, prepared similarly according to Example 3, Steps A-E) in tetrahydrofuran (1 mL) at 25° C. was treated with sodium hydride (2.1 mg, 0.053 mmol). The resulting suspension was stirred for 30 minutes. The reaction mixture was poured into 10 mL of saturated aqueous NH$_4$Cl and extracted with 3×15 mL EtOAc. The combined organics were rinsed with 10 mL of brine, dried with MgSO$_4$, filtered, and concentrated to dryness. Purification was achieved by chromatography on silica using 10-35% EtOAc/hexane to afford 3-amino-5-(3-chloro-5-fluorophenoxy)-4-(difluoromethyl)benzo[b]thiophene 1,1-dioxide as a yellow solid (12.7 mg, 77%).

Step B: Preparation of 3-amino-5-(3-chloro-5-fluorophenoxy)-4-(difluoromethyl)-2,3-dihydrobenzo[b]thiophene 1,1-dioxide: A solution of 5-(3-chloro-5-fluoro-phenoxy)-4-(difluoromethyl)-1,1-dioxo-benzothiophen-3-amine (10 mg, 0.027 mmol) in methanol (4.0 mL) at 25° C. was treated with sodium borohydride (20.1 mg, 0.53 mmol). Additional portions of sodium borohydride were added until the reaction was complete. The reaction mixture was quenched with 2 mL of water and concentrated to dryness. The residue was poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 20-60% EtOAc/hexane to afford Compound 17 as a white solid (3.9 mg, 39%). LCMS ESI (+) (M+H) m/z 378, 380; $^1$H NMR (400 MHz, CDCl$_3$): δ 7.80 (d, 1H), 7.22 (t, 1H), 7.06 (dt, 1H), 7.00 (dt, 1H), 6.87-6.84 (m, 1H), 6.70 (dt, 1H), 5.16-5.03 (br s, 1H), 3.75 (dd, 1H), 3.49 (dd, 1H), 2.20-1.97 (br s, 2H).

Example 18

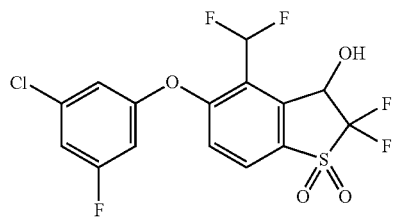 [SMILES: O=S1(=O)c2ccc(Oc3cc(F)cc(Cl)c3)c(C(F)F)c2C(O)C1(F)F]

5-(3-Chloro-5-fluorophenoxy)-4-(difluoromethyl)-2,2-difluoro-3-hydroxy-2,3-dihydrobenzo[b]thiophene 1,1-dioxide (Compound 18)

A solution of 5-(3-chloro-5-fluoro-phenoxy)-4-(difluoromethyl)-2,2-difluoro-1,1-dioxo-benzothiophen-3-one (27 mg, 0.066 mmol, prepared similarly according to Example 3, Steps A-G) in methanol (1.3 mL) at 0° C. was treated with sodium borohydride (2.7 mg, 0.073 mmol) and stirred at 0° C. for 1 hour. The reaction mixture was quenched by the addition of 0.5 mL of water and 0.25 mL of saturated NH$_4$Cl. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 10-30% EtOAc/hexane to afford Compound 18 as a thin film (8.6 mg, 31%). LCMS ESI (−) (M−H) m/z 413, 415; $^1$H NMR (400 MHz, CDCl$_3$): δ 7.93 (d, 1H), 7.25 (t, 1H), 7.21-7.17 (m, 1H), 7.06 (ddd, 1H), 6.92-6.89 (m, 1H), 6.75 (dt, 1H), 5.67 (dd, 1H), 3.10 (dd, 1H).

Examples 19 and 20

Compound 19

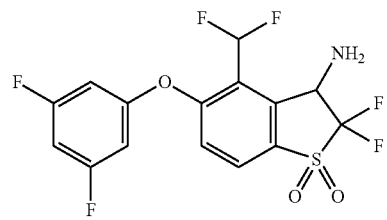

Compound 20

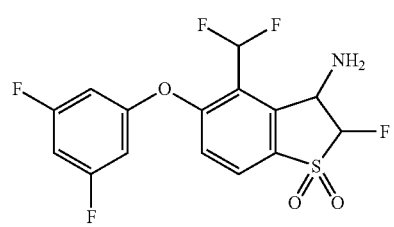

3-Amino-4-(difluoromethyl)-5-(3,5-difluorophenoxy)-2,2-difluoro-2,3-dihydrobenzo[b]thiophene 1,1-dioxide (Compound 19) and 3-amino-4-(difluoromethyl)-5-(3,5-difluorophenoxy)-2-fluoro-2,3-dihydrobenzo[b]thiophene 1,1-dioxide (Compound 20)

A solution of 4-(difluoromethyl)-5-(3,5-difluorophenoxy)-1,1-dioxo-benzothiophen-3-amine (24.4 mg, 0.07 mmol, prepared similarly according to Example 17, Step A) in acetonitrile (1.3 mL) at 25° C. was treated with sodium carbonate (15.8 mg, 0.15 mmol). The resulting suspension was stirred for 5 minutes and then Selectfluor® (53 mg, 0.15 mmol) was added. The reaction mixture was stirred at 25° C. for 1.5 hours. Volatiles were removed by concentration under reduced pressure. The residue was dissolved in 2 mL of MeOH and treated with sodium borohydride (5.1 mg, 0.14 mmol). The reaction mixture was allowed to stir for 1 hour at 25° C. Volatiles were removed by concentration under reduced pressure and the residue was poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 60-100% CH$_2$Cl$_2$/hexane to afford 3-amino-4-(difluoromethyl)-5-(3,5-difluorophenoxy)-2,2-difluoro-2,3-dihydrobenzo[b]thiophene 1,1-dioxide (Compound 19) as a thin film (6.0 mg, 22%) and 3-amino-4-(difluoromethyl)-5-(3,5-difluorophenoxy)-2-fluoro-2,3-dihydrobenzo[b]thiophene 1,1-dioxide (Compound 20) as a white solid (5.6 mg, 21%).

Data for 3-amino-4-(difluoromethyl)-5-(3,5-difluoro-2,3-dihydrobenzo[b]thiophene 1,1-dioxide (Compound 19): HPLC retention time=3.07 minutes; LCMS ESI (+) (M+H) m/z 398; $^1$H NMR (400 MHz, CDCl$_3$): δ 7.90 (d, 1H), 7.28 (dd, 1H), 7.18-7.14 (m, 1H), 6.76 (tt, 1H), 6.67-6.60 (m, 2H), 4.98 (dt, 1H), 2.01 (br d, 2H).

Data for 3-amino-4-(difluoromethyl)-5-(3,5-difluorophenoxy)-2-fluoro-2,3-dihydrobenzo[b]thiophene 1,1-dioxide (Compound 20): HPLC retention time=2.64 minutes; LCMS ESI (+) (M+H) m/z 380; $^1$H NMR (400 MHz, CDCl$_3$): δ 7.87 (d, 1H), 7.44 (dd, 1H), 7.15 (d, 1H), 6.73 (tt, 1H), 6.64-6.57 (m, 2H), 5.58 (dd, 1H), 5.17-5.07 (m, 1H), 2.02-1.93 (m, 2H).

Example 21

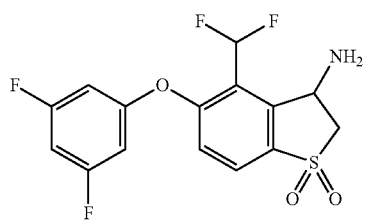 [SMILES: NC1CS(=O)(=O)c2ccc(Oc3cc(F)cc(F)c3)c(C(F)F)c21]

3-Amino-4-(difluoromethyl)-5-(3,5-difluorophenoxy)-2-fluoro-2,3-dihydrobenzo[b]thiophene 1,1-dioxide (Compound 21)

LCMS ESI (+) (M+H) m/z 362; $^1$H NMR (400 MHz, CDCl$_3$): δ 7.81 (d, 1H), 7.22 (t, 1H), 7.10-7.06 (m, 1H), 6.72 (tt, 1H), 6.63-6.56 (m, 2H), 5.14-5.07 (m, 1H), 3.75 (dd, 1H), 3.49 (dd, 1H), 2.12-2.04 (m, 2H).

Examples 22 and 23

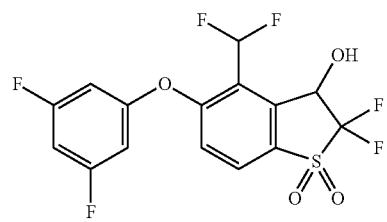
Compound 22

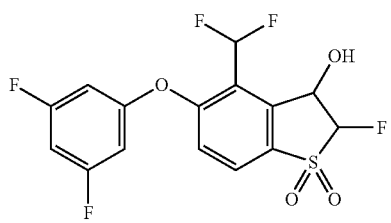
Compound 23

4-(Difluoromethyl)-5-(3,5-difluorophenoxy)-2,2-difluoro-3-hydroxy-2,3-dihydrobenzo[b]thiophene 1,1-dioxide (Compound 22) and 4-(difluoromethyl)-5-(3,5-difluorophenoxy)-2-fluoro-3-hydroxy-2,3-dihydrobenzo[b]thiophene 1,1-dioxide (Compound 23)

A solution of 4-(difluoromethyl)-5-(3,5-difluorophenoxy)-1,1-dioxo-benzothiophen-3-one (19 mg, 0.053 mmol, prepared similarly according to Example 3, Steps A-F) in acetonitrile (2.1 mL) at 25° C. was treated with sodium carbonate (12.3 mg, 0.12 mmol). The resulting suspension was stirred for 5 minutes. Selectfluor® (41 mg, 0.12 mmol) was added and the reaction mixture was stirred at 25° C. for 1.5 hours. Volatiles were removed by concentration under reduced pressure. The residue was dissolved in 2 mL of MeOH and treated with sodium borohydride (2.0 mg, 0.053 mmol). The reaction mixture was allowed to stir for 3 hours at room temperature. Volatiles were removed by concentration under reduced pressure and the residue was poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 0-10% EtOAc/CH$_2$Cl$_2$ to afford 4-(difluoromethyl)-5-(3,5-difluorophenoxy)-2,2-difluoro-3-hydroxy-2,3-dihydrobenzo[b]thiophene 1,1-dioxide (Compound 22) as a thin film (1.7 mg, 8%) and 4-(difluoromethyl)-5-(3,5-difluorophenoxy)-2-fluoro-3-hydroxy-2,3-dihydrobenzo[b]thiophene 1,1-dioxide (Compound 23) as a white solid (3.6 mg, 18%).

Data for 4-(difluoromethyl)-5-(3,5-difluorophenoxy)-2,2-difluoro-3-hydroxy-2,3-dihydrobenzo[b]thiophene 1,1-dioxide (Compound 22): HPLC retention time=2.96 minutes; LCMS ESI (−) (M−H) m/z 397; $^1$H NMR (400 MHz, CDCl$_3$): δ 7.93 (d, 1H), 7.25 (t, 1H), 7.23-7.19 (m, 1H), 6.78 (tt, 1H), 6.68-6.61 (m, 2H), 5.67 (dd, 1H), 3.09 (dd, 1H).

Data for 4-(difluoromethyl)-5-(3,5-difluorophenoxy)-2-fluoro-3-hydroxy-2,3-dihydrobenzo[b]thiophene 1,1-dioxide (Compound 23): HPLC retention time=2.73 minutes;

LCMS ESI (−) (M−H) m/z 379; 1H NMR (400 MHz, CDCl₃): δ 7.89 (d, 1H), 7.29 (t, 1H), 7.19 (d, 1H), 6.74 (tt, 1H), 6.65-6.58 (m, 2H), 5.87-5.80 (m, 1H), 5.66 (dd, 1H), 2.98 (ddd, 1H).

Example 24

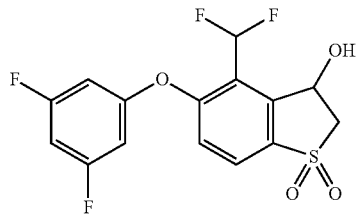 [SMILES: O=S1(=O)CC(O)c2c1ccc(Oc1cc(F)cc(F)c1)c2C(F)F]

4-(Difluoromethyl)-5-(3,5-difluorophenoxy)-3-hydroxy-2,3-dihydrobenzo[b]thiophene 1,1-dioxide (Compound 24)

4-(Difluoromethyl)-5-(3,5-difluorophenoxy)benzo[b]thiophen-3(2H)-one 1,1-dioxide was prepared similarly according to Example 15, Steps A-F, substituting 3,5-difluorophenol for 3-fluoro-5-hydroxy-benzonitrile. Reduction proceeded similarly as described in Example 15. Purification was achieved by chromatography on silica using 20-50% EtOAc/hexane to afford Compound 24 as a beige solid (5.6 mg, 58%). LCMS ESI (+) (M+H) m/z 363; ¹H NMR (400 MHz, CDCl₃): δ 7.85 (d, 1H), 7.25 (t, 1H), 7.16 (dt, 1H), 6.73 (tt, 1H), 6.63-6.56 (m, 1H), 5.90-5.86 (m, 1H), 5.90-5.85 (m, 1H), 3.78 (ddd, 1H), 3.67 (dd, 1H), 2.89 (t, 1H).

Example 25

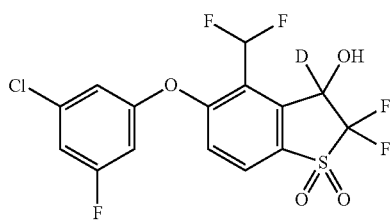 [SMILES: [2H]C1(O)c2c(ccc(Oc3cc(F)cc(Cl)c3)c2C(F)F)S(=O)(=O)C1(F)F]

5-(3-Chloro-5-fluorophenoxy)-4-(difluoromethyl)-2,2-difluoro-3-hydroxy-2,3-dihydrobenzo[b]thiophene 1,1-dioxide-3-d (Compound 25)

A solution of 5-(3-chloro-5-fluoro-phenoxy)-4-(difluoromethyl)-2,2-difluoro-1,1-dioxo-benzothiophen-3-one (40 mg, 0.097 mmol, prepared similarly according to Example 3, Steps A-G) in CD₃OD (1.9 mL) at 0° C. was treated with sodium borodeuteride (4 mg, 0.097 mmol) and stirred at 0° C. for 1 hour. The reaction mixture was quenched by the addition of 0.5 mL of water and 0.25 mL of saturated NH₄Cl. Volatiles were removed by concentration under reduced pressure. The reaction mixture was poured into 10 mL of water and extracted with 3×15 mL EtOAc. The combined organics were rinsed with 10 mL of brine, dried with MgSO₄, filtered, and concentrated to dryness. Purification was achieved by chromatography on silica using 10-30% EtOAc/hexane to give Compound 25 (7.0 mg, 17%). LCMS ESI (−) (M−H) m/z 414, 416; ¹H NMR (400 MHz, CDCl₃): δ 7.95-7.92 (m, 1H), 7.25 (t, 1H), 7.21-7.17 (m, 1H), 7.06 (ddd, 1H), 6.92-6.89 (m, 1H), 6.75 (dt, 1H), 3.07 (d, 1H).

Examples 26 and 27

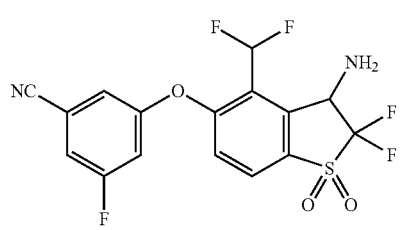

Compound 26

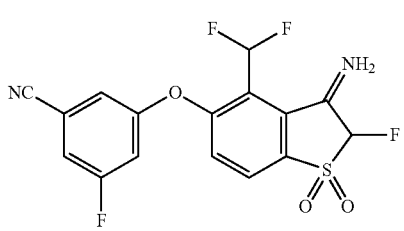

Compound 27

3-((3-Amino-4-(difluoromethyl)-2,2-difluoro-1, 1-dioxido-2,3-dihydrobenzo[b]thiophen-5-yl)oxy)-5-fluorobenzonitrile (Compound 26) and 3-((4-(difluoromethyl)-2-fluoro-3-imino-1,1-dioxido-2,3-dihydrobenzo[b]thiophen-5-yl)oxy)-5-fluorobenzonitrile (Compound 27)

Step A: Preparation of 3-[4-(difluoromethyl)-2,2-difluoro-3-imino-1,1-dioxo-benzothiophen-5-yl]oxy-5-fluoro-benzonitrile: A solution of 3-[3-amino-4-(difluoromethyl)-1,1-dioxo-benzothiophen-5-yl]oxy-5-fluoro-benzonitrile (25.4 mg, 0.07 mmol, prepared similarly according to Example 17, Step A) in acetonitrile (2.8 mL) at 25° C. was treated with sodium carbonate (14.7 mg, 0.14 mmol). The resulting suspension was stirred for 5 minutes. Selectfluor® (49 mg, 0.14 mmol) was added and the reaction mixture left to stir at 25° C. for 1.5 hours. Solution quickly turns from orange to yellow upon Selectfluor® addition. Volatiles were removed by concentration under reduced pressure and the residue was poured into 20 mL of water and extracted with 3×15 mL 30% isopropyl alcohol/CHCl₃. The combined organics were rinsed with 10 mL of brine, dried with MgSO₄, filtered, and concentrated to dryness. The product was used without further purification. LCMS ESI (+) (M+H) m/z 403.

Step B: Preparation of 3-((3-amino-4-(difluoromethyl)-2,2-difluoro-1,1-dioxido-2,3-dihydrobenzo[b]thiophen-5-yl)oxy)-5-fluorobenzonitrile (Compound 26) and 3-((4-(difluoromethyl)-2-fluoro-3-imino-1,1-dioxido-2,3-dihydrobenzo[b]thiophen-5-yl)oxy)-5-fluorobenzonitrile (Compound 27): A solution of 3-[4-(difluoromethyl)-2,2-difluoro-3-imino-1,1-dioxo-benzothiophen-5-yl]oxy-5-fluoro-benzonitrile and 3-((4-(difluoromethyl)-2-fluoro-3-imino-1,1-dioxido-2,3-dihydrobenzo[b]thiophen-5-yl)oxy)-5-fluorobenzonitrile (17.7 mg) in methanol (2.0 mL) at 0° C. was treated with sodium borohydride (1.7 mg, 0.044 mmol) and stirred for 1 hour. The reaction mixture was quenched by the addition of 0.5 mL of water. Volatiles were removed by concentration under reduced pressure. The reaction mixture was poured into 10 mL of water and extracted with 3×15 mL EtOAc. The combined organics were rinsed with 10 mL of brine, dried with MgSO₄, filtered, and concentrated to dryness. Purification was achieved by chromatography on silica using 0-15% EtOAc/CHCl₃ to afford 3-amino-5-(3-chloro-5-fluorophenoxy)-4-(difluoromethyl)-2,2-difluoro-2,3-dihydrobenzo[b]thiophene 1,1-dioxide (Compound 26) as a thin film (5.4 mg, 30%) and 3-((4-(difluoromethyl)-2-fluoro-3-imino-1,1-dioxido-2,3-dihydrobenzo[b]thiophen-5-yl)oxy)-5-fluorobenzonitrile (Compound 27) as a thin film (1.8 mg, 11%).

Data for 3-((3-amino-4-(difluoromethyl)-2,2-difluoro-1,1-dioxido-2,3-dihydrobenzo[b]thiophen-5-yl)oxy)-5-fluorobenzonitrile (Compound 26): HPLC retention time=2.92 minutes; LCMS ESI (+) (M+H) m/z 405; 1H NMR (400 MHz, CDCl₃): δ 7.95 (d, 1H), 7.31-7.27 (m, 1H), 7.30 (dd, 1H), 7.19-7.14 (m, 2H), 7.07 (dt, 1H), 5.00-4.92 (m, 1H), 2.03 (d, 2H).

Data for 3-((4-(difluoromethyl)-2-fluoro-3-imino-1,1-dioxido-2,3-dihydrobenzo[b]thiophen-5-yl)oxy)-5-fluorobenzonitrile (Compound 27): HPLC retention time=2.68 minutes; LCMS ESI (+) (M+H) m/z 385; ¹H NMR (400 MHz, CDCl₃): δ 11.26-11.22 (m, 1H), 8.09 (dd, 1H), 8.06 (d, 1H), 7.04 (d, 1H), 7.27-7.23 (m, 1H), 7.15-7.13 (m, 1H), 7.06 (dt, 1H), 5.87 (dd, 1H).

Example 28

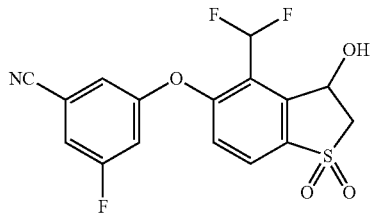 [SMILES: N#Cc1cc(F)cc(Oc2ccc3c(c2C(F)F)C(O)CS3(=O)=O)c1]

3-((4-(Difluoromethyl)-3-hydroxy-1,1-dioxido-2,3-dihydrobenzo[b]thiophen-5-yl)oxy)-5-fluorobenzonitrile (Compound 28)

LCMS ESI (+) (M–H) m/z 370; ¹H NMR (400 MHz, CDCl₃): δ 7.89 (d, 1H), 7.28-7.25 (m, 1H), 7.20 (t, 1H), 7.17-7.13 (m, 2H), 7.04 (dt, 1H), 5.90-5.85 (m, 1H), 3.79 (dd, 1H), 3.69 (dd, 1H), 2.93 (t, 1H).

Example 29

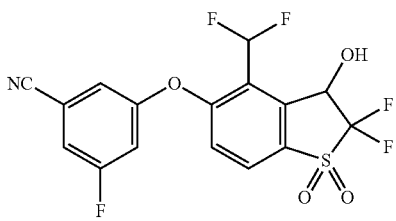 [SMILES: N#Cc1cc(F)cc(Oc2ccc3c(c2C(F)F)C(O)C(F)(F)S3(=O)=O)c1]

3-((4-(Difluoromethyl)-2,2-difluoro-3-hydroxy-1,1-dioxido-2,3-dihydrobenzo[b]thiophen-5-yl)oxy)-5-fluorobenzonitrile (Compound 29)

LCMS ESI (–) (M–H) m/z 404; ¹H NMR (400 MHz, CDCl₃): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H).

Example 30

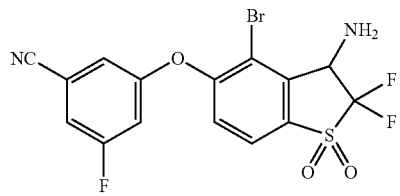 [SMILES: N#Cc1cc(F)cc(Oc2ccc3c(c2Br)C(N)C(F)(F)S3(=O)=O)c1]

3-Amino-4-bromo-5-(3,5-difluorophenoxy)-2,2-difluoro-2,3-dihydrobenzo[b]thiophene 1,1-dioxide (Compound 30)

Step A: Preparation of 2-bromo-3-fluoro-6-iodobenzamide: 2-Bromo-3-fluoro-6-iodobenzoic acid (2.33 g, 6.76 mmol) was dissolved in tetrahydrofuran (20 mL) and cooled to 0° C. The solution was treated with DMF (10 drops) followed by dropwise addition of thionyl chloride (1.0 mL, 10 mmol) then stirred for 10 minutes. The reaction was warmed to ambient temperature and stirred for 2 hours. The mixture was recooled to 0° C. and treated with concentrated ammonium hydroxide (5 mL) and the mixture was allowed to warm to ambient temperature with the bath and stirred overnight. The reaction mixture was concentrated in vacuo, then redissolved in saturated NaHCO₃ and ethyl acetate. The layers were separated and the organic phase was washed with saturated NaHCO₃, saturated NaCl, dried over Na₂SO₄ and concentrated in vacuo to give a white solid (2.2 g, 94%).

Step B: Preparation of 2-bromo-3-fluoro-6-iodobenzonitrile: 2-Bromo-3-fluoro-6-iodobenzamide (10 g, 29 mmol) was suspended in phosphorus oxychloride (41 mL), treated with triethylamine (12.2 mL, 87.2 mmol), then the mixture was heated to 75° C. for 3 hours. The reaction mixture was cooled to ambient temperature with the bath and stirred overnight. The reaction mixture was concentrated in vacuo to remove excess POCl₃, then the semi-dry residue was treated with ice and some water. The resulting mixture was stirred until the ice melted and a beige solid was collected by filtration, washed with water and air-dried (8.04 g, quant.).

Step C: Preparation of S-(3-bromo-2-cyano-4-fluorophenyl) ethanethioate: 2-Bromo-3-fluoro-6-iodobenzonitrile (6.5 g, 20 mmol) and 4,5-bis(diphenylphosphino)-9,9-dimethylxanthene (1.38 g, 2.4 mmol) were suspended in 2:1 toluene/acetone (80 mL). The mixture was sparged with argon, then treated with tris(dibenzylideneacetone)dipalladium (1.0 g, 1.1 mmol) and potassium ethanethioate (2.84 g, 24.9 mmol). The mixture was sealed under argon and heated to 70° C. for 3 hours, then stirred at ambient temperature overnight. The reaction was filtered through celite. The retained solids were washed with methylene chloride and the filtrate was concentrated in vacuo. The crude product was chromatographed on SiO₂ eluting with a gradient of ethyl acetate and hexane to give S-(3-bromo-2-cyano-4-fluorophenyl) ethanethioate as a dark brown solid (4.0 g, 73%). This material was used without further purification.

Step D: Preparation of 2-bromo-3-fluoro-6-(methylthio) benzonitrile: A solution of S-(3-bromo-2-cyano-4-fluorophenyl) ethanethioate (500 mg, 1.8 mmol) in methanol (9.1 mL) at 25° C. was sparged with nitrogen for 3 minutes and then treated with cesium carbonate (594 mg, 1.82 mmol) and stirred at 25° C. until completely dissolved. The reaction mixture was treated with iodomethane (0.15 mL, 2.4 mmol) and stirred for 1 hour. Volatiles were removed by concentration under reduced pressure. The reaction mixture was poured into 20 mL of water and extracted with 3×20 mL EtOAc. The combined organics were rinsed with 10 mL of brine, dried with $MgSO_4$, filtered, and concentrated to dryness. Purification was achieved by chromatography on silica using 5-25% EtOAc/hexane to afford 2-bromo-3-fluoro-6-(methylthio)benzonitrile as a yellow solid (388 mg, 86%).

Step E: Preparation of 2-bromo-3-fluoro-6-(methylsulfonyl)benzonitrile: A solution of 2-bromo-3-fluoro-6-methylsulfanyl-benzonitrile (286 mg, 1.16 mmol) in dichloromethane (11.6 mL) at 25° C. was treated with 3-chloroperbenzoic acid (~70% by wt, 716 mg, 2.9 mmol) and stirred at 25° C. for 6 hours. An additional equivalent of 3-chloroperbenzoic acid (286 mg, 1.16 mmol) was added to drive the reaction to completion. The reaction mixture was poured into 10 mL of 1 N NaOH and extracted with 3×20 mL $CH_2Cl_2$. The combined organics were rinsed with 20 mL of brine, dried with $MgSO_4$, filtered, and concentrated to dryness to obtain a yellow solid. The yellow solid was used without further purification. LCMS ESI (+) (M+$NH_4$) m/z 295, 297.

Step F: Preparation of 3-((4-bromo-2,2-difluoro-3-imino-1,1-dioxido-2,3-dihydrobenzo[b]thiophen-5-yl)oxy)-5-fluorobenzonitrile: 2-Bromo-3-fluoro-6-(methylsulfonyl)benzonitrile was advanced sequentially through a series of steps described previously: Example 3 (step E), Example 17 (step A), and Example 26 (step A).

Step G: Preparation of 3-amino-4-bromo-5-(3,5-difluorophenoxy)-2,2-difluoro-2,3-dihydrobenzo[b]thiophene 1,1-dioxide: Reduction proceeded similarly as described in Example 26, Step B. Purification was achieved by chromatography on silica using 5-30% EtOAc/hexane to afford Compound 30 as a white solid (7.0 mg, 39%). LCMS ESI (+) (M+H) m/z 426, 428; $^1$H NMR (400 MHz, $CDCl_3$): δ 7.78 (d, 1H), 7.18 (d, 1H), 6.72 (tt, 1H), 6.63-6.54 (m, 2H), 4.70 (dt, 1H), 1.92 (d, 2H).

Examples 31 and 32

Compound 31

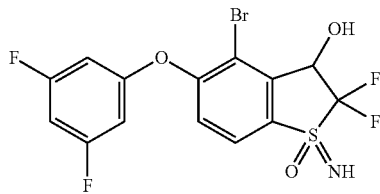

Compound 32

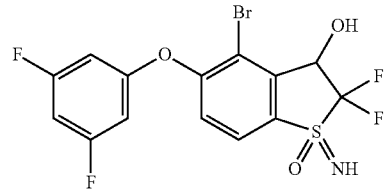

4-Bromo-5-(3,5-difluorophenoxy)-2,2-difluoro-3-hydroxy-1-imino-2,3-dihydro-1H-1$\lambda^4$-benzo[b]thiophene 1-oxide (Compound 31) and 4-bromo-5-(3,5-difluorophenoxy)-2,2-difluoro-3-hydroxy-1-imino-2,3-dihydro-1H-1$\lambda^4$-benzo[b]thiophene 1-oxide (Compound 32)

Step A: Preparation of 2-bromo-3-fluoro-6-(methylsulfinyl)benzonitrile: A solution of 2-bromo-3-fluoro-6-methylsulfanyl-benzonitrile (102 mg, 0.4 mmol) in methanol (10 mL) and water (5 mL) at 25° C. was treated with Oxone® (127.6 mg, 0.21 mmol) and stirred overnight at 25° C. The reaction mixture was concentrated to a thick slurry and poured into 20 mL of water and extracted with 3×20 mL EtOAc. The combined organics were rinsed with 10 mL of brine, dried with $MgSO_4$, filtered, and concentrated to dryness to obtain an off-white solid. The off-white solid was used without further purification. LCMS ESI (+) (M+H) m/z 262, 264.

Step B: Preparation of 2-bromo-3-(3,5-difluorophenoxy)-6-(methylsulfinyl)benzonitrile: A solution of 2-bromo-3-fluoro-6-methylsulfinyl-benzonitrile (335 mg, 1.3 mmol), 3,5-difluorophenol (141 mg, 1.1 mmol), and cesium bicarbonate (211 mg, 1.1 mmol) in N,N-dimethylformamide (6.4 mL) was stirred at 80° C. for 4 hours. The reaction mixture was poured into 60 mL of water and extracted with 3×20 mL $Et_2O$. The combined organics were rinsed with 20 mL of brine, dried with $MgSO_4$, filtered, and concentrated to dryness. Purification was achieved by chromatography on silica using 20-70% EtOAc/hexane to afford a whites solid (259 mg, 54%). LCMS ESI (+) (M+H) m/z 372, 374.

Step C: Preparation of N-((3-bromo-2-cyano-4-(3,5-difluorophenoxy)phenyl)(methyl)(oxo)-$\lambda^6$-sulfanylidene)-2,2,2-trifluoroacetamide: A suspension of 2-bromo-3-(3,5-difluorophenoxy)-6-methylsulfinyl-benzonitrile (259 mg, 0.70 mmol), trifluoroacetamide (157 mg, 1.4 mmol), magnesium oxide (112 mg, 2.8 mmol), and bis(rhodium(α,α,α',α'-tetramethyl-1,3-benezenedipropionic acid)) (21 mg, 0.028 mmol) in dichloromethane (4.6 mL) at 25° C. was treated with (diacetoxyiodo)benzene (336 mg, 1.0 mmol) and stirred at 25° C. Over the course of the reaction, additional portions of all reactants except the sulfoxide were added to help drive the reaction to completion (judged by LCMS). When complete, the reaction mixture was filtered through a pad of celite to remove insolubles ($CH_2Cl_2$ was used to rinse the filtered insolubles). The filtrate was concentrated and purification achieved by chromatography on silica using 10-50% EtOAc/hexane to afford a tan solid (265 mg, 79%). LCMS ESI (+) (M+H) m/z 483, 485.

Step D: Preparation of 4-bromo-5-(3,5-difluorophenoxy)-1-imino-1,2-dihydro-3H-1$\lambda^4$-benzo[b]thiophen-3-one 1-oxide: A solution of N-((3-bromo-2-cyano-4-(3,5-difluorophenoxy)phenyl)(methyl)(oxo)-$\lambda^6$-sulfanylidene)-2,2,2-trifluoroacetamide (265 mg, 0.55 mmol) in tetrahydrofuran (11 mL) at 25° C. was treated with sodium hydride (33 mg, 0.82 mmol). The resulting suspension was stirred for 1 hour. Initially, the reaction was quenched by the addition of 0.5 mL of water followed by 0.2 mL of saturated aqueous NH$_4$Cl. Then volatiles were removed and the resulting residue dissolved in 10 mL of MeOH and 4 mL of 10% aqueous HCl. The resulting mixture was stirred for 3 hours at room temperature. The reaction mixture was concentrated and the residue poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 20-85% EtOAc/hexane to afford a beige solid (55 mg, 26%). LCMS ESI (+) (M+H) m/z 388, 390.

Step E: Preparation of 4-bromo-5-(3,5-difluorophenoxy)-2,2-difluoro-1-imino-1,2-dihydro-3H-1λ$^4$-benzo[b]thiophen-3-one 1-oxide: A solution of 4-bromo-5-(3,5-difluorophenoxy)-1-imino-1,2-dihydro-3H-1λ$^4$-benzo[b]thiophen-3-one 1-oxide (21.6 mg, 0.056 mmol) in acetonitrile (1.1 mL) at 25° C. was treated with sodium carbonate (13 mg, 0.12 mmol) and stirred 5 minutes. Selectfluor® (43 mg, 0.12 mmol) was then added and the reaction mixture left to stir at 25° C. for 4 hours. Volatiles were removed by concentration under reduced pressure and the residue was poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. The product residue was used without further purification. LCMS ESI (+) (M+H) m/z 424, 426.

Step F: Preparation of 4-bromo-5-(3,5-difluorophenoxy)-2,2-difluoro-3-hydroxy-1-imino-2,3-dihydro-1H-1λ$^4$-benzo[b]thiophene 1-oxide (Compound 31) and 4-bromo-5-(3,5-difluorophenoxy)-2,2-difluoro-3-hydroxy-1-imino-2,3-dihydro-1H-1λ$^4$-benzo[b]thiophene 1-oxide (Compound 32): A solution of 4-bromo-5-(3,5-difluorophenoxy)-2,2-difluoro-1-imino-1,2-dihydro-3H-1λ$^4$-benzo[b]thiophen-3-one 1-oxide (23 mg, 0.055 mmol) in methanol (1 mL) at 0° C. was treated with sodium borohydride (2.3 mg, 0.06 mmol) and stirred at 0° C. for 1 hour. The reaction mixture was quenched by the addition of 0.5 mL of water and 0.25 mL of saturated aqueous NH$_4$Cl. Volatiles were removed by concentration under reduced pressure. The reaction mixture was poured into 10 mL water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 15-45% EtOAc/hexane to afford 4-bromo-5-(3,5-difluorophenoxy)-2,2-difluoro-3-hydroxy-1-imino-2,3-dihydro-1H-1λ$^4$-benzo[b]thiophene 1-oxide (Compound 31) as a white solid (4.5 mg, 19%) and 4-bromo-5-(3,5-difluorophenoxy)-2,2-difluoro-3-hydroxy-1-imino-2,3-dihydro-1H-1λ$^4$-benzo[b]thiophene 1-oxide (Compound 32) as a white solid (4.6 mg, 20%).

Data for 4-bromo-5-(3,5-difluorophenoxy)-2,2-difluoro-3-hydroxy-1-imino-2,3-dihydro-1H-1λ$^4$-benzo[b]thiophene 1-oxide (Compound 31): Retention time=2.59 minutes; LCMS ESI (+) (M+H) m/z 426, 428; $^1$H NMR (400 MHz, CDCl$_3$): δ 7.88 (d, 1H), 7.22 (d, 1H), 6.71 (tt, 1H), 6.62-6.55 (m, 2H), 5.31 (dd, 1H), 3.43 (br s, 1H), 3.03 (d, 1H).

Data for 4-bromo-5-(3,5-difluorophenoxy)-2,2-difluoro-3-hydroxy-1-imino-2,3-dihydro-1H-1λ$^4$-benzo[b]thiophene 1-oxide (Compound 32): Retention time=2.69 minutes; LCMS ESI (+) (M+H) m/z 426, 428; 1H NMR (400 MHz, CDCl$_3$): δ 7.81 (d, 1H), 7.22 (d, 1H), 6.70 (tt, 1H), 6.61-6.54 (m, 2H), 5.35 (t, 1H), 3.75 (br s, 1H), 3.27 (d, 1H).

Example 33

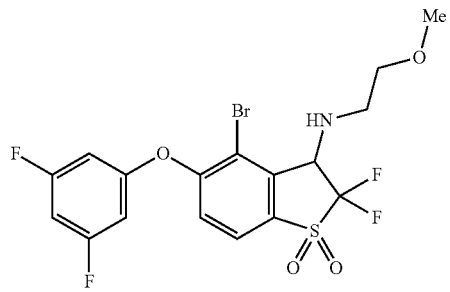 [SMILES: COCCNC1c2c(ccc(Oc3cc(F)cc(F)c3)c2Br)S(=O)(=O)C1(F)F]

4-Bromo-5-(3,5-difluorophenoxy)-2,2-difluoro-3-((2-methoxyethyl)amino)-2,3-dihydrobenzo[b]thiophene 1,1-dioxide (Compound 33)

Step A: Preparation of 4-bromo-5-(3,5-difluorophenoxy)-3-((2-methoxyethyl)amino)benzo[b]thiophene 1,1-dioxide: A solution of 4-bromo-5-(3,5-difluorophenoxy)-1,1-dioxobenzothiophen-3-amine (16.8 mg, 0.043 mmol, prepared similarly according to Example 30) in benzene (1.0 mL) was treated with 2-methoxyethylamine (3.3 mg, 0.043 mmol) and stirred at 95° C. under reflux using Dean-Stark trap for 3 hours. Volatiles were removed by concentration under reduced pressure. The resulting residue was purified by chromatography on silica using 20-50% EtOAc/hexane to afford a tan solid (11 mg, 58%). LCMS ESI (+) (M+H) m/z 446, 448.

Step B: Preparation of 4-bromo-5-(3,5-difluorophenoxy)-2,2-difluoro-3-((2-methoxyethyl)amino)-2,3-dihydrobenzo[b]thiophene 1,1-dioxide: Fluorination proceeded similarly as described in Example 26, Step A. The isolated solid was used without further purification. LCMS ESI (+) (M+H) m/z 482, 484.

Step C: Preparation of 4-bromo-5-(3,5-difluorophenoxy)-2,2-difluoro-3-((2-methoxyethyl)amino)-2,3-dihydrobenzo[b]thiophene 1,1-dioxide: A solution of 4-bromo-5-(3,5-difluorophenoxy)-2,2-difluoro-3-((2-methoxyethyl)amino)-2,3-dihydrobenzo[b]thiophene 1,1-dioxide (12 mg, 0.02 mmol) in methanol (1 mL) at 0° C. was treated with sodium borohydride (0.9 mg, 0.02 mmol) and stirred at 25° C. for 30 minutes. Additional equivalents of sodium borohydride (8 equivalents) were added to drive the reaction to completion. The reaction mixture was quenched by the addition of 0.5 mL of water and 0.25 mL of saturated NH$_4$Cl. Volatiles were removed by concentration under reduced pressure. The resulting mixture was poured into 10 mL water and extracted with 3×15 mL EtOAc. The combined organics were rinsed with 10 mL of brine, dried with MgSO$_4$, filtered, and concentrated to dryness. Purification was achieved by chromatography on silica using 20-35% EtOAc/hexane to afford Compound 33 as a white solid (2.6 mg, 22%). LCMS ESI (+) (M+H) m/z 484, 486; $^1$H NMR (400 MHz, CDCl$_3$): δ 7.75 (d, 1H), 7.16 (d, 1H), 6.71 (tt, 1H), 6.62-6.55 (m, 2H), 4.60 (dd, 1H), 3.55 (t, 2H), 3.35 (s, 3H), 3.21-3.06 (m, 2H), 2.10-2.03 (m, 1H).

Example 34

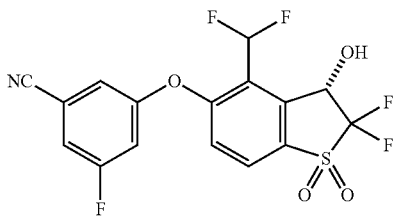 [SMILES: N#Cc1cc(F)cc(Oc2ccc3c(c2C(F)F)[C@H](O)C(F)(F)S3(=O)=O)c1]

(S)-3-((4-(Difluoromethyl)-2,2-difluoro-3-hydroxy-1,1-dioxido-2,3-dihydrobenzo[b]thiophen-5-yl)oxy)-5-fluorobenzonitrile (Compound 34)

Reduction proceeded similarly as described in Example 9. Purification of the racemic mixture was achieved by chromatography on silica using 10-40% EtOAc/hexane to afford racemic 3-((4-(difluoromethyl)-2,2-difluoro-3-hydroxy-1,1-dioxido-2,3-dihydrobenzo[b]thiophen-5-yl)oxy)-5-fluorobenzonitrile as a white solid (8 mg, 73%). Resolution of the enantiomers was achieved using preparative SFC chromatography under the following conditions: ChiralPak AS(—H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 34 was recovered as the second peak (retention time: 1.84 minutes) eluting from the column. LCMS ESI (−) (M−H) m/z 404; $^1$H NMR (400 MHz, CDCl$_3$): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H).

Example 35

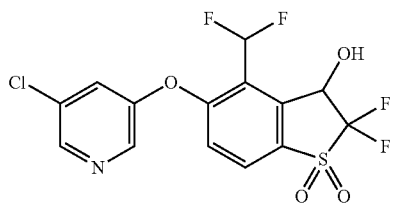 [SMILES: O=S1(=O)c2ccc(Oc3cncc(Cl)c3)c(C(F)F)c2C(O)C1(F)F]

5-((5-Chloropyridin-3-yl)oxy)-4-(difluoromethyl)-2,2-difluoro-3-hydroxy-2,3-dihydrobenzo[b]thiophene 1,1-dioxide (Compound 35)

5-((5-Chloropyridin-3-yl)oxy)-4-(difluoromethyl)-2,2-difluorobenzo[b]thiophen-3(2H)-one 1,1-dioxide was prepared similarly according to Example 3, Steps E-G, substituting 5-chloropyridin-3-ol for 3-fluoro-5-hydroxybenzonitrile. Reduction proceeded similarly as described in Example 9. Purification was achieved by chromatography on silica using 0-50% EtOAc/dichloromethane to afford Compound 35 as a white solid (11 mg, 30%). LCMS ESI (+) (M+H) m/z 398, 400; $^1$H NMR (400 MHz, CDCl$_3$): δ 8.55 (d, 1H), 8.38 (d, 1H), 7.96 (d, 1H), 7.46 (t, 1H), 7.29 (t, 1H), 7.16-7.13 (m, 1H), 5.67 (dd, 1H), 3.24 (dd, 1H).

Example 36

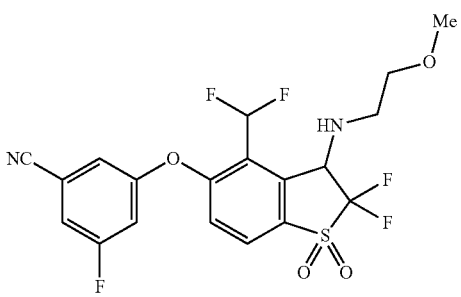 [SMILES: COCCNC1c2c(ccc(Oc3cc(F)cc(C#N)c3)c2C(F)F)S(=O)(=O)C1(F)F]

3-((4-(Difluoromethyl)-2,2-difluoro-3-((2-methoxyethyl)amino)-1,1-dioxido-2,3-dihydrobenzo[b]thiophen-5-yl)oxy)-5-fluorobenzonitrile (Compound 36)

3-((4-(Difluoromethyl)-2,2-difluoro-3-((2-methoxyethyl)imino)-1,1-dioxido-2,3-dihydrobenzo[b]thiophen-5-yl)oxy)-5-fluorobenzonitrile was prepared similarly according to Example 33, Steps A-B. Reduction proceeded similarly as described in Example 33, Step C. Purification was achieved by chromatography on silica using 5-25% EtOAc/hexane to afford Compound 36 as a thin film (5.1 mg, 51%). LCMS ESI (+) (M+H) m/z 463; $^1$H NMR (400 MHz, CDCl$_3$): δ 7.91 (d, 1H), 7.39 (t, 1H), 7.29-7.24 (m, 1H), 7.19-7.14 (m, 2H), 7.05 (dt, 1H), 4.94-4.87 (m, 1H), 3.53 (t, 2H), 3.37 (s, 3H), 3.17-3.07 (m, 2H), 2.28-2.20 (m, 1H).

Example 37

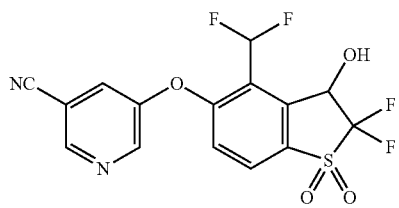 [SMILES: N#Cc1cncc(Oc2ccc3c(c2C(F)F)C(O)C(F)(F)S3(=O)=O)c1]

5-((4-(Difluoromethyl)-2,2-difluoro-3-hydroxy-1,1-dioxido-2,3-dihydrobenzo[b]thiophen-5-yl)oxy)nicotinonitrile (Compound 37)

5-((4-(Difluoromethyl)-2,2-difluoro-1,1-dioxido-3-oxo-2,3-dihydrobenzo[b]thiophen-5-yl)oxy)nicotinonitrile was prepared similarly according to Example 3, Steps E-G, substituting 5-hydroxynicotinonitrile for 3-fluoro-5-hydroxy-benzonitrile. Reduction proceeded similarly as described in Example 9. Purification was achieved by chromatography on silica using 10-50% EtOAc/CHCl$_3$ to afford Compound 37 as a white solid (12 mg, 29%). LCMS ESI (+) (M+H) m/z 389; $^1$H NMR (400 MHz, CD$_3$OD): δ 8.81 (d, 1H), 8.71 (d, 1H), 8.08 (d, 1H), 8.04 (dd, 1H), 7.42 (d, 1H), 7.38 (t, 1H), 5.69 (d, 1H).

Example 38

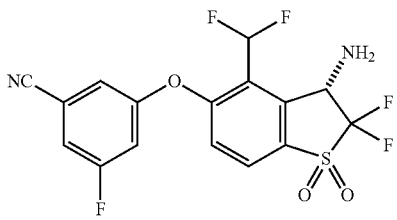 [SMILES: N#Cc1cc(F)cc(Oc2ccc3c(c2C(F)F)[C@H](N)C(F)(F)S3(=O)=O)c1]

(S)-3-((3-Amino-4-(difluoromethyl)-2,2-difluoro-1,1-dioxido-2,3-dihydrobenzo[b]thiophen-5-yl)oxy)-5-fluorobenzonitrile (Compound 38)

Step A: Preparation of (R)—N—((S)-5-(3-cyano-5-fluorophenoxy)-4-(difluoromethyl)-2,2-difluoro-1,1-dioxido-2,3-dihydrobenzo[b]thiophen-3-yl)-2-methylpropane-2-sulfinamide: 3-[4-(Difluoromethyl)-2,2-difluoro-1,1,3-trioxo-benzothiophen-5-yl]oxy-5-fluoro-benzonitrile was prepared previously according to Example 3, Steps A-G. A solution of 3-[4-(difluoromethyl)-2,2-difluoro-1,1,3-trioxo-benzothiophen-5-yl]oxy-5-fluoro-benzonitrile (100 mg, 0.25 mmol) and (R)-2-methylpropane-2-sulfinamide (36 mg, 0.30 mmol) in tetrahydrofuran (2.5 mL) was treated with titanium (IV) ethoxide (105 μL, 0.50 mmol) and heated to 50° C. for 3 hours. The reaction mixture was cooled to 0° C. and treated with sodium triacetoxyborohydride (52.6 mg, 0.25 mmol). After 1 hour an additional portion of sodium triacetoxyborohydride (52.6 mg, 0.25 mmol) was added to drive the reaction to completion. Following an additional 2 hours of reaction, the ice bath was removed and the vigorously stirred reaction mixture was quenched by the addition of 2.5 mL of brine. After 20 minutes, the resulting suspension was filtered through celite and the filter cake washed extensively with EtOAc. The filtrate was poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 10-40% EtOAc/CHCl$_3$ to afford a white solid (62 mg, 49%). LCMS ESI (+) (M+H) m/z 507.

Step B: Preparation of (S)-3-((3-amino-4-(difluoromethyl)-2,2-difluoro-1,1-dioxido-2,3-dihydrobenzo[b]thiophen-5-yl)oxy)-5-fluorobenzonitrile: A solution of (R)—N—((S)-5-(3-cyano-5-fluorophenoxy)-4-(difluoromethyl)-2,2-difluoro-1,1-dioxido-2,3-dihydrobenzo[b]thiophen-3-yl)-2-methylpropane-2-sulfinamide (62 mg, 0.12 mmol) in methanol (1.2 mL) at 25° C. was treated with a solution of 4 M HCl in dioxane (230 μL, 1.22 mmol) and stirred at 25° C. After 2 hours, volatiles were removed by concentration under reduced pressure. The reaction mixture was poured into 10 mL of saturated aqueous NaHCO$_3$ and extracted with 3×10 mL EtOAc. The combined organics were rinsed with 10 mL of brine, dried with MgSO$_4$, filtered, and concentrated to dryness. Purification was achieved by chromatography on silica using 10-35% EtOAc/hexane to afford Compound 38 as a white foam (37 mg, 76%). LCMS ESI (+) (M+H) m/z 405; $^1$H NMR (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.01-4.91 (dd, 1H), 2.06-1.99 (m, 2H).

Example 39

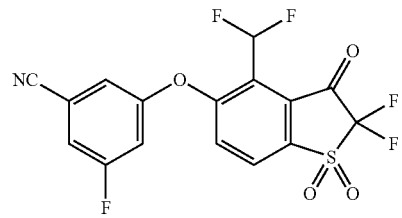 [SMILES: N#Cc1cc(F)cc(Oc2ccc3c(c2C(F)F)C(=O)C(F)(F)S3(=O)=O)c1]

3-((4-(Difluoromethyl)-2,2-difluoro-1,1-dioxido-3-oxo-2,3-dihydrobenzo[b]thiophen-5-yl)oxy)-5-fluorobenzonitrile (Compound 39)

Prepared according to Example 3. Compound 39 exists as a hydrate in (CD$_3$)$_2$SO. $^1$H NMR (400 MHz, (CD$_3$)$_2$SO): δ 8.79 (s, 2H), 8.27 (d, 1H), 7.78-7.73 (m, 1H), 7.72 (t, 1H), 7.55-7.47 (m, 3H).

Example 40

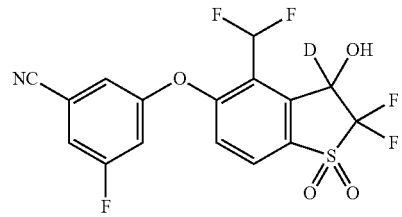 [SMILES: [2H]C1(O)c2c(ccc(Oc3cc(F)cc(C#N)c3)c2C(F)F)S(=O)(=O)C1(F)F]

3-((4-(Difluoromethyl)-2,2-difluoro-3-hydroxy-1,1-dioxido-2,3-dihydrobenzo[b]thiophen-5-yl-3-d)oxy)-5-fluorobenzonitrile (Compound 40)

Prepared similarly as described in Example 25. Purification was achieved by chromatography on silica using 10-40% EtOAc/hexane to afford Compound 40 as a thin film (32 mg, 90%). LCMS ESI (−) (M−H) m/z 405; 1H NMR (400 MHz, CDCl$_3$): δ 7.98 (d, 1H), 7.33-7.30 (m, 1H), 7.23 (t, 1H), 7.22-7.18 (m, 2H), 7.08 (dt, 1H), 3.12 (s, 1H).

Example 41

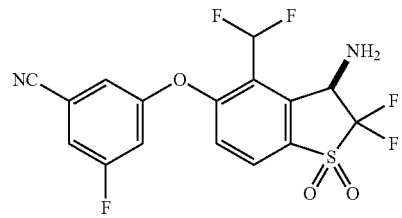 [SMILES: N#Cc1cc(F)cc(Oc2ccc3c(c2C(F)F)[C@@H](N)C(F)(F)S3(=O)=O)c1]

(R)-3-((3-Amino-4-(difluoromethyl)-2,2-difluoro-1,1-dioxido-2,3-dihydrobenzo[b]thiophen-5-yl)oxy)-5-fluorobenzonitrile (Compound 41)

Prepared similarly according to Example 38, substituting (S)-2-methylpropane-2-sulfinamide for (R)-2-methylpropane-2-sulfinamide. Purification was achieved by chromatography on silica using 10-35% EtOAc/hexanes to afford Compound 41 as a white foam (31 mg, 68%). LCMS ESI (+) (M+H) m/z 405; ¹H NMR (400 MHz, CDCl₃): δ 7.94 (d, 1H), 7.30 (d, 1H), 7.31-7.27 (m, 1H), 7.19-7.14 (m, 2H), 7.08 (dt, 1H), 5.02-4.89 (m, 1H), 2.12-1.92 (m, 2H).

Example 42

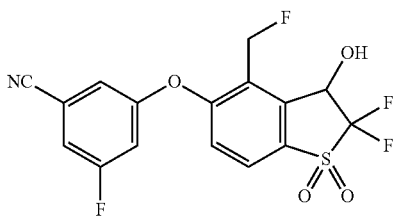 [SMILES: N#Cc1cc(F)cc(Oc2ccc3c(c2CF)C(O)C(F)(F)S3(=O)=O)c1]

3-((2,2-Difluoro-4-(fluoromethyl)-3-hydroxy-1,1-dioxido-2,3-dihydrobenzo[b]thiophen-5-yl)oxy)-5-fluorobenzonitrile (Compound 42)

Step A: Preparation of (2-bromo-3,6-difluorophenyl)methanol: A solution of 2-bromo-3,6-difluoro-benzaldehyde (1 g, 4.5 mmol) in methanol (9.0 mL) at 0° C. was treated with sodium borohydride (205 mg, 5.4 mmol) and stirred at 0° C. for 1 hour. The reaction mixture was quenched by the addition of 2 mL of water and 1 mL of saturated aqueous NH₄Cl. Volatiles were removed by concentration under reduced pressure. The residue was poured into 20 mL of water and extracted with 3×20 mL EtOAc. The combined organics were rinsed with 10 mL of brine, dried with MgSO₄, filtered, and concentrated to dryness. The product was used without further purification. LCMS ESI (+) (M-OH) m/z 205, 207.

Step B: Preparation of 3-((2,2-difluoro-4-(fluoromethyl)-3-hydroxy-1,1-dioxido-2,3-dihydrobenzo[b]thiophen-5-yl)oxy)-5-fluorobenzonitrile: Prepared similarly according to Example 3, Steps A-H, substituting (2-bromo-3,6-difluorophenyl)methanol for 3,6-difluoro-benzaldehyde. Purification was achieved by chromatography on silica using 10-45% EtOAc/hexane to afford Compound 42 as a white solid (7.7 mg, 69%). LCMS ESI (+) (M+NH₄) m/z 405; ¹H NMR (400 MHz, CDCl₃): δ 7.90 (d, 1H), 7.29-7.25 (m, 1H), 7.19 (d, 1H), 7.16-7.14 (m, 1H), 7.06-7.01 (m, 1H), 5.75 (d, 2H), 5.58 (br d, 1H), 3.30-3.22 (m, 1H).

Example 43

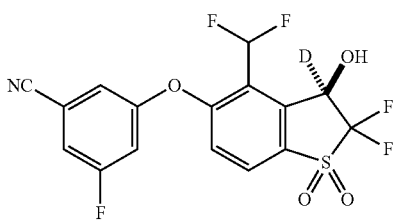 [SMILES: [2H][C@@]1(O)c2c(ccc(Oc3cc(F)cc(C#N)c3)c2C(F)F)S(=O)(=O)C1(F)F]

(R)-3-((4-(Difluoromethyl)-2,2-difluoro-3-hydroxy-1,1-dioxido-2,3-dihydrobenzo[b]thiophen-5-yl-3-d)oxy)-5-fluorobenzonitrile (Compound 43)

A solution of 3-[4-(difluoromethyl)-2,2-difluoro-1,1,3-trioxo-benzothiophen-5-yl]oxy-5-fluoro-benzonitrile (1 g, 2.48 mmol) in dicholoromethane (40 mL) cooled to 0° C. was treated with d-2 formic acid (95% wt in deuterium oxide, 280 µL, 7.44 mmol) and triethylamine (690 µL, 4.96 mmol). The resulting mixture was sparged with nitrogen for 5 minutes. Then, under continuous stream of nitrogen, [N-[(1S,2S)-2-(amino-κN)-1,2-diphenylethyl]-4-methyl-benzenesulfonamidato-κN]chloro[(1,2,3,4,5,6-η)-1,3,5-trimethylbenzene]-ruthenium (15.4 mg, 0.025 mmol, also known as RuCl[(S,S)-Tsdpen](mesitylene)) was added. The reaction vessel was sealed and transferred to a 4° C. refrigerator where the vessel remained for 24 hours. The reaction mixture was poured into 50 mL of water and extracted with 3×20 mL CH₂Cl₂. The combined organics were rinsed with 10 mL of saturated aqueous NaHCO₃, dried with MgSO₄, filtered, and concentrated to dryness. Purification was achieved by chromatography on silica using 10-40% EtOAc/hexane to give Compound 43. Enrichment of the desired enantiomer was achieved by crystallization using the following procedure: The sample was heated in a minimum amount of chloroform until chomogeneous. Upon cooling, solid precipitated. The solid was filtered and the filtrate was concentrated. The process was repeated 2 more times with a realization of about 2 fold improvement in % ee. A starting enantiomeric excess of about 65% was improved to about 94% over 3 crystallizations. Enantiomeric excess was evaluated using ¹⁹F NMR analysis of the corresponding Mosher ester. Compound 43 was isolated as a white solid (300 mg, 30% yield, >95% deuterium incorporation, 94% ee). LCMS ESI (−) (M−H) m/z 405; ¹H NMR (400 MHz, CDCl₃): δ 7.98 (d, 1H), 7.33-7.30 (m, 1H), 7.23 (t, 1H), 7.22-7.18 (m, 2H), 7.08 (dt, 1H), 3.12 (s, 1H).

Example 44

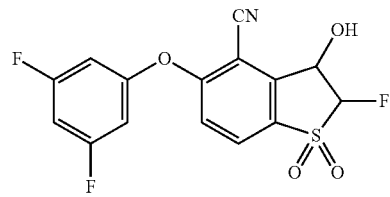 [SMILES: N#Cc1c(Oc2cc(F)cc(F)c2)ccc2c1C(O)C(F)S2(=O)=O]

5-(3,5-Difluorophenoxy)-2-fluoro-3-hydroxy-2,3-dihydrobenzo[b]thiophene-4-carbonitrile 1,1-dioxide (Compound 44)

Step A: Preparation of 4-bromo-5-(3,5-difluorophenoxy)-2-fluorobenzo[b]thiophen-3(2H)-one 1,1-dioxide: A solution of 4-bromo-5-(3,5-difluorophenoxy)-1,1-dioxo-benzothiophen-3-one (200 mg, 0.51 mmol, prepared similarly according to Example 1, Steps A-C) in acetonitrile (12.5 mL) was treated with Selectfluor® (1.14 g, 3.1 mmol) and heated at 120° C. by microwave irradiation for 2.5 hours. The resulting residue was purified by chromatography on silica using 5-20% EtOAc/hexane to afford the title compound as an off-white solid (25 mg, 12%).

Step B: Preparation of 4-bromo-5-(3,5-difluorophenoxy)-2-fluoro-3-hydroxy-2,3-dihydrobenzo[b]thiophene 1,1-dioxide: A solution of 4-bromo-5-(3,5-difluorophenoxy)-2-fluorobenzo[b]thiophen-3(2H)-one 1,1-dioxide (25 mg, 0.06 mmol) in dicholoromethane (6 mL) cooled to 0° C. was treated with formic acid (6.9 µL, 0.18 mmol) and triethylamine (17 µL, 0.12 mmol). The resulting mixture was sparged with nitrogen for 5 minutes. Then, under continuous stream of nitrogen, N-[(1R,2R)-1,2-diphenyl-2-(2-(4-methylbenzyloxy)ethylamino)-ethyl]-4-methylbenzene sulfonamide(chloro)ruthenium(II) (1.0 mg, 0.0015 mmol, also known as RuCl[(R,R)-Ts-DENEB]) was added. The reaction vessel was sealed and transferred to a 4° C. refrigerator where the vessel remained for 24 hours. The reaction mixture was poured into 30 mL of water and extracted with 3×10 mL CH$_2$Cl$_2$. The combined organics were rinsed with 10 mL of saturated aqueous NaHCO$_3$, dried with MgSO$_4$, filtered, and concentrated to dryness. Purification was achieved by chromatography on silica using 10-50% EtOAc/hexane to afford a white solid (18 mg, 72%). LCMS ESI (+) (M+NH$_4$) m/z 426, 428; $^1$H NMR (400 MHz, CD$_3$CN): δ 7.85 (d, 1H), 7.37 (d, 1H), 6.89-6.82 (m, 1H), 6.78-6.70 (m, 2H), 5.79 (dd, 1H), 5.57 (t, 1H), 4.45 (d, 1H).

Step C: Preparation of 5-(3,5-difluorophenoxy)-2-fluoro-3-hydroxy-2,3-dihydrobenzo[b]thiophene-4-carbonitrile 1,1-dioxide (Compound 44): A solution of copper(I) cyanide (2.9 mg, 0.03 mmol) in 1-methyl-2-pyrrolidone (0.5 mL) was treated with 4-bromo-5-(3,5-difluorophenoxy)-2-fluoro-3-hydroxy-2,3-dihydrobenzo[b]thiophene 1,1-dioxide (10 mg, 0.025 mmol) and heated at 160° C. by microwave irradiation for 1 hour and 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-40% EtOAc/hexane to afford Compound 44 as a white solid (5.4 mg, 60%). LCMS ESI (+) (M+NH$_4$) m/z 373; $^1$H NMR (400 MHz, CD$_3$CN): δ 8.02 (d, 1H), 7.27 (d, 1H), 7.01-6.87 (m, 3H), 5.88-5.73 (m, 2H), 4.91 (d, 1H).

Example 45

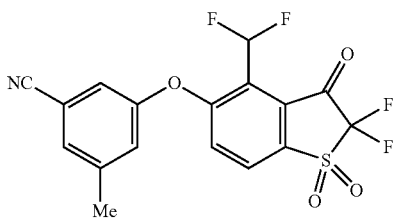 [SMILES: Cc1cc(C#N)cc(Oc2ccc3c(c2C(F)F)C(=O)C(F)(F)S3(=O)=O)c1]

3-((4-(Difluoromethyl)-2,2-difluoro-1,1-dioxido-3-oxo-2,3-dihydrobenzo[b]thiophen-5-yl)oxy)-5-methylbenzonitrile (Compound 45)

Prepared similarly according to Example 3, Steps A-F, substituting 3-hydroxy-5-methylbenzonitrile for 3-fluoro-5-hydroxy-benzonitrile. Purification was achieved by chromatography on silica using 0-15% EtOAc/CH$_2$Cl$_2$ to afford to give Compound 45 as an off-white solid (292 mg, 94%). $^1$H NMR (400 MHz, CDCl$_3$): δ 8.13 (d, 1H), 7.67 (t, 1H), 7.53 (d, 1H), 7.43 (s, 1H), 7.21 (s, 1H), 7.15 (s, 1H), 2.45 (s, 3H).

Example 46

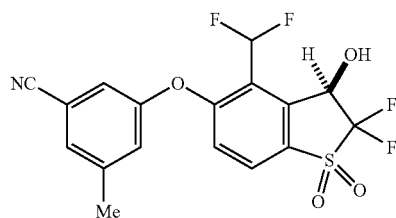 [SMILES: Cc1cc(C#N)cc(Oc2ccc3c(c2C(F)F)[C@@H](O)C(F)(F)S3(=O)=O)c1]

(R)-3-((4-(Difluoromethyl)-2,2-difluoro-3-hydroxy-1,1-dioxido-2,3-dihydrobenzo[b]thiophen-5-yl)oxy)-5-methylbenzonitrile (Compound 46)

A solution of 3-((4-(difluoromethyl)-2,2-difluoro-1,1-dioxido-3-oxo-2,3-dihydrobenzo[b]thiophen-5-yl)oxy)-5-methylbenzonitrile (287 mg, 0.72 mmol) in dicholoromethane (11.4 mL) cooled to 0° C. was treated with formic acid (81 µL, 2.2 mmol) and triethylamine (200 µL, 1.4 mmol). The resulting mixture was sparged with nitrogen for 5 minutes. Then, under continuous stream of nitrogen, [N-[(1S,2S)-2-(amino-κN)-1,2-diphenylethyl]-4-methylbenzenesulfonamidato-κN]chloro[(1,2,3,4,5,6-η)-1,3,5-trimethylbenzene]-ruthenium (9 mg, 0.014 mmol, also known as RuCl[(S,S)-Tsdpen](mesitylene)) was added. The reaction vessel was sealed and transferred to a 4° C. refrigerator where the vessel remained for 24 hours. The reaction mixture was poured into 50 mL of water and extracted with 3×20 mL CH$_2$Cl$_2$. The combined organics were rinsed with 10 mL of saturated aqueous NaHCO$_3$, dried with MgSO$_4$, filtered, and concentrated to dryness. Purification was achieved by chromatography on silica using 10-40% EtOAc/hexane. Enrichment of the desired enantiomer was achieved under crystallization by the following procedure. The sample was heated in a minimum amount of 1:1 hexane/CH$_2$Cl$_2$ solution until homogeneous. Upon cooling, solid precipitated. The solid was filtered and the filtrate concentrated. The process was repeated 2 more times. A starting enantiomeric excess of about 60% was improved to about 90% over 3 crystallizations. Enantiomeric excess was evaluated using $^{19}$F NMR analysis of the corresponding Mosher ester. Compound 46 was isolated as a white solid was isolated (58 mg, 20% yield, 90% ee). LCMS ESI (+) (M+NH$_4$) m/z 419; $^1$H NMR (400 MHz, CDCl$_3$): δ 7.91 (d, 1H), 7.41 (s, 1H), 7.27 (t, 1H), 7.21 (s, 1H), 7.13 (s, 1H), 7.10 (d, 1H), 5.71-5.64 (m, 1H), 3.04 (br d, 1H), 2.44 (s, 3H).

Example 47

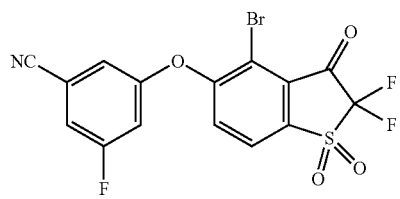 [SMILES: N#Cc1cc(F)cc(Oc2ccc3c(c2Br)C(=O)C(F)(F)S3(=O)=O)c1]

3-((4-Bromo-2,2-difluoro-1,1-dioxido-3-oxo-2,3-dihydrobenzo[b]thiophen-5-yl)oxy)-5-fluorobenzonitrile (Compound 47)

Prepared according to Example 1, Steps A-H, substituting 3-hydroxy-5-methylbenzonitrile for 3-fluoro-5-hydroxybenzonitrile. Purification was achieved by chromatography on silica using 0-10% EtOAc/CH$_2$Cl$_2$ to afford Compound 47 as an off-white solid (292 mg, 94%). LCMS ESI (+) (M+H2O+NH4) m/z 467, 469; $^1$H NMR (400 MHz, CDCl$_3$): δ 8.05 (d, 1H), 7.55 (d, 1H), 7.30 (d, 1H), 7.13 (s, 1H), 7.07-7.02 (m, 1H).

Examples 48 and 49

Compound 48

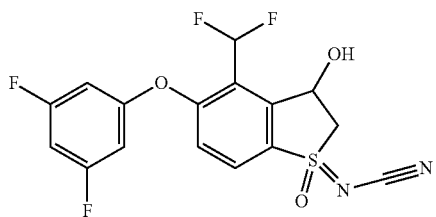

Compound 49

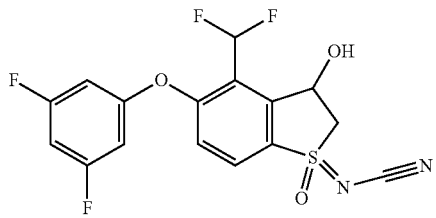

N-(4-(Difluoromethyl)-5-(3,5-difluorophenoxy)-3-hydroxy-1-oxido-2,3-dihydro-1λ$^4$-benzo[b]thiophen-1-ylidene)cyanamide (Compound 48) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 49)

Step A: Preparation of N-((2-cyano-3-(difluoromethyl)-4-fluorophenyl)(methyl)-λ$^4$-sulfanylidene)cyanamide: 2-(Difluoromethyl)-3-fluoro-6-(methylthio)benzonitrile was prepared similarly according to Example 3, Step A-C. (Diacetoxyiodo)benzene (890 mg, 2.76 mmol) was added to an ice-cold suspension of 2-(difluoromethyl)-3-fluoro-6-methylsulfanyl-benzonitrile (500 mg, 2.3 mmol) and cyanamide (126 mg, 3 mmol) in acetonitrile (23 mL). The ice bath was removed and the suspension slowly became a yellow solution. After 3 hours, the reaction mixture was poured into 100 mL of water containing and extracted with 3×30 mL EtOAc. The EtOAc was washed with brine, dried over MgSO$_4$, filtered, and evaporated. Purification was achieved by chromatography on silica using 60-100% EtOAc/hexane to afford a beige solid (360 mg, 61%). LCMS ESI (+) (M+H) m/z 258.

Step B: Preparation of N-((2-cyano-3-(difluoromethyl)-4-fluorophenyl)(methyl)(oxo)-λ$^6$-sulfanylidene)cyanamide: A solution of N-((2-cyano-3-(difluoromethyl)-4-fluorophenyl)(methyl)-λ$^4$-sulfanylidene)cyanamide (360 mg, 1.40 mmol) and ruthenium(III) trichloride (5.8 mg, 0.028 mmol) in a 1:1:2 mixture of CH$_3$CN/CCl$_4$/H$_2$O (26 mL) was treated with sodium periodate (449 mg, 2.1 mmol) and stirred at 25° C. for 30 minutes. The reaction mixture was poured into 100 mL of water and extracted with 3×20 mL EtOAc. The EtOAc was washed with brine, dried over MgSO$_4$, filtered, and evaporated. The product residue was used without further purification. LCMS ESI (+) (M+H) m/z 274.

Step C: Preparation of N-(3-amino-4-(difluoromethyl)-5-(3,5-difluorophenoxy)-1-oxido-1λ$^4$-benzo[b]thiophen-1-ylidene)cyanamide: A solution of N-((2-cyano-3-(difluoromethyl)-4-fluorophenyl)(methyl)(oxo)-λ$^6$-sulfanylidene)cyanamide (390 mg, 1.40 mmol), 3,5-difluorophenol (186 mg, 1.43 mmol), and cesium bicarbonate (830 mg, 4.28 mmol) in N, N-dimethylformamide (3.6 mL) was stirred at 50° C. overnight. The reaction mixture was quenched by diluting with 40 mL of water and extracting with 6×15 mL Et$_2$O. The combined organics were rinsed with 10 mL of brine, dried with MgSO$_4$, filtered, and concentrated to dryness. The crude product was used without further purification. LCMS ESI (+) (M+H) m/z 384.

Step D: Preparation of N-(4-(difluoromethyl)-5-(3,5-difluorophenoxy)-1-oxido-3-oxo-2,3-dihydro-1λ$^4$-benzo[b]thiophen-1-ylidene)cyanamide: A solution of N-(3-amino-4-(difluoromethyl)-5-(3,5-difluorophenoxy)-1-oxido-1λ$^4$-benzo[b]thiophen-1-ylidene)cyanamide (347 mg, 0.91 mmol) in methanol (7 mL) at 25° C. was treated with 1 M aqueous HCl (2.72 mL, 2.72 mmol). The resulting mixture was stirred at 40° C. for 1 hour. Volatiles were removed by concentration under reduced pressure and the residue poured into 30 mL of water and extracted with 3×15 mL 30% isopropyl alcohol/CHCl$_3$. The combined organics were rinsed with 10 mL of brine, dried with MgSO$_4$, filtered, and concentrated to dryness. The product residue was used without further purification. LCMS ESI (+) (M+H) m/z 385.

Step E: Preparation of N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 48) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 49): A solution of N-(4-(difluoromethyl)-5-(3,5-difluorophenoxy)-1-oxido-3-oxo-2,3-dihydro-1λ$^4$-benzo[b]thiophen-1-ylidene)cyanamide (60 mg, 0.16 mmol) in methanol (1.6 mL) at 0° C. was treated with sodium borohydride (5.9 mg, 0.16 mmol) and stirred at 0° C. for 30 minutes. The reaction mixture was quenched by the addition of 0.5 mL of water and 0.25 mL of saturated aqueous NH$_4$Cl. Volatiles were removed by concentration under reduced pressure. The reaction mixture was poured into 10 mL water and extracted with 3×10 mL 30% isopropyl alcohol/CHCl$_3$. The combined organics were rinsed with 10 mL of brine, dried with MgSO$_4$, filtered, and concentrated to dryness. Purification was achieved by chromatography on silica using 10-40% EtOAc/CHCl$_3$ to afford N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 48) as a thin film (1.1 mg, 1.8%) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 49) as a thin film (0.9 mg, 1.5%).

Data for N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 48): HPLC retention time=2.62 minutes; LCMS ESI (+) (M+H) m/z 387; $^1$H NMR (400 MHz, CDCl$_3$): δ 8.01 (d, 1H), 7.28 (t, 1H), 7.21

(d, 1H), 6.83-6.76 (m, 1H), 6.69-6.63 (m, 2H), 6.03-5.97 (m, 1H), 4.20 (dd, 1H), 3.88 (dd, 1H), 3.15-3.11 (m, 1H).

Data for N-(4-(difluoromethyl)-5-(3,5-difluorophenoxy)-3-hydroxy-1-oxido-2,3-dihydro-1λ⁴-benzo[b]thiophen-1-ylidene)cyanamide (Compound 49): HPLC retention time=2.56 minutes; LCMS ESI (+) (M+H) m/z 387; ¹H NMR (400 MHz, CDCl₃): δ 7.97 (d, 1H), 7.26 (t, 1H), 7.21 (d, 1H), 6.83-6.76 (m, 1H), 6.70-6.63 (m, 2H), 5.99 (t, 1H), 4.08-4.02 (m, 1H), 3.98 (dd, 1H), 3.20-3.15 (m, 1H).

Example 50

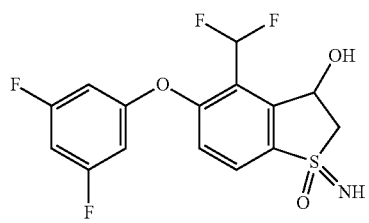 [SMILES: N=S1(=O)CC(O)c2c1ccc(Oc1cc(F)cc(F)c1)c2C(F)F]

4-(Difluoromethyl)-5-(3,5-difluorophenoxy)-3-hydroxy-1-imino-2,3-dihydro-1H-1λ⁴-benzo[b]thiophene 1-oxide (Compound 50)

Step A: Preparation of 4-(difluoromethyl)-5-(3,5-difluorophenoxy)-1-imino-1,2-dihydro-3H-1λ⁴-benzo[b]thiophen-3-one 1-oxide: A solution of N-(4-(difluoromethyl)-5-(3,5-difluorophenoxy)-1-oxido-3-oxo-2,3-dihydro-1λ⁴-benzo[b]thiophen-1-ylidene)cyanamide (80 mg, 0.21 mmol) in 1,4-dioxane (1.3 mL) was treated with aqueous concentrated HCl (0.6 mL, 7.2 mmol) and heated to 120° C. by microwave irradiation for 30 minutes. Volatiles were removed by concentration under reduced pressure. The reaction mixture was poured into 10 mL of water and extracted with 3×20 mL EtOAc. The combined organics were rinsed with 10 mL of brine, dried with MgSO₄, filtered, and concentrated to dryness. Purification was achieved by chromatography on silica using 20-60% EtOAc/hexane to afford an off-white solid (35.4 mg, 48%).

Step B: Preparation of 4-(difluoromethyl)-5-(3,5-difluorophenoxy)-3-hydroxy-1-imino-2,3-dihydro-1H-1λ⁴-benzo[b]thiophene 1-oxide: A solution of 4-(difluoromethyl)-5-(3,5-difluorophenoxy)-1-imino-1-oxo-benzothiophen-3-one (35 mg, 0.1 mmol) in methanol (2 mL) at 0° C. was treated with sodium borohydride (3.7 mg, 0.1 mmol) and stirred at 0° C. for 30 minutes. The reaction was quenched by the addition of 0.5 mL of water and 0.25 mL saturated aqueous NH₄Cl. Volatiles were removed by concentration under reduced pressure. The reaction mixture was poured into 10 mL of water and extracted with 3×10 mL 30% isopropyl alcohol/CHCl₃. The combined organics were rinsed with 10 mL of brine, dried with MgSO₄, filtered, and concentrated to dryness. Purification was achieved by chromatography on silica using 0-4% MeOH/CHCl₃ (6.8 mg, 19%). HPLC retention time=2.27 minutes; LCMS ESI (+) (M+H) m/z 362; ¹H NMR (400 MHz, CDCl³): δ 7.80 (d, 1H), 7.17 (t, 1H), 7.12 (d, 1H), 6.74-6.67 (m, 1H), 6.62-6.55 (m, 2H), 5.80-5.74 (m, 1H), 3.80 (dd, 1H), 3.75-3.69 (m, 2H), 3.41-3.34 (m, 1H).

Example 51

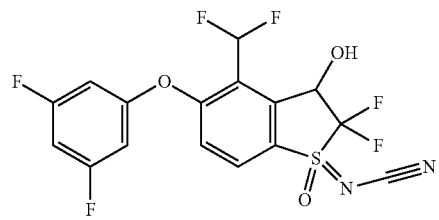 [SMILES: N#CN=S1(=O)c2ccc(Oc3cc(F)cc(F)c3)c(C(F)F)c2C(O)C1(F)F]

N-(4-(Difluoromethyl)-5-(3,5-difluorophenoxy)-2,2-difluoro-3-hydroxy-1-oxido-2,3-dihydro-1λ⁴-benzo[b]thiophen-1-ylidene)cyanamide (Compound 51)

Step A: Preparation of 4-(difluoromethyl)-5-(3,5-difluorophenoxy)-2,2-difluoro-1-imino-1,2-dihydro-3H-1λ⁴-benzo[b]thiophen-3-one 1-oxide: A solution of N-(4-(difluoromethyl)-5-(3,5-difluorophenoxy)-1-oxido-3-oxo-2,3-dihydro-1λ⁴-benzo[b]thiophen-1-ylidene)cyanamide (54 mg, 0.14 mmol) in acetonitrile (1.4 mL) at 25° C. was treated with sodium carbonate (32.7 mg, 0.31 mmol). Selectfluor® (109 mg, 0.31 mmol) was added and the reaction mixture left to stir at 25° C. for 1.5 hours. Volatiles were removed by concentration under reduced pressure and the residue was poured into 30 mL of water and extracted with 3×20 mL EtOAc. The combined organics were rinsed with 10 mL of brine, dried with MgSO₄, filtered, and concentrated to dryness. Purification was achieved by chromatography on silica using 0%-4% MeOH/CHCl₃ to afford an off-white solid (16 mg, 27%). LCMS ESI (+) (M+H) m/z 421.

Step B: Preparation of N-(4-(difluoromethyl)-5-(3,5-difluorophenoxy)-2,2-difluoro-3-hydroxy-1-oxido-2,3-dihydro-1λ⁴-benzo[b]thiophen-1-ylidene)cyanamide: A solution of [4-(difluoromethyl)-5-(3,5-difluorophenoxy)-2,2-difluoro-1,3-dioxo-benzothiophen-1-ylidene]cyanamide (16.1 mg, 0.038 mmol) in tetrahydrofuran (1.5 mL) at 25° C. was treated with sodium triacetoxyborohydride (12.2 mg, 0.058 mmol) and stirred at 25° C. for 1 hour. Volatiles were removed by concentration under reduced pressure. The reaction mixture was poured into 10 mL of water and extracted with 3×10 mL EtOAc. The combined organics were rinsed with 10 mL of brine, dried with MgSO₄, filtered, and concentrated to dryness. Purification was achieved by chromatography on silica using 0-20% EtOAc/CHCl₃ to afford Compound 51 as a white solid (6.9 mg, 43%). HPLC retention time=2.90 minutes; LCMS ESI (+) (M+H) m/z 423; ¹H NMR (400 MHz, CDCl₃): δ 8.07-8.00 (m, 1H), 7.42-7.13 (m, 2H), 6.87-6.80 (m, 1H), 6.73-6.66 (m, 2H), 5.83-5.76 (m, 1H), 3.78-3.66 (m, 1H).

Examples 52 and 53

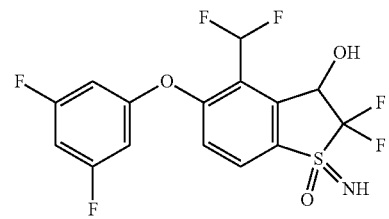

Compound 52

Compound 53

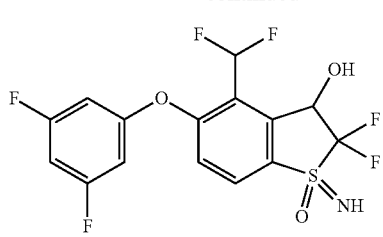

4-(Difluoromethyl)-5-(3,5-difluorophenoxy)-2,2-difluoro-3-hydroxy-1-imino-2,3-dihydro-1H-1λ⁴-benzo[b]thiophene 1-oxide (Compound 52) and 4-(Difluoromethyl)-5-(3,5-difluorophenoxy)-2,2-difluoro-3-hydroxy-1-imino-2,3-dihydro-1H-1λ⁴-benzo[b]thiophene 1-oxide (Compound 53)

Step A: Preparation of 4-(difluoromethyl)-5-(3,5-difluorophenoxy)-2,2-difluoro-1-imino-1,2-dihydro-3H-1λ⁴-benzo[b]thiophen-3-one 1-oxide: A solution of 4-(difluoromethyl)-5-(3,5-difluorophenoxy)-1-imino-1-oxo-benzothiophen-3-one (22.7 mg, 0.063 mmol) in acetonitrile (1.3 mL) at 25° C. was treated with sodium carbonate (14.7 mg, 0.14 mmol). Selectfluor® (49 mg, 0.14 mmol) was added and the reaction mixture left to stir at 25° C. for 1.5 hour. Volatiles were removed by concentration under reduced pressure and the residue was poured into 30 mL of water and extracted with 3×20 mL EtOAc. The combined organics were rinsed with 10 mL of brine, dried with MgSO₄, filtered, and concentrated to dryness. The product was used without further purification. LCMS ESI (−) (M−H) m/z 394.

Step B: Preparation of 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 52) and 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 53): A solution of 4-(difluoromethyl)-5-(3,5-difluorophenoxy)-2,2-difluoro-1-imino-1,2-dihydro-3H-1λ⁴-benzo[b]thiophen-3-one 1-oxide (27.3 mg, 0.069 mmol) in methanol (1.4 mL) at 0° C. was treated with sodium borohydride (2.9 mg, 0.076 mmol) and stirred at 0° C. for 30 minutes. The reaction mixture was quenched by the addition of 0.25 mL of saturated aqueous NH₄Cl and 0.5 mL of water. Volatiles were removed by concentration under reduced pressure. The reaction mixture was poured into 20 mL of water and extracted with 3×15 mL EtOAc. The combined organics were rinsed with 10 mL of brine, dried with MgSO₄, filtered, and concentrated to dryness. Purification was achieved by chromatography on silica using 15-20% EtOAc/CHCl₃ to afford 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 52) as a white solid (2.7 mg, 10%) and 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 53) as a white solid (1.7 mg, 6.2%).

Data for 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 52): Retention time=2.54 minutes; LCMS ESI (+) (M+H) m/z 398; ¹H NMR (400 MHz, CDCl₃): δ 8.02 (d, 1H), 7.22 (t, 1H), 7.19 (d, 1H), 6.79-6.72 (m, 1H), 6.66-6.59 (m, 2H), 5.60 (t, 1H), 3.39 (br s, 1H), 3.12 (d, 1H).

Data for 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 53): Retention time=2.65 minutes; LCMS ESI (+) (M+H) m/z 398; ¹H NMR (400 MHz, CDCl₃): δ 7.95 (d, 1H), 7.23 (t, 1H), 7.19 (d, 1H), 6.79-6.72 (m, 1H), 6.66-6.59 (m, 2H), 5.64 (t, 1H), 3.68 (br s, 1H), 3.33 (d, 1H).

Example 54

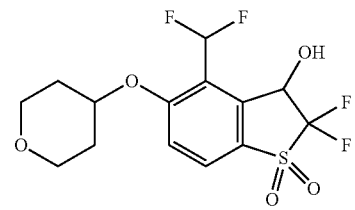 [SMILES: O=S1(=O)c2ccc(OC3CCOCC3)c(C(F)F)c2C(O)C1(F)F]

4-(Difluoromethyl)-2,2-difluoro-3-hydroxy-5-((tetrahydro-2H-pyran-4-yl)oxy)-2,3-dihydrobenzo[b]thiophene 1,1-dioxide (Compound 54)

Step A: Preparation of 2-(difluoromethyl)-6-(methylthio)-3-((tetrahydro-2H-pyran-4-yl)oxy)benzonitrile: A solution of tetrahydro-4-pyranol (160 μL, 1.66 mmol) in dimethyl sulfoxide (3.7 mL) at 25° C. was treated with sodium hydride, 60% dispersion in mineral oil (60.8 mg, 1.52 mmol) and stirred at 25° C. for 2 hours. 2-(Difluoromethyl)-3-fluoro-6-methylsulfanyl-benzonitrile (300 mg, 1.38 mmol) was added directly to the opaque solution of the alkoxide. After 2.5 hours, the reaction mixture was poured into 30 mL of water and extracted with 3×15 mL EtOAc. The combined organics were rinsed with 10 mL of brine, dried with MgSO₄, filtered, and concentrated to dryness. Purification was achieved by chromatography on silica using 30-80% EtOAc/hexane to afford a white solid (253 mg, 61%). LCMS ESI (+) (M+H) m/z 300.

Step B: Preparation of 2-(difluoromethyl)-6-(methylsulfonyl)-3-((tetrahydro-2H-pyran-4-yl)oxy)benzonitrile: A solution of 2-(difluoromethyl)-6-(methylthio)-3-((tetrahydro-2H-pyran-4-yl)oxy)benzonitrile (175 mg, 0.58 mmol) in dichloromethane (5.8 mL) at 25° C. was treated with 3-chloroperbenzoic acid (~70% by wt, 346 mg, 1.4 mmol) and stirred at 25° C. for 2 hours. The reaction mixture was poured into 20 mL of 1 M NaOH and extracted with 3×20 mL CH₂Cl₂. The combined organics were rinsed with 20 mL of brine, dried with MgSO₄, filtered, and concentrated to dryness. The resulting white solid was used without further purification. LCMS ESI (+) (M+NH₄) m/z 349.

Step C: Preparation of 4-(difluoromethyl)-5-((tetrahydro-2H-pyran-4-yl)oxy)benzo[b]thiophen-3(2H)-one 1,1-dioxide: A solution of 2-(difluoromethyl)-6-(methylsulfonyl)-3-((tetrahydro-2H-pyran-4-yl)oxy)benzonitrile (193 mg, 0.58 mmol) in tetrahydrofuran (12 mL) at 25° C. was treated with sodium hydride (35 mg, 0.87 mmol) and stirred at 25° C. for 2 hours. The reaction mixture was treated with 12 mL of a 3:1 mixture of MeOH/10% aqueous HCl. The resulting mixture was stirred for 1 hour and then the volatile portion was removed by concentration under reduced pressure. The reaction mixture was extracted with 3×20 mL EtOAc. The combined organics were rinsed with 10 mL of brine, dried with MgSO₄, filtered, and concentrated to dryness. Purification was achieved by chromatography on silica using 30-70% EtOAc/hexane to afford a white solid (48 mg, 25%). LCMS ESI (+) (M+H) m/z 333.

Step D: Preparation of 4-(difluoromethyl)-2,2-difluoro-5-((tetrahydro-2H-pyran-4-yl)oxy)benzo[b]thiophen-3(2H)-one 1,1-dioxide: A solution of 4-(difluoromethyl)-5-((tetrahydro-2H-pyran-4-yl)oxy)benzo[b]thiophen-3(2H)-one 1,1-dioxide (48 mg, 0.14 mmol) in acetonitrile (2.9 mL) at 25° C. was treated with sodium carbonate (33.7 mg, 0.32 mmol). Selectfluor® (113 mg, 0.32 mmol) was added and the reaction mixture left to stir at 25° C. for 1.5 hours. Volatiles were removed by concentration under reduced pressure and the residue was poured into 30 mL of water and extracted with 3×20 mL EtOAc. The combined organics were rinsed with 10 mL of brine, dried with MgSO$_4$, filtered, and concentrated to dryness. The product was used without further purification. LCMS ESI (+) (M+H) m/z 369.

Step E: Preparation of 4-(difluoromethyl)-2,2-difluoro-3-hydroxy-5-((tetrahydro-2H-pyran-4-yl)oxy)-2,3-dihydrobenzo[b]thiophene 1,1-dioxide: A solution of 4-(difluoromethyl)-2,2-difluoro-5-((tetrahydro-2H-pyran-4-yl)oxy)benzo[b]thiophen-3(2H)-one 1,1-dioxide (50 mg, 0.14 mmol) in methanol (2.8 mL) at 0° C. was treated with sodium borohydride (5.1 mg, 0.14 mmol) and stirred at 0° C. for 30 minutes. The reaction mixture was quenched by the addition of 0.5 mL of saturated aqueous NH$_4$Cl and 1.0 mL of water. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 30-80% EtOAc/hexane to afford Compound 54 as a white solid (12 mg, 23%). LCMS ESI (+) (M+H) m/z 387; $^1$H NMR (400 MHz, CD$_3$OD): δ 7.99 (d, 1H), 7.57 (d, 1H), 7.26 (t, 1H), 5.57-5.52 (m, 1H), 4.95-4.88 (m, 1H), 3.98-3.91 (m, 2H), 3.67-3.60 (m, 2H), 2.32-2.03 (m, 2H), 1.86-1.76 (m, 2H).

Example 55

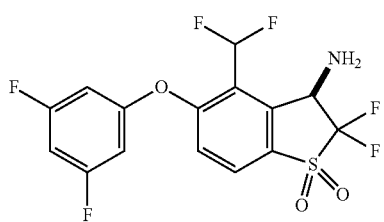 [SMILES: N[C@@H]1c2c(ccc(Oc3cc(F)cc(F)c3)c2C(F)F)S(=O)(=O)C1(F)F]

(R)-3-Amino-4-(difluoromethyl)-5-(3,5-difluorophenoxy)-2,2-difluoro-2,3-dihydrobenzo[b]thiophene 1,1-dioxide (Compound 55)

Prepared similarly according to Example 41. Purification was achieved by chromatography on silica using 5-25% EtOAc/hexane to afford Compound 55 as a white solid (44.1 mg, 86%). LCMS ESI (+) (M+H) m/z 398; $^1$H NMR (400 MHz, CDCl$_3$): δ 7.90 (d, 1H), 7.29 (t, 1H), 7.16 (d, 1H), 6.76 (tt, 1H), 6.67-6.60 (m, 2H), 5.02-4.93 (m, 1H), 2.01 (br d, 2H).

Example 56

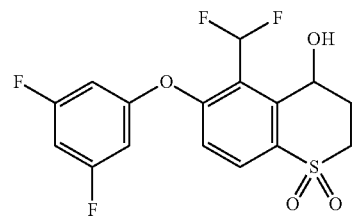 [SMILES: O=S1(=O)CCC(O)c2c1ccc(Oc1cc(F)cc(F)c1)c2C(F)F]

5-(Difluoromethyl)-6-(3,5-difluorophenoxy)-4-hydroxythiochromane 1,1-dioxide (Compound 56)

Step A: Preparation of 6-(benzylthio)-2-(difluoromethyl)-3-fluorobenzonitrile: A solution of 2-(difluoromethyl)-3,6-difluoro-benzonitrile (1.5 g, 7.93 mmol) in acetonitrile (40 mL, previously sparged with nitrogen for 5 minutes) at −40° C. was treated with sodium phenylmethanethiolate (1.16 g, 7.9 mmol) in 2 portions over 10 minutes. The resulting suspension was stirred initially at −40° C. and then allowed to slowly warm towards room temperature (the reaction remained immersed in the acetone bath during this time). The reaction was quenched when the temperature reached 10° C. The reaction mixture was poured into 300 mL of water and extracted with 3×100 mL Et$_2$O. The combined organics were rinsed with 20 mL of brine, dried with MgSO$_4$, filtered, and concentrated to dryness. Purification was achieved using reverse phase chromatography (Biotage Isolera One unit, C18 Flash 40+M column, 40-95% CH$_3$CN/water) to afford an off-white solid (650 mg, 28%). LCMS ESI (−) (M−H) m/z 293.

Step B: Preparation of 6-(benzylthio)-2-(difluoromethyl)-3-(3,5-difluorophenoxy)benzonitrile: A solution of 6-(benzylthio)-2-(difluoromethyl)-3-fluorobenzonitrile (800 mg, 2.73 mmol) and cesium hydrogen carbonate (582 mg, 3.0 mmol) in N,N-dimethylformamide (6.8 mL) was treated with 3,5-difluorophenol (355 mg, 2.73 mmol) and stirred at 100° C. for 2 hours. The reaction mixture was poured into 70 mL of water and extracted with 3×30 mL Et$_2$O. The combined organics were rinsed with 10 mL of brine, dried with MgSO$_4$, filtered, and concentrated to dryness. The product residue was used without further purification. LCMS ESI (+) (M+NH$_4$) m/z 421.

Step C: Preparation of 6-(benzylthio)-2-(difluoromethyl)-3-(3,5-difluorophenoxy)benzaldehyde: A solution of 6-(benzylthio)-2-(difluoromethyl)-3-(3,5-difluorophenoxy)benzonitrile (550 mg, 1.36 mmol) in dichloromethane (9 mL) at 0° C. was treated with diisobutylalumane (~1.0 M in heptane, 2.05 mL, 2.05 mmol) and stirred at 0° C. for 1 hour. Additional diisobutylalumane (600 μL, ~1.0 M in heptane) was added. After stirring for an additional 30 minutes, the reaction mixture was quenched by the addition of 8.5 mL of 10% aqueous HCl. The resulting mixture was stirred vigorously for 1 hour. Then the sample was treated with 8.5 mL of 20% aqueous potassium sodium tartrate and stirred vigorously an additional hour. The reaction mixture was basified with 10% aqueous NaOH. The reaction mixture was extracted with 3×20 mL CH$_2$Cl$_2$. The combined organics were rinsed with 20 mL of brine, dried with MgSO$_4$, filtered, and concentrated to dryness. The product residue was used without further purification. LCMS ESI (−) (M−H) m/z 405.

Step D: Preparation of 1-(6-(benzylthio)-2-(difluoromethyl)-3-(3,5-difluorophenoxy)phenyl)prop-2-en-1-ol: A solution of 6-(benzylthio)-2-(difluoromethyl)-3-(3,5-difluorophenoxy)benzaldehyde (91 mg, 0.22 mmol) in tetrahydrofuran (2.2 mL) at 0° C. was treated with vinylmagnesium bromide (~1.0 M in tetrahydrofuran, 220 µL, 0.22 mmol) and stirred at 0° C. for 30 minutes. The reaction was quenched by the addition of 10 mL of saturated aqueous NH₄Cl. The reaction mixture warmed to room temperature and was then poured into 10 mL of water and extracted with 3×15 mL EtOAc. The combined organics were rinsed with 10 mL of brine, dried with MgSO₄, filtered, and concentrated to dryness. Purification was achieved by chromatography on silica using 30-70% CH₂Cl₂/hexane to afford a yellow solid (83 mg, 85%). LCMS ESI (−) (M−H) m/z 433.

Step E: Preparation of 1-(6-(benzylthio)-2-(difluoromethyl)-3-(3,5-difluorophenoxy)phenyl)prop-2-en-1-one: A solution of 1-(6-(benzylthio)-2-(difluoromethyl)-3-(3,5-difluorophenoxy)phenyl)prop-2-en-1-ol (83 mg, 0.19 mmol) in dichloromethane (1.9 mL) at 25° C. was treated with Dess-Martin periodinane (101 mg, 0.24 mmol) and stirred at 25° C. for 3 hours. The reaction mixture was diluted with water (2 mL) and treated with sodium thiosulfate pentahydrate (130 mg, 0.53 mmol). The resulting mixture was stirred for 30 minutes and was then poured into 20 mL of water and extracted with 3×10 mL CH₂Cl₂. The combined organics were rinsed with 10 mL of brine, dried with MgSO₄, filtered, and concentrated to dryness. The product residue was used without further purification. LCMS ESI (+) (M+H) m/z 433.

Step F: Preparation of 5-(difluoromethyl)-6-(3,5-difluorophenoxy)thiochroman-4-one: A vigorously stirred solution of 1-(6-(benzylthio)-2-(difluoromethyl)-3-(3,5-difluorophenoxy)phenyl)prop-2-en-1-one (21 mg, 0.05 mmol) in benzene (0.5 mL) at 25° C. was treated with aluminum chloride (10.8 mg, 0.08 mmol). After 1 hour, the reaction was quenched by the addition of ice chips. The reaction mixture was then diluted with 10 mL of CH₂Cl₂, poured into 10 mL of 1 M HCl and extracted with 3×10 mL CH₂Cl₂. The combined organics were rinsed with 10 mL of brine, dried with MgSO₄, filtered, and concentrated to dryness. Purification was achieved by chromatography on silica using 5-25% EtOAc/hexane to afford a thin film (3.3 mg, 20%). LCMS ESI (−) (M−H) m/z 341.

Step G: Preparation of 5-(difluoromethyl)-6-(3,5-difluorophenoxy)thiochroman-4-ol: A solution of 5-(difluoromethyl)-6-(3,5-difluorophenoxy)thiochroman-4-one (3.3 mg, 0.01 mmol) in methanol (1 mL) at 25° C. was treated with sodium borohydride (0.36 mg, 0.01 mmol) and stirred at 25° C. for 1 hour. The reaction mixture was quenched by the addition of 0.25 mL of saturated NH₄Cl. Volatiles were removed by concentration under reduced pressure. The reaction mixture was poured into 10 mL of water and extracted with 3×10 mL EtOAc. The combined organics were rinsed with 10 mL of brine, dried with MgSO₄, filtered, and concentrated to dryness. The intermediate product residue was dissolved in dichloromethane (1 mL) and treated with 3-chloroperbenzoic acid (~70% by wt, 5.9 mg, 0.024 mmol). The reaction mixture stirred at 25° C. for 1.5 hours and was then poured into 10 mL of 1:1 mixture of 1 M NaOH and 20% Na₂S₂O₃ and extracted with 3×10 mL CH₂Cl₂. The combined organics were rinsed with 10 mL of brine, dried with MgSO4, filtered, and concentrated to dryness. Purification was achieved by chromatography on silica using 25-75% EtOAc/hexane to afford Compound 56 as a white solid (2.2 mg, 60%). LCMS ESI (+) (M+NH₄) m/z 394; ¹H NMR (400 MHz, CDCl₃): δ 8.08 (d, 1H), 7.31 (t, 1H), 7.10 (d, 1H), 6.71 (tt, 1H), 6.61-6.54 (m, 2H), 5.52-5.48 (m, 1H), 4.05 (td, 1H), 3.32 (ddd, 1H), 2.84-2.74 (m, 1H), 2.73-2.64 (m, 2H).

Example 57

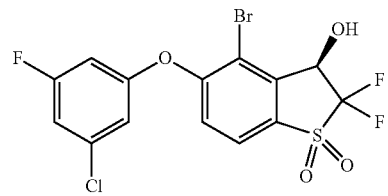 [SMILES: O=S1(=O)c2ccc(Oc3cc(F)cc(Cl)c3)c(Br)c2[C@@H](O)C1(F)F]

(3R)-4-Bromo-5-(3-chloro-5-fluoro-phenoxy)-2,2-difluoro-1,1-dioxo-3H-benzothiophen-3-ol (Compound 57)

Step A: Preparation of 4-bromo-5-(3-chloro-5-fluoro-phenoxy)-2,2-difluoro-1,1-dioxo-benzothiophen-3-one: Sodium carbonate (130 mg, 1.23 mmol) was added all at once to 4-bromo-5-(3-chloro-5-fluoro-phenoxy)-1,1-dioxo-benzothiophen-3-one (226 mg, 0.56 mmol) in acetonitrile (6 mL) at room temperature under nitrogen and stirred for 45 minutes. Selectfluor® (434 mg, 1.23 mmol) was then added all at once. The resulting mixture was stirred for an additional 1 hour, concentrated to dryness in vacuo, diluted with water (20 mL), and extracted with ethyl acetate (3×25 mL). The organic layer was washed with brine (20 mL), dried over MgSO₄, filtered, and concentrated in vacuo. The crude product was purified on silica gel (10 g SNAP, 14 CV, 10-60% ethyl acetate/hexane) affording 4-bromo-5-(3-chloro-5-fluoro-phenoxy)-2,2-difluoro-1,1-dioxo-benzothiophen-3-one (196 mg, 0.44 mmol, 80% yield) as a white solid.

Step B: Preparation of (3R)-4-bromo-5-(3-chloro-5-fluoro-phenoxy)-2,2-difluoro-1,1-dioxo-3H-benzothiophen-3-ol (Compound 57): Chloro{[(1S,2S)-(+)-2-amino-1,2-diphenylethyl](4-toluenesulfonyl)amido}(p-cymene)ruthenium(II) (RuCl(p-cymene)[(S,S)-Ts-DPEN], 0.5 mg, 0.0008 mmol) was added all at once to a degassed mixture of 4-bromo-5-(3-chloro-5-fluoro-phenoxy)-2,2-difluoro-1,1-dioxo-benzothiophen-3-one (16 mg, 0.04 mmol), triethylamine (6 µL, 0.04 mmol) and formic acid (2 µL, 0.05 mmol) in dichloromethane (350 µL) at room temperature in a reaction vial equipped with a stir bar under a stream of nitrogen. The reaction vial was then tightly sealed with a teflon lined cap and stirred for 2 hours. The reaction mixture was purified directly on silica gel (10 g SNAP, 14 CV, 5-60% EtOAc/hexane) affording (3R)-4-bromo-5-(3-chloro-5-fluoro-phenoxy)-2,2-difluoro-1,1-dioxo-3H-benzothiophen-3-ol (12 mg, 0.03 mmol, 77% yield) as a clear oil. LCMS ESI (−) m/z 441, 443, 445 (M−H); ¹H NMR (CDCl₃, 400 MHz) δ: 7.80 (d, 1H), 7.22 (d, 1H), 7.02-7.00 (m, 1H), 6.87-6.86 (m, 1H), 6.72 (dt, 1H), 5.38 (d, 1H).

Example 58

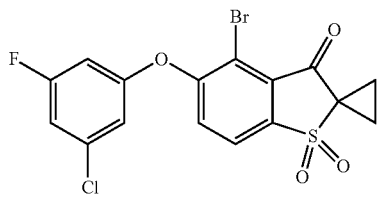 [SMILES: O=C1c2c(ccc(Oc3cc(F)cc(Cl)c3)c2Br)S(=O)(=O)C12CC2]

4-Bromo-5-(3-chloro-5-fluoro-phenoxy)-1,1-dioxo-spiro[benzothiophene-2,1'-cyclopropane]-3-one (Compound 58)

1,2-Dibromoethane (13 µL, 0.15 mmol) was added to 4-bromo-5-(3-chloro-5-fluoro-phenoxy)-1, 1-dioxo-benzothiophen-3-one (40 mg, 0.10 mmol) and potassium carbonate (41 mg, 0.30 mmol) in N,N-dimethylformamide (1.0 mL) at room temperature. The reaction mixture was stirred overnight in a sealed reaction vial and then warmed to 50° C. for additional 24 hours. After cooling to room temperature, the reaction mixture was diluted with water (5 mL), and extracted with diethyl ether (4×5 mL). The organic layer was washed with water (3×5 mL), brine (10 mL), dried over MgSO$_4$, filtered and concentrated in vacuo. The residue was purified on silica gel (10 g SNAP, 14 CV, 10-100% ethyl acetate/hexane) affording 4-bromo-5-(3-chloro-5-fluoro-phenoxy)-1,1-dioxo-spiro[benzothiophene-2,1'-cyclopropane]-3-one (6 mg, 0.015 mmol, 15% yield). LCMS ESI (−) m/z 475, 477, 479 (M+HCO2-); $^1$H NMR (CDCl$_3$, 400 MHz) δ: 8.00 (d, 1H), 7.46 (d, 1H), 6.99-6.96 (m, 1H), 6.81-6.80 (m, 1H), 6.67 (dt, 1H), 2.08-2.04 (m, 2H), 1.96-1.93 (m, 2H).

Example 59

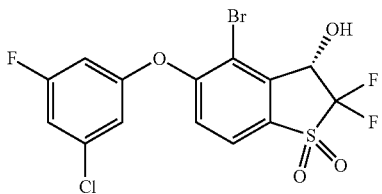

(3S)-4-Bromo-5-(3-chloro-5-fluoro-phenoxy)-2,2-difluoro-1,1-dioxo-3H-benzothiophen-3-ol (Compound 59)

An ice cold solution of N-[(1S,2S)-1,2-diphenyl-2-(2-(4-methylbenzyloxy)ethylamino)-ethyl]-4-methylbenzene sulfonamide(chloro)ruthenium(II) ((S,S)-Ts-DENEB™, 0.8 mg, 0.001 mmol) in dichloromethane (0.3 mL) was added dropwise to an ice cold solution of 4-bromo-5-(3-chloro-5-fluoro-phenoxy)-2,2-difluoro-1,1-dioxo-benzothiophen-3-one (26 mg, 0.06 mmol), triethylamine (16 µL, 0.12 mmol) and formic acid (7 µL, 0.18 mmol) under nitrogen. The reaction vial was then placed in a 4° C. fridge for 18 hours. The reaction mixture was purified directly on silica gel (10 g SNAP, 14 CV, 5-60% ethyl acetate/hexane) affording Compound 59 (21 mg, 0.047 mmol, 80% yield). The e.e. was determined to be 83% by $^{19}$F NMR analysis of the corresponding Mosher ester. LCMS ESI (−) m/z 441, 443, 445 (M−H); $^1$H NMR (CDCl$_3$, 400 MHz): δ 7.80 (d, 1H), 7.22 (d, 1H), 7.02-7.00 (m, 1H), 6.87-6.86 (m, 1H), 6.72 (dt, 1H), 5.38 (d, 1H).

Example 60

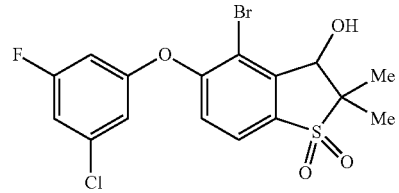 [SMILES: CC1(C)C(O)c2c(ccc(Oc3cc(F)cc(Cl)c3)c2Br)S1(=O)=O]

4-Bromo-5-(3-chloro-5-fluoro-phenoxy)-2,2-dimethyl-1,1-dioxo-3H-benzothiophen-3-ol (Compound 60)

Step A: Preparation of 4-bromo-5-(3-chloro-5-fluoro-phenoxy)-2,2-dimethyl-1,1-dioxo-benzothiophen-3-one: Iodomethane (31 µL, 0.49 mmol) was added all at once to 4-bromo-5-(3-chloro-5-fluoro-phenoxy)-1,1-dioxo-benzothiophen-3-one (40 mg, 0.10 mmol) and potassium carbonate (41 mg, 0.30 mmol) in N,N-dimethylformamide (1.0 mL) at room temperature and then stirred for 2 hours. The reaction mixture was diluted with water (5 mL), and extracted with ethyl acetate (3×10 mL). The organic layer was washed with brine (10 mL), dried over MgSO$_4$, filtered and concentrated in vacuo. The crude product was used directly in the next reaction without purification. LCMS ESI (+) m/z 433, 435, 437 (M+H).

Step B: Preparation of 4-bromo-5-(3-chloro-5-fluoro-phenoxy)-2,2-dimethyl-1,1-dioxo-3H-benzothiophen-3-ol (Compound 60): Sodium borohydride (4 mg, 0.10 mmol) was added all at once to 4-bromo-5-(3-chloro-5-fluoro-phenoxy)-2,2-dimethyl-1,1-dioxo-benzothiophen-3-one (43 mg, 0.10 mmol) in methanol (2.0 mL) at room temperature and stirred for 10 minutes. The reaction was quenched with saturated ammonium chloride (2 mL) and extracted with ethyl acetate (3×5 mL). The organic layer was washed with brine (5 mL), dried over MgSO$_4$, filtered and concentrated in vacuo. The residue was purified on silica gel (10 g SNAP, 14 CV, 5-45% ethyl acetate/hexane) affording 4-bromo-5-(3-chloro-5-fluoro-phenoxy)-2,2-dimethyl-1,1-dioxo-3H-benzothiophen-3-ol (20 mg, 0.046 mmol, 47% yield over 2 steps). LCMS ESI (−) m/z 479, 481, 483 (M+HCO$_2^-$); $^1$H NMR (CDCl$_3$, 400 MHz): δ 7.73 (dd, 1H), 7.16 (d, 1H), 6.98-6.95 (m, 1H), 6.83-6.82 (m, 1H), 6.66 (dt, 1H), 1.65 (s, 3H), 1.40 (s, 3H).

Example 61

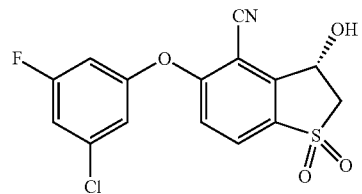 [SMILES: N#Cc1c(Oc2cc(F)cc(Cl)c2)ccc2c1[C@H](O)CS2(=O)=O]

(3S)-5-(3-Chloro-5-fluoro-phenoxy)-3-hydroxy-1,1-dioxo-2,3-dihydrobenzothiophene-4-carbonitrile (Compound 61)

Copper(I) cyanide (11 mg, 0.12 mmol) was added all at once to a solution of (3S)-4-bromo-5-(3-chloro-5-fluoro-phenoxy)-1,1-dioxo-2,3-dihydrobenzothiophen-3-ol (32 mg, 0.08 mmol) in 1-methyl-2-pyrrolidone (0.4 mL), then warmed to 160° C. in a sealed microwave vial by microwave irradiation. The reaction mixture was purified directly on reverse phase silica gel (12+M, 14 CV, 20-100% acetonitrile/water) affording (3S)-5-(3-chloro-5-fluoro-phenoxy)-3-hydroxy-1,1-dioxo-2,3-dihydrobenzothiophene-4-carbonitrile (23 mg, 0.064 mmol, 81% yield). The e.e. was determined to be 83% by $^{19}$F NMR analysis of the corresponding Mosher ester. LCMS ESI (−) m/z 352, 354 (M−H); $^{1}$H NMR (CDCl$_3$, 400 MHz): δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H).

Example 62

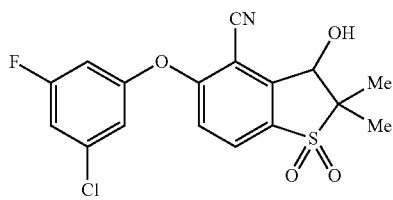 [SMILES: CC1(C)C(O)c2c(ccc(Oc3cc(F)cc(Cl)c3)c2C#N)S1(=O)=O]

5-(3-Chloro-5-fluoro-phenoxy)-3-hydroxy-2,2-dimethyl-1,1-dioxo-3H-benzothiophene-4-carbonitrile (Compound 62)

To copper (I) cyanide (5 mg, 0.05 mmol) in a microwave reaction vial equipped with a stir bar was added a solution of 4-bromo-5-(3-chloro-5-fluoro-phenoxy)-2,2-dimethyl-1,1-dioxo-3H-benzothiophen-3-ol (17 mg, 0.04 mmol) in 1-methyl-2-pyrrolidone (0.25 mL). The reaction vial was sealed with a crimp cap and warmed to 160° C. under microwave irradiation for 75 minutes. The reaction mixture was purified directly on reverse phase silica gel (12+M, 14 CV, 20-100% acetonitrile/water) affording 5-(3-chloro-5-fluoro-phenoxy)-3-hydroxy-2,2-dimethyl-1,1-dioxo-3H-benzothiophene-4-carbonitrile (10 mg, 0.026 mmol, 67% yield). LCMS ESI (−) m/z 380, 382 (M−H); $^{1}$H NMR (CDCl$_3$, 400 MHz): δ 7.91 (d, 1H), 7.10-7.06 (m, 2H), 6.97-6.96 (m, 1H), 6.81 (dt, 1H), 1.55 (s, 3H), 1.49 (s, 3H).

Example 63

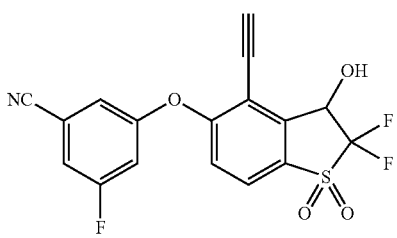 [SMILES: C#Cc1c(Oc2cc(F)cc(C#N)c2)ccc2c1C(O)C(F)(F)S2(=O)=O]

3-((4-Ethynyl-2,2-difluoro-3-hydroxy-1,1-dioxido-2,3-dihydrobenzo[b]thiophen-5-yl)oxy)-5-fluorobenzonitrile (Compound 63)

Step A: Preparation of methyl 3-(3-cyano-5-fluoro-phenoxy)-6-methylsulfonyl-2-(2-trimethylsilylethynyl)benzoate: A mixture of methyl 2-bromo-3-(3-cyano-5-fluoro-phenoxy)-6-methylsulfonyl-benzoate (500 mg, 1.2 mmol), trimethylsilyl acetylene (1.7 mL, 11.7 mmol), bis(triphenylphosphine)palladium(II) dichloride (164 mg, 0.23 mmol), N, N-diisopropylethylamine (0.6 mL, 3.5 mmol) and CuI (89 mg, 0.47 mmol) in a sealed tube under argon was heated at 95° C. overnight. After cooling to room temperature, the reaction mixture was concentrated under reduced pressure. The residue was purified by flash column chromatography with EtOAc/hexane (0% to 50%) to give methyl 3-(3-cyano-5-fluoro-phenoxy)-6-methylsulfonyl-2-(2-trimethylsilylethynyl)benzoate (186 mg, 0.42 mmol, 36% yield). LCMS ESI (+) m/z 446 (M+H), 463 (M+NH$_4$).

Step B: Preparation of 3-(4-ethynyl-1,1,3-trioxo-benzothiophen-5-yl)oxy-5-fluoro-benzonitrile: To a solution of methyl 3-(3-cyano-5-fluoro-phenoxy)-6-methylsulfonyl-2-(2-trimethylsilylethynyl)benzoate (176 mg, 0.4 mmol) in tetrahydrofuran (10 mL) at room temperature was added tetrabutylammonium fluoride (1 M in tetrahydrofuran, 0.5 mL). The reaction was stirred at room temperature for 10 minutes. Additional tetrabutylammonium fluoride (1 M in tetrahydrofuran, 0.3 mL) was added. The reaction mixture was stirred at room temperature for 40 minutes, then diluted with EtOAc, washed with saturated NaHCO$_3$ and brine, dried over MgSO$_4$, filtered, and concentrated. The residue was purified by flash column chromatography with EtOAc/hexane (0% to 60%) to give 3-(4-ethynyl-1,1,3-trioxo-benzothiophen-5-yl)oxy-5-fluoro-benzonitrile (46 mg, 0.13 mmol, 34% yield). LCMS ESI (+) m/z 391 (M+NH$_4$).

Step C: Preparation of 3-(4-ethynyl-2,2-difluoro-1,1,3-trioxo-benzothiophen-5-yl)oxy-5-fluoro-benzonitrile: To a solution of 3-(4-ethynyl-1,1,3-trioxo-benzothiophen-5-yl)oxy-5-fluoro-benzonitrile (12 mg, 0.04 mmol) in acetonitrile (4 mL) at room temperature was added sodium carbonate (12 mg, 0.11 mmol) and Selectfluor® (38 mg, 0.11 mmol). The reaction mixture was stirred at room temperature for 40 minutes. Additional Selectfluor (38 mg, 0.1 mmol) was added and stirring was continued at room temperature for additional 40 minutes. The reaction mixture was concentrated under reduced pressure, diluted with EtOAc, washed with saturated NaHCO$_3$ and brine, dried over MgSO$_4$, filtered, and concentrated. The crude product was used in the next step without further purification. LCMS ESI (+) m/z 395 (M+NH$_4$).

Step D: Preparation of 3-((4-ethynyl-2,2-difluoro-3-hydroxy-1,1-dioxido-2,3-dihydrobenzo[b]thiophen-5-yl)oxy)-5-fluorobenzonitrile (Compound 63): To a solution of 3-(4-ethynyl-2,2-difluoro-1,1,3-trioxo-benzothiophen-5-yl)oxy-5-fluoro-benzonitrile (7 mg, 0.02 mmol) in tetrahydrofuran (2.5 mL) at room temperature was added sodium triacetoxyborohydride (12 mg, 0.06 mmol). The reaction was stirred at room temperature for 1 hour. Additional sodium triacetoxyborohydride (12 mg, 0.06 mmol) was added. The reaction mixture was stirred for additional 1 hour and directly purified by preparative TLC with EtOAc/hexane (35%) to give Compound 63 (6 mg, 0.02 mmol, 85% yield). LCMS ESI (+) m/z 397 (M+NH$_4$); $^{1}$H NMR (400 MHz, CDCl$_3$): δ 7.85 (d, 1H), 7.27-7.23 (m, 2H), 7.15 (s, 1H), 7.04 (d, 1H), 5.46 (dd, 1H), 3.69 (s, 1H), 3.13 (d, 1H).

Example 64

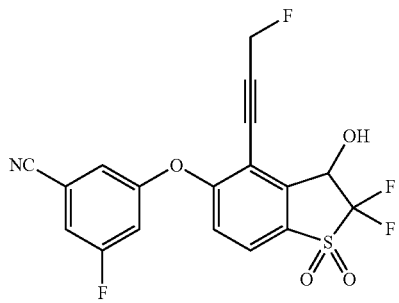 [SMILES: N#Cc1cc(F)cc(Oc2ccc3c(c2C#CCF)C(O)C(F)(F)S3(=O)=O)c1]

3-[[2,2-Difluoro-4-(3-fluoroprop-1-ynyl)-3-hydroxy-1,1-dioxo-3H-benzothiophen-5-yl]oxy]-5-fluoro-benzonitrile (Compound 64)

Step A: Preparation of 3-(3-cyano-5-fluoro-phenoxy)-2-(3-hydroxyprop-1-ynyl)-6-methylsulfonyl-benzoate: A mixture of methyl 2-bromo-3-(3-cyano-5-fluoro-phenoxy)-6-methylsulfonyl-benzoate (650 mg, 1.52 mmol), propargyl alcohol (0.18 mL, 3.0 mmol), bis(triphenylphosphine)palladium(II) dichloride (53 mg, 0.08 mmol), N, N-diisopropylethylamine (0.8 mL, 4.6 mmol) and CuI (29 mg, 0.15 mmol) in a sealed tube under argon was heated at 90° C. overnight. After cooling to room temperature, the mixture was concentrated under reduced pressure. Dichloromethane was added and the resulting suspension was filtered. The filtrate was concentrated and the residue was purified by flash column chromatography with EtOAc/hexane (0% to 80%) to give methyl 3-(3-cyano-5-fluoro-phenoxy)-2-(3-hydroxyprop-1-ynyl)-6-methylsulfonyl-benzoate (130 mg, 0.32 mmol, 21% yield). LCMS ESI (+) m/z 421 (M+NH$_4$).

Step B: Preparation of methyl 3-(3-cyano-5-fluoro-phenoxy)-2-(3-fluoroprop-1-ynyl)-6-methylsulfonyl-benzoate: To a solution of methyl 3-(3-cyano-5-fluoro-phenoxy)-2-(3-hydroxyprop-1-ynyl)-6-methylsulfonyl-benzoate (18 mg, 0.04 mmol) in dichloromethane (1 mL) at room temperature was added diethylaminosulfur trifluoride (0.01 mL, 0.09 mmol). The reaction mixture was stirred at room temperature for 1.5 hours and directly purified by preparative TLC to give methyl 3-(3-cyano-5-fluoro-phenoxy)-2-(3-fluoroprop-1-ynyl)-6-methylsulfonyl-benzoate (14 mg, 0.03 mmol, 77% yield). LCMS ESI (+) m/z 423 (M+NH$_4$).

Step C: Preparation of 3-fluoro-5-[4-(3-fluoroprop-1-ynyl)-1,1,3-trioxo-benzothiophen-5-yl]oxy-benzonitrile: To a solution of methyl 3-(3-cyano-5-fluoro-phenoxy)-2-(3-fluoroprop-1-ynyl)-6-methylsulfonyl-benzoate (14 mg, 0.03 mmol) in THF (3 mL) was added sodium hydride (10 mg, 0.25 mmol). The reaction was stirred at room temperature for 2 hours and 15 minutes. The reaction mixture was poured into ice cold 1:1 brine and 10% citric acid, and extracted with EtOAc. The organic layer was dried over MgSO$_4$, filtered, and concentrated. The residue was purified by preparative TLC (50% EtOAc/hexane) to give 3-fluoro-5-[4-(3-fluoroprop-1-ynyl)-1,1,3-trioxo-benzothiophen-5-yl]oxy-benzonitrile (11 mg, 0.03 mmol, 85% yield). LCMS ESI (−) m/z 372 (M−H).

Step D: Preparation of 3-[2,2-difluoro-4-(3-fluoroprop-1-ynyl)-1,1,3-trioxo-benzothiophen-5-yl]oxy-5-fluoro-benzonitrile: To a mixture of 3-fluoro-5-[4-(3-fluoroprop-1-ynyl)-1,1,3-trioxo-benzothiophen-5-yl]oxy-benzonitrile (11 mg, 0.03 mmol), sodium carbonate (12 mg, 0.12 mmol), and Selectfluor® (63 mg, 0.18 mmol) was added acetonitrile (2 mL). The reaction was stirred at room temperature for 1.5 hours and directly purified by preparative TLC with EtOAc/hexane (50%) to give 3-[2,2-difluoro-4-(3-fluoroprop-1-ynyl)-1,1,3-trioxo-benzothiophen-5-yl]oxy-5-fluoro-benzonitrile (6 mg, 0.015 mmol, 50% yield).

Step E: Preparation of 3-[[2,2-difluoro-4-(3-fluoroprop-1-ynyl)-3-hydroxy-1,1-dioxo-3H-benzothiophen-5-yl]oxy]-5-fluoro-benzonitrile (Compound 64): To a solution of 3-[2,2-difluoro-4-(3-fluoroprop-1-ynyl)-1,1,3-trioxo-benzothiophen-5-yl]oxy-5-fluoro-benzonitrile (6 mg, 0.01 mmol) in THF (1 mL) was added sodium triacetoxyborohydride (10 mg, 0.05 mmol). The reaction mixture was stirred at room temperature for 2 hours and then directly purified by preparative TLC with 60% EtOAc/hexane to give Compound 64 (4.4 mg, 0.01 mmol, 73% yield). LCMS ESI (−) m/z 410 (M−H); $^1$H NMR (400 MHz, CDCl$_3$): δ 7.85 (d, 1H), 7.28-7.25 (m, 1H), 7.23 (d, 1H), 7.16-7.14 (m, 1H), 7.05 (dt, 1H), 5.43 (d, 1H), 5.19 (d, 2H), 3.27 (s, 1H).

Example 65

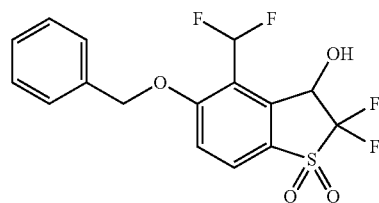 [SMILES: O=S1(=O)c2ccc(OCc3ccccc3)c(C(F)F)c2C(O)C1(F)F]

5-Benzyloxy-4-(difluoromethyl)-2,2-difluoro-1,1-dioxo-3H-benzothiophen-3-ol (Compound 65)

Step A: Preparation of 3-benzyloxy-2-(difluoromethyl)-6-methylsulfonyl-benzonitrile: To a solution of phenylmethanol (0.04 mL, 0.4 mmol) in tetrahydrofuran (4 mL) at room temperature was added sodium hydride (8 mg, 60%, 0.2 mmol). After stirring at room temperature for 15 minutes, (difluoromethyl)-3-fluoro-6-methylsulfonyl-benzonitrile (50 mg, 0.2 mmol) was added. The reaction mixture was stirred at room temperature overnight and purified directly by preparative TLC with EtOAc/hexane (40%) followed by flash column chromatography with EtOAc/hexane (20% to 80%) to give 3-benzyloxy-2-(difluoromethyl)-6-methylsulfonyl-benzonitrile (28 mg, 0.083 mmol, 41% yield). LCMS ESI (+) m/z 355 (M+NH$_4$).

Step B: Preparation of 5-benzyloxy-4-(difluoromethyl)-1,1-dioxo-benzothiophen-3-one: To a solution of 3-benzyloxy-2-(difluoromethyl)-6-methylsulfonyl-benzonitrile (27 mg, 0.08 mmol) in tetrahydrofuran (3 mL) at room temperature was added sodium hydride (25 mg, 60%, 0.6 mmol). The reaction was stirred at room temperature overnight. Aqueous KHSO$_4$ (10%, 10 mL) was added. The reaction mixture was stirred at room temperature for 30 minutes and extracted with EtOAc. The organic layer was dried over MgSO$_4$, filtered, and concentrated. The residue was purified by flash column chromatography with EtOAc/hexane (40%) to give 5-benzyloxy-4-(difluoromethyl)-1,1-dioxo-benzothiophen-3-one (6 mg, 0.018 mmol, 22% yield). LCMS ESI (+) m/z 356 (M+NH$_4$).

Step C: Preparation of 5-benzyloxy-4-(difluoromethyl)-2,2-difluoro-1,1-dioxo-benzothiophen-3-one: A mixture of 5-benzyloxy-4-(difluoromethyl)-1,1-dioxo-benzothiophen-3-one (6 mg, 0.02 mmol), Selectfluor® (38 mg, 0.11 mmol) and sodium carbonate (8 mg, 0.08 mmol) in acetonitrile (3 mL) was stirred at room temperature for 4 hours. The reaction mixture was purified directly by preparative TLC to give 5-benzyloxy-4-(difluoromethyl)-2,2-difluoro-1,1-dioxo-benzothiophen-3-one (4 mg, 0.01 mmol, 60% yield). LCMS ESI (+) m/z 410 (M+H$_2$O+NH$_4$).

Step D: Preparation of 5-benzyloxy-4-(difluoromethyl)-2,2-difluoro-1,1-dioxo-3H-benzothiophen-3-ol: To a solution of 5-benzyloxy-4-(difluoromethyl)-2,2-difluoro-1,1-dioxo-benzothiophen-3-one (4 mg, 0.011 mmol) in tetrahydrofuran (1.5 mL) at room temperature was added sodium triacetoxyborohydride (5 mg, 0.02 mmol). The reaction mixture was stirred at room temperature for 30 minutes and purified directly by preparative TLC to give Compound 65 (3 mg, 0.008 mmol, 75% yield). LCMS ESI (+) m/z 394 (M+NH$_4$); $^1$H NMR (400 MHz, CDCl$_3$): δ 7.92 (d, 1H), 7.46-7.10 (m, 7H), 5.61 (d, 1H), 5.26 (s, 2H), 3.00 (s, 1H).

Example 66

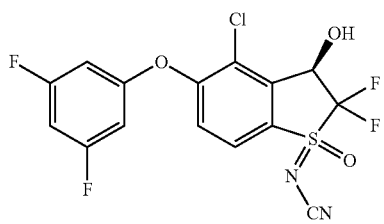 [SMILES: N#CN=S1(=O)c2ccc(Oc3cc(F)cc(F)c3)c(Cl)c2[C@@H](O)C1(F)F]

N-((3R)-4-Chloro-5-(3,5-difluorophenoxy)-2,2-difluoro-3-hydroxy-1-oxido-2,3-dihydro-1λ$^4$-benzo[b]thiophen-1-ylidene)cyanamide (Compound 66)

Step A: Preparation of 2-chloro-3-fluoro-6-(methylthio)benzonitrile: A vial containing a clear solution of 2-chloro-3,6-difluoro-benzonitrile (1.00 g, 5.8 mmol) in N,N-dimethylformamide (DMF, 5 mL) was flushed with nitrogen, cooled in ice, and treated with sodium sulfide (472 mg, 6.1 mmol). The stirred yellow suspension was allowed to slowly warm to ambient temperature. After 3 hours, the reaction mixture was treated with dimethyl sulfate (0.60 mL, 6.3 mmol). The yellow suspension turned milky white. The reaction mixture was partitioned between EtOAc and water. The EtOAc was washed with brine, dried over MgSO$_4$, filtered, and evaporated. The residue was chromatographed on a Biotage 50 g SNAP column with a 10% to 40% EtOAc/hexane gradient to afford 2-chloro-3-fluoro-6-(methylthio)benzonitrile (430 mg, 2.13 mmol, 37% yield) as a fluffy white solid.

Step B: Preparation of N-((3-chloro-2-cyano-4-fluorophenyl)(methyl)-λ$^4$-sulfanylidene)cyanamide: (Diacetoxyiodo)benzene (755 mg, 2.4 mmol) was added to an ice-cold suspension of 2-chloro-3-fluoro-6-(methylthio)benzonitrile (430 mg, 2.1 mmol) and cyanamide (107 mg, 2.6 mmol) in acetonitrile (20 mL). The suspension slowly became a yellow solution. The mixture was allowed to warm to ambient temperature. After 1.25 hours, the reaction mixture was partitioned between EtOAc and dilute aqueous NaCl. The EtOAc layer was washed with brine, dried over MgSO$_4$, filtered, and evaporated. The residue was chromatographed on a Biotage 25 g SNAP column with a 40% to 100% EtOAc/hexane gradient to afford N-((3-chloro-2-cyano-4-fluorophenyl)(methyl)-λ$^4$-sulfanylidene)cyanamide (390 mg, 1.6 mmol, 76% yield) as a white solid.

Step C: Preparation of N-((3-chloro-2-cyano-4-fluorophenyl)(methyl)(oxo)-λ$^6$-sulfanylidene)cyanamide: Sodium periodate (398 mg, 1.9 mmol) was added to N-((3-chloro-2-cyano-4-fluorophenyl)(methyl)-λ$^4$-sulfanylidene)cyanamide (150 mg, 0.6 mmol) and ruthenium (III) chloride (3.9 mg, 0.02 mmol) in a mixture of carbon tetrachloride (3 mL), acetonitrile (3 mL), and water (6 mL). This was stirred at ambient temperature. After 15 minutes, the reaction mixture was partitioned between dichloromethane and water. The dichloromethane was washed with brine, dried over MgSO$_4$, filtered, and evaporated to afford N-((3-chloro-2-cyano-4-fluorophenyl)(methyl)(oxo)-λ$^6$-sulfanylidene)cyanamide (170 mg, 0.66 mmol, quantitative yield) as a grey solid.

Step D: Preparation of N-(3-amino-4-chloro-5-(3,5-difluorophenoxy)-1-oxido-1λ$^4$-benzo[b]thiophen-1-ylidene)cyanamide: Sodium hydrogen carbonate (166 mg, 2 mmol) was added to a vial containing a solution of N-((3-chloro-2-cyano-4-fluorophenyl)(methyl)(oxo)-λ$^6$-sulfanylidene)cyanamide (170 mg, 0.66 mmol) and 3,5-difluorophenol (172 mg, 1.3 mmol) in DMF (2 mL). The sealed vial was heated at 70° C. After 3.5 hours, the reaction mixture was partitioned between EtOAc and water. The EtOAc was washed with 2 portions of brine, dried over MgSO$_4$, filtered, and evaporated. The residue was chromatographed on a Biotage 25 g SNAP column with a 40% to 100% EtOAc/hexane gradient to afford N-(3-amino-4-chloro-5-(3,5-difluorophenoxy)-1-oxido-1λ$^4$-benzo[b]thiophen-1-ylidene)cyanamide (100 mg, 0.27 mmol, 41% yield) as a pale yellow solid. LCMS ESI-API (+) m/z 368 (M+H).

Step E: Preparation of N-(4-chloro-5-(3,5-difluorophenoxy)-1-oxido-3-oxo-2,3-dihydro-1λ$^4$-benzo[b]thiophen-1-ylidene)cyanamide: Hydrochloric acid (1.0 M, 0.65 mL, 0.65 mmol) was added to a solution of N-(3-amino-4-chloro-5-(3,5-difluorophenoxy)-1-oxido-1λ$^4$-benzo[b]thiophen-1-ylidene)cyanamide (80 mg, 0.22 mmol) in methanol (7 mL). The mixture was stirred at 40° C. After 30 minutes, the cooled reaction mixture was treated with water and the resulting solid was collected by vacuum filtration to afford N-(4-chloro-5-(3,5-difluorophenoxy)-1-oxido-3-oxo-2,3-dihydro-1λ$^4$-benzo[b]thiophen-1-ylidene)cyanamide (80 mg, 0.22 mmol, 100% yield) as a tan solid. LCMS ESI-API (+) m/z 369 (M+H).

Step F: Preparation of N-(4-chloro-5-(3,5-difluorophenoxy)-2,2-difluoro-1-oxido-3-oxo-2,3-dihydro-1λ$^4$-benzo[b]thiophen-1-ylidene)cyanamide: 1-(Chloromethyl)-4-fluoro-1,4-diazoniabicyclo[2.2.2]octane ditetrafluoroborate (190 mg, 0.54 mmol) was added to a mixture of N-(4-chloro-5-(3,5-difluorophenoxy)-1-oxido-3-oxo-2,3-dihydro-1λ$^4$-benzo[b]thiophen-1-ylidene)cyanamide (90 mg, 0.24 mmol) and sodium carbonate (57 mg, 0.54 mmol) in acetonitrile (5 mL). This was stirred at ambient temperature. After 30 minutes, the reaction mixture was partitioned between EtOAc and water. The EtOAc was washed with brine, dried over MgSO$_4$, filtered, and evaporated. The residue was chromatographed on a Biotage 10 g SNAP column with a 20% to 80% EtOAc/hexane gradient to afford N-(4-chloro-5-(3,5-difluorophenoxy)-2,2-difluoro-1-oxido-3-oxo-2,3-dihydro-1λ$^4$-benzo[b]thiophen-1-ylidene)cyanamide (401 mg, 0.1 mmol, 41% yield). LCMS ESI-API (+) m/z 423 (M+H+H$_2$O).

Step G: Preparation of N-((3R)-4-chloro-5-(3,5-difluorophenoxy)-2,2-difluoro-3-hydroxy-1-oxido-2,3-dihydro-1λ$^4$-benzo[b]thiophen-1-ylidene)cyanamide: N-[(1R,2R)-1,2-Diphenyl-2-(2-(4-methylbenzyloxy)ethylamino)-ethyl]-4- methylbenzene sulfonamide(chloro)ruthenium(II) ((R,R)-Ts-DENEB™, 1.3 mg, 0.002 mmol) was added to a flask containing an ice-cold, nitrogen-sparged solution of N-(4-chloro-5-(3,5-difluorophenoxy)-2,2-difluoro-1-oxido-3-oxo-2,3-dihydro-1λ⁴-benzo[b]thiophen-1-ylidene)cyanamide (41 mg, 0.1 mmol), triethylamine (0.03 mL, 0.2 mmol), and formic acid (0.009 mL, 0.25 mmol) in dichloromethane (5 mL). The flask was sealed and kept in a 4° C. refrigerator over a weekend. The reaction mixture was evaporated and the residue was chromatographed on a Biotage 10 g SNAP column with a 20% to 80% EtOAc/hexane gradient to afford N-((3R)-4-chloro-5-(3,5-difluorophenoxy)-2,2-difluoro-3-hydroxy-1-oxido-2,3-dihydro-1λ⁴-benzo[b]thiophen-1-ylidene)cyanamide (12.5 mg, 0.03 mmol, 31% yield) as a colorless film. LCMS ESI (+) m/z 407, 409 (M+H); ¹H NMR (400 MHz, CDCl₃): δ 7.89-7.81 (m, 1H), 7.31-7.26 (m, 1H), 6.78 (t, 1H), 6.65 (d, 2H), 5.59-5.51 (m, 1H), 4.60-4.38 (br s, 1H).

Example 67

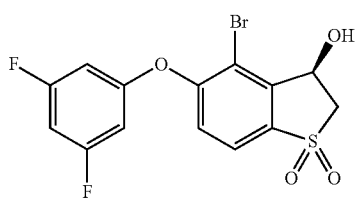 [SMILES: O=S1(=O)C[C@H](O)c2c1ccc(Oc1cc(F)cc(F)c1)c2Br]

(R)-4-Bromo-5-(3,5-difluorophenoxy)-3-hydroxy-2,3-dihydrobenzo[b]thiophene 1,1-dioxide (Compound 67)

Step A: Preparation of 4-bromo-5-(3,5-difluorophenoxy)benzo[b]thiophen-3(2H)-one 1,1-dioxide: Prepared analogously to Example 1, Steps A-G utilizing 3,5-difluorophenol in Step F. ¹H NMR (400 MHz, CDCl₃): δ 7.95-7.92 (m, 1H), 7.48-7.45 (m, 1H), 6.73-6.67 (m, 1H), 6.58-6.53 (m, 2H), 4.20 (s, 2H).

Step B: Preparation of (R)-4-bromo-5-(3,5-difluorophenoxy)-3-hydroxy-2,3-dihydrobenzo[b]thiophene 1,1-dioxide: 4-Bromo-5-(3,5-difluorophenoxy)benzo[b]thiophen-3(2H)-one 1,1-dioxide (267 mg, 0.69 mmol) was dissolved in dichloromethane (freshly degassed by sparging with nitrogen, 3.4 mL) and the solution was treated with triethylamine (0.19 mL, 1.37 mmol) and formic acid (0.08 mL, 2.1 mmol). This solution was cooled to 0° C. and treated with a pre-cooled (0° C.) solution of RuCl(p-cymene)(S,S)-Ts-DPEN (4.4 mg, 0.01 mmol) dissolved in dichloromethane (3.4 mL). The resultant solution was placed in the refrigerator and allowed to stand at 4° C. for 15 hours. The reaction mixture was concentrated to a small volume and chromatographed on SiO₂ eluting with a gradient of ethyl acetate/hexane. The product was collected and concentrated to a colorless oil. Diethyl ether and hexane were added and the mixture was reconcentrated to form of (R)-4-bromo-5-(3,5-difluorophenoxy)-3-hydroxy-2,3-dihydrobenzo[b]thiophene 1,1-dioxide as a white solid (248 mg, 92%, >95% ee by Mosher ester analysis). ¹H NMR (400 MHz, CDCl₃): δ 7.72 (d, 1H), 7.21 (d, 1H), 6.71-6.64 (m, 1H), 6.57-6.52 (m, 2H), 5.60 (t, 1H), 3.83-3.78 (m, 1H), 3.71-3.67 (m, 1H), 2.88 (d, 1H).

Example 68

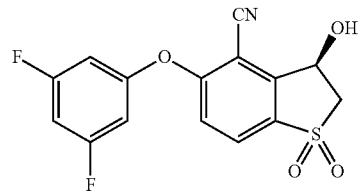

(R)-5-(3,5-difluorophenoxy)-3-hydroxy-2,3-dihydrobenzo[b]thiophene-4-carbonitrile 1,1-dioxide (Compound 68)

A solution of (R)-4-bromo-5-(3,5-difluorophenoxy)-3-hydroxy-2,3-dihydrobenzo[b]thiophene 1,1-dioxide (51.7 mg, 0.13 mmol) dissolved in 1-methyl-2-pyrrolidinone (0.52 mL) was treated with copper (I) cyanide (16.6 mg, 0.19 mmol). Argon was bubbled through the solution for several minutes, then the mixture was heated to 160° C. for 60 minutes in the microwave reactor. After cooling, the mixture was diluted with Et₂O and water. After separation, the aqueous was washed with Et₂O, then the combined organics were washed five times with water, saturated NaHCO₃, saturated NaCl, dried over Na₂SO₄ and concentrated in vacuo. The crude material was redissolved in a small amount of methylene chloride and after a few minutes a precipitate began to form. The supernant was removed and the remaining solids were washed several times with cold 1:1 methylene chloride/hexane. The solids were suspended in hexane, filtered and air-dried. (R)-5-(3,5-Difluorophenoxy)-3-hydroxy-2,3-dihydrobenzo[b]thiophene-4-carbonitrile 1,1-dioxide was obtained as a white solid (22.5 mg, 51%, >86% ee by Mosher ester analysis). ¹H NMR (400 MHz, CDCl₃): δ 7.89 (d, 1H), 7.15 (d, 1H), 6.83-6.76 (m, 1H), 6.71-6.67 (m, 2H), 5.78-5.74 (m, 1H), 3.94-3.89 (m, 1H), 3.67-3.63 (m, 1H), 3.27-3.24 (m, 1H).

Example 69

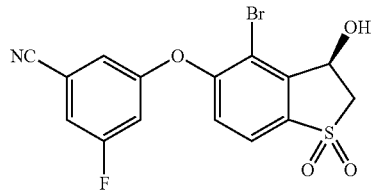

(R)-3-((4-Bromo-3-hydroxy-1,1-dioxido-2,3-dihydrobenzo[b]thiophen-5-yl)oxy)-5-fluorobenzonitrile (Compound 69)

Preparation of (R)-5-(3,5-difluorophenoxy)-3-hydroxy-2,3-dihydrobenzo[b]thiophene-4-carbonitrile 1,1-dioxide: Prepared analogously as described in Example 67, Step B using 3-((4-bromo-1,1-dioxido-3-oxo-2,3-dihydrobenzo[b]thiophen-5-yl)oxy)-5-fluorobenzonitrile (Example 1, Step G) (66%, >98% ee by Mosher ester analysis).

¹H NMR (400 MHz, CDCl₃): δ 7.77 (d, 1H), 7.25 (d, 1H), 7.22-7.19 (m, 1H), 7.06-7.05 (m, 1H), 6.99-6.96 (m, 1H), 5.62-5.59 (m, 1H), 3.85-3.80 (m, 1H), 3.71-3.69 (m, 1H), 2.90 (d, 1H).

Example 70

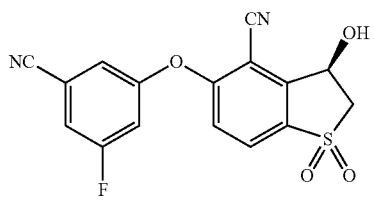 [SMILES: N#Cc1cc(F)cc(Oc2ccc3c(c2Br)[C@@H](O)CS3(=O)=O)c1]

(R)-5-(3-Cyano-5-fluorophenoxy)-3-hydroxy-2,3-dihydrobenzo[b]thiophene-4-carbonitrile 1,1-dioxide (Compound 70)

Prepared analogously as described in Example 68 using (R)-3-((4-bromo-3-hydroxy-1,1-dioxido-2,3-dihydrobenzo[b]thiophen-5-yl)oxy)-5-fluorobenzonitrile (57%, >88% ee by Mosher ester analysis). ¹H NMR (400 MHz, CDCl₃): δ 7.94 (d, 1H), 7.35-7.31 (m, 1H), 7.24-7.22 (m, 1H), 7.16 (d, 1H), 7.16-7.12 (m, 1H), 5.80-5.73 (m, 1H), 3.96-3.90 (m, 1H), 3.68-3.63 (m, 1H), 3.48-3.46 (m, 1H).

Example 71

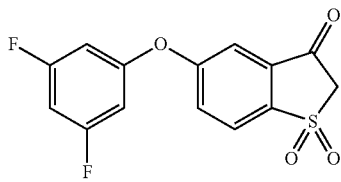 [SMILES: O=C1CS(=O)(=O)c2ccc(Oc3cc(F)cc(F)c3)cc21]

5-(3,5-Difluorophenoxy)benzo[b]thiophen-3(2H)-one 1,1-dioxide (Compound 71)

A solution of 4-bromo-5-(3,5-difluorophenoxy)-1,1-dioxo-benzothiophen-3-one (60 mg, 0.15 mmol) was dissolved in MeOH (0.45 mL) and cooled to 0° C. The solution was treated with sodium borohydride (5.8 mg, 0.15 mmol) and the mixture was stirred at 0° C. for 1 hour. The mixture was treated with additional sodium borohydride (1 mg, 0.03 mmol) and stirred for an additional 30 minutes. The reaction was quenched by careful addition of 10% KHSO₄ and the mixture was stirred at 0° C. for 1 hour. The pH was adjusted to 7-8 with saturated NaHCO₃ and the aqueous was extracted three times with ethyl acetate. The combined organic layers were washed with saturated NaHCO₃, saturated NaCl, dried over Na₂SO₄ and concentrated in vacuo. The crude material was chromatographed on SiO₂ eluting with a gradient of ethyl acetate/hexane to give Compound 71 (11.9 mg, 25%). ¹H NMR (400 MHz, CDCl₃): δ 8.24 (d, 1H), 7.89-7.86 (dd, 1H), 7.11 (d, 1H), 6.70-6.65 (m, 1H), 6.59-6.51 (m, 2H), 3.10 (s, 2H).

Example 72

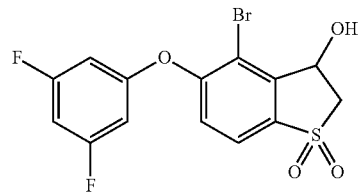

4-Bromo-5-(3,5-difluorophenoxy)-3-hydroxy-2,3-dihydrobenzo[b]thiophene 1,1-dioxide (Compound 72)

Prepared analogously as described in Example 71 to give Compound 72 (40 mg, 66%). ¹H NMR (400 MHz, CDCl₃): δ 7.72 (d, 1H), 7.20 (d, 1H), 6.70-6.65 (m, 1H), 6.58-6.52 (m, 2H), 5.62-5.58 (m, 1H), 3.83-3.78 (m, 1H), 3.71-3.67 (m, 1H), 2.93 (d, 1H).

Example 73

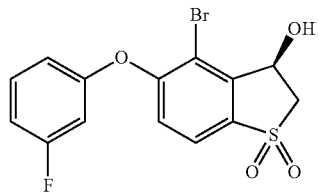 [SMILES: O=S1(=O)C[C@H](O)c2c1ccc(Oc1cccc(F)c1)c2Br]

(R)-4-bromo-5-(3-fluorophenoxy)-3-hydroxy-2,3-dihydrobenzo[b]thiophene 1,1-dioxide (Compound 73)

Prepared analogously as described in Example 1, Step A-G utilizing 3-fluorophenol in Step F, followed by Example 67, Step B (92%, >96% ee by Mosher ester analysis). ¹H NMR (400 MHz, CDCl₃): δ 7.66 (d, 1H), 7.40-7.35 (m, 1H), 7.10 (d, 1H), 6.97-6.93 (m, 1H), 6.83-6.76 (m, 2H), 5.62-5.59 (m, 1H), 3.82-3.77 (m, 1H), 3.70-3.66 (m, 1H), 2.96 (d, 1H).

Example 74

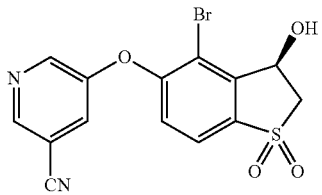 [SMILES: N#Cc1cncc(Oc2ccc3c(c2Br)[C@@H](O)CS3(=O)=O)c1]

(R)-5-((4-bromo-3-hydroxy-1,1-dioxido-2,3-dihydrobenzo[b]thiophen-5-yl)oxy)nicotinonitrile (Compound 74)

Prepared analogously as described in Example 1, Step A-G utilizing 5-hydroxynicotinonitrile in Step F, followed by Example 67, Step B (70%, >96% ee by Mosher ester analysis). ¹H NMR (400 MHz, CDCl₃+CD₃OD): δ 8.69 (d, 1H), 8.61-8.60 (d, 1H), 7.79 (d, 1H), 7.55-7.54 (m, 1H), 7.29 (d, 1H), 5.57 (d, 1H), 3.84-3.79 (m, 1H), 3.70-3.66 (m, 1H).

Example 75

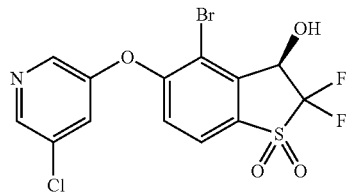

(R)-4-bromo-5-((5-chloropyridin-3-yl)oxy)-2,2-difluoro-3-hydroxy-2,3-dihydrobenzo[b]thiophene 1,1-dioxide (Compound 75)

Prepared analogously as described in Example 1 using 5-chloropyridin-3-ol in Step F (42% ee by Mosher ester analysis). ¹H NMR (400 MHz, CDCl₃): δ 8.50 (s, 1H), 8.33 (s, 1H), 7.81 (d, 1H), 7.41-7.40 (m, 1H), 7.19 (d, 1H), 5.41-5.37 (m, 1H), 3.45-3.40 (m, 1H).

Example 76

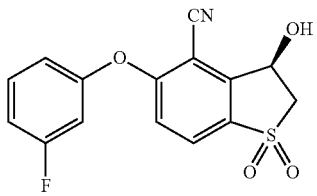 [SMILES: N#Cc1c(Oc2cccc(F)c2)ccc2c1[C@@H](O)CS2(=O)=O]

(R)-5-(3-fluorophenoxy)-3-hydroxy-2,3-dihydrobenzo[b]thiophene-4-carbonitrile 1,1-dioxide (Compound 76)

Prepared analogously as described in Example 68 utilizing (R)-4-bromo-5-(3-fluorophenoxy)-3-hydroxy-2,3-dihydrobenzo[b]thiophene 1,1-dioxide (>94% ee by Mosher ester analysis). ¹H NMR (400 MHz, CDCl₃): δ 7.83 (d, 1H), 7.48-7.42 (m, 1H), 7.08-7.03 (m, 1H), 7.06 (d, 1H), 6.94-6.87 (m, 2H), 5.78-5.73 (m, 1H), 3.93-3.88 (m, 1H), 3.66-3.62 (m, 1H), 3.56 (d, 1H).

Example 77

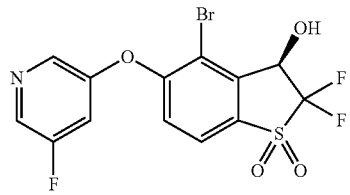 [SMILES: O=S1(=O)c2ccc(Oc3cncc(F)c3)c(Br)c2[C@@H](O)C1(F)F]

(R)-4-bromo-2,2-difluoro-5-((5-fluoropyridin-3-yl)oxy)-3-hydroxy-2,3-dihydrobenzo[b]thiophene 1,1-dioxide (Compound 77)

Prepared analogously as described in Example 1 utilizing 5-fluoropyridin-3-ol in Step F. ¹H NMR (400 MHz, CDCl₃): δ 8.43 (d, 1H), 8.29 (d, 1H), 7.82 (d, 1H), 7.21 (d, 1H), 7.18-7.14 (dt, 1H), 5.41-5.37 (m, 1H), 3.29-3.28 (m, 1H).

Example 78

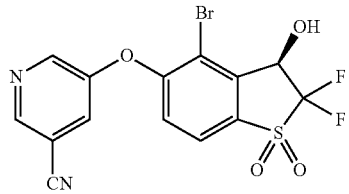 [SMILES: N#Cc1cncc(Oc2ccc3c(c2Br)[C@@H](O)C(F)(F)S3(=O)=O)c1]

(R)-5-((4-Bromo-2,2-difluoro-3-hydroxy-1,1-dioxido-2,3-dihydrobenzo[b]thiophen-5-yl)oxy)nicotinonitrile (Compound 78)

Prepared analogously as described in Example 1 utilizing 5-hydroxynicotinonitrile in Step F. ¹H NMR (400 MHz, CDCl₃): δ 8.76 (s, 1H), 8.64 (d, 1H), 7.87 (d, 1H), 7.59-7.58 (m, 1H), 7.27 (d, 1H), 5.42-5.36 (m, 1H), 3.36-3.32 (m, 1H).

Example 79

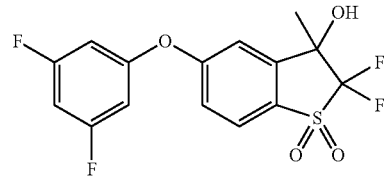 [SMILES: CC1(O)c2cc(Oc3cc(F)cc(F)c3)ccc2S(=O)(=O)C1(F)F]

5-(3,5-Difluorophenoxy)-2,2-difluoro-3-hydroxy-3-methyl-2,3-dihydrobenzo[b]thiophene 1,1-dioxide (Compound 79)

4-Bromo-5-(3,5-difluorophenoxy)-2,2-difluorobenzo[b]thiophen-3(2H)-one 1,1-dioxide (25 mg, 0.06 mmol) was dissolved in tetrahydrofuran (THF, 0.21 mL), cooled to 0° C., and treated with methylmagnesium chloride (3M in THF, 0.039 mL, 0.12 mmol). The solution was stirred at 0° C. for 2 hours, then quenched with 10% KHSO₄. The volatile solvents were removed with a stream of nitrogen gas, and the aqueous was treated with ethyl acetate. After separation, the aqueous was washed with ethyl acetate and the combined organics were washed with water, saturated aqueous NaHCO₃, saturated aqueous NaCl, dried over Na₂SO₄ and concentrated in vacuo. The crude material was chromatographed on SiO₂ eluting with a gradient of ethyl acetate/hexane to give 5-(3,5-difluorophenoxy)-2,2-difluoro-3-hydroxy-3-methyl-2,3-dihydrobenzo[b]thiophene 1,1-dioxide as a colorless film (22.5 mg, 87%). LCMS ESI (−) m/z 407 (M+HCOOH-H); ¹H NMR (400 MHz, CDCl₃): δ 7.81 (d, 1H), 7.28 (d, 1H), 7.24-7.21 (m, 1H), 6.76-6.70 (1H), 6.65-6.95 (m, 2H), 2.80 (m, 1H), 1.75 (m, 3H).

Example 80

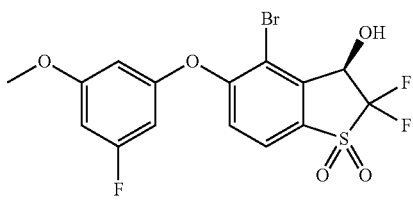 [SMILES: COc1cc(F)cc(Oc2ccc3c(c2Br)[C@@H](O)C(F)(F)S3(=O)=O)c1]

(R)-4-Bromo-2,2-difluoro-5-(3-fluoro-5-methoxyphenoxy)-3-hydroxy-2,3-dihydrobenzo[b]thiophene 1,1-dioxide (Compound 80)

Step A: Preparation of 2-bromo-3-fluoro-6-iodobenzoic acid: A stirred mixture of 2-bromo-3-fluorobenzoic acid (25 g, 114 mmol), palladium (II) acetate (1.28 g, 5.71 mmol), iodine (29 g, 114 mmol), diacetoxy iodobenzene (36.8 g, 114 mmol) and dimethylformamide (560 mL) was sparged with nitrogen for 5 minutes. The mixture was then heated at 120° C. under nitrogen for 16 hours. After cooling, the reaction mixture was poured into ice water. The solution was treated with aqueous 10% $Na_2S_2O_3$ to remove residual iodine color. The mixture was extracted with methyl t-butyl ether. The combined organic layers were washed with water and saturated NaCl, dried over $Na_2SO_4$ and concentrated in vacuo. The yellow oil was triturated 10% ethyl acetate/hexane to give a solid, which was collected by filtration. The filtrate was concentrated and triturated again with 10% ethyl acetate/hexane. The combined solids of 2-bromo-3-fluoro-6-iodobenzoic acid (30.7 g) were used in the next step without further purification.

Step B: Preparation of methyl 2-bromo-3-fluoro-6-iodobenzoate: To a stirred solution of 2-bromo-3-fluoro-6-iodobenzoic acid (30.7 g, 89 mmol) in dimethylformamide (220 mL), fine mesh potassium carbonate (36.9 g, 267 mmol) and iodomethane (16.6 mL, 267 mmol) were added. The reaction mixture was stirred at ambient temperature for 2 hours. The reaction mixture was poured into cold water and extracted with methyl t-butyl ether. The combined organic layers were washed with water and brine, dried over sodium sulfate and concentrated in vacuo. The residue was treated with 15% ethyl acetate/hexane and stirred. The precipitated solid (18.5 g) was collected by filtration. The filtrate was concentrated in vacuo. The residue was purified by chromatography on silica gel eluting with a gradient of ethyl acetate/hexane to give additional desired product (5.3 g). The two isolated fractions of methyl 2-bromo-3-fluoro-6-iodobenzoate were combined (23.8 g) and carried forward.

LCMS ESI (+) m/z 359 (M+H); $^1$H NMR (400 MHz, $CDCl_3$): δ 7.74-7.70 (m, 1H), 6.93-6.89 (m, 1H), 4.00 (s, 3H).

Step C: Preparation of methyl 6-(acetylthio)-2-bromo-3-fluorobenzoate: A mixture of methyl 2-bromo-3-fluoro-6-iodobenzoate (17.5 g, 48.6 mmol) and 4,5-bis(diphenylphosphino)-9,9-dimethylxanthene (Xantphos, 3.38 g, 5.84 mmol) were suspended in 2:1 toluene/acetone (195 mL). The mixture was sparged with nitrogen for five minutes followed by addition of tris(dibenzylideneacetone)dipalladium(0) (2.67 g, 2.92 mmol) and potassium ethanethioate (6.93 g, 60.8 mmol). The mixture was heated at 70° C. for 3 hours. After cooling, the reaction mixture was filtered through a pad of celite. The filtrate was concentrated in vacuo to orange oil, which was purified by column chromatography on silica gel eluting with a gradient ethyl acetate/hexane) to give methyl 6-(acetylthio)-2-bromo-3-fluorobenzoate (14.6 g, 98%). $^1$H NMR (400 MHz, $CDCl_3$): δ 7.44-7.41 (m, 1H), 7.25-7.21 (m, 1H), 3.95 (s, 3H), 2.41 (s, 3H).

Step D: Preparation of methyl 2-bromo-3-fluoro-6-(methylthio)benzoate: A stirred solution of methyl 6-(acetylthio)-2-bromo-3-fluorobenzoate (22.2 g, 72.3 mmol) in MeOH (360 mL) was degassed by sparging with nitrogen. Solid cesium carbonate (30.6 g, 94 mmol) was added. The solution was stirred at ambient temperature for 1 hour. Iodomethane (22.5 mL, 361 mmol) was added and the reaction mixture was stirred at ambient temperature overnight under nitrogen, and then filtered through a pad of celite. The filtrate was concentrated in vacuo and redissolved in methyl t-butyl ether and water. The layers were separated. The organic layer was washed with brine and dried over $Na_2SO_4$. Crude methyl 2-bromo-3-fluoro-6-(methylthio)benzoate (20.7 g, quant.) was used in the next step without further purification. $^1$H NMR (400 MHz, $CDCl_3$): δ 7.38-7.35 (m, 1H), 7.16-7.11 (m, 1H), 3.98 (s, 3H), 2.45 (s, 3H).

Step E: Preparation of methyl 2-bromo-3-fluoro-6-(methylsulfonyl)benzoate: A solution of methyl 2-bromo-3-fluoro-6-(methylthio)-benzoate (20.7 g, 74 mmol) dissolved in MeOH (370 mL) was added dropwise to a solution of Oxone® (137 g, 222 mmol) in water (370 mL). The mixture was stirred at ambient temperature for 14 hours. The reaction mixture was filtered and the solids were washed with methanol. The filtrate was concentrated under reduced pressure to remove the volatile solvents. The residual aqueous mixture was extracted three times with ethyl acetate. The combined organic layers were washed with water and brine, dried over $Na_2SO_4$ and concentrated in vacuo. The crude product was purified by column chromatography on silica gel eluting with a gradient of ethyl acetate/hexane. After concentration in vacuo, methyl 2-bromo-3-fluoro-6-(methylsulfonyl)benzoate was obtained as a pale yellow solid (15.5 g). $^1$H NMR (400 MHz, $CDCl_3$): δ 8.04-8.01 (m, 1H), 7.37-7.33 (m, 1H), 4.02 (s, 3H), 3.17 (s, 3H).

Step F: Preparation of methyl 2-bromo-3-(3-fluoro-5-methoxyphenoxy)-6-(methylsulfonyl)benzoate: Methyl 2-bromo-3-fluoro-6-(methylsulfonyl)benzoate (200 mg, 0.64 mmol) was treated with 3-fluoro-5-methoxy-phenol (137 mg, 0.96 mmol) and dimethylformamide (2.5 mL). The solution was treated with in a single portion with sodium bicarbonate (108 mg, 1.29 mmol) and the mixture was heated to 90° C. for 18 hours. The reaction was cooled, diluted with $Et_2O$ and water and then separated. The aqueous was washed with $Et_2O$ and the combined organics were washed five times with 10% $K_2CO_3$, saturated $NaHCO_3$, saturated NaCl, dried over $Na_2SO_4$. After concentration in vacuo, methyl 2-bromo-3-(3-fluoro-5-methoxyphenoxy)-6-(methylsulfonyl)benzoate was obtained as an orange film (quant.). $^1$H NMR (400 MHz, $CDCl_3$): δ 7.92 (d, 1H), 7.02 (d, 1H), 6.54-6.51 (dt, 1H), 6.41-6.37 (m, 2H), 4.04 (s, 3H), 3.80 (s, 3H), 3.17 (s, 3H).

Step G: Preparation of 4-bromo-5-(3-fluoro-5-methoxyphenoxy)benzo[b]thiophen-3(2H)-one 1,1-dioxide: Sodium hydride (60% in mineral oil, 92 mg, 2.3 mmol) was washed with three portions of hexanes, then suspended in tetrahydrofuran (11 mL) and cooled to 0° C. The suspension was treated dropwise with a solution of methyl 2-bromo-3-(3-fluoro-5-methoxy-phenoxy)-6-methylsulfonyl-benzoate (331 mg, 0.76 mmol) dissolved in tetrahydrofuran (12 mL). The suspension was stirred at 0° C. for 5 minutes, then warmed to ambient temperature and stirred for 2 hours. The reaction mixture was poured slowly into cold 10% KHSO$_4$ and swirled vigorously. The pH of the resultant aqueous phase was ~2. The suspension was concentrated in vacuo to remove tetrahydrofuran, then the mixture was diluted with ethyl acetate. The layers were separated and the aqueous was washed with ethyl acetate. The combined organic layer was washed with water, saturated NaHCO$_3$, saturated NaCl, dried over Na$_2$SO$_4$. After concentration in vacuo, 4-bromo-5-(3-fluoro-5-methoxyphenoxy)benzo[b]thiophen-3(2H)-one 1,1-dioxide was isolated as a yellow solid (199 mg, 65%). $^1$H NMR (400 MHz, CDCl$_3$): δ 7.84 (d, 1H), 7.36 (d, 1H), 6.49-6.45 (dt, 1H), 6.33-6.28 (m, 2H), 3.75 (s, 3H), 2.89 (s, 2H).

Step H: Preparation of 4-bromo-2,2-difluoro-5-(3-fluoro-5-methoxyphenoxy)benzo[b]thiophen-3(2H)-one 1,1-dioxide: A suspension of 4-bromo-5-(3-fluoro-5-methoxy-phenoxy)-1,1-dioxo-benzothiophen-3-one (100 mg, 0.25 mmol) dissolved in acetonitrile (1.3 mL) was treated with sodium carbonate (79 mg, 0.75 mmol) and Selectfluor® (265 mg, 0.75 mmol), then the resulting suspension was stirred at ambient temperature for 2 hours, then cooled to 0° C. and stirred for 2 hours. The mixture was concentrated in vacuo at ambient temperature, then the residue was diluted with ethyl acetate and water. The layers were separated and the aqueous was washed with ethyl acetate. The combined organics were washed with saturated NaHCO$_3$, saturated NaCl, dried over Na$_2$SO$_4$ and concentrated in vacuo to a waxy, light yellow solid. This material was chromatographed on SiO$_2$ eluting with a gradient of ethyl acetate/hexane. 4-Bromo-2,2-difluoro-5-(3-fluoro-5-methoxyphenoxy)benzo[b]thiophen-3(2H)-one 1,1-dioxide was isolated as a pale yellow solid (84 mg, 77%). $^1$H NMR (400 MHz, CDCl$_3$): δ 7.93 (d, 1H), 7.46 (d, 1H), 6.60-6.55 (m, 1H), 6.48-6.43 (m, 2H), 3.81 (s, 3H).

Step I: Preparation of (R)-4-bromo-2,2-difluoro-5-(3-fluoro-5-methoxyphenoxy)-3-hydroxy-2,3-dihydrobenzo[b]thiophene 1,1-dioxide (Compound 80): 4-Bromo-2,2-difluoro-5-(3-fluoro-5-methoxyphenoxy)benzo[b]thiophen-3(2H)-one 1,1-dioxide (77 mg, 0.18 mmol) was dissolved in dichloromethane (pre-sparged with nitrogen gas, 0.8 mL), then the solution was treated with triethylamine (49 µL, 0.35 mmol) and formic acid (20 µL, 0.53 mmol). This solution was cooled to 0° C. and treated with a pre-cooled (0° C.) solution of N-[(1R,2R)-1,2-diphenyl-2-(2-(4-methylbenzyloxy)ethylamino)-ethyl]-4-methylbenzene sulfonamide (chloro)ruthenium(II) (1.15 mg, 0.002 mmol) dissolved in dichloromethane (0.8 mL). The resultant suspension was placed in the refrigerator and allowed to stand at 4° C. for 100 hours. The reaction mixture was concentrated to a small volume and chromatographed on SiO$_2$, eluting with a stepped gradient of ethyl acetate/chloroform. The desired compound was collected and concentrated in vacuo. The oil was redissolved in methylene chloride and hexane, then concentrated in vacuo to a white solid (34 mg, 43%). (R)-4-Bromo-2,2-difluoro-5-(3-fluoro-5-methoxyphenoxy)-3-hydroxy-2,3-dihydrobenzo[b]thiophene 1,1-dioxide was obtained with >79% ee by Mosher ester analysis. LCMS ESI (−) m/z 437, 439 (M−H); $^1$H NMR (400 MHz, CDCl$_3$) δ 7.75 (d, 1H), 7.17 (d, 1H), 6.56-6.51 (m, 1H), 6.42-6.37 (m, 2H), 5.42-5.35 (m, 1H), 3.80 (s, 3H), 2.99-2.95 (m, 1H).

Example 81

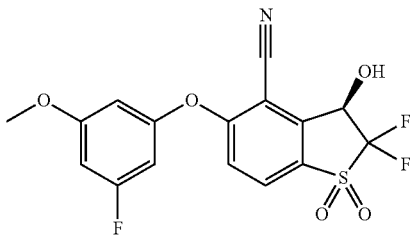 [SMILES: COc1cc(F)cc(Oc2ccc3c(c2C#N)[C@@H](O)C(F)(F)S3(=O)=O)c1]

(R)-2,2-difluoro-5-(3-fluoro-5-methoxyphenoxy)-3-hydroxy-2,3-dihydrobenzo[b]thiophene-4-carbonitrile 1,1-dioxide (Compound 81)

A solution of (R)-4-bromo-2,2-difluoro-5-(3-fluoro-5-methoxyphenoxy)-3-hydroxy-2,3-dihydrobenzo[b]thiophene 1,1-dioxide (20 mg, 0.05 mmol)] dissolved in 1-methyl-2-pyrrolidinone (0.32 mL) was treated with copper (I) cyanide (5.3 mg, 0.06 mmol). Argon gas was bubbled through the solution for several minutes, then the solution was heated to 160° C. for 90 minutes in the microwave reactor. After cooling, the mixture was diluted with ethyl acetate and water. After separation, the aqueous was washed with ethyl acetate, then the combined organics were washed with water, saturated NaHCO$_3$, saturated NaCl, dried over Na$_2$SO$_4$ and concentrated in vacuo to a dark residue. The crude material was chromatographed on SiO$_2$, eluting with a stepped gradient of ethyl acetate/CHCl$_3$. (R)-2,2-Difluoro-5-(3-fluoro-5-methoxyphenoxy)-3-hydroxy-2,3-dihydrobenzo[b]thiophene-4-carbonitrile 1,1-dioxide was obtained as a white solid (7.2 mg, 37%, >79% ee by Mosher ester analysis). LCMS ESI (−) m/z 384 (M−H); $^1$HNMR (400 MHz, CDCl$_3$) δ 7.92 (d, 1H), 7.17 (d, 1H), 6.64-6.60 (m, 1H), 6.50-6.45 (m, 2H), 6.57-6.51 (m, 1H), 3.82 (s, 3H), 3.80-3.74 (m, 1H).

Example 82

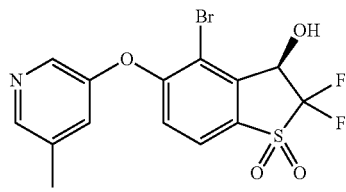 [SMILES: Cc1cncc(Oc2ccc3c(c2Br)[C@@H](O)C(F)(F)S3(=O)=O)c1]

(R)-4-bromo-2,2-difluoro-3-hydroxy-5-((5-methylpyridin-3-yl)oxy)-2,3-dihydrobenzo[b]thiophene 1,1-dioxide (Compound 82)

Prepared analogously as described in Example 1 utilizing 5-methylpyridin-3-ol in Step F. $^1$H NMR (400 MHz, CDCl$_3$): δ 8.38-8.36 (m, 1H), 8.14 (d, 1H), 7.72 (d, 1H), 7.24-7.22 (m, 1H), 7.01 (d, 1H), 5.41-5.37 (m, 1H), 4.14-4.08 (m, 1H), 2.40 (s, 3H).

Example 83

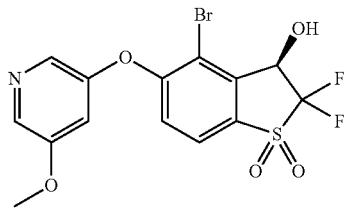 [SMILES: COc1cncc(Oc2ccc3c(c2Br)[C@@H](O)C(F)(F)S3(=O)=O)c1]

(R)-4-bromo-2,2-difluoro-3-hydroxy-5-((5-methoxypyridin-3-yl)oxy)-2,3-dihydrobenzo[b]thiophene 1,1-dioxide (Compound 83)

Prepared analogously as described in Example 1 utilizing 5-methoxypyridin-3-ol in Step F. $^1$H NMR (400 MHz, CDCl$_3$): δ 8.26-8.23 (m, 1H), 7.95-7.93 (m, 1H), 7.73 (d, 1H), 7.06 (d, 1H), 6.95-6.92 (m, 1H), 5.42-5.35 (m, 1H), 4.03-3.97 (m, 1H), 3.88 (s, 3H).

Example 84

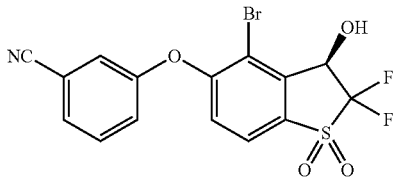 [SMILES: N#Cc1cccc(Oc2ccc3c(c2Br)[C@@H](O)C(F)(F)S3(=O)=O)c1]

(R)-3-((4-bromo-2,2-difluoro-3-hydroxy-1,1-dioxido-2,3-dihydrobenzo[b]thiophen-5-yl)oxy)benzonitrile (Compound 84)

Prepared analogously as described in Example 1 utilizing 3-hydroxybenzonitrile in Step F. $^1$H NMR (400 MHz, CDCl$_3$): δ 7.80 (d, 1H), 7.59-7.54 (m, 2H), 7.37-7.35 (m, 1H), 7.32-7.27 (m, 1H), 7.15 (d, 1H), 5.42-5.37 (m, 1H), 3.11 (d, 1H).

Example 85

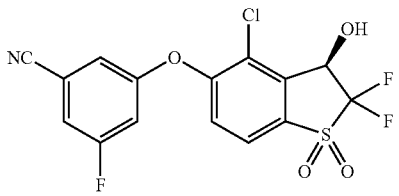 [SMILES: N#Cc1cc(F)cc(Oc2ccc3c(c2Cl)[C@@H](O)C(F)(F)S3(=O)=O)c1]

(R)-3-((4-chloro-2,2-difluoro-3-hydroxy-1,1-dioxido-2,3-dihydrobenzo[b]thiophen-5-yl)oxy)-5-fluorobenzonitrile (Compound 85)

Step A: Preparation of 2-chloro-3-fluoro-6-iodobenzoic acid: 2-chloro-3-fluoro-benzoic acid (25.3 g, 144 mmol) was combined with palladium (II) acetate (1.62 g, 7.24 mmol), iodine (36.7 g, 144 mmol), and diacetoxy iodobenzene (46.6 g, 144 mmol) and the solids were slurried in dimethylformamide (700 mL). The resulting suspension was sparged with argon, then heated to 120° C. under nitrogen for 16 hours. The reaction was cooled and poured into water (2.5 L). Methyl t-butyl ether (800 mL) was added and the layers were separated. The aqueous was re-extracted with fresh methyl t-butyl ether (400 mL). The combined organic layers were washed with 1M Na$_2$S$_2$O$_3$, water, saturated NaCl, dried over Na$_2$SO$_4$ and concentrated in vacuo. The crude oil was dissolved in ethyl acetate (20 mL) and diluted with hexane (180 mL) and the solution was stirred overnight. The undesired solid was removed by filtration and washed with hexanes. Crude 2-chloro-3-fluoro-6-iodobenzoic acid was obtained, after concentration of the filtrate, as yellow oil (40 g, 94%). $^1$H NMR (400 MHz, CDCl$_3$): δ 7.74-7.70 (m, 1H), 7.01-6.96 (m, 1H).

Step B: Preparation of methyl 2-chloro-3-fluoro-6-iodobenzoate: 2-Chloro-3-fluoro-6-iodobenzoic acid (40.0 g, 133 mmol) was dissolved in DMF (300 mL), then treated with fine mesh potassium carbonate (55 g, 400 mmol) and iodomethane (24.9 mL, 400 mmol). The suspension was stirred at ambient temperature for 3.5 hours, then concentrated in vacuo to remove iodomethane. The mixture was poured into cold water (600 mL) and extracted twice with methyl t-butyl ether (200 mL). The combined organics were washed with water, saturated NaCl, dried over Na$_2$SO$_4$ and concentrated in vacuo. The resulting oil was dissolved in hexanes, then concentrated onto SiO$_2$ (100 g). Separately, a pad of silica gel was pre-equilibrated with hexane, then the crude solid was placed on the top of this filter column. The column was eluted with a stepped gradient of hexane/Et$_2$O. Fractions containing the desired product were concentrated in vacuo. The resultant oil was treated with hexane and concentrated to produce methyl 2-chloro-3-fluoro-6-iodobenzoate as a white solid (31 g, 74%). $^1$H NMR (400 MHz, CDCl$_3$): δ 7.70-7.67 (m, 1H), 6.97-6.93 (m, 1H), 4.00 (s, 3H).

Step C: Preparation of methyl 6-(acetylthio)-2-chloro-3-fluorobenzoate: Methyl 2-chloro-3-fluoro-6-iodobenzoate (15.3 g, 48.7 mmol) and 4,5-bis(diphenylphosphino)-9,9-dimethylxanthene (Xantphos, 3.38 g, 5.84 mmol) were suspended in 2:1 toluene/acetone (170 mL). The mixture was sparged with argon, then treated with tris(dibenzylideneacetone)dipalladium (Pd$_2$dba$_3$, 2.67 g, 2.9 mmol) and potassium ethanethiolate (6.93 g, 60.8 mmol). The mixture was sealed in a tube, stirred vigorously, and heated to 70° C. for 3 hours. After cooling, the mixture was filtered through a pad of celite on cellulose, then concentrated in vacuo to dark orange oil. This oil was redissolved in methylene chloride and concentrated onto Na$_2$SO$_4$ (200 g). The sodium sulfate powder with adhered crude product was dry-loaded onto a large column of SiO$_2$ pre-equilibrated with hexane. The column was eluted under slight vacuum with a stepwise gradient of ethyl acetate/hexane. Methyl 6-(acetylthio)-2-chloro-3-fluorobenzoate was obtained as orange oil after concentration in vacuo (11.9 g, 93%).

Step D: Preparation of methyl 2-chloro-3-fluoro-6-(methylthio)benzoate: A solution of methyl 6-(acetylthio)-2-chloro-3-fluorobenzoate (11.9 g, 45.5 mmol) was dissolved in MeOH (225 mL), degassed with bubbling argon for 5 minutes, then the solution was treated with cesium carbonate (19.3 g, 59.1 mmol). The suspension was stirred at ambient temperature for 4 hours. The reaction mixture was treated with iodomethane (14.2 mL, 227 mmol) and stirred under argon for 60 hours. The mixture was concentrated in vacuo and redissolved in a mixture of Et$_2$O and water. The layers were separated and the aqueous was washed with Et$_2$O. The combined organic layers were washed with saturated NaHCO$_3$, saturated NaCl, dried over Na$_2$SO$_4$ and concentrated in vacuo to dark oil (9.08 g, 85%).

Step E: Preparation of methyl 2-chloro-3-fluoro-6-(methylsulfonyl)benzoate: A solution of methyl 2-chloro-3-fluoro-6-(methylthio)benzoate (9.08 g, 32.5 mmol) dissolved in MeOH (160 mL) was added dropwise to a slurry of Oxone® (60.1 g, 97.6 mmol) dissolved water (160 mL). The mixture was stirred at ambient temperature for 22 hours. The suspended solids were removed by filtration and washed with water. The filtered solids were resuspended in ethyl acetate, then re-filtered. The solids were suspended once again in ethyl acetate, stirred 10 minutes and then filtered. The combined filtrates were concentrated to a yellow solid. This solid was triturated with MeOH (ca. 75 mL), filtered and washed with MeOH and then air-dried. Methyl 2-chloro-3-fluoro-6-(methylsulfonyl)benzoate was obtained as a white solid (5.04 g, 49%). $^1$H NMR (400 MHz, CDCl$_3$): δ 8.00-7.97 (m, 1H), 7.41-7.37 (m, 1H), 4.03 (s, 3H), 3.18 (s, 3H).

Step F: Preparation of methyl 2-chloro-3-(3-cyano-5-fluorophenoxy)-6-(methylsulfonyl)benzoate: Methyl 2-chloro-3-fluoro-6-(methylsulfonyl)benzoate (200 mg, 0.75 mmol) was treated with 3-fluoro-5-hydroxy-benzonitrile (205 mg, 1.5 mmol) and DMF (2.5 mL). The solution was treated with in a single portion with sodium bicarbonate (126 mg, 1.5 mmol) and the mixture was heated to 90° C. for 16 hours. The reaction was cooled, diluted with Et$_2$O and water, then separated. The aqueous was washed with Et$_2$O. The combined organics were washed with water, three times with 10% K$_2$CO$_3$, saturated NaCl, dried over Na$_2$SO$_4$ and concentrated in vacuo to an light orange solid (262 mg, 91%). $^1$H NMR (400 MHz, CDCl$_3$): δ 7.99 (d, 1H), 7.25-7.22 (m, 1H), 7.19 (d, 1H), 7.10-7.09 (m, 1H), 7.03-7.00 (dt, 1H), 4.04 (s, 3H), 3.21 (s, 3H).

Step G: Preparation of 3-((4-chloro-1,1-dioxido-3-oxo-2,3-dihydrobenzo[b]thiophen-5-yl)oxy)-5-fluorobenzonitrile: Sodium hydride (60% in mineral oil, 81 mg, 2.0 mmol) was rinsed with three times with hexane, then resuspended in tetrahydrofuran (3.5 mL). The suspension was cooled to 0° C. and treated dropwise with a solution of methyl 2-chloro-3-(3-cyano-5-fluorophenoxy)-6-(methylsulfonyl)benzoate (260 mg, 0.68 mmol) in tetrahydrofuran (3.7 mL). After the addition, the mixture was removed from the ice bath and stirred at ambient temperature for 2 hours. The reaction was quenched with 10% KHSO$_4$ to about pH 2, and concentrated in vacuo to remove volatile solvents. Ethyl acetate was added, the solids were redissolved and the pH of the aqueous was adjusted to about 3-4 with 10% KHSO$_4$. After separation, the aqueous was washed twice with ethyl acetate, then the combined organics were washed twice with water, saturated NaCl, dried over Na$_2$SO$_4$ and concentrated in vacuo to a pale yellow solid (183 mg, 77%). $^1$H NMR (400 MHz, CDCl$_3$): δ 7.95 (d, 1H), 7.56 (d, 1H), 7.24-7.21 (m, 1H), 7.05-7.04 (m, 1H), 6.99-6.96 (dt, 1H), 4.21 (s, 2H).

Step H: Preparation of 3-((4-chloro-2,2-difluoro-1,1-dioxido-3-oxo-2,3-dihydrobenzo[b]thiophen-5-yl)oxy)-5-fluorobenzonitrile: A solution of 3-((4-chloro-1,1-dioxido-3-oxo-2,3-dihydrobenzo[b]thiophen-5-yl)oxy)-5-fluorobenzonitrile (70 mg, 0.20 mmol) in acetonitrile (1.15 mL) was treated with Selectfluor® (211 mg, 0.60 mmol) and sodium carbonate (63.3 mg, 0.60 mmol) and the resulting suspension was stirred at ambient temperature for 2 hours. The mixture was diluted with water and ethyl acetate and then separated. The aqueous was washed with ethyl acetate. The combined organics were washed with saturated NaHCO$_3$, saturated NaCl, dried over Na$_2$SO$_4$ and concentrated in vacuo to a light yellow film. The crude product was chromatographed on SiO$_2$ eluting with a gradient of ethyl acetate/hexane. 3-((4-Chloro-2,2-difluoro-1,1-dioxido-3-oxo-2,3-dihydrobenzo[b]thiophen-5-yl)oxy)-5-fluorobenzonitrile was obtained as a yellow solid (111 mg, quant). 3-((4-Chloro-2,2-difluoro-1,1-dioxido-3-oxo-2,3-dihydrobenzo[b]thiophen-5-yl)oxy)-5-fluorobenzonitrile was observed as about 4:1 mixture of ketone and hydrate in CDCl$_3$ and both sets of signals are described together below. $^1$H NMR (400 MHz, CDCl$_3$): δ 8.01 (d, 1H), 7.83 (d, 0.25H), 7.62 (d, 1H), 7.32-7.28 (m, 1.2H), 7.14-7.11 (m, 1.2H), 7.07-7.00 (m, 1.3H).

Step I: Preparation of (R)-3-((4-chloro-2,2-difluoro-3-hydroxy-1,1-dioxido-2,3-dihydrobenzo[b]thiophen-5-yl)oxy)-5-fluorobenzonitrile: 3-((4-Chloro-2,2-difluoro-1,1-dioxido-3-oxo-2,3-dihydrobenzo[b]thiophen-5-yl)oxy)-5-fluorobenzonitrile (107 mg, 0.28 mmol) was dissolved in dichloromethane (freshly sparged with nitrogen, 1.25 mL) and the solution was treated with triethylamine (77 μL, 0.55 mmol) and formic acid (31 μL, 0.83 mmol). This solution was cooled to 0° C. and treated with a pre-cooled (0° C.) solution of (R,R)-Ts-DENEB™ (1.8 mg, 2.8 μmol) dissolved in dichloromethane (1.25 mL). The resultant suspension was placed in the refrigerator and allowed to stand at 4° C. for 30 hours. The reaction was concentrated with a stream of nitrogen gas, then chromatographed on SiO$_2$ eluting with a gradient of ethyl acetate/chloroform. (R)-3-((4-Chloro-2,2-difluoro-3-hydroxy-1,1-dioxido-2,3-dihydrobenzo[b]thiophen-5-yl)oxy)-5-fluorobenzonitrile was obtained as light yellow oil which slowly solidified (116 mg, quant., >88% ee by Mosher ester analysis). LCMS ESI (−) m/z 388, 390 (M−H); $^1$H NMR (400 MHz, CDCl$_3$): δ 7.82 (d, 1H), 7.32 (d, 1H), 7.25-7.23 (m, 1H), 7.12-7.10 (m, 1H), 7.03-7.00 (dt, 1H), 5.44 (d, 1H), 3.39-3.25 (m, 1H).

Example 86

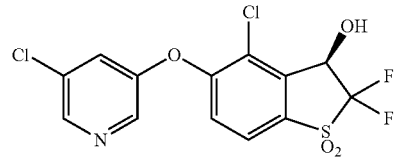 [SMILES: O=S1(=O)c2ccc(Oc3cncc(Cl)c3)c(Cl)c2[C@@H](O)C1(F)F]

(R)-4-Chloro-5-((5-chloropyridin-3-yl)oxy)-2,2-difluoro-3-hydroxy-2,3-dihydrobenzo[b]thiophene 1,1-dioxide (Compound 86)

Prepared analogously as described in Example 85 utilizing 5-chloropyridin-3-ol in Step F. $^1$H NMR (400 MHz, CDCl$_3$): δ 8.50 (d, 1H), 8.33 (d, 1H), 7.78 (d, 1H), 7.41-7.40 (m, 1H), 7.22 (d, 1H), 5.47-5.42 (m, 1H), 3.45 (d, 1H).

Example 87

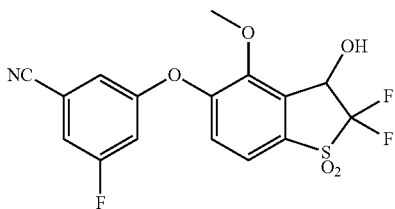 [SMILES: COc1c(Oc2cc(F)cc(C#N)c2)ccc2c1C(O)C(F)(F)S2(=O)=O]

3-((2,2-Difluoro-3-hydroxy-4-methoxy-1,1-dioxido-2,3-dihydrobenzo[b]thiophen-5-yl)oxy)-5-fluorobenzonitrile (Compound 87)

Step A: Preparation of methyl 3-(3-cyano-5-fluorophenoxy)-2-fluoro-6-(methylsulfonyl)benzoate: Prepared analogously as described in Example 1, Steps A-F utilizing 2,3-difluorobenzoic acid in Step A. $^1$H NMR (400 MHz, CDCl$_3$): δ 7.90 (dd, 1H), 7.31-7.27 (dd, 1H), 7.24-7.21 (m, 1H), 7.12-7.11 (m, 1H), 7.04-7.01 (m, 1H), 4.02 (s, 3H), 3.27 (s, 3H).

Step B: Preparation of 3-fluoro-5-((4-methoxy-1,1-dioxido-3-oxo-2,3-dihydrobenzo[b]thiophen-5-yl)oxy)benzonitrile: Sodium hydride (60% in mineral oil, 79 mg, 2.0 mmol) was washed three times with hexane, then resuspended in tetrahydrofuran (3.4 mL). The suspension was cooled to 0° C. and treated dropwise with a solution of methyl 3-(3-cyano-5-fluorophenoxy)-2-fluoro-6-(methylsulfonyl)benzoate (242 mg, 0.66 mmol) dissolved in tetrahydrofuran (3.4 mL). After the addition, the mixture was removed from the ice bath and stirred at ambient temperature for 60 hours. The reaction was quenched with methanol, then 10% KHSO$_4$ was added to adjust pH to about 2, and concentrated in vacuo. Ethyl acetate was added, then the pH of the aqueous was adjusted to about 3-4 with saturated NaHCO$_3$. The layers were separated and the aqueous was washed twice with ethyl acetate. The combined organics were washed twice with water, saturated NaCl, dried over Na$_2$SO$_4$ and concentrated in vacuo to yellow oil. The crude product was chromatographed on SiO$_2$ eluting with a gradient of ethyl acetate/hexane to give two products. The crude material was carried forward as a mixture (151 mg).

Step C: Preparation of 3-((2,2-difluoro-4-methoxy-1,1-dioxido-3-oxo-2,3-dihydrobenzo[b]thiophen-5-yl)oxy)-5-fluorobenzonitrile: A solution of 3-fluoro-5-((4-methoxy-1,1-dioxido-3-oxo-2,3-dihydrobenzo[b]thiophen-5-yl)oxy)benzonitrile (151 mg, 0.45 mmol) in acetonitrile (2.6 mL) was treated with Selectfluor® (479 mg, 1.35 mmol) and sodium carbonate (143 mg, 1.35 mmol) and the resulting suspension was stirred at ambient temperature for 16 hours. Additional Selectfluor® (160 mg, 0.45 mmol) was added and the mixture was stirred at ambient temperature for an additional 2 hours. The reaction mixture was diluted with water and ethyl acetate and then separated. The aqueous was washed with ethyl acetate. The combined organics were washed with saturated NaHCO$_3$, saturated NaCl, dried over Na$_2$SO$_4$ and concentrated in vacuo to yellow oil. The crude product was chromatographed on SiO$_2$ eluting with a gradient of ethyl acetate/hexane. The sample was not sufficiently purified by this method. The mixture was re-chromatographed on SiO$_2$ eluting with a gradient of methylene chloride/chloroform then with ethyl acetate/chloroform. 3-((2,2-Difluoro-4-methoxy-1,1-dioxido-3-oxo-2,3-dihydrobenzo[b]thiophen-5-yl)oxy)-5-fluorobenzonitrile was obtained as a white solid (75 mg, 43%). $^1$H NMR (400 MHz, CDCl$_3$): δ 7.78 (d, 1H), 7.66 (d, 1H), 7.25-7.21 (m, 1H), 7.07-7.06 (m, 1H), 6.98-6.94 (m, H), 4.07 (s, 3H).

Step D: Preparation of 3-((2,2-difluoro-3-hydroxy-4-methoxy-1,1-dioxido-2,3-dihydrobenzo[b]thiophen-5-yl)oxy)-5-fluorobenzonitrile: 3-((2,2-Difluoro-4-methoxy-1,1-dioxido-3-oxo-2,3-dihydrobenzo[b]thiophen-5-yl)oxy)-5-fluorobenzonitrile (28.6 mg, 0.07 mmol) was dissolved in a mixture of MeOH (0.28 mL) and ethyl acetate (0.28 mL), cooled to 0° C. and treated with sodium borohydride (5.5 mg, 0.15 mmol). The mixture was stirred at 0° C. and allowed to warm to ambient temperature with the bath overnight. The reaction was cooled to 0° C. and treated with 1N KHSO$_4$ and stirred for 20 minutes. The reaction was neutralized with saturated NaHCO$_3$, diluted with ethyl acetate and separated. The aqueous was washed with ethyl acetate and the combined organics were washed with saturated NaHCO$_3$, saturated NaCl, dried over Na$_2$SO$_4$ and concentrated in vacuo. The crude product was chromatographed on silica gel eluting with a gradient of ethyl acetate/hexane. 3-((2,2-Difluoro-3-hydroxy-4-methoxy-1,1-dioxido-2,3-dihydrobenzo[b]thiophen-5-yl)oxy)-5-fluorobenzonitrile was obtained as a white solid (11 mg, 38%). LCMS ESI (−) m/z 430 (M+HCOOH-H); $^1$H NMR (400 MHz, CDCl$_3$): δ 7.62 (d, 1H), 7.32 (d, 1H), 7.21-7.18 (m, 1H), 7.08-7.06 (m, 1H), 6.97-6.93 (m, 1H), 5.47-5.43 (m, 1H), 4.02 (s, 3H), 3.10-3.08 (m, 1H).

Example 88

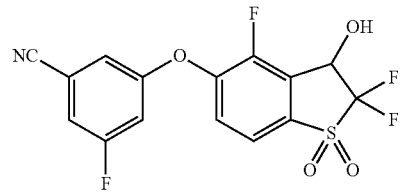 [SMILES: N#Cc1cc(F)cc(Oc2ccc3c(c2F)C(O)C(F)(F)S3(=O)=O)c1]

3-Fluoro-5-((2,2,4-trifluoro-3-hydroxy-1,1-dioxido-2,3-dihydrobenzo[b]thiophen-5-yl)oxy)benzonitrile (Compound 88)

Step A: Preparation of methyl 3-(3-cyano-5-fluorophenoxy)-2-fluoro-6-(methylsulfonyl)benzoate: Prepared analogously as described in Example 1, Steps A-F utilizing 2,3-difluorobenzoic acid in Step A. $^1$H NMR (400 MHz, CDCl$_3$): δ 7.90 (dd, 1H), 7.31-7.27 (dd, 1H), 7.24-7.21 (m, 1H), 7.12-7.11 (m, 1H), 7.04-7.01 (m, 1H), 4.02 (s, 3H), 3.27 (s, 3H).

Step B: Preparation of 3-fluoro-5-((4-fluoro-1,1-dioxido-3-oxo-2,3-dihydrobenzo[b]thiophen-5-yl)oxy)benzonitrile: Sodium hydride (60% in mineral oil, 79 mg, 2.0 mmol) was washed three times with hexane, then resuspended in tetrahydrofuran (3.4 mL). The suspension was cooled to 0° C. and treated dropwise with a solution of methyl 3-(3-cyano-5-fluorophenoxy)-2-fluoro-6-(methylsulfonyl)benzoate (242 mg, 0.66 mmol) in tetrahydrofuran (3.4 mL). After the addition, the mixture was removed from the ice bath and stirred at ambient temperature for 60 hours. The reaction was quenched with methanol, then 10% KHSO$_4$ was added to adjust pH to about 2, and concentrated in vacuo. Ethyl acetate was added, then the pH of the aqueous was adjusted to about 3-4 with saturated NaHCO$_3$. The layers were separated and the aqueous was washed twice with ethyl acetate. The combined organics were washed twice with water, saturated NaCl, dried over Na$_2$SO$_4$ and concentrated in vacuo to a yellow oil. The crude product was chromatographed on SiO₂ eluting with a gradient of ethyl acetate/hexane to give two products, which was carried forward as a mixture (151 mg).

Step C: Preparation of 3-fluoro-5-((2,2,4-trifluoro-1,1-dioxido-3-oxo-2,3-dihydrobenzo[b]thiophen-5-yl)oxy)benzonitrile: A solution of (3-fluoro-5-((4-fluoro-1,1-dioxido-3-oxo-2,3-dihydrobenzo[b]thiophen-5-yl)oxy)benzonitrile (151 mg, 0.45 mmol) in acetonitrile (2.6 mL) was treated with Selectfluor® (479 mg, 1.35 mmol) and sodium carbonate (143 mg, 1.35 mmol) and the resulting suspension was stirred at ambient temperature for 16 hours. Additional Selectfluor® (160 mg, 0.45 mmol) was added and the mixture was stirred at ambient temperature for an additional 2 hours. The reaction mixture was diluted with water and ethyl acetate and then separated. The aqueous was washed with ethyl acetate. The combined organics were washed with saturated NaHCO₃, saturated NaCl, dried over Na₂SO₄ and concentrated in vacuo to yellow oil. The crude product was chromatographed on SiO₂ eluting with a gradient of ethyl acetate/hexane. The mixture was re-chromatographed on SiO₂ eluting with a gradient of methylene chloride/chloroform then with ethyl acetate/chloroform. 3-Fluoro-5-((2,2,4-trifluoro-1,1-dioxido-3-oxo-2,3-dihydrobenzo[b]thiophen-5-yl)oxy)benzonitrile was isolated as a yellow film (16 mg, 10%). ¹H NMR (400 MHz, CDCl₃): δ 7.92 (d, 1H), 7.78-7.74 (m, 1H), 7.29 (d, 1H), 7.16-7.14 (m, 1H), 7.09-7.05 (m, 1H).

Step D: Preparation of 3-fluoro-5-((2,2,4-trifluoro-3-hydroxy-1,1-dioxido-2,3-dihydrobenzo[b]thiophen-5-yl)oxy)benzonitrile: 3-Fluoro-5-((2,2,4-trifluoro-1,1-dioxido-3-oxo-2,3-dihydrobenzo[b]thiophen-5-yl)oxy)benzonitrile (16 mg, 0.04 mmol) was dissolved in dichloromethane (freshly sparged with nitrogen gas, 0.2 mL) and the solution was treated with triethylamine (12 μL, 0.09 mmol) and formic acid (4.9 μL, 0.13 mmol). This solution was cooled to 0° C. and treated with a pre-cooled (0° C.) solution of (R,R)-Ts-DENEB (0.3 mg, 0.4 μmol) dissolved in dichloromethane (0.2 mL). The resultant suspension was placed in the refrigerator and allowed to stand at 4° C. for 102 hours. The mixture was concentrated in vacuo and chromatographed on silica gel eluting with a gradient of ethyl acetate/methylene chloride. 3-Fluoro-5-((2,2,4-trifluoro-3-hydroxy-1,1-dioxido-2,3-dihydrobenzo[b]thiophen-5-yl)oxy)benzonitrile was obtained as a colorless film (5 mg, 31%). LCMS ESI (−) m/z 418 (M+HCOOH-H); ¹H NMR (400 MHz, CDCl₃): δ 7.72 (d, 1H), 7.44-7.40 (m, 1H), 7.25-7.22 (m, 1H), 7.13-7.10 (m, 1H), 7.05-7.01 (m, 1H), 5.51 (d, 1H).

Example 89

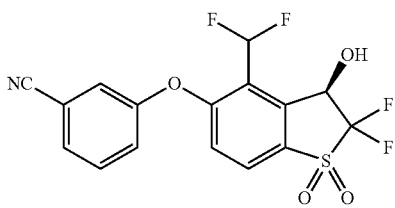 [SMILES: N#Cc1cccc(Oc2ccc3c(c2C(F)F)[C@@H](O)C(F)(F)S3(=O)=O)c1]

(R)-3-((4-(difluoromethyl)-2,2-difluoro-3-hydroxy-1,1-dioxido-2,3-dihydrobenzo[b]thiophen-5-yl)oxy)benzonitrile (Compound 89)

Step A: Preparation of 3-((4-(difluoromethyl)-2,2-difluoro-1,1-dioxido-3-oxo-2,3-dihydrobenzo[b]thiophen-5-yl)oxy)benzonitrile: Prepared analogously as described in Example 3, Steps A-G utilizing 3-hydroxybenzonitrile in Step E. ¹H NMR (400 MHz, CDCl₃): δ 8.14 (d, 1H), 7.68 (t, 1H), 7.64-7.59 (m, 2H), 7.52 (d, 1H), 7.42-7.40 (m, 1H), 7.37-7.33 (m, 1H).

Step B: Preparation of (R)-3-((4-(difluoromethyl)-2,2-difluoro-3-hydroxy-1,1-dioxido-2,3-dihydrobenzo[b]thiophen-5-yl)oxy)benzonitrile: 3-((4-(Difluoromethyl)-2,2-difluoro-1,1-dioxido-3-oxo-2,3-dihydrobenzo[b]thiophen-5-yl)oxy)benzonitrile (11.7 mg, 0.03 mmol) was added as a solid to a pre-cooled (0° C.) solution of triethylamine (8.5 μL, 0.06 mmol), formic acid (3.4 μL, 0.09 mmol) and (R,R)-Ts-DENEB™ (0.2 mg, 0.3 μmol) in dichloromethane (freshly sparged with nitrogen gas, 0.2 mL). The resultant suspension was placed in the refrigerator and allowed to stand at 4° C. for 48 hours. The solvent was removed in a stream of nitrogen gas and the crude product was chromatographed on SiO₂ eluting with a gradient of ethyl acetate/hexane. (R)-3-((4-(Difluoromethyl)-2,2-difluoro-3-hydroxy-1,1-dioxido-2,3-dihydrobenzo[b]thiophen-5-yl)oxy)benzonitrile was isolated as a white semi-solid (7 mg, 59%). ¹H NMR (400 MHz, CDCl₃): δ 7.92 (d, 1H), 7.62-7.57 (m, 2H), 7.42-7.40 (m, 1H), 7.35-7.31 (m, 1H), 7.28 (t, J=53 Hz, 1H), 7.11 (d, 1H), 5.69-5.65 (m, 1H), 3.33-3.32 (m, 1H).

Example 90

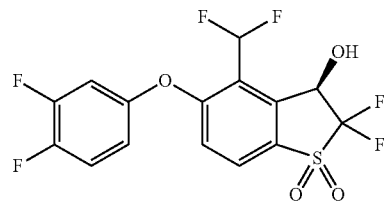 [SMILES: O=S1(=O)c2ccc(Oc3ccc(F)c(F)c3)c(C(F)F)c2[C@@H](O)C1(F)F]

(R)-4-(Difluoromethyl)-5-(3,4-difluorophenoxy)-2,2-difluoro-3-hydroxy-2,3-dihydrobenzo[b]thiophene 1,1-dioxide (Compound 90)

Prepared analogously as described in Example 89 utilizing 3,4-difluorophenol in Example 3, Step E. ¹H NMR (400 MHz, CDCl₃+CD₃OD): δ 7.80 (d, 1H), 7.23-7.15 (m, 1H), 7.20 (t, 1H), 7.02 (d, 1H), 6.94-6.88 (m, 1H), 6.80-6.75 (m, 1H), 5.50 (d, 1H).

Example 91

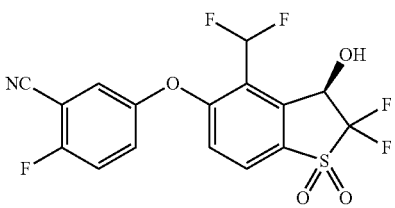 [SMILES: N#Cc1cc(Oc2ccc3c(c2C(F)F)[C@@H](O)C(F)(F)S3(=O)=O)ccc1F]

(R)-5-((4-(Difluoromethyl)-2,2-difluoro-3-hydroxy-1,1-dioxido-2,3-dihydrobenzo[b]thiophen-5-yl)oxy)-2-fluorobenzonitrile (Compound 91)

Prepared analogously as described in Example 89 utilizing 2-fluoro-5-hydroxybenzonitrile in Example 3, Step E. ¹H NMR (400 MHz, CDCl₃+CD₃OD): δ 7.83 (d, 1H), 7.33-7.23 (m, 3H), 7.18 (t, 1H), 7.01 (d, 1H), 5.51-5.48 (m, 1H).

Example 92

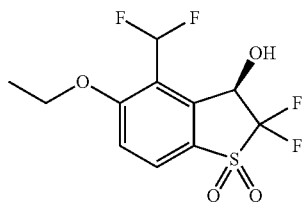 [SMILES: CCOc1ccc2c(c1C(F)F)[C@@H](O)C(F)(F)S2(=O)=O]

(R)-4-(Difluoromethyl)-5-ethoxy-2,2-difluoro-3-hydroxy-2,3-dihydrobenzo[b]thiophene 1,1-dioxide (Compound 92)

Step A: Preparation of 2-(difluoromethyl)-3-ethoxy-6-(methylsulfonyl)benzonitrile: 2-(Difluoromethyl)-3-fluoro-6-(methylsulfonyl)benzonitrile (Example 3, Step D) (200 mg, 0.80 mmol) was dissolved in tetrahydrofuran (1.6 mL) and absolute EtOH (1.6 mL), then the mixture was treated with 3N NaOH (0.27 mL, 0.80 mmol) and stirred at ambient temperature for 90 minutes. The mixture was neutralized with 10% citric acid (0.29 mL) and the volatile solvents were removed in a stream of nitrogen gas. The residue was redissolved in ethyl acetate and water and then separated. The aqueous was washed with ethyl acetate and the combined organics were washed with saturated NaHCO₃, saturated NaCl, dried over Na₂SO₄ and concentrated in vacuo. 2-(Difluoromethyl)-3-ethoxy-6-(methylsulfonyl)benzonitrile was isolated as an off-white solid (181 mg, 82%). ¹H NMR (400 MHz, CDCl₃): δ 8.27 (d, 1H), 7.28 (d, 1H), 7.18 (t, 1H), 4.25 (q, 2H), 3.31 (s, 3H), 1.52 (t, 3H).

Step B: Preparation of 4-(difluoromethyl)-5-ethoxy-2,2-difluorobenzo[b]thiophen-3(2H)-one 1,1-dioxide: Prepared analogously as described in Example 3, Steps F and G, utilizing 2-(difluoromethyl)-3-ethoxy-6-(methylsulfonyl)benzonitrile in Step F. ¹H NMR (400 MHz, CDCl₃): δ 8.15 (d, 1H), 7.61 (d, 1H), 7.52 (t, 1H), 4.30 (q, 2H), 1.55 (t, 3H).

Step C: Preparation of (R)-4-(difluoromethyl)-5-ethoxy-2,2-difluoro-3-hydroxy-2,3-dihydrobenzo[b]thiophene 1,1-dioxide: Prepared analogously as described in Example 89, Step B utilizing 4-(difluoromethyl)-5-ethoxy-2,2-difluorobenzo[b]thiophen-3(2H)-one 1,1-dioxide (96%). ¹H NMR (400 MHz, CDCl₃): δ 7.93 (d, 1H), 7.24 (d, 1H), 7.21 (t, 1H), 5.63-5.58 (m, 1H), 4.23 (q, 2H), 2.94-2.89 (m, 1H), 1.51 (t, 3H).

Example 93

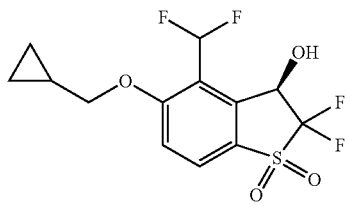 [SMILES: O=S1(=O)c2ccc(OCC3CC3)c(C(F)F)c2[C@@H](O)C1(F)F]

(R)-5-(Cyclopropylmethoxy)-4-(difluoromethyl)-2,2-difluoro-3-hydroxy-2,3-dihydrobenzo[b]thiophene 1,1-dioxide (Compound 93)

Step A: Preparation of 3-(cyclopropylmethoxy)-2-(difluoromethyl)-6-(methylsulfonyl)benzonitrile: 2-(Difluoromethyl)-3-fluoro-6-methylsulfonyl-benzonitrile (Example 3, Step D) (200 mg, 0.80 mmol) was added to a solution of tetrahydrofuran (1.6 mL) and cyclopropanemethanol (174 mg, 2.4 mmol). The mixture was treated with 3N NaOH (0.27 mL, 0.80 mmol), then stirred at ambient temperature for 16 hours. The reaction was neutralized with 10% KHSO₄ (0.29 mL) and the solvent was removed with a stream of nitrogen gas. The residue was redissolved in ethyl acetate and water and then separated. The aqueous was washed with ethyl acetate and the combined organics were washed with saturated NaHCO₃, saturated NaCl, dried over Na₂SO₄ and concentrated in vacuo. 3-(Cyclopropylmethoxy)-2-(difluoromethyl)-6-(methylsulfonyl)benzonitrile was obtained as an off-white solid (187 mg, 77%). ¹H NMR (400 MHz, CDCl₃): δ 8.25 (d, 1H), 7.25 (d, 1H), 7.22 (t, 1H), 4.02 (d, 2H), 3.31 (s, 3H), 1.35-1.24 (m, 1H), 0.75-0.70 (m, 2H), 0.43-0.39 (m, 2H).

Step B: Preparation of 5-(cyclopropylmethoxy)-4-(difluoromethyl)-2,2-difluorobenzo[b]thiophen-3(2H)-one 1,1-dioxide: Prepared analogously as described in Example 3, Steps F and G, utilizing 3-(cyclopropylmethoxy)-2-(difluoromethyl)-6-(methylsulfonyl)benzonitrile in Step F. ¹H NMR (400 MHz, CDCl₃): δ 8.13 (d, 1H), 7.59 (d, 1H), 7.54 (t, 1H), 4.10 (d, 2H), 1.38-1.23 (m, 1H), 0.76-0.69 (m, 2H), 0.47-0.41 (m, 2H).

Step C: Preparation of (R)-5-(cyclopropylmethoxy)-4-(difluoromethyl)-2,2-difluoro-3-hydroxy-2,3-dihydrobenzo[b]thiophene 1,1-dioxide: Prepared analogously as described in Example 89, Step B utilizing 5-(cyclopropylmethoxy)-4-(difluoromethyl)-2,2-difluorobenzo[b]thiophen-3(2H)-one 1,1-dioxide (11%). ¹H NMR (400 MHz, CDCl₃): δ 7.92 (d, 1H), 7.26 (t, 1H), 7.21 (d, 1H), 5.63-5.59 (m, 1H), 4.01-3.98 (m, 2H), 2.95-2.92 (m, 1H), 1.37-1.27 (m, 1H), 0.74-0.70 (m, 2H), 0.42-0.38 (m, 2H).

Example 94

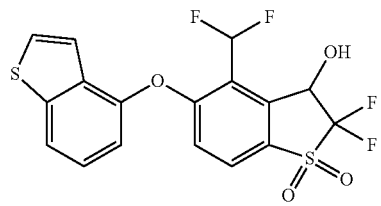 [SMILES: O=S1(=O)c2ccc(Oc3cccc4sccc34)c(C(F)F)c2C(O)C1(F)F]

5-(Benzo[b]thiophen-4-yloxy)-4-(difluoromethyl)-2,2-difluoro-3-hydroxy-2,3-dihydrobenzo[b]thiophene 1,1-dioxide (Compound 94)

Step A: Preparation of 3-(benzo[b]thiophen-4-yloxy)-2-(difluoromethyl)-6-(methylsulfonyl)benzonitrile: Sodium hydrogen carbonate (34 mg, 0.4 mmol) was added to a vial containing 2-(difluoromethyl)-3-fluoro-6-(methylsulfonyl)benzonitrile (50 mg, 0.2 mmol) and benzothiophen-4-ol (36 mg, 0.24 mmol) in DMF (1 mL). The vial was sealed and heated at 60° C. After 3 hours, the reaction mixture was partitioned between EtOAc and water. The EtOAc was washed with brine, dried over MgSO4, filtered, and evaporated. The residue was chromatographed on a Biotage 10 g SNAP column with a 10% to 80% EtOAc/hexane to afford 3-(benzo[b]thiophen-4-yloxy)-2-(difluoromethyl)-6-(methylsulfonyl)benzonitrile (55 mg, 0.14 mmol, 72% yield).

Step B: Preparation of 5-(benzo[b]thiophen-4-yloxy)-4-(difluoromethyl)benzo[b]thiophen-3(2H)-one 1,1-dioxide: Sodium hydride (60%, 16.8 mg, 0.42 mmol) was added to a solution of 3-(benzothiophen-4-yloxy)-2-(difluoromethyl)-6-(methylsulfonyl)benzonitrile (53 mg, 0.14 mmol) in tetrahydrofuran (5 mL). Gas evolution was observed, along with a color change from colorless to orange. After 30 minutes, the reaction mixture was evaporated, the residue was taken up in methanol (5 mL), and treated with hydrochloric acid (1.0 M, 5 mL, 5 mmol). The reaction mixture was concentrated and the aqueous slurry was partitioned between EtOAc and water. The EtOAc was washed with brine, dried over MgSO$_4$, filtered, and evaporated. The residue was chromatographed on a Biotage 10 g SNAP column with a 10% to 80% EtOAc:hexane gradient to afford 5-(benzo[b]thiophen-4-yloxy)-4-(difluoromethyl)benzo[b]thiophen-3(2H)-one 1,1-dioxide (12 mg, 0.03 mmol, 23% yield).

Step C: Preparation of 5-(benzo[b]thiophen-4-yloxy)-4-(difluoromethyl)-2,2-difluorobenzo[b]thiophen-3(2H)-one 1,1-dioxide: 1-(Chloromethyl)-4-fluoro-1-propyl-piperazine-1,4-diium ditetrafluoroborate (24.5 mg, 0.07 mmol) was added to a mixture of 5-(benzo[b]thiophen-4-yloxy)-4-(difluoromethyl)benzo[b]thiophen-3(2H)-one 1,1-dioxide (12 mg, 0.03 mmol) and sodium carbonate (7 mg, 0.07 mmol) in acetonitrile (3 mL). This was stirred at ambient temperature. After 1.5 hours, the reaction mixture was evaporated and the residue was partitioned between EtOAc and water. The EtOAc was washed with brine, dried over MgSO$_4$, filtered, and evaporated. The residue was chromatographed on a Biotage 10 g SNAP column with a 10% to 80% EtOAc/hexane to afford 5-(benzo[b]thiophen-4-yloxy)-4-(difluoromethyl)-2,2-difluorobenzo[b]thiophen-3(2H)-one 1,1-dioxide (10 mg, 0.024 mmol, 75% yield).

Step D: Preparation of 5-(benzo[b]thiophen-4-yloxy)-4-(difluoromethyl)-2,2-difluoro-3-hydroxy-2,3-dihydrobenzo[b]thiophene 1,1-dioxide: Sodium borohydride (1 mg, 0.03 mmol) was added to a solution of 5-(benzo[b]thiophen-4-yloxy)-4-(difluoromethyl)-2,2-difluorobenzo[b]thiophen-3 (2H)-one 1,1-dioxide (10 mg, 0.02 mmol) in methanol (2 mL). The resulting solution was stirred at ambient temperature. After 1 hour, the reaction mixture was evaporated and the residue was partitioned between EtOAc and water. The EtOAc was washed with brine, dried over MgSO4, filtered, and evaporated to afford Compound 94 (8.4 mg, 0.02 mmol, 85% yield). $^1$H NMR (400 MHz, CDCl$_3$): δ 7.85 (d, 1H), 7.78 (d, 1H), 7.50 (d, 1H), 7.47 (t, 1H), 7.42 (t, 1H), 7.17 (dd, 1H), 7.05 (dd, 1H), 6.96 (d, 1H), 5.73-5.67 (m, 1H), 3.20-3.13 (br s, 1H).

Example 95

5-((1H-Indazol-7-yl)oxy)-4-(difluoromethyl)-2,2-difluoro-3-hydroxy-2,3-dihydrobenzo[b]thiophene 1,1-dioxide (Compound 95)

5-((1H-Indazol-7-yl)oxy)-4-(difluoromethyl)-2,2-difluoro-3-hydroxy-2,3-dihydrobenzo[b]thiophene 1,1-dioxide was prepared according to Example 94, substituting 1H-indazol-7-ol for benzothiophen-4-ol in Step A. $^1$H NMR (400 MHz, CDCl$_3$): δ 8.17 (s, 1H), 7.83 (d, 1H), 7.72 (d, 1H), 7.42 (t, 1H), 7.22 (t, 1H), 7.12-7.07 (m, 2H), 5.69 (d, 1H).

Example 96

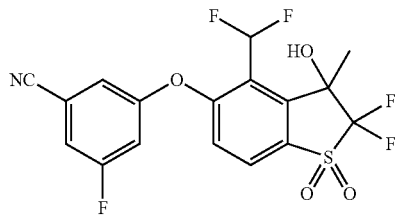

3-((4-(Difluoromethyl)-2,2-difluoro-3-hydroxy-3-methyl-1, 1-dioxido-2,3-dihydrobenzo[b]thiophen-5-yl)oxy)-5-fluorobenzonitrile (Compound 96)

3-((4-(Difluoromethyl)-2,2-difluoro-1,1-dioxido-3-oxo-2,3-dihydrobenzo[b]thiophen-5-yl)oxy)-5-fluorobenzonitrile was dissolved in toluene (0.26 mL) and treated with a solution of dimethyl zinc (1M in heptane, 0.14 mL, 0.14 mmol) and the mixture was stirred at 50° C. for 60 hours. The resulting heterogeneous reaction mixture was cooled to ambient temperature, quenched with saturated NH$_4$Cl and diluted with ethyl acetate. The layers were separated and the aqueous was washed twice with ethyl acetate. The combined organic layers were washed with saturated NaHCO$_3$, saturated NaCl, dried over Na$_2$SO$_4$ and concentrated in vacuo. The crude product mixture was chromatographed on SiO$_2$ eluting with a gradient of ethyl acetate/hexane. The desired product was recovered as a colorless film which was redissolved in methylene chloride, treated with hexanes and concentrated to form an off-white solid (19 mg, 75%). LCMS ESI (−) m/z 418 (M−H); $^1$H NMR (400 MHz, CDCl$_3$): δ 7.95-7.90 (d, 1H), 7.65 (t, 1H), 7.25-7.22 (m, 1H), 7.22-7.18 (d, 1H), 7.13-7.11 (m, 1H), 7.08-7.04 (m, 1H), 3.73 (brd s, 1H), 1.91-1.88 (m, 3H).

Example 97

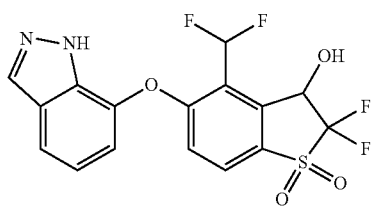 [SMILES: O=S1(=O)c2ccc(Oc3cccc4cn[nH]c34)c(C(F)F)c2C(O)C1(F)F]

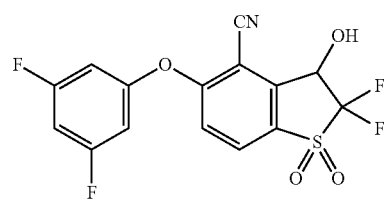 [SMILES: N#Cc1c(Oc2cc(F)cc(F)c2)ccc2c1C(O)C(F)(F)S2(=O)=O]

5-(3,5-Difluorophenoxy)-2,2-difluoro-3-hydroxy-2,3-dihydrobenzo[b]thiophene-4-carbonitrile 1,1-dioxide (Compound 97)

Compound 97 was prepared similarly according to Example 10. 3,5-Difluorophenol was substituted for 3-chloro-5-fluorophenol earlier in the synthesis. Purification was achieved by chromatography on silica using 0-15% EtOAc/CHCl$_3$ to afford Compound 97 as a beige solid (1.5 mg, 14%). LCMS ESI (−) (M−H) m/z 372; $^1$H NMR (400 MHz, CDCl$_3$): δ 7.97 (d, 1H), 7.20 (d, 1H), 6.87-6.81 (m, 1H), 6.76-6.69 (m, 2H), 5.55 (dd, 1H).

Example 98

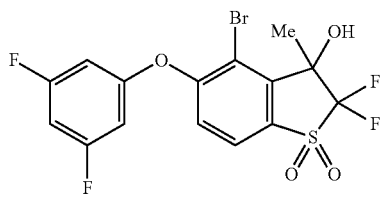 [SMILES: CC1(O)c2c(ccc(Oc3cc(F)cc(F)c3)c2Br)S(=O)(=O)C1(F)F]

4-Bromo-5-(3,5-difluorophenoxy)-2,2-difluoro-3-hydroxy-3-methyl-2,3-dihydrobenzo[b]thiophene 1,1-dioxide (Compound 98)

4-Bromo-5-(3,5-difluorophenoxy)-2,2-difluorobenzo[b]thiophen-3(2H)-one 1,1-dioxide was prepared similarly according to Example 8, Step A. 3,5-Difluorophenol was substituted for 3-chloro-5-fluorophenol earlier in the synthesis. A solution of 4-bromo-5-(3,5-difluorophenoxy)-2,2-difluorobenzo[b]thiophen-3(2H)-one 1,1-dioxide (77.0 mg, 0.18 mmol) in tetrahydrofuran (3.6 mL) at −50° C. was treated with methylmagnesium chloride (3.0 M in tetrahydrofuran, 80 µL, 0.24 mmol). After 30 minutes, additional methylmagnesium chloride (3.0 M in tetrahydrofuran, 80 µL, 0.24 mmol) was added over 5 minutes. The reaction mixture was allowed to warm to −30° C. and then quenched by the addition of 5 mL of saturated aqueous NH$_4$Cl. The reaction mixture was poured into 10 mL of water and extracted with 3×10 mL EtOAc. The combined organics were rinsed with 10 mL of brine, dried with MgSO$_4$, filtered, and concentrated to dryness. Purification was achieved by chromatography on silica using 5% to 20% EtOAc/hexane to afford Compound 98 as a thin film (24.3 mg, 30%). LCMS ESI (−) (M−H) m/z 439, 441; $^1$H NMR (400 MHz, CDCl$_3$): δ 7.78 (d, 1H), 7.16 (d, 1H), 6.75-6.69 (m, 1H), 6.62-6.54 (m, 2H), 3.04-2.98 (m, 1H), 1.95 (d, 3H).

Example 99

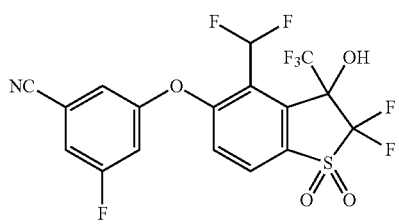

3-((4-(difluoromethyl)-2,2-difluoro-3-hydroxy-1,1-dioxido-3-(trifluoromethyl)-2,3-dihydrobenzo[b]thiophen-5-yl)oxy)-5-fluorobenzonitrile (Compound 99)

A solution of trimethyl(trifluoromethyl)silane solution (2.0 M in tetrahydrofuran, 150 µL, 0.30 mmol) and 3-[4-(difluoromethyl)-2,2-difluoro-1,1,3-trioxo-benzothiophen-5-yl]oxy-5-fluoro-benzonitrile (30.0 mg, 0.074 mmol) in tetrahydrofuran (350 µL) was treated with tetrabutylammonium fluoride (1.0 M in tetrahydrofuran, 7.4 µL, 0.0074 mmol) and stirred at 120° C. by microwave irradiation for 2 hours. The reaction mixture was poured into 10 mL of 1 M HCl and extracted with 3×15 mL EtOAc. The combined organics were rinsed with 10 mL of brine, dried with MgSO$_4$, filtered, and concentrated to dryness. Purification was achieved by chromatography on silica using 10-40% EtOAc/hexane to afford Compound 99 as a white solid (6.8 mg, 19%). LCMS ESI (−) (M−H) m/z 472; $^1$H NMR (400 MHz, CDCl$_3$): δ 8.03 (d, 1H), 7.57 (t, 1H), 7.37 (d, 1H), 7.29-7.25 (m, 1H), 7.17-7.14 (m, 1H), 7.08 (dt, 1H), 5.40-5.10 (m, 1H).

Example 100

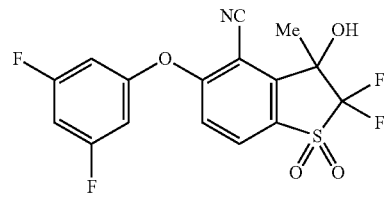 [SMILES: CC1(O)c2c(ccc(Oc3cc(F)cc(F)c3)c2C#N)S(=O)(=O)C1(F)F]

5-(3,5-Difluorophenoxy)-2,2-difluoro-3-hydroxy-3-methyl-2,3-dihydrobenzo[b]thiophene-4-carbonitrile 1,1-dioxide (Compound 100)

A solution of 4-bromo-5-(3,5-difluorophenoxy)-2,2-difluoro-3-hydroxy-3-methyl-2,3-dihydrobenzo[b]thiophene 1,1-dioxide (21.7 mg, 0.049 mmol) in 1-methyl-2-pyrrolidone (0.5 mL) was treated with copper (I) cyanide (5.7 mg, 0.064 mmol) and heated at 165° C. by microwave irradiation for 45 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-30% EtOAc/hexane to afford Compound 100 as a thin film (11.3 mg, 59%). LCMS ESI (−) (M−H) m/z 386; $^1$H NMR (400 MHz, CDCl$_3$): δ 7.93 (d, 1H), 7.13 (d, 1H), 6.83 (tt, 1H), 6.75-6.68 (m, 2H), 3.54 (s, 1H), 1.97 (d, 3H).

Example 101

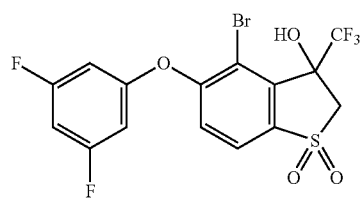 [SMILES: O=S1(=O)CC(O)(C(F)(F)F)c2c1ccc(Oc1cc(F)cc(F)c1)c2Br]

4-Bromo-5-(3,5-difluorophenoxy)-3-hydroxy-3-(trifluoromethyl)-2,3-dihydrobenzo[b]thiophene 1,1-dioxide (Compound 101)

Step A: Preparation of 2-bromo-3-fluoro-6-(methylthio) benzaldehyde: Glassware was flame-dried prior to reaction. A solution of 2-bromo-3-fluoro-6-methylsulfanyl-benzonitrile (480 mg, 1.95 mmol) in dichloromethane (19.5 mL) at 0° C. was treated with diisobutylaluminum hydride (~1.0 M in heptane, 3.9 mL, 3.9 mmol) by slow dropwise addition over 15 minutes. The reaction mixture was stirred at 0° C. until complete as shown by LCMS (~1 h) and then quenched by the addition of 8.5 mL of 10% aqueous HCl. The resulting mixture was stirred vigorously for 1 h, treated with 8.5 mL of 20% aqueous potassium sodium tartrate and stirred vigorously for an additional hour. The mixture was treated with 10% aqueous NaOH and extracted with 3×20 mL $CH_2Cl_2$. The combined organics were rinsed with 20 mL of brine, dried with $MgSO_4$, filtered, and concentrated. The residue (a yellow solid) was used without further purification.

Step B: Preparation of 1-(2-bromo-3-fluoro-6-(methylthio)phenyl)-2,2,2-trifluoroethan-1-ol: A solution of 2-bromo-3-fluoro-6-methylsulfanyl-benzaldehyde (470 mg, 1.89 mmol) and tetrabutylammonium fluoride (0.38 mL, 0.38 mmol) in THF (1.9 mL) at 0° C. was treated with trimethyl(trifluoromethyl)silane solution (~2.0 M in THF, 1.89 mL, 3.77 mmol) and stirred at 0° C. for 4 h. The reaction mixture was quenched by the addition of 5 mL of 1 M HCl and stirred for 30 minutes. Volatiles were removed by concentration under reduced pressure. The mixture was poured into 30 mL of water and extracted with 3×20 mL EtOAc. The combined organics were rinsed with 10 mL of brine, dried with $MgSO_4$, filtered, and concentrated. Purification was achieved by chromatography on silica using 10-20% EtOAc/hexane (346 mg, 57%).

Step C: Preparation of 1-(2-bromo-3-fluoro-6-(methylsulfonyl)phenyl)-2,2,2-trifluoroethan-1-ol: A solution of 1-(2-bromo-3-fluoro-6-methylsulfanyl-phenyl)-2,2,2-trifluoro-ethanol (346 mg, 1.08 mmol) in dichloromethane (10.8 mL) at 0° C. was treated with 3-chloroperbenzoic acid (668 mg, 2.71 mmol). The ice bath was removed and the reaction was stirred overnight at room temperature. The reaction mixture was partitioned with 10 mL of water and treated with sodium thiosulfate pentahydrate (269 mg, 1.08 mmol). The resulting mixture was left to stir for 30 minutes, poured into 20 mL of saturated aqueous $NaHCO_3$ and extracted with 3×20 mL EtOAc. The combined organics were rinsed with 10 mL of brine, dried with $MgSO_4$, filtered, and concentrated. Purification was achieved by chromatography on silica using 0-80% EtOAc/$CH_2Cl_2$ (349 mg, 92%).

Step D: Preparation of 1-(2-bromo-3-(3,5-difluorophenoxy)-6-(methylsulfonyl)phenyl)-2,2,2-trifluoroethan-1-ol: A solution of sodium bicarbonate (77 mg, 0.91 mmol), 1-(2-bromo-3-fluoro-6-methylsulfonyl-phenyl)-2,2,2-trifluoro-ethanol (320 mg, 0.91 mmol), and 3,5-difluorophenol (119 mg, 0.91 mmol) in DMF (3.65 mL) was heated to 80° C. for 2 h. The reaction mixture was poured into 30 mL of water and extracted with 3×20 mL $Et_2O$. The combined organics were rinsed with 10 mL of brine, dried with $MgSO_4$, filtered, and concentrated. Purification was achieved by chromatography on silica using 10-35% EtOAc/hexane.

Step E: Preparation of 1-(2-bromo-3-(3,5-difluorophenoxy)-6-(methylsulfonyl)phenyl)-2,2,2-trifluoroethan-1-one: A solution of 1-[2-bromo-3-(3,5-difluorophenoxy)-6-methylsulfonyl-phenyl]-2,2,2-trifluoro-ethanol (96 mg, 0.21 mmol) in dichloromethane (2.1 mL) at 25° C. was treated with (1,1-diacetoxy-3-oxo-1λ⁵-2-benziodoxol-1-yl) acetate (141 mg, 0.33 mmol) and stirred at 25° C. overnight. The reaction mixture was partitioned with 2 mL of water and treated with disodium dioxido-oxo-thioxo-λ⁶-sulfane pentahydrate (165.3 mg, 0.67 mmol). The resulting solution was stirred for 30 minutes. The reaction mixture was poured into 20 mL of saturated aqueous $NaHCO_3$ and extracted with 3×20 mL EtOAc. The combined organics were rinsed with 10 mL of brine, dried with $MgSO_4$, filtered, and concentrated. Purification was achieved by chromatography on silica using 10-30% EtOAc/hexane (34.1 mg, 36% yield).

Step F: Preparation of 4-bromo-5-(3,5-difluorophenoxy)-3-hydroxy-3-(trifluoromethyl)-2,3-dihydrobenzo[b]thiophene 1,1-dioxide: A solution of 1-[2-bromo-3-(3,5-difluorophenoxy)-6-methylsulfonyl-phenyl]-2,2,2-trifluoro-ethanone (34 mg, 0.074 mmol) in THF (0.74 mL) at 25° C. was treated with sodium hydride (2.7 mg, 0.11 mmol) and stirred at 25° C. until complete as shown by LCMS. The reaction mixture was poured into 10 mL of saturated aqueous $NH_4Cl$ and extracted with 3×20 mL EtOAc. The combined organics were rinsed with 10 mL of brine, dried with $MgSO_4$, filtered, and concentrated to dryness. Purification was achieved by chromatography on silica using 20-60% EtOAc/hexane to afford the desired product as a white solid (21.8 mg, 64%). LCMS ESI (−) (M−H) m/z 457, 459; $^1$H NMR (400 MHz, $CDCl_3$): δ 7.79 (d, 1H), 7.27 (d, 1H), 6.72 (tt, 1H), 6.62-6.55 (m, 2H), 4.71 (s, 1H), 4.16 (d, 1H), 3.83 (d, 1H).

Example 102

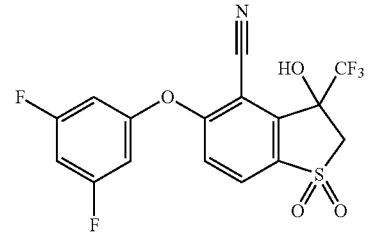 [SMILES: N#Cc1c(Oc2cc(F)cc(F)c2)ccc2c1C(O)(C(F)(F)F)CS2(=O)=O]

5-(3,5-Difluorophenoxy)-3-hydroxy-3-(trifluoromethyl)-2,3-dihydrobenzo[b]thiophene-4-carbonitrile 1,1-dioxide (Compound 102)

A solution of 4-bromo-5-(3,5-difluorophenoxy)-1,1-dioxo-3-(trifluoromethyl)-2H-benzothiophen-3-ol (18 mg, 0.039 mmol) in 1-methyl-2-pyrrolidone (0.5 mL) was treated with copper(I) cyanide (4.5 mg, 0.050 mmol) and stirred at 165° C. by microwave irradiation for 45 minutes. An additional portion of copper(I) cyanide (4.5 mg, 0.050 mmol) was added to the reaction mixture and it was subjected to heating at 175° C. by microwave irradiation for 45 minutes. The reaction mixture was poured into 30 mL of water and extracted with 3×10 mL $Et_2O$. The combined organics were rinsed with 10 mL of brine, dried with $MgSO_4$, filtered, and concentrated. Purification was achieved by chromatography on silica using 20-70% EtOAc/hexane to afford a white solid (9.8 mg, 62%). LCMS ESI (−) (M−H) m/z 404; $^1$H NMR (400 MHz, $CDCl_3$): δ 7.94 (d, 1H), 7.26 (d, 1H), 6.83 (tt, 1H), 6.76-6.69 (m, 2H), 4.26 (br s, 1H), 4.18 (d, 1H), 3.81 (d, 1H).

Example 103

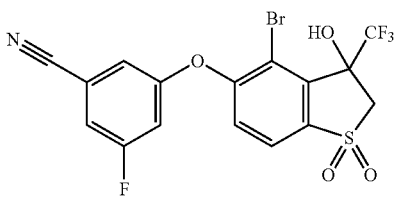 [SMILES: N#Cc1cc(F)cc(Oc2ccc3c(c2Br)C(O)(C(F)(F)F)CS3(=O)=O)c1]

3-((4-Bromo-3-hydroxy-1,1-dioxido-3-(trifluoromethyl)-2,3-dihydrobenzo[b]thiophen-5-yl)oxy)-5-fluorobenzonitrile (Compound 103)

Prepared similarly according to Example 101, Steps A-F, substituting 3,5-difluorophenol with 3-fluoro-5-hydroxybenzonitrile. Purification was achieved by chromatography on silica using 10-50% EtOAc/hexane. Compound 103 was isolated as a clear thin film (15.2 mg, 69%). LCMS ESI (−) (M−H) m/z 464, 466; $^1$H NMR (400 MHz, CDCl$_3$): δ 7.84 (d, 1H), 7.30 (d, 1H), 7.27-7.24 (m, 1H), 7.12-7.10 (m, 1H), 7.00 (dt, 1H), 4.63 (s, 1H), 4.18 (d, 1H), 3.85 (d, 1H).

Example 104

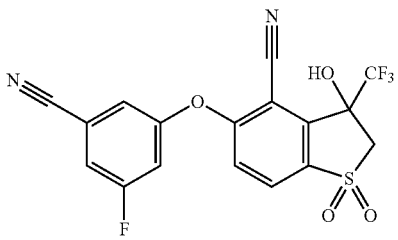 [SMILES: N#Cc1cc(F)cc(Oc2ccc3c(c2C#N)C(O)(C(F)(F)F)CS3(=O)=O)c1]

5-(3-Cyano-5-fluorophenoxy)-3-hydroxy-3-(trifluoromethyl)-2,3-dihydrobenzo[b]thiophene-4-carbonitrile 1,1-dioxide (Compound 104)

Prepared similarly according to Example 102. Purification was achieved by chromatography on silica using 20-60% EtOAc/hexane. Compound 104 was isolated as a clear thin film (2.3 mg, 19%). LCMS ESI (−) (M−H) m/z 411; $^1$H NMR (400 MHz, CDCl$_3$): δ 7.99 (d, 1H), 7.38-7.34 (m, 1H), 7.29-7.24 (m, 2H), 7.20-7.16 (dt, 1H), 4.75 (br s, 1H), 4.20 (d, 1H), 3.82 (d, 1H).

Example 105

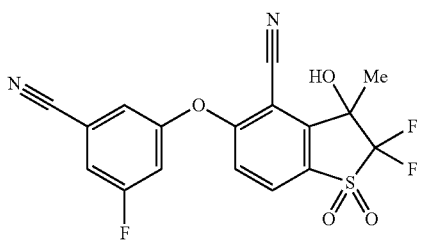 [SMILES: CC1(O)c2c(ccc(Oc3cc(F)cc(C#N)c3)c2C#N)S(=O)(=O)C1(F)F]

5-(3-Cyano-5-fluorophenoxy)-2,2-difluoro-3-hydroxy-3-methyl-2,3-dihydrobenzo[b]thiophene-4-carbonitrile 1,1-dioxide (Compound 105)

Step A: Preparation of 4-bromo-5-(3-bromo-5-fluorophenoxy)-2,2-difluoro-3-hydroxy-3-methyl-2,3-dihydrobenzo[b]thiophene 1,1-dioxide: Methylmagnesium chloride (~3.0 M in THF, 1.89 mL, 5.66 mmol) was mixed with lanthanum (III) chloride bis(lithium chloride) complex solution (0.6 M in THF, 11.1 mL, 6.66 mmol) and stirred at room temperature for 5 minutes. The resulting solution was cooled to −30° C. and then treated with 4-bromo-5-(3-bromo-5-fluoro-phenoxy)-2,2-difluoro-1,1-dioxo-benzothiophen-3-one (1.62 g, 3.33 mmol) in 10 mL of THF by slow dropwise addition over 20 minutes. Once the addition was complete, the reaction mixture was allowed to warm to −20° C. over 30 minutes. The reaction mixture was quenched by the addition of 10 mL of saturated aqueous NH$_4$Cl. The reaction mixture was poured into 30 mL of water and extracted with 3×30 mL EtOAc. The combined organics were rinsed with 10 mL of brine, dried with MgSO4, filtered, and concentrated to dryness. Purification was achieved by chromatography on silica using 15-20% EtOAc/hexane (769 mg, 46%).

Step B: Preparation of 5-(3-cyano-5-fluorophenoxy)-2,2-difluoro-3-hydroxy-3-methyl-2,3-dihydrobenzo[b]thiophene-4-carbonitrile 1,1-dioxide: A solution of 4-bromo-5-(3-bromo-5-fluoro-phenoxy)-2,2-difluoro-3-methyl-1,1-dioxo-benzothiophen-3-ol (32 mg, 0.064 mmol) in 1-methyl-2-pyrrolidone (1.3 mL) was treated with copper(I) cyanide (28.5 mg, 0.32 mmol) and stirred at 180° C. by microwave irradiation for 3 h. The reaction mixture was poured into 40 mL of water and extracted with 3×15 mL Et$_2$O. The combined organics were rinsed with 10 mL of brine, dried with MgSO$_4$, filtered, and concentrated to dryness. Purification was achieved by chromatography on silica using 10-30% EtOAc/hexane to afford Compound 105 as a white solid (13 mg, 52%). LCMS ESI (−) (M−H) m/z 393; $^1$H NMR (400 MHz, CDCl$_3$): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H).

Examples 106 and 107

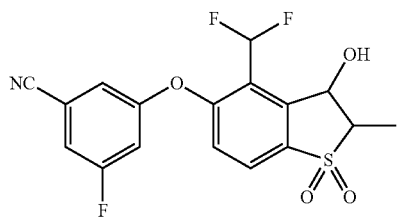 [SMILES: CC1C(O)c2c(ccc(Oc3cc(F)cc(C#N)c3)c2C(F)F)S1(=O)=O]

Isomer 1 of 3-((4-(difluoromethyl)-3-hydroxy-2-methyl-1,1-dioxido-2,3-dihydrobenzo[b]thiophen-5-yl)oxy)-5-fluorobenzonitrile (Compound 106) and isomer 2 of 3-((4-(difluoromethyl)-3-hydroxy-2-methyl-1,1-dioxido-2,3-dihydrobenzo[b]thiophen-5-yl)oxy)-5-fluorobenzonitrile (Compound 107)

Step A: Preparation of 3-((4-(difluoromethyl)-2-methyl-1,1-dioxido-3-oxo-2,3-dihydrobenzo[b]thiophen-5-yl)oxy)-5-fluorobenzonitrile: Prepared as described in Example 3

Step C to Step F, substituting sodium methanethiolate with sodium ethanethiolate in step C. LCMS ESI (−) m/z 380 (M−H).

Step B: Preparation of isomer 1 of 3-((4-(difluoromethyl)-3-hydroxy-2-methyl-1,1-dioxido-2,3-dihydrobenzo[b]thiophen-5-yl)oxy)-5-fluorobenzonitrile (Compound 106) and isomer 2 of 3-((4-(difluoromethyl)-3-hydroxy-2-methyl-1,1-dioxido-2,3-dihydrobenzo[b]thiophen-5-yl)oxy)-5-fluorobenzonitrile (Compound 107): A suspension of 3-((4-(difluoromethyl)-2-methyl-1,1-dioxido-3-oxo-2,3-dihydrobenzo[b]thiophen-5-yl)oxy)-5-fluorobenzonitrile (147 mg, 0.390 mmol) in methanol (4 mL) was treated with sodium borohydride (15 mg, 0.39 mmol) at ambient temperature. After stirring for 30 minutes, the reaction was quenched by slow addition of water. The mixture was partitioned between EtOAc and water. The aqueous layer was extracted with EtOAc. The combined organic layers were washed with brine, dried and concentrated. The residue was purified by flash chromatography on silica gel with 10-40% EtOAc/hexane to give Compound 106 (36 mg, 24) and Compound 107) (19 mg, 13%).

Data for isomer 1 of 3-((4-(difluoromethyl)-3-hydroxy-2-methyl-1,1-dioxido-2,3-dihydrobenzo[b]thiophen-5-yl)oxy)-5-fluorobenzonitrile (Compound 106): Retention time=1.52 minutes; LCMS ESI (+) (M+NH$_{4+}$) m/z 401; $^1$H NMR (400 MHz, CDCl$_3$): δ 7.89 (d, 1H), 7.27-7.24 (m, 1H), 7.21 (t, 1H), 7.16-7.11 (m, 2H), 7.06-7.02 (m, 1H), 5.34 (br s, 1H), 3.66-3.58 (m, 1H), 3.13 (br s, 1H), 1.55 (d, 3H).

Data for isomer 2 of 3-((4-(difluoromethyl)-3-hydroxy-2-methyl-1,1-dioxido-2,3-dihydrobenzo[b]thiophen-5-yl)oxy)-5-fluorobenzonitrile (Compound 107): Retention time=1.46 minutes; LCMS ESI (+) (M+NH$_4^+$) m/z 401; $^1$H NMR (400 MHz, DMSO-d6): δ 7.99 (d, 1H), 7.75-7.71 (m, 1H), 7.52-7.49 (m, 1H), 7.48-7.44 (m, 1H), 7.36 (d, 1H), 7.29 (t, 1H), 6.23 (d, 1H), 5.52 (t, 1H), 3.76-3.68 (m, 1H), 1.35 (d, 3H).

Example 108

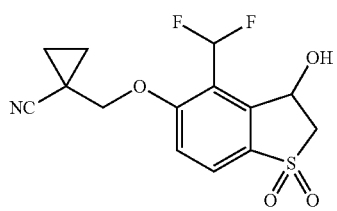 [SMILES: N#CC1(COc2ccc3c(c2C(F)F)C(O)CS3(=O)=O)CC1]

1-[[4-(difluoromethyl)-3-hydroxy-1,1-dioxo-2,3-dihydrobenzothiophen-5-yl]oxymethyl]cyclopropanecarbonitrile (Compound 108)

Step A: Preparation of 3-[(1-cyanocyclopropyl)methoxy]-2-(difluoromethyl)-6-methylsulfonyl-benzonitrile: 2-(Difluoromethyl)-3-fluoro-6-methylsulfonyl-benzonitrile (250 mg, 1.00 mmol) was added to a solution of THF (8 mL) and 1-(hydroxymethyl)cyclopropanecarbonitrile (195 mg, 2.01 mmol). The mixture was treated with 3 N NaOH (1.00 mL, 3.00 mmol) then stirred at ambient temperature for 16 hours. The reaction was partitioned between EtOAc and water. The aqueous layer was extracted with EtOAc. The combined organic layers were washed with brine, dried and concentrated. The residue was purified by flash chromatography on silica gel with 20-100% EtOAc/hexane to give 3-[(1-cyanocyclopropyl)methoxy]-2-(difluoromethyl)-6-methylsulfonyl-benzonitrile (248 mg, 76%). LCMS ESI (+) m/z 344 (M+NH$_4^+$).

Step B: Preparation of 1-[[4-(difluoromethyl)-1,1,3-trioxo-benzothiophen-5-yl]oxymethyl]cyclopropanecarbonitrile: Prepared as described in Example 3 Step F, substituting 3-(3-cyano-5-fluorophenoxy)-2-(difluoromethyl)-6-(methylsulfonyl)benzonitrile with 3-[(1-cyanocyclopropyl)methoxy]-2-(difluoromethyl)-6-methylsulfonyl-benzonitrile. LCMS ESI (−) m/z 326 (M−H).

Step C: 1-[[4-(difluoromethyl)-3-hydroxy-1,1-dioxo-2,3-dihydrobenzothiophen-5-yl]oxymethyl]cyclopropanecarbonitrile (Compound 108): Prepared as described in Example 15 substituting 5-(3-chloro-5-fluoro-phenoxy)-4-(difluoromethyl)-1,1-dioxo-benzothiophen-3-one with 1-[[4-(difluoromethyl)-1,1,3-trioxo-benzothiophen-5yl]oxymethyl]cyclopropanecarbonitrile. LCMS ESI (+) m/z 347 (M+NH$_4^+$);
$^1$H NMR (400 MHz, CDCl$_3$): δ 7.84 (d, 1H), 7.31 (t, 1H), 7.09 (d, 1H), 5.87-5.79 (m, 1H), 4.17-4.04 (m, 2H), 3.75-3.68 (m, 1H), 3.65-3.59 (m, 1H), 2.91-2.84 (m, 1H), 1.54-1.48 (m, 2H), 1.22-1.14 (m, 2H).

Example 109

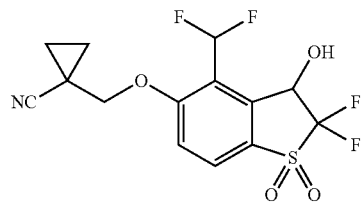 [SMILES: N#CC1(COc2ccc3c(c2C(F)F)C(O)C(F)(F)S3(=O)=O)CC1]

1-(((4-(difluoromethyl)-2,2-difluoro-3-hydroxy-1,1-dioxido-2,3-dihydrobenzo[b]thiophen-5-yl)oxy)methyl)cyclopropane-1-carbonitrile (Compound 109)

Prepared as described in Example 22 substituting 4-(difluoromethyl)-5-(3,5-difluorophenoxy)-1,1-dioxo-benzothiophen-3-one with 1-[[4-(difluoromethyl)-1,1,3-trioxo-benzothiophen-5-yl]oxymethyl]cyclopropanecarbonitrile. LCMS ESI (−) m/z 410 (M+HCO$_2^-$); $^1$H NMR (400 MHz, CDCl$_3$): δ 7.86 (d, 1H), 7.19 (t, 1H), 7.14 (d, 1H), 5.47 (d, 1H), 4.15-4.03 (m, 2H), 3.15 (s, 1H), 1.47-1.39 (m, 2H), 1.19-1.12 (m, 2H).

Example 110

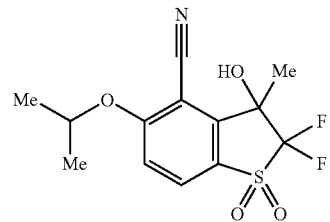 [SMILES: CC(C)Oc1ccc2c(c1C#N)C(C)(O)C(F)(F)S2(=O)=O]

2,2-Difluoro-3-hydroxy-5-isopropoxy-3-methyl-2,3-dihydrobenzo[b]thiophene-4-carbonitrile 1,1-dioxide (Compound 110)

Step A: Preparation of methyl 2-bromo-3-hydroxy-6-(methylsulfonyl)benzoate: A solution of methyl 2-bromo-3-fluoro-6-methylsulfonyl-benzoate (2.0 g, 6.43 mmol) in DMF (12.9 mL) was treated with potassium acetate (1.39 g, 14.1 mmol) and stirred at 100° C. for 6 h. The reaction mixture was poured into 200 mL of water containing 20 mL of 1 M HCl and extracted with 5×50 mL of 20% EtOAc in $Et_2O$. The combined organics were rinsed with 40 mL of brine, dried with $MgSO_4$, filtered, and concentrated to dryness. Purification was achieved by chromatography on silica using 40-90% EtOAc/hexane to afford a white solid (1.18 g, 59%).

Step B: Preparation of methyl 2-bromo-3-((4-methoxybenzyl)oxy)-6-(methylsulfonyl)benzoate: A solution of methyl 2-bromo-3-hydroxy-6-methylsulfonyl-benzoate (1.08 g, 3.49 mmol) and potassium carbonate (507 mg, 3.67 mmol) in DMF (10.6 mL) was treated with 4-methoxybenzyl chloride (0.5 mL, 3.67 mmol) and heated to 70° C. for 2 h. The reaction mixture was poured into 100 mL of water and extracted with 3×30 mL $Et_2O$. The combined organics were rinsed with 10 mL of brine, dried with $MgSO_4$, filtered, and concentrated. The product was used without further purification.

Step C: Preparation of 4-bromo-5-((4-methoxybenzyl)oxy)benzo[b]thiophen-3(2H)-one 1,1-dioxide: A solution of methyl 2-bromo-3-[(4-methoxyphenyl)methoxy]-6-methylsulfonyl-benzoate (1.55 g, 3.6 mmol) in THF (36.1 mL) at 25° C. was treated with sodium hydride (289 mg, 7.2 mmol) and stirred at 25° C. for 30 minutes. The reaction mixture was quenched by the addition of 30 mL of saturated aqueous $NH_4Cl$. Organic volatiles were removed by concentration under reduced pressure. The reaction mixture was poured into 30 mL of water and extracted with 3×30 mL EtOAc. The combined organics were rinsed with 10 mL of brine, dried with $MgSO_4$, filtered, and concentrated. The product was used without further purification.

Step D: Preparation of 4-bromo-2,2-difluoro-5-((4-methoxybenzyl)oxy)benzo[b]thiophen-3(2H)-one 1,1-dioxide: A solution of 4-bromo-5-[(4-methoxyphenyl)methoxy]-1,1-dioxo-benzothiophen-3-one (1.38 g, 3.47 mmol) in acetonitrile (35 mL) at 25° C. was treated sequentially with sodium carbonate (810 mg, 7.6 mmol) and Selectfluor® (2.7 g, 7.6 mmol). The reaction mixture was stirred at 25° C. for 1.5 h. Volatiles were removed under reduced pressure and the residue was poured into 30 mL of water and extracted with 3×30 mL EtOAc. The combined organics were rinsed with 10 mL of brine, dried with $MgSO_4$, filtered, and concentrated. Purification was achieved by chromatography on silica using 10-30% EtOAc/hexane.

Step E: Preparation of 4-bromo-2,2-difluoro-3-hydroxy-5-((4-methoxybenzyl)oxy)-3-methyl-2,3-dihydrobenzo[b]thiophene 1,1-dioxide: Methylmagnesium chloride (~3.0 M in THF, 1.15 mL, 3.45 mmol) was mixed with lanthanum (III) chloride bis(lithium chloride) complex solution (0.6 M in THF, 6.76 mL, 4.1 mmol) and stirred at room temperature for 5 minutes. The resulting solution was cooled to −30° C. and then treated with 4-bromo-2,2-difluoro-5-[(4-methoxyphenyl)methoxy]-1,1-dioxo-benzothiophen-3-one (878 mg, 2.0 mmol) in 10 mL of THF by slow dropwise addition over 20 minutes. Once the addition was complete, the reaction mixture was allowed to warm to −20° C. over 30 minutes. The reaction mixture was quenched by the addition of 10 mL of saturated aqueous $NH_4Cl$. The resulting mixture was poured into 30 mL of water and extracted with 3×30 mL EtOAc. The combined organics were rinsed with 10 mL of brine, dried with $MgSO_4$, filtered, and concentrated. The crude product was used without further purification.

Step F: Preparation of 2,2-difluoro-3,5-dihydroxy-3-methyl-2,3-dihydrobenzo[b]thiophene-4-carbonitrile 1,1-dioxide: A solution of copper(I) cyanide (10 mg, 0.11 mmol) in 1-methyl-2-pyrrolidone (0.5 mL) was treated with 4-bromo-2,2-difluoro-5-[(4-methoxyphenyl)methoxy]-3-methyl-1,1-dioxo-benzothiophen-3-ol (42 mg, 0.093 mmol) and stirred at 180° C. by microwave irradiation for 3 h. The reaction mixture was purified directly on reverse phase silica gel with 10-50% $CH_3CN$/water as eluent to give the desired product (18.1 mg, 70%).

Step G: Preparation of 2,2-difluoro-3-hydroxy-5-isopropoxy-3-methyl-2,3-dihydrobenzo[b]thiophene-4-carbonitrile 1,1-dioxide: A solution of 2,2-difluoro-3,5-dihydroxy-3-methyl-1,1-dioxo-benzothiophene-4-carbonitrile (18.1 mg, 0.066 mmol), triphenylphosphine (69.0 mg, 0.26 mmol) and 2-propanol (30.4 μL, 0.39 mmol) in THF (0.7 mL) was treated with diisopropyl azodicarboxylate (51.6 μL, 0.26 mmol) and stirred at 25° C. for 4 h. Volatiles were removed by concentration under reduced pressure. The residue was purified by chromatography on silica using 5-45% EtOAc/hexane. A second purification on reverse phase silica gel with 20-80% $CH_3CN$/water as eluent afforded Compound 110 as a white solid (9.9 mg, 47%). LCMS ESI (−) (M−H) m/z 316; $^1$H NMR (400 MHz, $CDCl_3$): δ 7.92 (d, 1H), 7.18 (d, 1H), 4.81 (m, 1H), 3.18 (s, 1H), 1.92 (d, 3H), 1.48 (t, 6H).

Examples 111 and 112

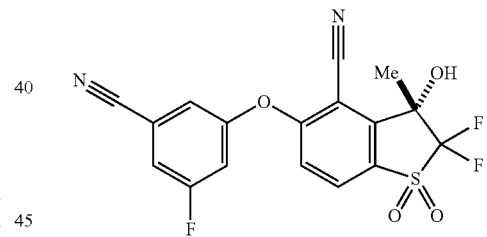

Compound 111

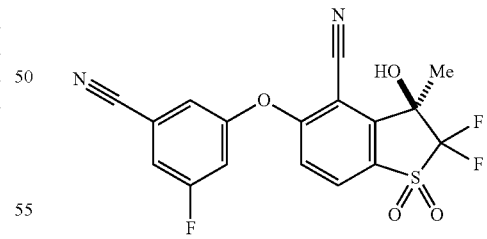

Compound 112

(S)-5-(3-Cyano-5-fluorophenoxy)-2,2-difluoro-3-hydroxy-3-methyl-2,3-dihydrobenzo[b]thiophene-4-carbonitrile 1,1-dioxide (Compound 111) and (R)-5-(3-cyano-5-fluorophenoxy)-2,2-difluoro-3-hydroxy-3-methyl-2,3-dihydrobenzo[b]thiophene-4-carbonitrile 1,1-dioxide (Compound 112)

The product made in Example 105 was separated with preparative SFC chromatography under the following conditions: ChiralPak AD-H (2×25 cm) column, 20% methanol with carbon dioxide at 100 bar, 70 mL/min flow rate, injection volume was 0.5 mL of a 20 mg/mL solution in methanol, peak detection at 220 nm. Compound 111 was recovered as the first peak (2.33 minutes, 178 mg, 45%) and Compound 112 as the second peak (3.00 minutes, 182 mg, 46%) from the column. MS and NMR data were identical to those reported for Example 105.

Example 113

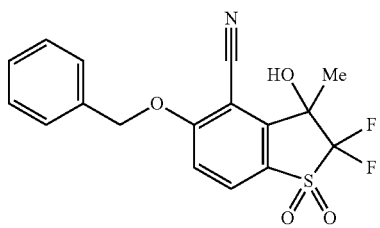 [SMILES: CC1(O)c2c(ccc(OCc3ccccc3)c2C#N)S(=O)(=O)C1(F)F]

5-(Benzyloxy)-2,2-difluoro-3-hydroxy-3-methyl-2,3-dihydrobenzo[b]thiophene-4-carbonitrile 1,1-dioxide (Compound 113)

Prepared similarly according to Example 110, Step G, substituting 2-propanol with benzyl alcohol. Purification was achieved by chromatography on silica using 5-10% EtOAc/CH$_2$Cl$_2$ to afford Compound 113 as a white solid (8.3 mg, 35%). LCMS ESI (−) (M+HCO2−) m/z 410; $^1$H NMR (400 MHz, (CD$_3$)$_2$CO): δ 8.23 (d, 1H), 7.74 (d, 1H), 7.57 (d, 2H), 7.48-7.36 (m, 3H), 6.54 (d, 1H), 5.54 (s, 2H), 1.86 (d, 3H).

Example 114

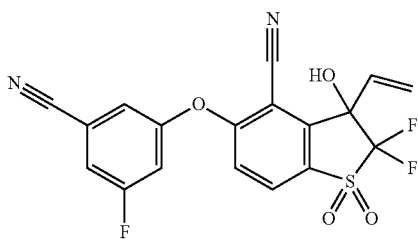 [SMILES: C=CC1(O)c2c(ccc(Oc3cc(F)cc(C#N)c3)c2C#N)S(=O)(=O)C1(F)F]

5-(3-Cyano-5-fluorophenoxy)-2,2-difluoro-3-hydroxy-3-vinyl-2,3-dihydrobenzo[b]thiophene-4-carbonitrile 1,1-dioxide (Compound 114)

Prepared similarly according to Example 105, Steps A-B, substituting methylmagnesium chloride with vinylmagnesium bromide. Purification was achieved by chromatography on silica using 5-40% EtOAc/hexane. A second purification on reverse phase silica gel using 20-80% CH$_3$CN/water as eluent afforded Compound 114 as a white solid (19 mg, 71%). LCMS ESI (−) (M−H) m/z 405; $^1$H NMR (400 MHz, CDCl$_3$): δ 8.00 (d, 1H), 7.39-7.35 (m, 1H), 7.26-7.24 (m, 1H), 7.18-7.13 (m, 2H), 6.12 (ddd, 1H), 5.86 (d, 1H), 5.73 (d, 1H), 3.45 (d, 1H).

Example 115

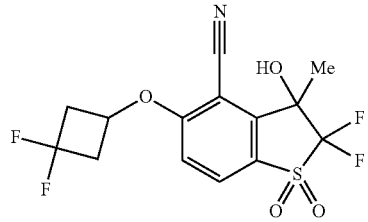 [SMILES: CC1(O)c2c(ccc(OC3CC(F)(F)C3)c2C#N)S(=O)(=O)C1(F)F]

5-(3,3-Difluorocyclobutoxy)-2,2-difluoro-3-hydroxy-3-methyl-2,3-dihydrobenzo[b]thiophene-4-carbonitrile 1,1-dioxide (Compound 115)

Prepared similarly according to Example 110, Step G, substituting 2-propanol with 3,3-difluorocyclobutanol. Purification was achieved by chromatography on silica using 0-5% EtOAc/CH$_2$Cl$_2$ to afford Compound 115 as a thin clear film (2.6 mg, 12%). LCMS ESI (−) (M−H) m/z 364; $^1$H NMR (400 MHz, CDCl$_3$): δ 7.97 (d, 1H), 7.02 (d, 1H), 4.90-4.81 (m, 1H), 3.29-3.17 (m, 2H), 3.10 (d, 1H), 3.02-2.87 (m, 2H), 1.93 (d, 3H).

Example 116

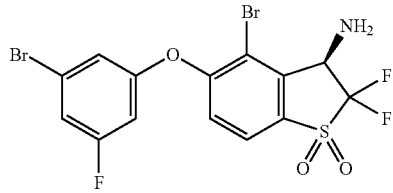 [SMILES: N[C@@H]1c2c(ccc(Oc3cc(F)cc(Br)c3)c2Br)S(=O)(=O)C1(F)F]

(R)-3-Amino-4-bromo-5-(3-bromo-5-fluorophenoxy)-2,2-difluoro-2,3-dihydrobenzo[b]thiophene 1,1-dioxide (Compound 116)

A solution of (R)—N—((R)-4-bromo-5-(3-bromo-5-fluorophenoxy)-2,2-difluoro-1,1-dioxido-2,3-dihydrobenzo[b]thiophen-3-yl)-2-methylpropane-2-sulfinamide (117 mg, 0.20 mmol) in methanol (2.0 mL) was treated with hydrogen chloride in dioxane (~4.0 M in dioxane, 0.5 mL, 2 mmol) and stirred at 25° C. overnight. Volatiles were removed by concentration under reduced pressure. The white solid residue was kept under high vacuum overnight and then assayed without further purification (102 mg, 98%). LCMS ESI (+) (M+H) m/z 486, 488, 490; $^1$H NMR (400 MHz, (CD$_3$)$_2$SO): δ 8.15 (d, 1H), 7.48 (d, 1H), 7.47 (ddd, 1H), 7.29-7.27 (m, 1H), 7.18 (dt, 1H), 5.04 (d, 1H).

Example 117

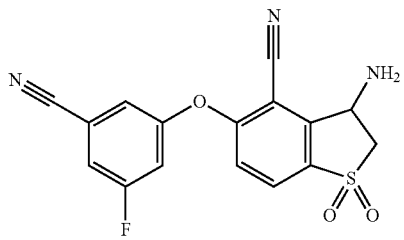 [SMILES: N#Cc1cc(F)cc(Oc2ccc3c(c2C#N)C(N)CS3(=O)=O)c1]

3-Amino-5-(3-cyano-5-fluorophenoxy)-2,3-dihydrobenzo[b]thiophene-4-carbonitrile 1,1-dioxide (Compound 117)

A mixture of 3-((3-amino-4-bromo-1,1-dioxidobenzo[b]thiophen-5-yl)oxy)-5-fluorobenzonitrile (24.9 mg, 0.063 mmol, prepared similarly according to Example 17, Step A) and zinc cyanide (8.1 mg, 0.069 mmol) in DMF (0.7 mL) was sparged with nitrogen for 3 minutes. The reaction mixture was then treated sequentially with dichloro[1;1'-bis(diphenylphosphino)ferrocene]palladium(II) dichloromethane adduct (5.1 mg, 0.0063 mmol) and zinc powder (4.1 mg, 0.063 mmol) under continuous nitrogen stream. The vessel was sealed and heated to 110° C. for 30 minutes. The reaction mixture was poured into 30 mL of water and extracted with 3×10 mL Et$_2$O. The combined organics were rinsed with 10 mL of brine, dried with MgSO4, filtered, and concentrated to dryness. Purification was achieved by chromatography on silica using 20-80% EtOAc/hexane. A second purification on silica using 10-35% EtOAc/CH$_2$Cl$_2$ afforded Compound 117 as a yellow solid (3.0 mg, 14%). LCMS ESI (−) (M−H) m/z 342; $^1$H NMR (400 MHz, (CD$_3$)$_2$CO): δ 7.99 (d, 1H), 7.66-7.61 (m, 2H), 7.56 (dt, 1H), 7.42 (d, 1H), 5.03 (br s, 1H), 3.95 (dd, 1H), 3.48 (dd, 1H), 2.40 (br s, 2H).

Example 118

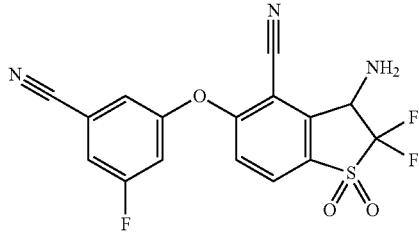 [SMILES: N#Cc1cc(F)cc(Oc2ccc3c(c2C#N)C(N)C(F)(F)S3(=O)=O)c1]

3-Amino-5-(3-cyano-5-fluorophenoxy)-2,2-difluoro-2,3-dihydrobenzo[b]thiophene-4-carbonitrile 1,1-dioxide (Compound 118)

Step A: Preparation of 3-amino-5-(3-cyano-5-fluorophenoxy)benzo[b]thiophene-4-carbonitrile 1,1-dioxide: A mixture of 3-((3-amino-4-bromo-1,1-dioxidobenzo[b]thiophen-5-yl)oxy)-5-fluorobenzonitrile (107 mg, 0.27 mmol) and zinc cyanide (95.1 mg, 0.81 mmol) in DMF (2.7 mL) was sparged with nitrogen for 3 minutes. The reaction mixture was then treated sequentially with 1,1'-bis(diphenylphosphino)ferrocene (29.5 mg, 0.054 mmol) and tris(dibenzylideneacetone)dipalladium(0) (24.7 mg, 0.027 mmol) under continuous nitrogen stream. The vessel was sealed and heated to 110° C. for 30 minutes. The reaction mixture was poured into 30 mL of water and extracted with 3×20 mL Et$_2$O. The combined organics were rinsed with 10 mL of brine, dried with MgSO$_4$, filtered, and concentrated to dryness. Purification was achieved by chromatography on silica using 20-60% EtOAc/hexane to afford a white solid (43 mg, 46%).

Step B: Preparation of 3-amino-5-(3-cyano-5-fluorophenoxy)-2,2-difluoro-2,3-dihydrobenzo[b]thiophene-4-carbonitrile 1,1-dioxide: A solution of Selectfluor® (45.9 mg, 0.13 mmol) and 3-amino-5-(3-cyano-5-fluoro-phenoxy)-1,1-dioxo-benzothiophene-4-carbonitrile (20 mg, 0.059 mmol) in acetonitrile (5.9 mL) at 25° C. was treated with sodium carbonate (13.7 mg, 0.13 mmol) and stirred at 25° C. until complete as shown by LCMS. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. The residue was dissolved in 20 mL of MeOH, cooled to 0° C., and treated with NaBH$_4$ (2.2 mg, 0.059 mmol). The reaction mixture was stirred for 10 minutes and quenched by the addition of 1 mL of saturated NH$_4$Cl. Volatiles were removed by concentration under reduced pressure. The mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 10-40% EtOAc/hexane to afford Compound 118 as a white foam (2.6 mg, 12%). LCMS ESI (+) (M+H) m/z 380; $^1$H NMR (400 MHz, (CD$_3$)$_2$CO): δ 8.20 (d, 1H), 7.62 (ddd, 1H), 7.55-7.53 (m, 1H), 7.45 (dt, 1H), 7.39 (d, 1H), 5.14-5.04 (m, 1H), 2.42 (br d, 2H).

Example 119: General Procedure for Determining Enantiomeric Excess

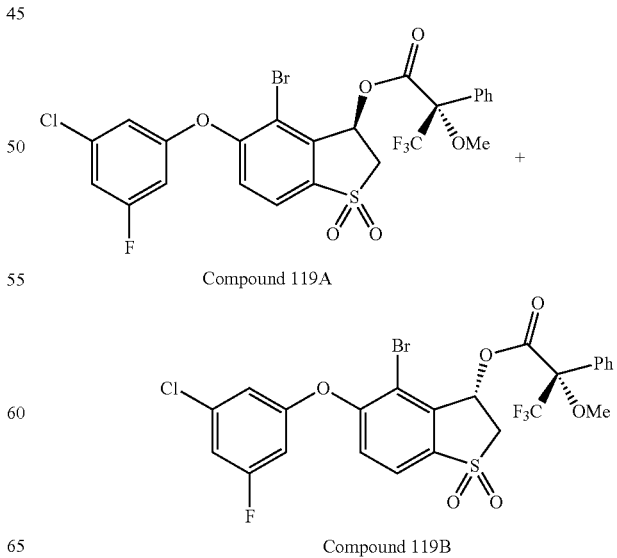

Compound 119A

Compound 119B (R)-4-bromo-5-(3-chloro-5-fluorophenoxy)-1,1-di-oxido-2,3-dihydrobenzo[b]thiophen-3-yl (S)-3,3,3-trifluoro-2-methoxy-2-phenylpropanoate (Compound 119A) and (S)-4-bromo-5-(3-chloro-5-fluorophenoxy)-1,1-dioxido-2,3-dihydrobenzo[b]thiophen-3-yl (S)-3,3,3-trifluoro-2-methoxy-2-phenylpropanoate (Compound 119B)

Mosher ester analysis: N,N-Diisopropylethylamine (1.7 µL, 0.01 mmol) was added to 4-bromo-5-(3-chloro-5-fluorophenoxy)-1,1-dioxo-2,3-dihydrobenzothiophen-3-ol (enantiomerically enriched, 2 mg, 0.005 mmol) and (2R)-3,3,3-trifluoro-2-methoxy-2-phenyl-propanoyl chloride (1.5 mg, 0.006 mmol) in CDCl$_3$ (0.5 mL) in a NMR tube followed by 4-(dimethylamino)pyridine (0.6 mg, 0.005 mmol). The reaction mixture was gently shaken for 2 minutes, then analyzed by $^{19}$FNMR to determine the ee of the corresponding alcohol. Diagnostic peaks in the $^{19}$FNMR are −71.4 ppm for the R-configured alcohol and −71.5 ppm for the S-configured alcohol. A ratio of 9:1 (R:S) was observed, translating to an enantiomeric excess of 80%.

Example 120

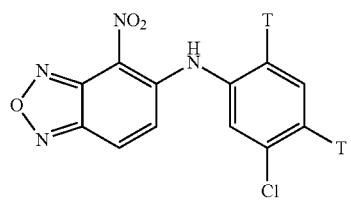

N-(3-Chlorophenyl-4,6-t$_2$)-4-nitrobenzo[c][1,2,5]oxadiazol-5-amine (Compound 120)

Step A: Synthesis of 3-chlorobenzen-4,6-t$_2$-amine: 3-Chloro-4,6-diiodoaniline (100 mg) was dissolved in methanol (3 mL) and added with triethylamine (0.1 mL) and submitted for overnight tritiation using 50Ci of tritium gas, at room temperature. Labile tritium was removed by dissolving the crude reaction mixture in methanol (3 mL) and bringing to dryness under vacuum. Labile removal was done in duplicate. The crude tritiated material was purified by preparative TLC (Silica gel, 1000µ) using hexane: ethyl acetate:acetic acid (85:14:1). The product band was eluted with ethyl acetate to give 3-chlorobenzen-4,6-t$_2$-amine (yield=600 mCi, radiochemical purity was >98%).

Step B: Synthesis of N-(3-chlorophenyl-4,6-t$_2$)-4-nitrobenzo[c][1,2,5]oxadiazol-5-amine (Compound 120): A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in N, N-dimethylformamide (1 mL) was heated at 60° C. for 1 hour. After cooling, the reaction mixture was partitioned between ethyl acetate and water. The aqueous layer was extracted with ethyl acetate. The combined organic layers were washed with water and brine, dried and concentrated. The residue was purified by preparative HPLC on an ACE-5 C18 Semi-prep column, 250×10 mm, 100 Å. Elution was carried out isocratically using 0.1% trifluoroacetic acid in water/acetonitrile (35:65) to give Compound 120 (478 mCi, 80%).

Example 121: HIF-2α Scintillation Proximity Assay (SPA)

The total assay volume was about 100 µL in the following configuration: 2-µL compound in DMSO, 88 µL buffer with protein and probe and 10 µL of SPA beads. The compound was diluted in a master plate consisting of a 10-point dose response with a 3-fold compound dilution from 100 µM to 5 nM. Assays were run on a 96-well plate in which one column, designated as the high signal control, contained DMSO with no compound and another column, designated as the low signal control, contained no protein. Prior to plating out of a compound, a buffer solution, containing 25 mM TRIS pH 7.5 (Sigma), 150 mM NaCl (Sigma), 15% Glycerol (Sigma), 0.15% BSA (Sigma), 0.001% Tween-20 (Sigma), 150 nM Compound 120 and 100 nM HIF-2α HIS TAG-PASB Domain, was prepared and allowed to equilibrate for 30 minutes. Compounds that were to be tested were then plated in to a 96-well white clear bottom Isoplate-96 SPA plate (Perkin Elmer). To each compound, 88 µL of the buffer solution was then added. The plate was covered with a plastic cover and then aluminum foil, placed onto a shaker and equilibrated for 1 hour. After equilibration, 10 µL of a 2 mg/mL solution of YSi Cu His tagged SPA beads (Perkin Elmer) were then added to each well of the plate, covered and equilibrated for another 2-hours. The plates were then removed from the shaker, placed into a 1450 LSC and luminescence counter MicroBeta Trilux (Perkin Elmer) to measure the extent of probe displacement. The percent inhibition was determined and IC$_{50}$ values were calculated using the Dotmatics system based on the following equation:

% inhibition=[(high control−sample)/(high control−low control)]×100.

Table 1 shows IC$_{50}$s of Compounds in Scintillation Proximity Assay (SPA).

TABLE 1

| Compound IC$_{50}$s in SPA | | |
|---|---|---|
| Compound Number | Mean SPA IC$_{50}$ (µM) | SD |
| 1 | 0.007 | N/A |
| 2 | 0.047 | 0.025 |
| 3 | <0.005 | N/A |
| 4 | 4.41 | N/A |
| 5 | 4.86 | N/A |
| 6 | 2.44 | 1.35 |
| 7 | 0.061 | 0.07 |
| 8 | 1.41 | N/A |
| 9 | 0.002 | N/A |
| 10 | 0.045 | 0.024 |
| 11 | <0.005 | N/A |
| 12 | 0.20 | N/A |
| 13 | 0.015 | N/A |
| 14 | <0.005 | N/A |
| 15 | 0.1 | N/A |
| 16 | 1.88 | N/A |
| 17 | 7.88 | 6.72 |
| 18 | <0.005 | N/A |
| 19 | <0.005 | N/A |
| 20 | 1.54 | N/A |
| 21 | 11.8 | N/A |
| 22 | <0.005 | N/A |
| 23 | 0.27 | N/A |
| 24 | 0.077 | N/A |
| 25 | <0.005 | N/A |
| 26 | <0.005 | N/A |
| 27 | 5.84 | 0.89 |
| 28 | 0.70 | N/A |
| 29 | 0.014 | 0.009 |
| 30 | <0.005 | N/A |
| 31 | 4.14 | 1.9 |
| 32 | 0.239 | 0.009 |
| 33 | <0.005 | N/A |
| 34 | 4.87 | N/A |
| 35 | 0.23 | N/A |
| 36 | 2.89 | 0.092 |
| 37 | 0.12 | N/A |

TABLE 1-continued

Compound IC$_{50}$s in SPA

| Compound Number | Mean SPA IC$_{50}$ (µM) | SD |
|---|---|---|
| 38 | 13.4 | N/A |
| 39 | 2.42 | N/A |
| 40 | 0.034 | N/A |
| 41 | 0.069 | N/A |
| 42 | 0.086 | N/A |
| 43 | <0.005 | N/A |
| 44 | 1.64 | N/A |
| 45 | 18.7 | N/A |
| 46 | <0.005 | N/A |
| 47 | 9.69 | N/A |
| 48 | 1.47 | N/A |
| 49 | 17.4 | N/A |
| 50 | 14.2 | N/A |
| 51 | 0.02 | N/A |
| 52 | 0.029 | N/A |
| 53 | 0.059 | N/A |
| 54 | 1.92 | N/A |
| 55 | 0.033 | N/A |
| 56 | 4.1 | N/A |
| 57 | <0.005 | N/A |
| 58 | 6.32 | N/A |
| 59 | 0.06 | 0.066 |
| 60 | 21.9 | N/A |
| 61 | 12.9 | N/A |
| 62 | 19.6 | N/A |
| 63 | 0.059 | N/A |
| 64 | 10.9 | N/A |
| 65 | 0.565 | N/A |
| 66 | 0.17 | N/A |
| 67 | 4.66 | N/A |
| 68 | 0.125 | 0.057 |
| 69 | 13.4 | N/A |
| 70 | 12.9 | N/A |
| 71 | 17.6 | 3.5 |
| 72 | 17.1 | 4.7 |
| 73 | 13.7 | 0.03 |
| 74 | 10.2 | N/A |
| 75 | 0.12 | 0.024 |
| 76 | 0.75 | 0.18 |
| 77 | 0.31 | 0.17 |
| 78 | 0.12 | N/A |
| 79 | 6.86 | 1.0 |
| 80 | 0.057 | N/A |
| 81 | 0.067 | 0.005 |
| 82 | 2.93 | N/A |
| 83 | 14.3 | N/A |
| 84 | 0.017 | 0.007 |
| 85 | 0.011 | N/A |
| 86 | 0.38 | 0.10 |
| 87 | 0.94 | N/A |
| 88 | 0.98 | N/A |
| 89 | 0.034 | N/A |
| 90 | 0.024 | N/A |
| 91 | 0.072 | N/A |
| 92 | 15.5 | N/A |
| 93 | 1.89 | N/A |
| 94 | 0.011 | N/A |
| 95 | 1.76 | N/A |
| 96 | 0.20 | N/A |
| 97 | 0.046 | N/A |
| 98 | 0.083 | N/A |
| 99 | 4.4 | N/A |
| 100 | 0.041 | N/A |
| 101 | 3.0 | N/A |
| 102 | 4.6 | N/A |
| 103 | 38 | N/A |
| 104 | 6.3 | N/A |
| 105 | <0.005 | N/A |
| 106 | 47 | N/A |
| 107 | 40 | N/A |
| 108 | 19 | N/A |
| 109 | 20 | N/A |
| 110 | 29 | N/A |
| 111 | 13.8 | N/A |
| 112 | 0.009 | N/A |
| 113 | 16.7 | N/A |
| 114 | >100 | N/A |
| 115 | 6.7 | N/A |
| 116 | 0.063 | N/A |
| 117 | 59 | N/A |
| 118 | 1.23 | N/A |

SD: standard deviation.
SDs and Means were calculated using the Python programming language version 2.7.5 with Numpy library 1.7.1. When a compound was tested multiple times, any number less than 5 nM or more than 100 µM was excluded from the standard deviation or IC$_{50}$ calculation.
N/A: SD is not calculated for compounds with IC$_{50}$ less than 5 nM or having a single data point.

The following compounds were synthesized and tested using the SPA described above, and were found to have an IC$_{50}$ value of greater than 100 µM:

| Structure | IUPAC Name |
|---|---|
| (structure: 4-bromo-5-(3,5-difluorophenoxy)-benzo[b]thiophene derivative with 3-OH, 1-imino, 1-oxide) | [4-bromo-5-(3,5-difluorophenoxy)-3-hydroxy-1-imino-2,3-dihydro-1λ$^4$-benzo[b]thiophene 1-oxide |
| (structure: 3-cyano-5-fluorophenoxy benzothiophene derivative with difluoro, hydroxy, hydroxypropynyl, 1,1-dioxo groups) | 3-[[2,2-difluoro-3-hydroxy-4-(3-hydroxyprop-1-ynyl)-1,1-dioxo-3H-benzothiophen-5-yl]oxy]-5-fluoro-benzonitrile |

| Structure | IUPAC Name |
|---|---|
| 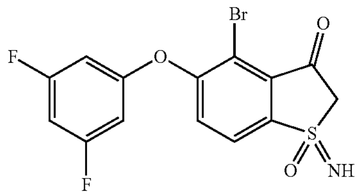 [SMILES: N=S1(=O)CC(=O)c2c1ccc(Oc1cc(F)cc(F)c1)c2Br] | 4-bromo-5-(3,5-difluorophenoxy)-1-imino-1-oxo-benzothiophen-3-one |
| 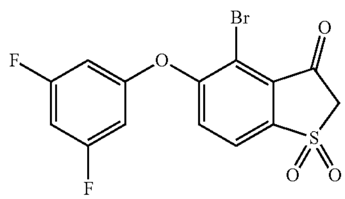 [SMILES: O=C1CS(=O)(=O)c2ccc(Oc3cc(F)cc(F)c3)c(Br)c21] | 4-bromo-5-(3,5-difluorophenoxy)-1,1-dioxo-benzothiophen-3-one |
| | (3R)-4-bromo-5-[(5-chloro-3-pyridyl)oxy]-1,1-dioxo-2,3-dihydrobenzothiophen-3-ol |
| | 5-(3,5-difluorophenoxy)-3-hydroxy-1-imino-2,3-dihydro-1H-1$\lambda^4$-benzo[b]thiophene-4-carbonitrile 1-oxide |
| 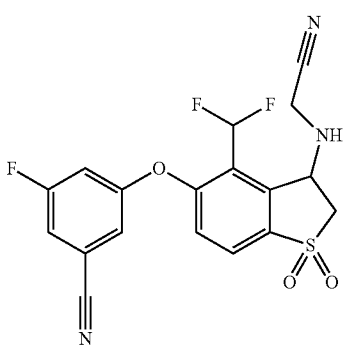 [SMILES: N#CCNC1CS(=O)(=O)c2ccc(Oc3cc(F)cc(C#N)c3)c(C(F)F)c21] | 3-[[3-(cyanomethylamino)-4-(difluoromethyl)-1,1-dioxo-2,3-dihydrobenzothiophen-5-yl]oxy]-5-fluoro-benzonitrile |
| 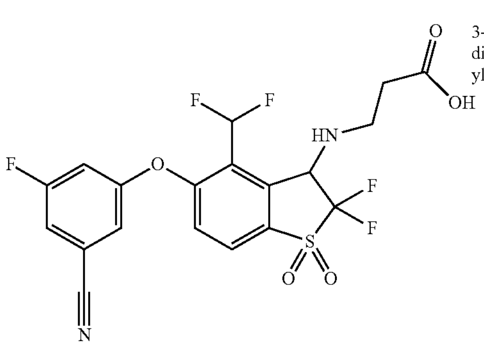 | 3-[[5-(3-cyano-5-fluoro-phenoxy)-4-(difluoromethyl)-2,2-difluoro-1,1-dioxo-3H-benzothiophen-3-yl]amino]propanoic acid |

| Structure | IUPAC Name |
|---|---|
| 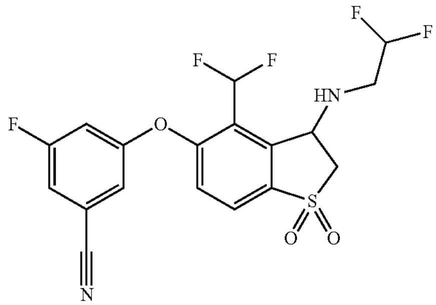 [SMILES: N#Cc1cc(F)cc(Oc2ccc3c(c2C(F)F)C(NCC(F)F)CS3(=O)=O)c1] | 3-[[3-(2,2-difluoroethylamino)-4-(difluoromethyl)-1,1-dioxo-2,3-dihydrobenzothiophen-5-yl]oxy]-5-fluoro-benzonitrile |
| 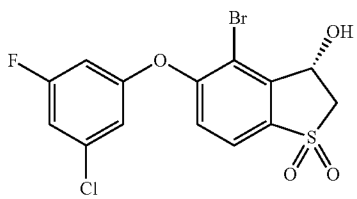 [SMILES: O=S1(=O)C[C@@H](O)c2c1ccc(Oc1cc(F)cc(Cl)c1)c2Br] | (3S)-4-bromo-5-(3-chloro-5-fluoro-phenoxy)-1,1-dioxo-2,3-dihydrobenzothiophen-3-ol |
| 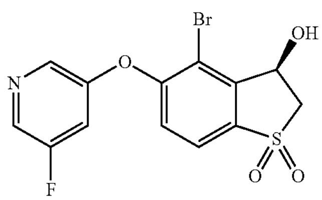 [SMILES: O=S1(=O)C[C@H](O)c2c1ccc(Oc1cncc(F)c1)c2Br] | (3R)-4-bromo-5-[(5-fluoro-3-pyridyl)oxy]-1,1-dioxo-2,3-dihydrobenzothiophen-3-ol |
| 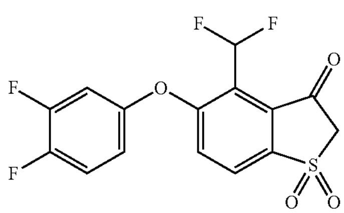 [SMILES: O=C1CS(=O)(=O)c2ccc(Oc3ccc(F)c(F)c3)c(C(F)F)c21] | 4-(difluoromethyl)-5-(3,4-difluorophenoxy)-1,1-dioxo-benzothiophen-3-one |
| 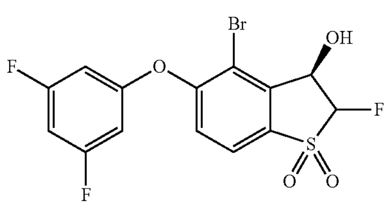 [SMILES: O=S1(=O)c2ccc(Oc3cc(F)cc(F)c3)c(Br)c2[C@@H](O)C1F] | (3R)-4-bromo-5-(3,5-difluorophenoxy)-2-fluoro-1,1-dioxo-2,3-dihydrobenzothiophen-3-ol |
| 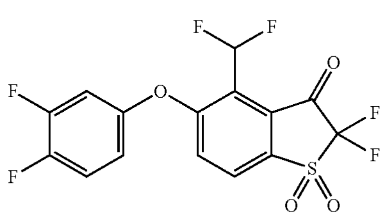 [SMILES: O=C1c2c(ccc(Oc3ccc(F)c(F)c3)c2C(F)F)S(=O)(=O)C1(F)F] | 4-(difluoromethyl)-5-(3,4-difluorophenoxy)-2,2-difluoro-1,1-dioxo-benzothiophen-3-one |

The following compounds were synthesized and tested in the SPA described above, and were found to have an IC$_{50}$ value between 25 and 100 μM:

| Structure | IUPAC Name |
|---|---|
| 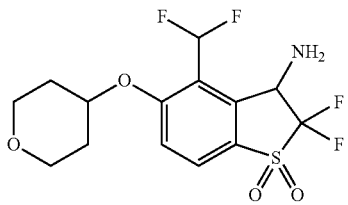 [SMILES: NC1c2c(ccc(OC3CCOCC3)c2C(F)F)S(=O)(=O)C1(F)F] | 4-(difluoromethyl)-2,2-difluoro-1,1-dioxo-5-tetrahydropyran-4-yloxy-3H-benzothiophen-3-amine |
| 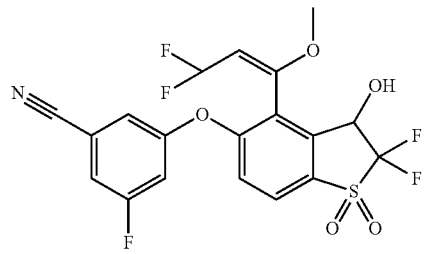 [SMILES: CO/C(=C/C(F)F)c1c(Oc2cc(F)cc(C#N)c2)ccc2c1C(O)C(F)(F)S2(=O)=O] | 3-[[4-[(E)-3,3-difluoro-1-methoxy-prop-1-enyl]-2,2-difluoro-3-hydroxy-1,1-dioxo-3H-benzothiophen-5-yl]oxy]-5-fluoro-benzonitrile |
| 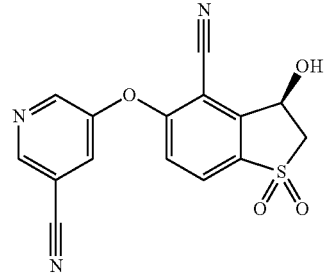 [SMILES: N#Cc1cncc(Oc2ccc3c(c2C#N)[C@@H](O)CS3(=O)=O)c1] | 5-[[(3R)-4-cyano-3-hydroxy-1,1-dioxo-2,3-dihydrobenzothiophen-5-yl]oxy]pyridine-3-carbonitrile |
| 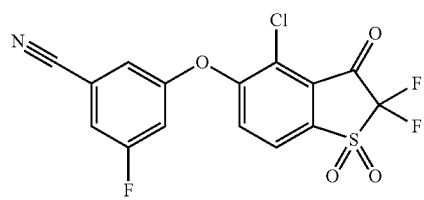 [SMILES: N#Cc1cc(F)cc(Oc2ccc3c(c2Cl)C(=O)C(F)(F)S3(=O)=O)c1] | 3-(4-chloro-2,2-difluoro-1,1,3-trioxo-benzothiophen-5-yl)oxy-5-fluoro-benzonitrile |
| 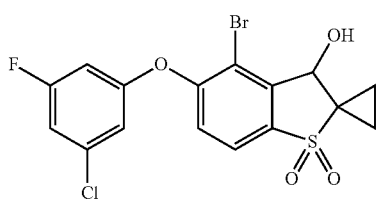 [SMILES: O=S1(=O)c2ccc(Oc3cc(F)cc(Cl)c3)c(Br)c2C(O)C12CC2] | 4-bromo-5-(3-chloro-5-fluoro-phenoxy)-1,1-dioxo-spiro[3H-benzothiophene-2,1'-cyclopropane]-3-ol |
| 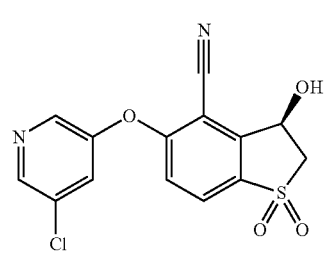 [SMILES: N#Cc1c(Oc2cncc(Cl)c2)ccc2c1[C@@H](O)CS2(=O)=O] | (3R)-5-[(5-chloro-3-pyridyl)oxy]-3-hydroxy-1,1-dioxo-2,3-dihydrobenzothiophene-4-carbonitrile |

| Structure | IUPAC Name |
|---|---|
| 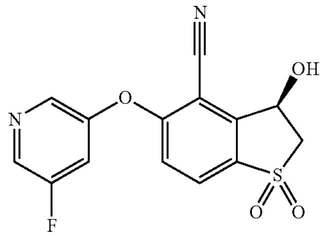 [SMILES: N#Cc1c(Oc2cncc(F)c2)ccc2c1[C@@H](O)CS2(=O)=O] | (3R)-5-[(5-fluoro-3-pyridyl)oxy]-3-hydroxy-1,1-dioxo-2,3-dihydrobenzothiophene-4-carbonitrile |
| 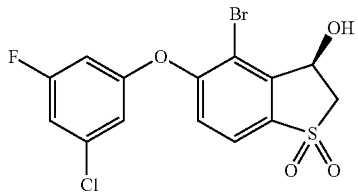 [SMILES: O=S1(=O)C[C@H](O)c2c1ccc(Oc1cc(F)cc(Cl)c1)c2Br] | (3R)-4-bromo-5-(3-chloro-5-fluoro-phenoxy)-1,1-dioxo-2,3-dihydrobenzothiophen-3-ol |
| 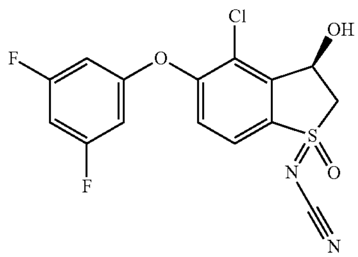 [SMILES: N#CN=S1(=O)C[C@H](O)c2c1ccc(Oc1cc(F)cc(F)c1)c2Cl] | [(3R)-4-chloro-5-(3,5-difluorophenoxy)-3-hydroxy-1-oxo-2,3-dihydrobenzothiophen-1-ylidene]cyanamide |
| 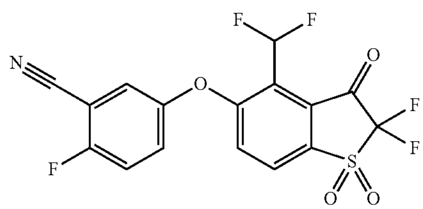 [SMILES: N#Cc1cc(Oc2ccc3c(c2C(F)F)C(=O)C(F)(F)S3(=O)=O)ccc1F] | 5-[4-(difluoromethyl)-2,2-difluoro-1,1,3-trioxo-benzothiophen-5-yl]oxy-2-fluoro-benzonitrile |
| 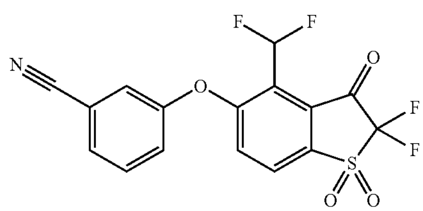 [SMILES: N#Cc1cccc(Oc2ccc3c(c2C(F)F)C(=O)C(F)(F)S3(=O)=O)c1] | 3-[4-(difluoromethyl)-2,2-difluoro-1,1,3-trioxo-benzothiophen-5-yl]oxybenzonitrile |
| 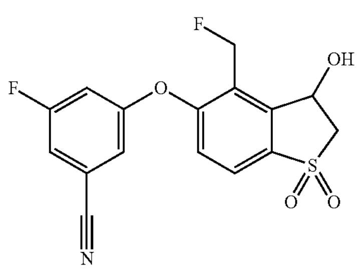 [SMILES: N#Cc1cc(F)cc(Oc2ccc3c(c2CF)C(O)CS3(=O)=O)c1] | 3-fluoro-5-[[4-(fluoromethyl)-3-hydroxy-1,1-dioxo-2,3-dihydrobenzothiophen-5-yl]oxy]benzonitrile |

Example 122: VEGF ELISA Assay

About 7500 of 786-O cells in 180 μL of growth medium were seeded into each well of a 96 well plate with white clear bottom on the first day (07-200-566, Fisher Scientific) in the layout presented in FIG. 9.

Four hours later, serial dilutions of 10× compound stocks were made in growth medium from 500×DMSO stocks, and 20 μL of those 10× stocks were added to each well to make final concentrations as follows (μM): 20, 6.7, 2.2, 0.74, 0.25, 0.082, 0.027, 0.009, 0.003, 0.001, 0. Each concentration had duplicated wells. About twenty hours later, the growth medium was removed by suction and each well was supplied with 180 μL of growth medium. About 20 μl freshly-made 10× compound stocks were added to each well. About twenty four hours later, cell culture medium was removed for the determination of VEGF concentration using an ELISA kit purchased from R&D systems by following the manufacturer's suggested method. The $EC_{50}$ was calculated by GraphPad Prism using the dose-response-inhibition (four parameter) equation. The cell seeded plate was then subjected to CellTiter-Glo luminescence cell viability assay (Promega) by adding about 50 μL of Celltiter Glo reagent into each well and shaking the plate for 8 minutes at 550 rpm (Thermomixer R, Eppendorf). The luminescence signals were read in a plate reader (3 second delay, 0.5 second/well integration time, Synergy 2 multi Detection Microplate reader) immediately.

Table 2 shows $EC_{50}$s of selected compounds in VEGF ELISA Assay.

TABLE 2

$EC_{50}$s of Selected Compounds in VEGF ELISA Assay

| Compound Number | Mean VEGF ELISA $EC_{50}$ (μM) | SD |
|---|---|---|
| 1 | 0.064 | N/A |
| 3 | 0.062 | 0.06 |
| 7 | 0.33 | N/A |
| 9 | 0.065 | 0.009 |
| 11 | 0.125 | N/A |
| 14 | 0.089 | N/A |
| 18 | 0.029 | N/A |
| 19 | 0.087 | N/A |
| 22 | 0.009 | N/A |
| 26 | 0.20 | N/A |
| 29 | 0.014 | 0.003 |
| 41 | 0.68 | 0.02 |
| 43 | 0.009 | N/A |
| 52 | 0.09 | N/A |
| 53 | 0.067 | N/A |
| 57 | 0.045 | N/A |
| 75 | 0.178 | N/A |
| 78 | 0.33 | N/A |
| 85 | 0.077 | N/A |
| 100 | 0.018 | N/A |
| 105 | 0.048 | N/A |
| 112 | 0.031 | N/A |

SD: standard deviation.
SDs and Means were calculated using the Python programming language version 2.7.5 with Numpy library 1.7.1. When a compound was tested multiple times, any number less than 5 nM or more than 100 μM was excluded from the standard deviation or $EC_{50}$ calculation.
N/A: SD is not calculated for compounds with $EC_{50}$ less than 5 nM or having a single data point.

Example 123: Luciferase Assay

The 786-O-Hif-Luc single clone cells were obtained by infecting 786-O cells (ATCC® CRL-1932™) with commercial lentivirus that delivers a luciferase gene driven by multiple HIF responsive elements (Cignal Lenti HIF Reporter (luc): CLS-007L, Qiagen) at multiplicity of infection (MOI) of 25 for about 24 hours and then the cells were replenished with fresh medium (Dulbecco's Modified Eagle's Medium (DMEM, D5796, Sigma) supplemented with 10% FBS (F6178, Sigma), 100 units penicillin, and 100 μg streptomycin/mL (P4333, Sigma)) for another 24 hours. A pool of infected cells were then selected against 2 μg/mL of puromycin (P8833, Sigma) for 10 days followed by limited dilution to select single clones. The clones were tested for their response to HIF-2α inhibitors and the ones that showed the biggest dynamic range (786-O-Hif-Luc) were expanded and used for the luciferase assay. For the luciferase assay, about 7500 of 786-O-Hif-Luc cells in about 90 μL growth medium were seeded into each well of a 96 well white opaque plate (08-771-26, Fisher Scientific) a day before treatment with the layout presented in FIG. 10.

On treatment day, serial dilutions of 10× compound stocks were prepared in growth medium from 500×DMSO stocks, and 10 μL of the 10× stocks were added to each well to make final concentrations as follows (μM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated by using Dotmatics software.

Table 3 shows $EC_{50}$s of selected compounds in Luciferase Assay.

TABLE 3

$EC_{50}$s of Selected Compounds in Luciferase Assay

| Compound Number | Mean Luciferease $EC_{50}$ (μM) | SD |
|---|---|---|
| 1 | 0.023 | N/A |
| 2 | 0.226 | N/A |
| 3 | 0.007 | 0.002 |
| 6 | 4.85 | N/A |
| 7 | 0.45 | 0.014 |
| 9 | 0.05 | 0.009 |
| 10 | 4.17 | 1.75 |
| 11 | 0.13 | N/A |
| 12 | 3.72 | N/A |
| 13 | 0.45 | N/A |
| 14 | 0.075 | N/A |
| 15 | 0.73 | N/A |
| 17 | 6.89 | N/A |
| 18 | 0.017 | 0.02 |
| 19 | 0.068 | N/A |
| 22 | 0.013 | N/A |
| 23 | 0.124 | N/A |
| 24 | 0.72 | N/A |
| 25 | 0.01 | N/A |
| 26 | 0.11 | N/A |
| 28 | 1.43 | 0.83 |
| 29 | 0.004 | N/A |
| 30 | 1.7 | 1.0 |
| 31 | 0.54 | N/A |
| 32 | 0.29 | N/A |
| 33 | 1.78 | N/A |
| 34 | 0.02 | N/A |
| 35 | 0.15 | N/A |
| 37 | 0.17 | N/A |
| 39 | 2.79 | 2.6 |
| 40 | 0.012 | N/A |
| 41 | 0.14 | 0.006 |
| 42 | 0.126 | N/A |
| 43 | 0.006 | N/A |
| 44 | 0.79 | N/A |
| 46 | 0.1 | N/A |
| 48 | 1.88 | N/A |
| 51 | 1.5 | 0.001 |
| 52 | 0.069 | N/A |
| 53 | 0.039 | N/A |
| 54 | 1.54 | N/A |
| 55 | 0.057 | N/A |
| 57 | 0.037 | 0.005 |
| 59 | 0.17 | N/A |
| 63 | 0.19 | N/A |
| 65 | 0.51 | N/A |
| 66 | 2.16 | N/A |
| 68 | 0.37 | N/A |
| 70 | 0.40 | N/A |
| 75 | 0.098 | 0.12 |
| 76 | 0.49 | N/A |
| 77 | 0.126 | 0.063 |
| 78 | 0.095 | 0.077 |
| 80 | 0.41 | N/A |

TABLE 3-continued

EC$_{50}$s of Selected Compounds in Luciferase Assay

| Compound Number | Mean Luciferase EC$_{50}$ (µM) | SD |
|---|---|---|
| 81 | 15.0 | N/A |
| 82 | 1.42 | N/A |
| 84 | 0.033 | 0.003 |
| 85 | 0.047 | 0.007 |
| 86 | 0.425 | N/A |
| 87 | 1.1 | N/A |
| 88 | 0.88 | N/A |
| 89 | 0.033 | N/A |
| 90 | 0.079 | N/A |
| 91 | 0.31 | N/A |
| 93 | 1.16 | N/A |
| 94 | 0.455 | N/A |
| 95 | 6.89 | N/A |
| 97 | 0.427 | N/A |
| 98 | 0.296 | N/A |
| 100 | 0.022 | N/A |
| 105 | 0.048 | N/A |
| 109 | 6.7 | N/A |
| 110 | 5.4 | N/A |
| 112 | 0.018 | N/A |
| 116 | 0.8 | N/A |
| 118 | 4.6 | N/A |

SD: standard deviation.
SDs and means were calculated using the Python programming language version 2.7.5 with Numpy library 1.7.1. When a compound was tested multiple times, any number less than 5 nM or more than 100 µM was excluded from the standard deviation or EC$_{50}$ calculation.
N/A: SD is not calculated for compounds with EC$_{50}$ less than 5 nM or having a single data point.

Example 124: In Vivo PK/PD Study

Compound 3 was formulated with 10% absolute ethanol, 30% PEG400, 60% water containing 0.5% methylcellulose and 0.5% Tween80®. About 5×10$^6$ renal cell carcinoma 786-O tumor cells (ATCC® CRL-1932™, VHL and HIF-1α null cell line) in PBS and Matrigel (1:1 in volume) were injected subcutaneously in the right flanks of SCID/Biege mice at 6-7 weeks of age for xenograft development. When the xenografts reached about 450 mm$^3$ in size, the tumor-bearing mice were randomly divided into two groups (4 mice in each group). The animals were treated with either vehicle or Compound 3 at 10 mg/kg by oral gavage three times at 12 hour intervals. Animals were sacrificed at 12 hours post last dose. Tumors and plasma were collected from each animal. Total RNA was extracted from the tumors. The mRNA levels of HIF-2α and its respective target genes were determined by qRT-PCR.

Tumor mRNA for HIF-2α and two HIF-2α specific target genes (PAI-1 and CCND1) displayed a significant reduction in response to Compound 3 treatment (FIG. 1). The levels of mRNA for HIF-1α and two HIF-1α specific target genes (PGK1 and PDK1) exhibited no significant changes in response to Compound 3 treatment. These data indicated that Compound 3 selectively inhibited the expression of genes regulated by HIF-2α in the 786-O xenograft.

Figure 2:
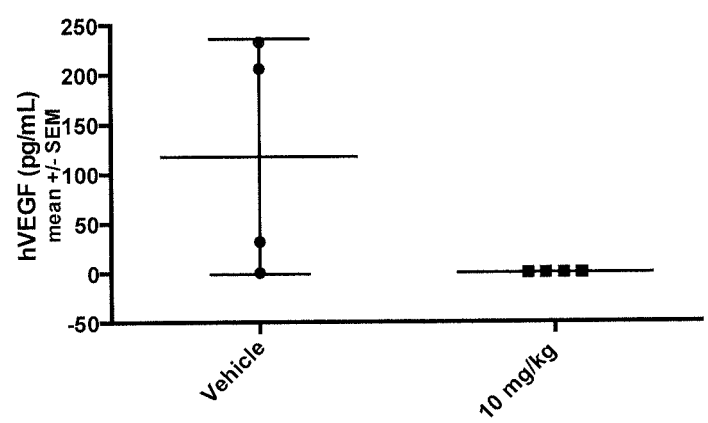
FIG. 2 shows treatment of renal cell carcinoma 786-O xenograft bearing mice at 0 mg/kg (denoted as "Vehicle") and 10 mg/kg of Compound 3, three times each at 12 hour intervals.

The plasma level of human VEGFA was determined by ELISA assay. FIG. 2 showed that Compound 3 treatment led to undetectable level of human VEGFA (hVEGF) in the plasma of 786-O tumor-bearing mice.

Example 125: In Vivo Efficacy Study

Figure 3:
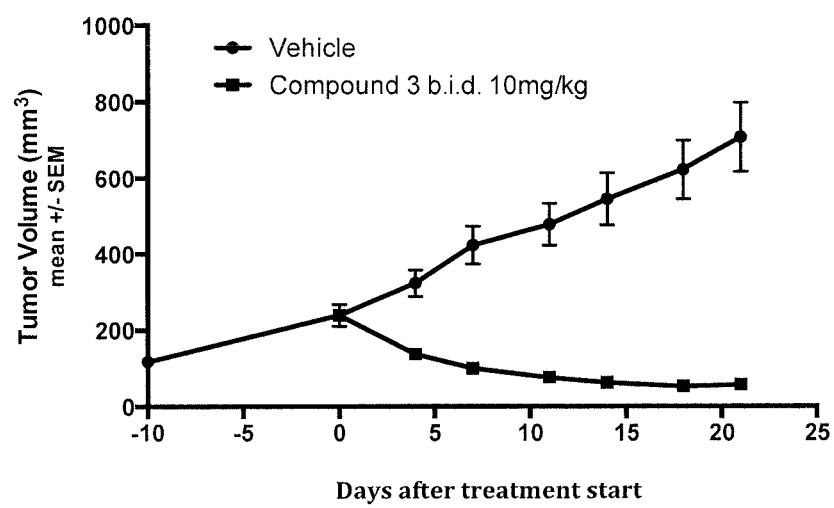
FIG. 3 shows treatment of 786-O xenograft bearing mice at 0 mg/kg (denoted as "Vehicle") and 10 mg/kg of Compound 3, twice a day at 12 h interval (b.i.d.) for 21 days.
Figure 4:
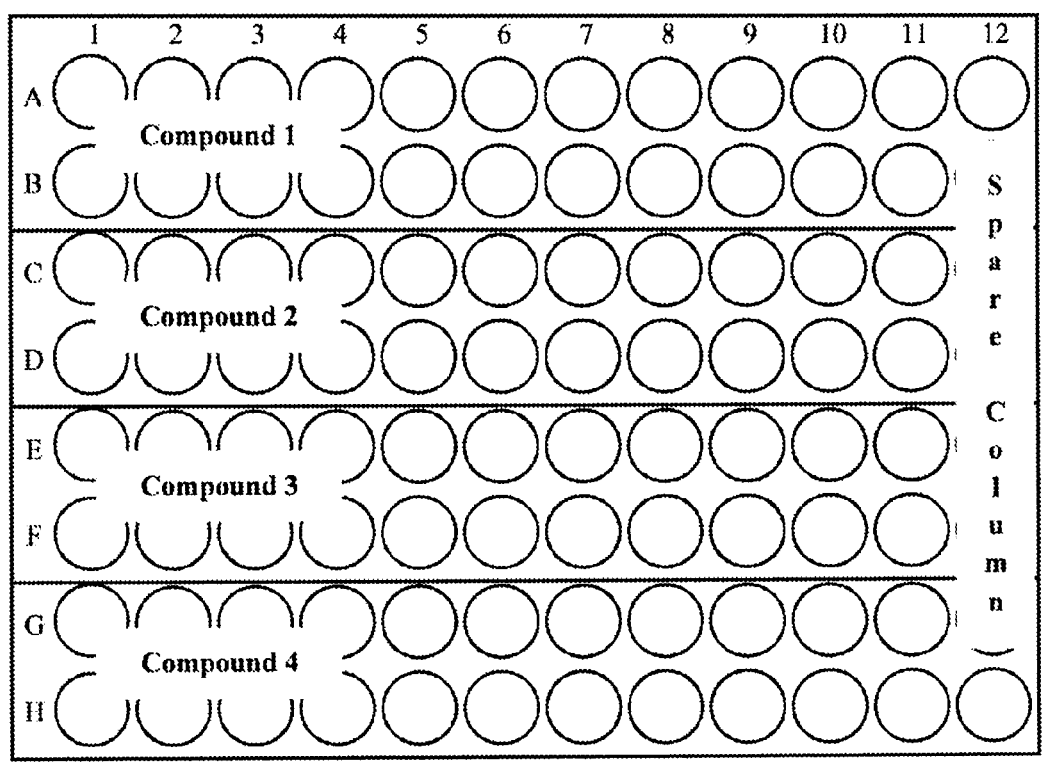
FIG. 4 depicts a 96-well plate layout of an ELISA assay.
Figure 5:
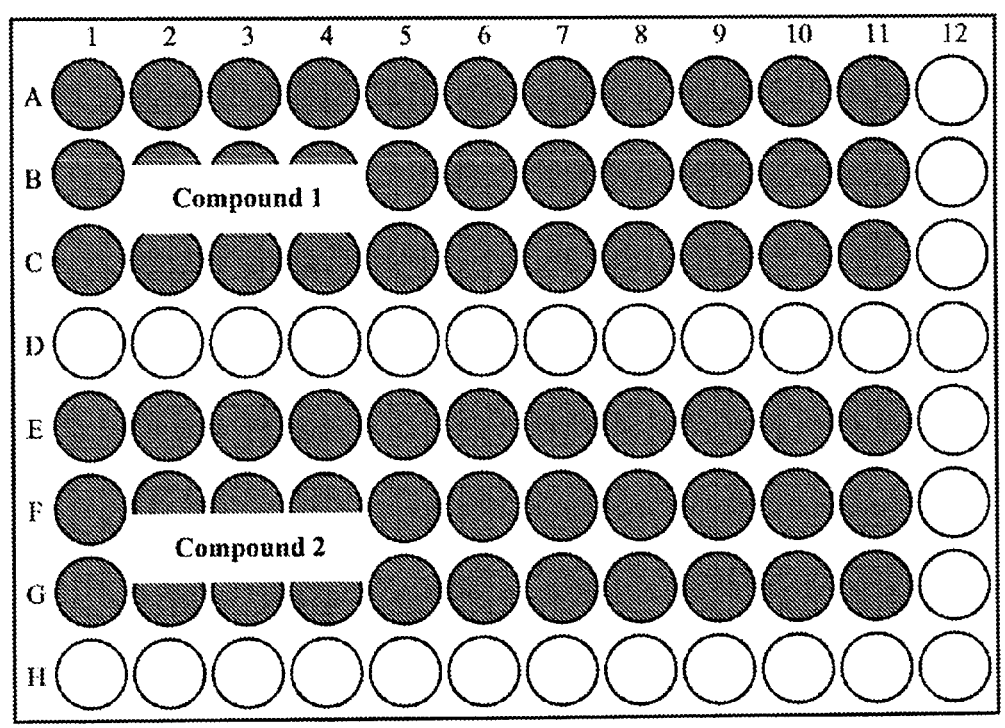
FIG. 5 depicts a 96-well plate layout of a luciferase assay.

Compound 3 was formulated with 10% absolute ethanol, 30% PEG400, 60% water containing 0.5% methylcellulose and 0.5% Tween80®. About 5×10$^6$ 786-O renal cell carcinoma cells (ATCC® CRL-1932™) in PBS and Matrigel (1:1 in volume) were inoculated subcutaneously in the right flank of SCID/Biege mice at 6-7 weeks of age for tumor development. When the xenografts reached about 250 mm$^3$ in size, the tumor-bearing mice were randomly grouped into 2 groups (8 mice in each group) and treated by oral gavage with vehicle and Compound 3 at 10 mg/kg twice a day dosing (b.i.d.) for twenty-one days. Tumor sizes were measured twice weekly in two dimensions using a caliper and the volume were expressed in mm$^3$ using the formula V=0.5× a× b$^2$ wherein a and b were the long and short diameters of the tumor, respectively. As shown in FIG. 3 and Table 4, Compound 3 treatment led to a statistically significant reduction of tumor size in the renal cell carcinoma 786-O xenograft model (all data displayed as mean with the standard error of the mean (SEM)).

TABLE 4

786-O Xenograft Study: Tumor sizes after 21 days of dosing

| Treatment groups | Vehicle Group | Compound 3 Group |
|---|---|---|
| Dose | | 10 mg/kg b.i.d. |
| Tumor size (mm$^3$) Mean ± SEM | 709 ± 91 | 57 ± 5.6 |

What is claimed is:

1. A compound of Formula I:

or a pharmaceutically acceptable salt thereof,
wherein:
R$_1$ is alkyl, C1-C10 heteroalkyl, C3-C8 cycloalkyl, C5-C8 heterocycloalkyl or a monocyclic aromatic ring having 6 to 10 ring atoms;
R$_2$ is nitro, cyano, halo, substituted alkyl, C1-C10 heteroalkyl, alkynyl or alkenyl;
R$_3$ is hydrogen, hydroxy or amino;
each of R$_4$ is independently selected from the group consisting of hydrogen, halo, alkyl, C1-C10 heteroalkyl and C3-C8 cycloalkyl, or two R$_4$ groups and the carbon(s) to which they are attached form C3-C8 cycloalkyl or C5-C8 heterocycloalkyl;
R$_5$ is O or NR$_6$, wherein R$_6$ is selected from the group consisting of hydrogen, alkyl, and cyano;
R$_7$ is hydrogen, deuterium, or alkyl, or R$_3$ and R$_7$ in combination form oxo; and
n is 1 or 2;
wherein:
said C1-C10 heteroalkyl contains 1, 2 or 3 chain atoms selected from O, N and S; and
said C5-C8 heterocycloalkyl contains 1, 2 or 3 ring atoms selected from O, N and S.

2. The compound of claim 1, wherein R$_1$ is phenyl or pyridyl.

3. The compound of claim 1, wherein R$_2$ is cyano, halo, alkynyl, fluoroalkyl or substituted alkyl.

4. The compound of claim 1, wherein $R_3$ is hydroxy or amino, $R_2$ is fluoroalkyl, at least one $R_4$ is fluoro, and n is 1.

5. The compound of claim 1, wherein at least one $R_4$ is fluoro.

6. The compound of claim 1, having the structure of Formula II:

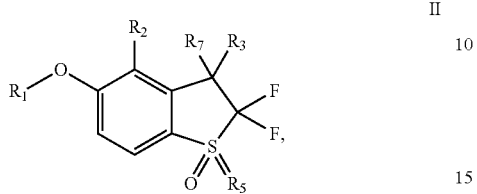

or a pharmaceutically acceptable salt thereof.

7. The compound of claim 6, wherein $R_1$ is phenyl or pyridyl.

8. The compound of claim 6, wherein $R_2$ is cyano, halo, fluoroalkyl or substituted alkyl.

9. The compound of claim 6, wherein $R_3$ is hydroxy or amino.

10. The compound of claim 6, wherein $R_5$ is O, N—CN or NH.

11. The compound of claim 10, wherein $R_7$ is hydrogen or deuterium and $R_3$ is hydroxy.

12. The compound of claim 1, having the structure of Formula III:

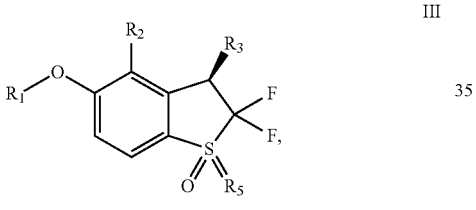

or a pharmaceutically acceptable salt thereof.

13. The compound of claim 12, wherein $R_1$ is phenyl or pyridyl.

14. The compound of claim 12, wherein $R_3$ is hydroxy or $NH_2$.

15. The compound of claim 14, wherein $R_5$ is O, N—CN or NH.

16. The compound of claim 14, wherein $R_5$ is O and said compound has an enantiomeric excess of at least about 80%.

17. A compound selected from the group consisting of:

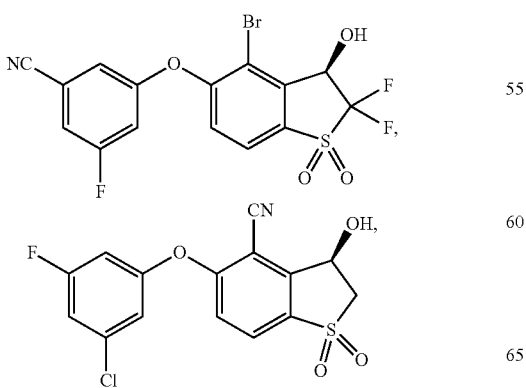

-continued

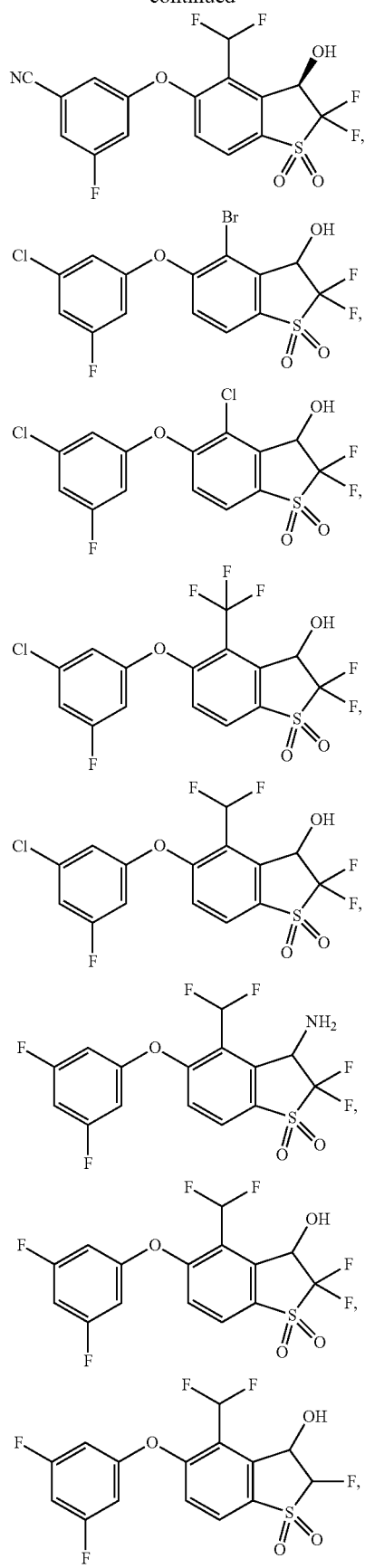

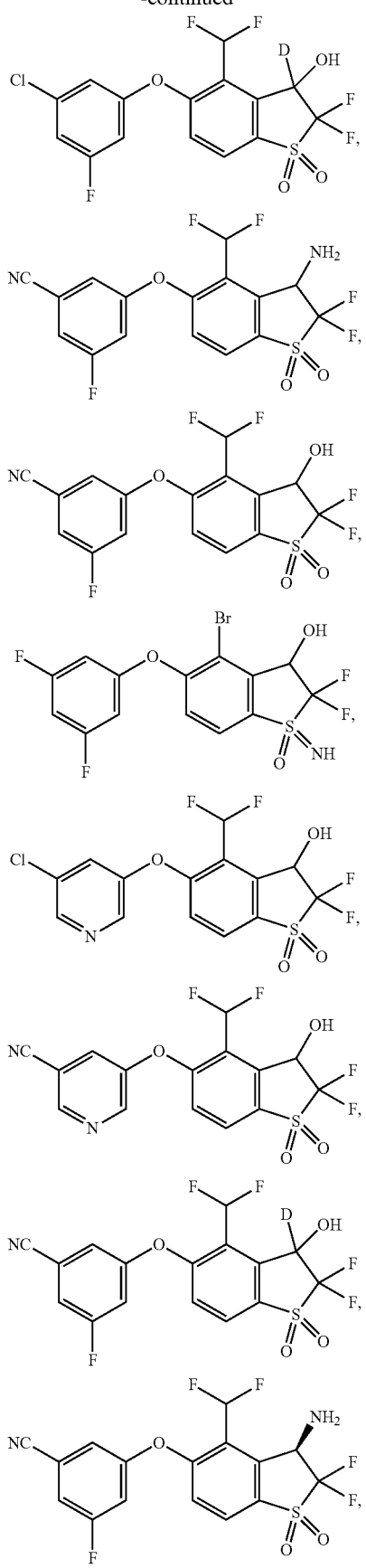
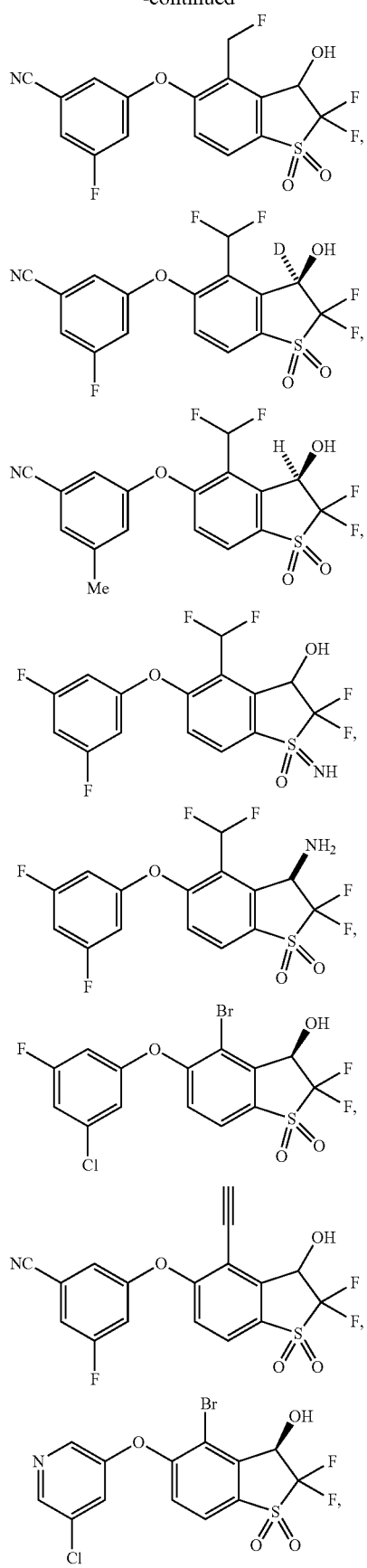

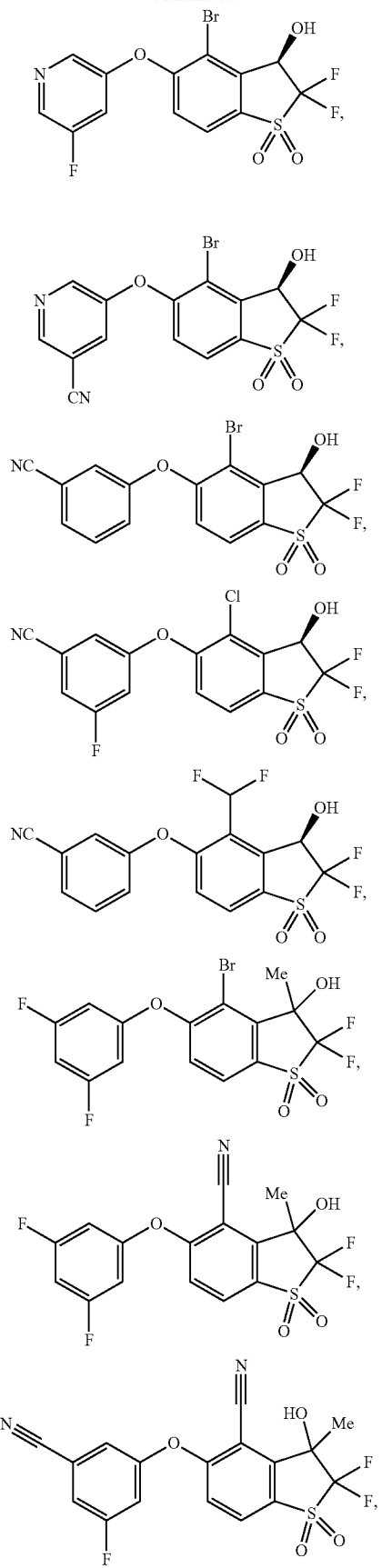

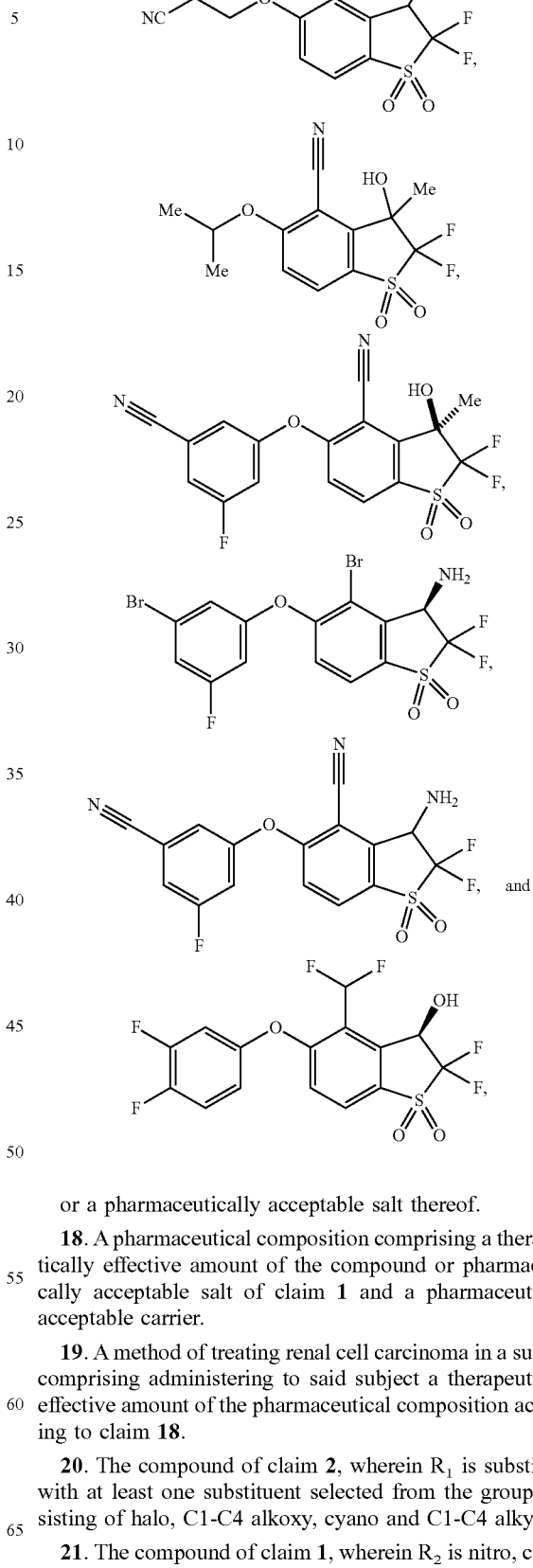

or a pharmaceutically acceptable salt thereof.

18. A pharmaceutical composition comprising a therapeutically effective amount of the compound or pharmaceutically acceptable salt of claim 1 and a pharmaceutically acceptable carrier.

19. A method of treating renal cell carcinoma in a subject, comprising administering to said subject a therapeutically effective amount of the pharmaceutical composition according to claim 18.

20. The compound of claim 2, wherein $R_1$ is substituted with at least one substituent selected from the group consisting of halo, C1-C4 alkoxy, cyano and C1-C4 alkyl.

21. The compound of claim 1, wherein $R_2$ is nitro, cyano, halo, haloalkyl, C1-C10 heteroalkyl, alkynyl or alkenyl.

22. A compound of Formula I:

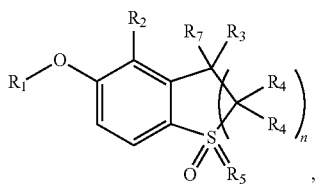

or a pharmaceutically acceptable salt thereof,
wherein:
$R_1$ is phenyl or pyridyl;
$R_2$ is nitro, cyano, halo, alkyl, C1-C10 heteroalkyl, alkynyl or alkenyl;
$R_3$ is hydrogen, hydroxy or amino;
each of $R_4$ is independently selected from the group consisting of hydrogen, halo, alkyl, C1-C10 heteroalkyl and C3-C8 cycloalkyl, or two $R_4$ groups and the carbon(s) to which they are attached form C3-C8 cycloalkyl or C5-C8 heterocycloalkyl;
$R_5$ is O or $NR_6$, wherein $R_6$ is selected from the group consisting of hydrogen, alkyl, and cyano;
$R_7$ is hydrogen, deuterium, or alkyl, or $R_3$ and $R_7$ in combination form oxo; and
n is 1 or 2;
wherein:
said C1-C10 heteroalkyl contains 1, 2 or 3 chain atoms selected from O, N and S; and
said C5-C8 heterocycloalkyl contains 1, 2 or 3 ring atoms selected from O, N and S.

23. A compound of Formula I:

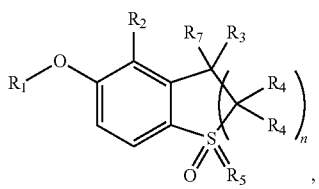

or a pharmaceutically acceptable salt thereof,
wherein:
$R_1$ is alkyl, C1-C10 heteroalkyl, C3-C8 cycloalkyl, C5-C8 heterocycloalkyl or a monocyclic aromatic ring having 6 to 10 ring atoms;
$R_2$ is nitro, cyano, halo, alkyl, C1-C10 heteroalkyl, alkynyl or alkenyl;
$R_3$ is hydrogen, hydroxy or amino;
each of $R_4$ is independently selected from the group consisting of hydrogen, halo, alkyl, C1-C10 heteroalkyl and C3-C8 cycloalkyl, or two $R_4$ groups and the carbon(s) to which they are attached form C3-C8 cycloalkyl or C5-C8 heterocycloalkyl;
$R_5$ is O or $NR_6$, wherein $R_6$ is selected from the group consisting of hydrogen, alkyl, and cyano;
$R_7$ is hydrogen, deuterium, or alkyl, or $R_3$ and $R_7$ in combination form oxo; and
n is 1 or 2;

wherein:
at least one $R_4$ is fluoro;
said C1-C10 heteroalkyl contains 1, 2 or 3 chain atoms selected from O, N and S; and
said C5-C8 heterocycloalkyl contains 1, 2 or 3 ring atoms selected from O, N and S.

24. A compound of Formula II:

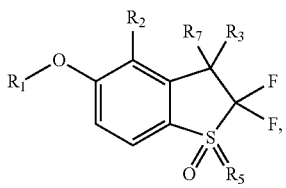

or a pharmaceutically acceptable salt thereof,
wherein:
$R_1$ is alkyl, C1-C10 heteroalkyl, C3-C8 cycloalkyl, C5-C8 heterocycloalkyl or a monocyclic aromatic ring having 6 to 10 ring atoms;
$R_2$ is nitro, cyano, halo, alkyl, C1-C10 heteroalkyl, alkynyl or alkenyl;
$R_3$ is hydrogen, hydroxy or amino;
$R_5$ is O or $NR_6$, wherein $R_6$ is selected from the group consisting of hydrogen, alkyl, and cyano; and
$R_7$ is hydrogen, deuterium, or alkyl, or $R_3$ and $R_7$ in combination form oxo;
wherein:
said C1-C10 heteroalkyl contains 1, 2 or 3 chain atoms selected from O, N and S; and
said C5-C8 heterocycloalkyl contains 1, 2 or 3 ring atoms selected from O, N and S.

25. The compound of claim 1, wherein:
$R_1$ is alkyl, C3-C8 cycloalkyl, phenyl or pyridyl;
$R_2$ is nitro, cyano, halo, substituted alkyl, alkynyl or alkenyl; and
each of $R_4$ is independently selected from the group consisting of hydrogen, halo, alkyl and C3-C8 cycloalkyl, or two $R_4$ groups and the carbon(s) to which they are attached form C3-C8 cycloalkyl.

26. The compound of claim 22, wherein:
$R_2$ is nitro, cyano, halo, alkyl, alkynyl or alkenyl; and
each of $R_4$ is independently selected from the group consisting of hydrogen, halo, alkyl and C3-C8 cycloalkyl, or two $R_4$ groups and the carbon(s) to which they are attached form C3-C8 cycloalkyl.

27. The compound of claim 23, wherein:
$R_1$ is alkyl, C3-C8 cycloalkyl, phenyl or pyridyl;
$R_2$ is nitro, cyano, halo, alkyl, alkynyl or alkenyl; and
each of $R_4$ is independently selected from the group consisting of hydrogen, halo, alkyl and C3-C8 cycloalkyl, or two $R_4$ groups and the carbon(s) to which they are attached form C3-C8 cycloalkyl.

28. The compound of claim 24, wherein:
$R_1$ is alkyl, C3-C8 cycloalkyl, phenyl or pyridyl; and
$R_2$ is nitro, cyano, halo, alkyl, alkynyl or alkenyl.

* * * * *